United States Patent
Thompson et al.

(10) Patent No.: US 12,211,607 B2
(45) Date of Patent: Jan. 28, 2025

(54) MANAGEMENT OF PSYCHIATRIC OR MENTAL CONDITIONS USING DIGITAL OR AUGMENTED REALITY WITH PERSONALIZED EXPOSURE PROGRESSION

(71) Applicants: BehaVR, LLC, Elizabethtown, KY (US); FrontAct Co., Ltd., Tokyo (JP)

(72) Inventors: Aprilia Thompson, Elizabethtown, KY (US); Brandon Hedges, Elizabethtown, KY (US); Christina Zaluski, Marlborough, MA (US); Eleanor Anderson, Elizabethtown, KY (US); Georgia Mitsi, Marlborough, MA (US); Joyce Tsai, Marlborough, MA (US); Morgan Taylor, Elizabethtown, KY (US); Risa Weisberg Hawkins, Elizabethtown, KY (US); Sarah Zadd, Elizabethtown, KY (US); Todd Grinnell, Marlborough, MA (US)

(73) Assignees: BehaVR, LLC, Elizabethtown, KY (US); FrontAct Co., Ltd., Tokyo (JP)

( * ) Notice: Subject to any disclaimer, the term of this patent is extended or adjusted under 35 U.S.C. 154(b) by 0 days.

(21) Appl. No.: 18/073,407

(22) Filed: Dec. 1, 2022

(65) Prior Publication Data
US 2023/0170075 A1 Jun. 1, 2023

Related U.S. Application Data

(63) Continuation of application No. PCT/US2022/051549, filed on Dec. 1, 2022.
(Continued)

(51) Int. Cl.
*G16H 20/70* (2018.01)
*G06F 3/01* (2006.01)
*G16H 40/67* (2018.01)

(52) U.S. Cl.
CPC ............ *G16H 20/70* (2018.01); *G06F 3/011* (2013.01); *G16H 40/67* (2018.01)

(58) Field of Classification Search
None
See application file for complete search history.

(56) References Cited

U.S. PATENT DOCUMENTS 10,286,179 B2  5/2019  Giap et al.
10,885,719 B1  1/2021  Ravindran et al.
(Continued)

OTHER PUBLICATIONS

HackerEarth, "Decision Tree", Accessed via web.archive.org for Jul. 9, 2021. (Year: 2021).*
(Continued)

*Primary Examiner* — Anne-Marie K Alderson
(74) *Attorney, Agent, or Firm* — Morgan, Lewis & Bockius LLP

(57) ABSTRACT

Systems and methods for implementing an exposure progression that improves an ability of a subject to manage a psychiatric or mental condition of the subject are provided. An exposure progression includes a plurality of categories in a hierarchical order. Each category is associated with one or more experiences, and each experience is associated with a digital reality scene that manifests a challenge. In some embodiments, the hierarchical order is generated or modified dynamically based at least in part on the level of success that a subject has had in one or more challenges, producing an exposure progression that it not only tailored to each subject but also with personalized timing and/or nature of the exposure practice.

33 Claims, 44 Drawing Sheets

Related U.S. Application Data

(60) Provisional application No. 63/415,876, filed on Oct. 13, 2022, provisional application No. 63/284,862, filed on Dec. 1, 2021.

(56) References Cited

U.S. PATENT DOCUMENTS

| | | |
|---|---|---|
| 11,101,031 B2 | 8/2021 | Hill et al. |
| 2008/0294013 A1* | 11/2008 | Gobeyn .................. A61B 5/445 600/300 |
| 2010/0010371 A1* | 1/2010 | Zayfert .................. G16H 20/70 600/558 |
| 2010/0223568 A1 | 9/2010 | Quek et al. |
| 2017/0326332 A1* | 11/2017 | Giap ..................... G06T 19/006 |
| 2018/0103867 A1* | 4/2018 | Stephens ................ A61B 5/486 |
| 2019/0198153 A1* | 6/2019 | Hill ........................ G16H 20/70 |
| 2019/0252080 A1 | 8/2019 | Liu |
| 2019/0385711 A1* | 12/2019 | Shriberg ................ G16H 50/20 |
| 2020/0023157 A1 | 1/2020 | Lewis et al. |
| 2020/0253527 A1 | 8/2020 | Ellison |
| 2020/0402642 A1 | 12/2020 | Hasselberg et al. |
| 2021/0383913 A1* | 12/2021 | Tablan ................... G10L 15/26 |
| 2022/0008745 A1* | 1/2022 | Kirchner ................ G06F 3/011 |
| 2022/0223067 A1* | 7/2022 | Franz ..................... G09B 5/065 |
| 2022/0310247 A1* | 9/2022 | Freeman ............... A61B 5/0205 |
| 2023/0005595 A1* | 1/2023 | Garriga Calleja ..... G16H 50/20 |

OTHER PUBLICATIONS

Chesham et. al., Meta-Analysis of the Efficacy of Virtual Reality Exposure Therapy for Social Anxiety, 2018, Behaviour Change (2018), 35, 152-166. (Year: 2018).*

Foa, et. al., Emotional processing of fear: Exposure to corrective information. Psychological Bulletin, 99 (1), 20-35. (Year: 1986).*

Miloff et. al., Single-session gamified virtual reality exposure therapy for spider phobia vs. traditional exposure therapy: study protocol for a randomized controlled non-inferiority trial. Trials. Feb. 2, 2016;17:60. (Year: 2016).*

Written Opinion issued in related International Patent Application No. PCT/US2022/037751 dated Nov. 15, 2022.

International Search Report issued in corresponding International Patent Application No. PCT/US2022/051549 dated Mar. 6, 2023.

Written Opinion issued in corresponding International Patent Application No. PCT/US2022/051549 dated Mar. 6, 2023.

International Search Report issued in related International Patent Application No. PCT/US2022/037751 dated Nov. 15, 2022.

* cited by examiner

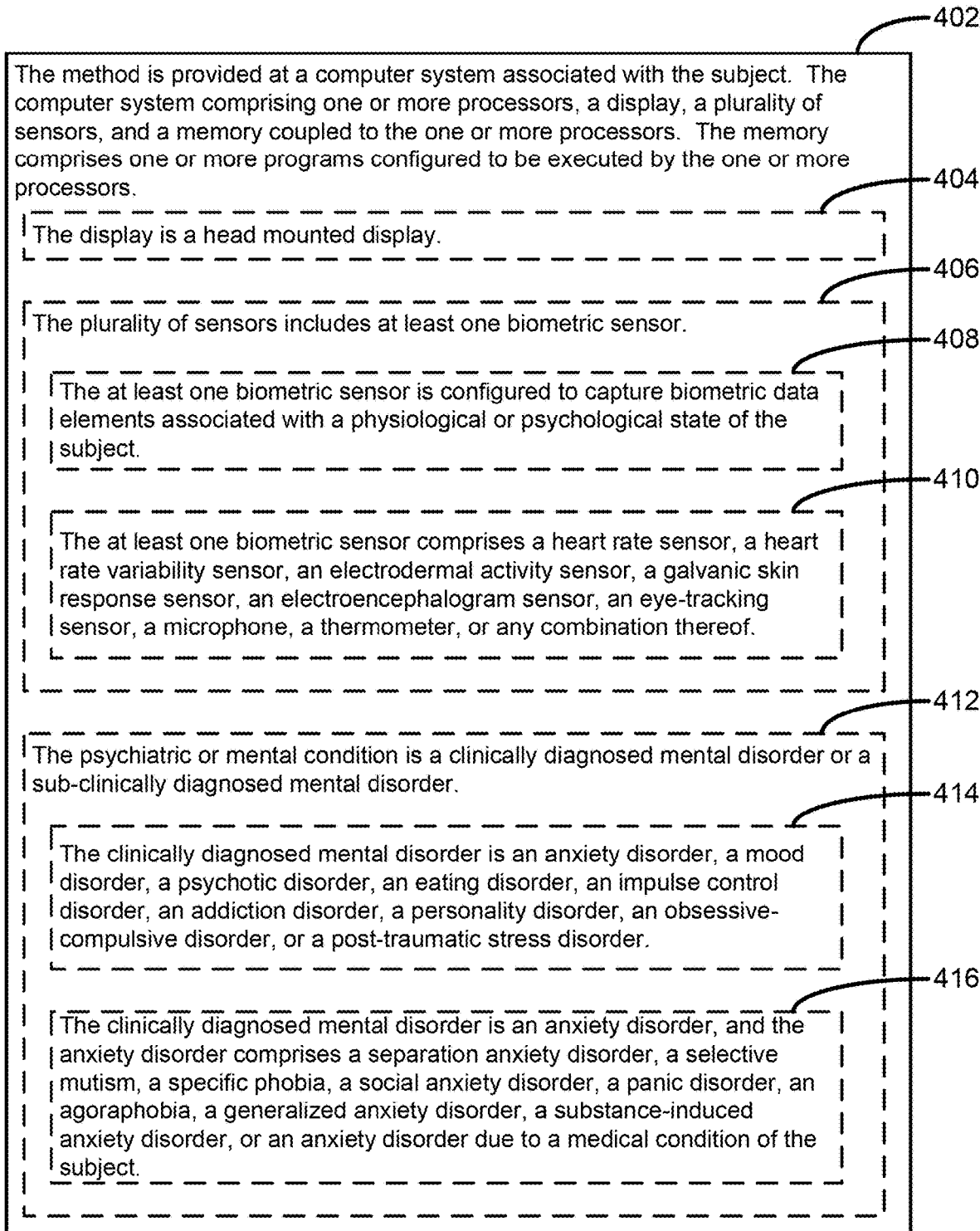

- 402: The method is provided at a computer system associated with the subject. The computer system comprising one or more processors, a display, a plurality of sensors, and a memory coupled to the one or more processors. The memory comprises one or more programs configured to be executed by the one or more processors.
  - 404: The display is a head mounted display.
  - 406: The plurality of sensors includes at least one biometric sensor.
    - 408: The at least one biometric sensor is configured to capture biometric data elements associated with a physiological or psychological state of the subject.
    - 410: The at least one biometric sensor comprises a heart rate sensor, a heart rate variability sensor, an electrodermal activity sensor, a galvanic skin response sensor, an electroencephalogram sensor, an eye-tracking sensor, a microphone, a thermometer, or any combination thereof.
  - 412: The psychiatric or mental condition is a clinically diagnosed mental disorder or a sub-clinically diagnosed mental disorder.
    - 414: The clinically diagnosed mental disorder is an anxiety disorder, a mood disorder, a psychotic disorder, an eating disorder, an impulse control disorder, an addiction disorder, a personality disorder, an obsessive-compulsive disorder, or a post-traumatic stress disorder.
    - 416: The clinically diagnosed mental disorder is an anxiety disorder, and the anxiety disorder comprises a separation anxiety disorder, a selective mutism, a specific phobia, a social anxiety disorder, a panic disorder, an agoraphobia, a generalized anxiety disorder, a substance-induced anxiety disorder, or an anxiety disorder due to a medical condition of the subject.

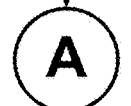

432 — The method comprises (A) obtaining a plurality of categories for the subject, wherein each respective category in the plurality of categories (i) is directed to improving the ability of the subject to manage the psychiatric or mental condition of the subject, (ii) is associated with a corresponding plurality of proposed experiences, and (iii) is associated with at least one respective gate criterion in a plurality of gate criteria, and wherein for each respective category in the plurality of categories, each respective proposed experience in the corresponding plurality of proposed experiences (i) is associated with a corresponding digital reality scene, in a corresponding plurality of digital reality scenes, that manifests a corresponding challenge, in a corresponding plurality of challenges, designed for the respective proposed experience of the respective category, and (ii) is associated with at least one biometric threshold in a plurality of biometric thresholds.

434 — A respective gate criteria of a respective category in the plurality of categories is set by a system administrator, the subject, a health care worker associated with the subject, a model, or a combination thereof.

436 — A respective gate criteria of a first category in the plurality of categories is set by a system administrator or a health care worker associated with the subject, and a respective gate criteria of a second category in the plurality of categories is set by the subject.

438 — The at least one respective gate criteria comprises a ranking gate criterion associated with a hierarchical ranking of each category in the plurality of categories.

440 — The at least one respective gate criteria comprises a medical practitioner gate criterion associated with an approval, from a medical practitioner associated with the subject, of the category in the plurality of categories corresponding to the at least one respective gate criteria.

588 — In the obtaining (A), the plurality of categories is originally arranged in an initial category hierarchy, thereby forming an initial exposure progression, wherein the initial category hierarchy is set by (i) a system administrator, (ii) the subject, (iii) a health care worker associated with the subject, (iv) a model, or (v) a combination thereof.

590 — The method further comprises (F) presenting, on the display prior to the presenting (B), a graph to represent an initial instance of the exposure progression, wherein the graph comprises a plurality of nodes and a plurality of edges, and wherein for each respective node in the plurality of nodes, the graph further comprises a corresponding plurality of experience graphics displayed adjacent to the respective node, wherein: each respective node in the plurality of nodes (i) corresponds to a respective category in the plurality of categories, (ii) is associated with a corresponding plurality of proposed experiences, and (iii) is associated with the at least one respective gate criterion in the plurality of gate criteria, for each respective node in the plurality of nodes, each respective experience graphic in the corresponding plurality of experience graphic (i) corresponds to a respective proposed experience in the plurality of proposed experiences, and (ii) is associated with the at least one biometric threshold in the plurality of biometric thresholds, each respective node in the plurality of nodes is connected by an edge in the plurality of edges to at least one other node in the graph, and each respective edge in the plurality of edges represents a progression within the graph between a respective initial node and a respective subsequent node in the graph upon successful completion by a subject of a required number of corresponding challenges associated with the respective initial node.

592 — For each respective node in the plurality of nodes, the graph further comprises a plurality of branches, wherein each experience graphic in the plurality of experience graphics is connected to the respective node in the plurality of nodes by a branch in the plurality of branches.

In the obtaining (A), the plurality of proposed experiences associated with the first category is originally arranged in an initial first experience hierarchy, thereby forming an initial first sub-progression, wherein the initial first experience hierarchy is set by (i) a system administrator, (ii) the subject, (iii) a health care worker associated with the subject, (iv) a model, or (v) a combination thereof.

The method further comprises (S) assessing whether a proposed experience immediately subsequent to the first proposed experience in the initial first sub-progression is appropriate for the subject to perform next.

The method further comprises (T) presenting, if the immediately subsequent proposed experience is appropriate for the subject to perform next, a digital reality scene that manifests a challenge designed for the immediately subsequent proposed experience in the initial first sub-progression.

The method further comprises (U) repeating the obtaining (C), and the determining (D) for the challenge designed for the immediately subsequent proposed experience in the initial exposure first sub-progression.

The method further comprises (V) recommending, if the immediately subsequent proposed experience is inappropriate for the subject to perform next, a proposed experience other than immediately subsequent proposed experience for the subject to perform next.

Fig. 4R

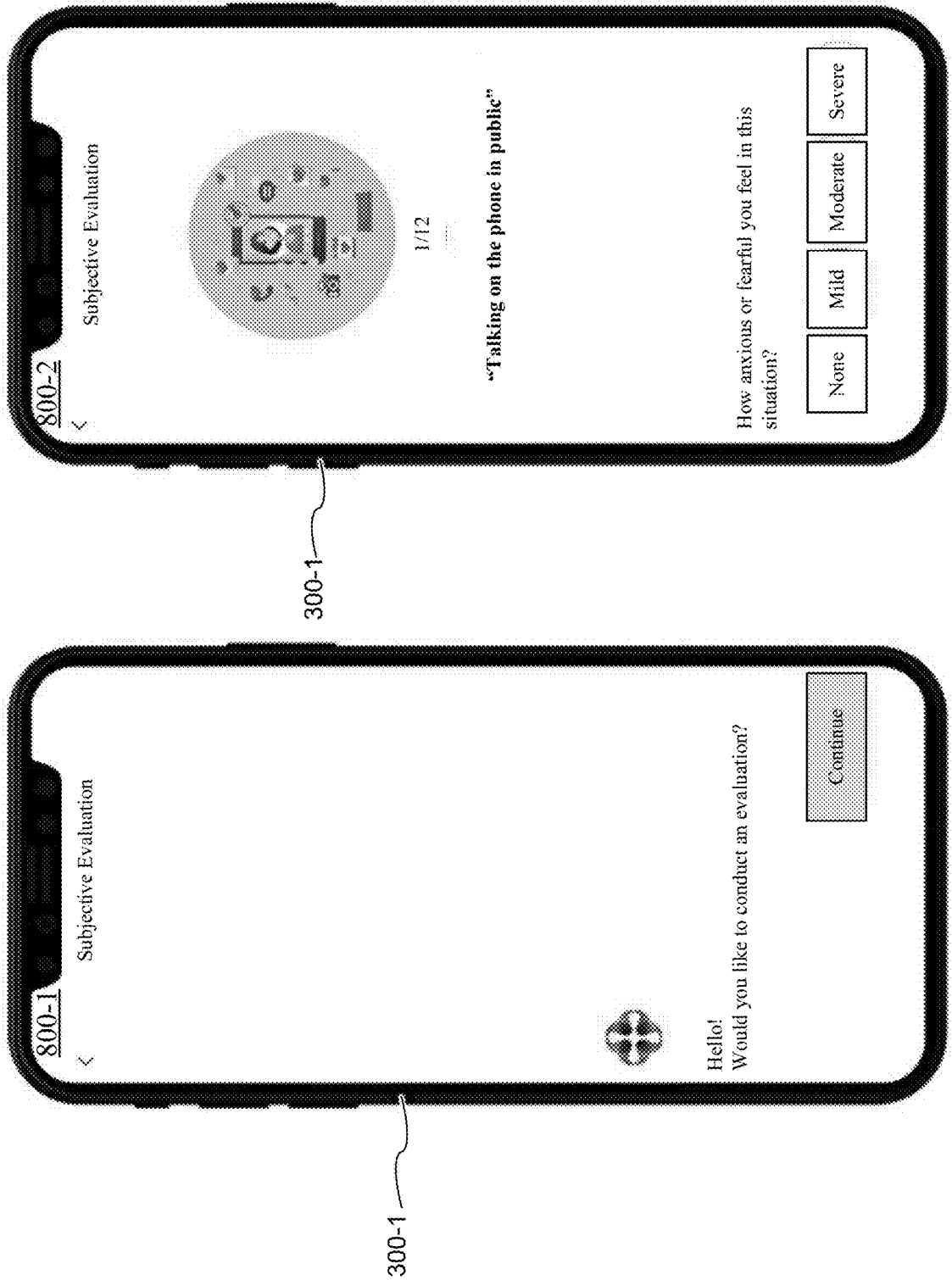

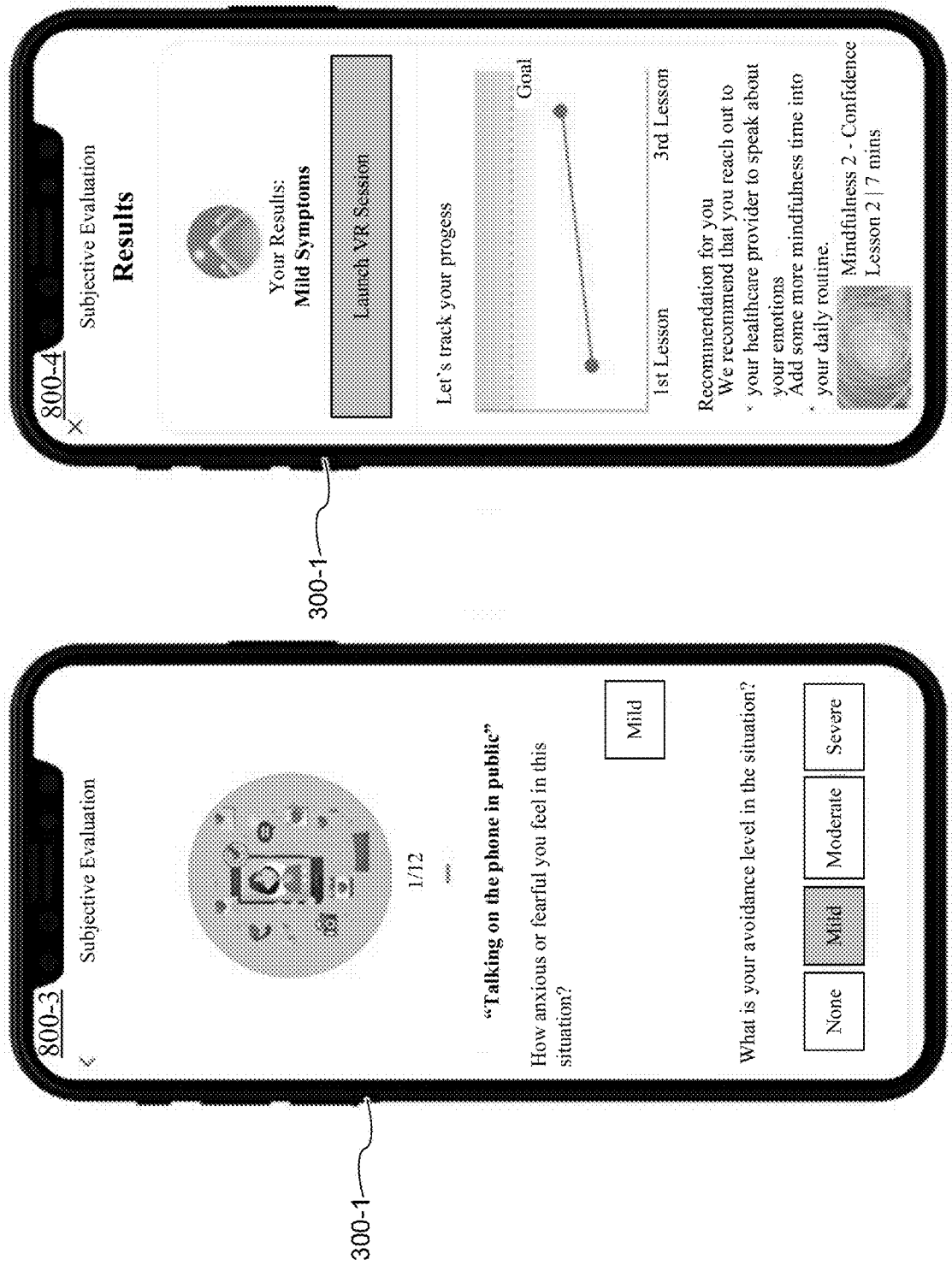

2200

| Time Period | Exemplary Lesson | Exemplary Content |
|---|---|---|
| 1 | Introduction to Cognitive Reframing: Part 1 | Users are introduced to the Woods of Wisdom for the first time, and learn about linking emotions and behaviors to anxious thoughts. |
| | Introduction to Cognitive Reframing: Part 2 | Users learn how to identify different types of anxious thoughts, and practice labeling thoughts. |
| | How to Record Thoughts | Users learn how to record both anxious thoughts and positive thoughts/affirmations in DR. They also unlock the ability to log thoughts via App. |
| 2 | Gathering Evidence | Users practice a reframing activity, such as by reframing a thought by gathering evidence for and against the thought. |
| 3 | Usefulness & Core Beliefs | Users practice identifying the usefulness and core belief activity associated with an anxious thought, such as by testing the usefulness of that core belief as it relates to them achieving his/her goals. |
| 4 | Creating Space | Users practice defusion activity, such as by learning how to create cognitive distance between themselves and his/her thoughts. |

Fig. 10A

| Key R=Required O=Optional | | Psychoeducation | Social Challenge (SC) | Mindfulness | Cognitive Reframing (CR) | Goal Setting |
|---|---|---|---|---|---|---|
| Week 1 | Chapter 1 | (R) Intro to program and to CBT + psychoeducation (~15 min) | | | | |
| Week 1 | Chapter 2 | (R) Intro to Mindfulness | | (R) Mindfulness | | |
| Week 1 | Chapter 3 | (R) Intro to Goals | | (O) Mindfulness | | (R) Long-term goal setting (O) Short-term goal setting in PWA |
| Week 2 | Chapter 4 | (R) Intro to Exposure and SC | (R) Fear ladder activity and first challenge | (R) Mindfulness | | (O) Long-term + short-term goal setting |
| Week 2 | Chapter 5 | | (R) SC Practice | (R) Mindfulness | | (O) Long-term + short-term goal setting |
| Week 2 | Chapter 6 | | (R) SC Practice | (O) Mindfulness | (R) Woods-Wisdom Tutorial + Anxious Thoughts + linking emotions/behaviors | (O) Long-term + short-term goal setting |
| Week 3 | Chapter 7 | (R) Intro to Cognitive Reframing Part 1 | (R) SC Practice | (O) Mindfulness | (R) CR Session – Label Types + Practice | (O) Long-term + short-term goal setting |
| Week 3 | Chapter 8 | (R) Intro to Cognitive Reframing Part 2 | (R) SC Practice | (O) Mindfulness | (R) CR Practice | (O) Long-term + short-term goal setting |
| Week 3 | Chapter 9 | | (R) SC Practice | (O) Mindfulness | (R) CR Practice | (O) Long-term + short-term goal setting |
| Week 4 | Chapter 10 | | (R) SC Practice | (O) Mindfulness | (R) CR Practice | (O) Long-term + short-term goal setting |
| Week 4 | Chapter 11 | (R) Gathering Evidence | (R) SC Practice | (O) Mindfulness | (R) CR Practice | (O) Long-term + short-term goal setting |
| Week 4 | Chapter 12 | | (R) SC Practice | (O) Mindfulness | (O) CR Practice | (O) Long-term + short-term goal setting |

| | | | | | |
|---|---|---|---|---|---|
| Week 5 | Chapter 13 | | (R) SC Practice | (O) Mindfulness | (R) CR Tutorial | (O) Long-term goal setting (R) Short-term goal setting |
| Week 5 | Chapter 14 | (R) Usefulness | | | (R) CR Practice | (O) Long-term + short-term goal setting |
| Week 5 | Chapter 15 | | (R) SC Practice | (O) Mindfulness | (O) CR Practice | (O) Long-term + short-term goal setting |
| Week 6 | Chapter 16 | | | (O) Mindfulness | (O) CR Practice | (O) Long-term + short-term goal setting |
| Week 6 | Chapter 17 | | (R) SC Practice | (O) Mindfulness | (O) CR Practice | (O) Long-term + short-term goal setting |
| Week 6 | Chapter 18 | | (R) SC Practice | (O) Mindfulness | (O) CR Practice | (O) Long-term + short-term goal setting |
| Week 7 | Chapter 19 | | (R) SC Practice | (O) Mindfulness | (O) CR Practice | (O) Long-term + short-term goal setting |
| Week 7 | Chapter 20 | | (R) SC Practice | (O) Mindfulness | (O) CR Practice | (O) Long-term + short-term goal setting |
| Week 7 | Chapter 21 | | (R) SC Practice | (O) Mindfulness | (O) CR Practice | (O) Long-term + short-term goal setting |
| Week 8 | Chapter 22 | (R) Maintenance + Values | (R) SC Practice | (O) Mindfulness | (O) CR Practice | (O) Long-term + short-term goal setting |
| Week 8 | Chapter 23 | | (R) SC Practice | (O) Mindfulness | (O) CR Practice | (O) Long-term + short-term goal setting |
| Week 8 | Chapter 24 | (R) Graduation | | (O) Mindfulness | (O) CR Practice | (O) Long-term + short-term goal setting |

A
| | Type | Logic function |
|---|---|---|
| 1 | 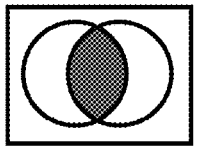 | $C = A \wedge B$ |
| 2 | 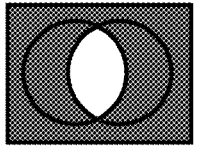 | $C = \sim(A \wedge B)$ |
| 3 | 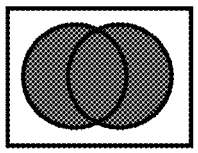 | $C = A \vee B$ |
| 4 | 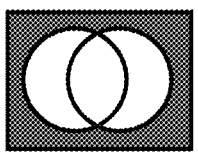 | $C = \sim(A \vee B)$ |
| 5 |  | $C = A \wedge \sim B,\ C = \sim A \wedge B,$ |
| 6 | 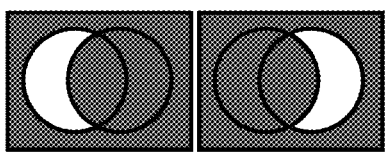 | $C = \sim A \vee B,\ C = A \vee \sim B,$ |
| 7 | 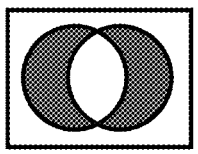 | $C = \sim(A \leftrightarrow B)$ |
| 8 | 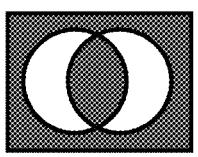 | $C = A \leftrightarrow B$ |
Fig. 14

MANAGEMENT OF PSYCHIATRIC OR MENTAL CONDITIONS USING DIGITAL OR AUGMENTED REALITY WITH PERSONALIZED EXPOSURE PROGRESSION

CROSS-REFERENCE TO RELATED APPLICATIONS

The present application claims priority to U.S. Provisional Patent Application No. 63/284,862, entitled "Management of Psychiatric or Mental Conditions Using Digital or Augmented Reality with Personalized Exposure Progression," filed Dec. 1, 2021, which is hereby incorporated by reference in its entirety for all purposes. Also, the present application claims priority to U.S. Provisional Patent Application No. 63/415,876, entitled "Management of Psychiatric or Mental Conditions Using Digital or Augmented Reality with Personalized Exposure Progression," filed Oct. 13, 2022, which is hereby incorporated by reference in its entirety for all purposes.

TECHNICAL FIELD

The present disclosure relates to systems, methods, and devices for preparing digital reality or augmented reality based regimens for the management of psychiatric or mental conditions exhibited by subjects.

BACKGROUND

Demand to access mental health care facilities and services that improve the mental health of patients is at an all-time high. However, evidence cannot be found that this increased access to mental health care facilities has also led to decreases in the prevalence of mental health issues. In fact, mental health problems in patients have increased in recent years. See Mojtabai et al., "Trends in Psychological Distress, Depressive Episodes and Mental-Health Treatment-Seeking in the United States: 2001-2012," Journal of Affective Disorders, 174, pg. 556.

Furthermore, increased demand to mental health care facilities causes a proportional increase in demand for health care practitioners and professionals to provide services at the mental health care facilities. Accordingly, health care practitioners and professionals are subjected to increased stress, both psychological and physiological, that prevents them from providing optimal service. See Ruiz-Fernandez et al., 2020, "Compassion Fatigue, Burnout, Compassion Satisfaction and Perceived Stress in Healthcare Professionals During the COVID-19 Health Crisis in Spain," Journal of Clinical Nursing, 29(21-22), pg. 4321-4430.

Conventional solutions to improving mental health are laborious and resource intensive for all parties involved. For instance, conventional solutions often require time-consuming and expensive in-person meetings between a clinician and a patient. Moreover, these in-person meetings do not readily allow a clinician to observe the patient in situations that expose an underlying mental health issue of the patient given the intimate and private nature of in-person meetings with the clinician.

Furthermore, conventional solutions lack satisfactory efficacy for treatment of certain mental health issues. For instance, while conventional in-person cognitive and/or behavioral exposure techniques have generally shown some efficacy, they lack significant efficacy, particularly for post-traumatic stress disorders (PTSD), social anxiety disorder (SAD), and panic disorder. See Carpenter et al., 2018, "Cognitive Behavioral Therapy for Anxiety and Related Disorders: A Meta-analysis of Randomized Placebo-controlled Trails," Depression and Anxiety, 25(56), pg. 502.

Coinciding with this, interactive computer implemented gaming and services are expanding. However, prior solutions to marry services to improve mental health with computer implemented gaming has been unsatisfactory. One cause of such dissatisfaction is the requirement that a therapist be present with a patient during a computer implemented therapeutic gaming session. See Freeman et al., 2017, "Virtual Reality in the Assessment, Understanding, and Treatment of Mental Health Disorders," Psychological Medicine, 47(14), pg. 2393. This requirement is burdensome on the temporal, spatial, and financial resources available to both the patient and the medical practitioner.

As such, there is a need for systems, methods, and devices that improve the mental health of subjects without overly burdening the subjects or their medical practitioners.

SUMMARY

Given the above background, what is needed in the art are systems and methods for preparing a regimen for improving an ability of a subject to manage a psychiatric or mental condition exhibited by the subject.

The present disclosure provides improved systems and methods for implementing an exposure progression that improves an ability of a subject to manage or improve a psychiatric or mental condition of the subject.

One aspect of the present disclosure is directed to providing systems, methods, and devices for implementing an exposure progression. The exposure progression is a sequence of events in a digital reality that is configured to improve an ability of a subject to manage a psychiatric or mental condition of the subject. For instance, in some embodiments, the sequence of events includes various experiences presented to a subject such as two or more experiences, three or more experiences, five or more experiences, 10 or more experiences, or the like. In this way, in some such embodiments, a method of the present disclosure is implemented at a computer system associated with the subject. The computer system includes one or more processors and a display for presenting at least the digital reality scene. In some embodiments, the computer system includes one or more speakers or headphones for presenting auditory aspects of a digital reality scene. Moreover, the computer system includes a plurality of sensors and a memory coupled to the one or more processors. The memory includes one or more programs configured to be executed by the one or more processors.

Accordingly, the method includes obtaining a plurality of categories for the subject. In some embodiments, each respective category in the plurality of categories is directed to improving a particular ability of the subject to manage the psychiatric or mental condition. In some embodiments the plurality of categories includes an exposure category, a cognitive reframing therapy (CBT) category, a mindfulness category, a general category, or a combination thereof. A non-limiting example of the exposure category includes a first social interaction and/or interaction anxiety category, a second public performance anxiety category, a third fear of being observed category, a fourth ingestion anxiety (e.g., anxiety associated with consumption of foods) category, a fifth assertiveness anxiety category, or a combination thereof. Another non-limiting example of a CBT category includes a sixth cognitive reframing category, a seventh usefulness category, an eight defusion category, or a combination there. Each respective category is associated with a corresponding plurality of proposed experiences. As such, each proposed experience in the corresponding plurality of proposed experiences is a task, or challenge, in the digital reality that is configured to improve the particular ability of the subject to manage the psychiatric or mental condition. A non-limiting example of an experience associated with the first social interaction and/or interaction anxiety category includes an exercise to improve interaction anxiety by being left alone (e.g., at a wedding, at a park, etc.) and having to interact with a stranger. Another non-limiting example of an experience associated with the CBT category includes a cognitive reframing exercise configured to identify catastrophic thoughts and assumptions of the subject regarding how the subject will be perceived that lead to interaction anxiety.

Furthermore, each respective category is associated with at least one respective gate criterion in a plurality of gate criteria. In some embodiments, a gate criterion is a condition precedent that must be achieved in order to deem the respective category complete for the subject. A non-limiting example of a condition precedent is a requirement that at least two proposed experiences in the corresponding plurality of proposed experiences be successfully completed by the subject before the subject is allowed to invoke a given category. Another non-limiting example of a condition precedent is a requirement that the subject must satisfy a threshold number of interactions with a digital reality object when interacting with an experience. In this way, each respective proposed experience in the corresponding plurality of proposed experiences is associated with a corresponding digital reality scene that manifests a corresponding challenge designed for the respective proposed experience of the respective category.

In some embodiments, each proposed experience is further associated with at least one biometric measurement and threshold in a plurality of biometric thresholds, which allows the method to correlate capturing at least one biometric data element from the subject during the digital reality scene. For instance, in some embodiments, the at least one biometric measurement includes a vocal feature associated with the subject (e.g., an entropy of a vocal signal obtained from the subject), or a spatial feature associated with the subject when interacting with the digital reality scene (e.g., movement of a hand of the subject when interacting with the digital reality scene). Accordingly, in some embodiments, the disclosed methods include presenting, on the display, a first digital reality scene that manifests a first challenge designed for a first proposed experience of a first category, which is based on the selection by the subject of the plurality of categories. In some embodiments, in coordination with this presentation of the first digital reality scene, the disclosed methods include obtaining a first plurality of data elements. In some embodiments, the first plurality of data elements includes a first set of biometric data elements. The first set of biometric data elements is obtained from a subset of sensors in the plurality of sensors. In some embodiments, the subset of sensors includes one sensor, at least two sensors, or at least four sensors. As such, the subset of sensors includes at least one biometric sensor configured to capture at least one biometric data element associated with the subject when the subject is completing the first challenge in the first digital reality scene. In some embodiments, the at least one biometric sensor includes a first biometric sensor that is a heart rate sensor, a heart rate variability sensor, a blood pressure sensor, an electrodermal activity sensor, a galvanic skin response sensor, an electroencephalogram sensor, an eye-tracking sensor, a recorder, a microphone, a thermometer, or any combination thereof. From this, in some such embodiments, the disclosed methods include determining if performance of the subject during the presenting satisfies or exceeds various biometric measurement thresholds, when each gate criterion in the at least one respective gate criterion associated with the first category is satisfied, or both. In some such embodiments, based on this determination, which includes an assessment of the at least one biometric data element, the disclosed methods include determining a second category in the plurality of categories for the subject to perform next that will best improve the ability of the subject to manage the psychiatric or mental condition based at least in part on an outcome of the determination if performance of the subject during the presenting satisfies or exceeds various biometric measurement thresholds. Accordingly, the disclosed methods implement the exposure progression from the first category to the second category that improves the ability of the subject to manage the psychiatric or mental condition of the subject by selecting the second category for the subject, as opposed to a third category that is less optimal for the subject in comparison to the second category.

In some embodiments, the plurality of categories in the obtaining the plurality of categories is originally arranged in an initial instance of the exposure progression that is set by a system administrator, the subject, a health care worker associated with the subject (e.g., a medical practitioner), a model (e.g., a computational model), or a combination thereof.

In some embodiments, the method further includes presenting, on the display prior to the presenting the first digital reality scene, a graph to represent the initial instance of the exposure progression. The graph includes a plurality of nodes and a plurality of edges. In some embodiments, for each respective node in the plurality of nodes, the graph further includes a corresponding plurality of experience graphics displayed adjacent to the respective node. In some embodiments, each respective node in the plurality of nodes corresponds to a respective category in the plurality of categories. Moreover, in some embodiments, each respective node is associated with a corresponding plurality of proposed experiences. Furthermore, each respective node is associated with the at least one respective gate criterion in the plurality of gate criteria. For each respective node in the plurality of nodes, each respective experience graphic in the corresponding plurality of experience graphics corresponds to a respective proposed experience in the plurality of proposed experiences and is associated with the at least one biometric threshold in the plurality of biometric thresholds. Additionally, in some embodiments, each respective node in the plurality of nodes is connected by an edge in the plurality of edges to at least one other node in the graph. Furthermore, in some embodiments, each respective edge in the plurality of edges represents a progression within the graph between a respective initial node and a respective subsequent node in the graph upon successful completion by a subject of a required number of corresponding challenges associated with the respective initial node.

In some embodiments, for each respective node in the plurality of nodes, the graph further includes a corresponding plurality of branches. Furthermore, each respective experience graphic in the corresponding plurality of experience graphics is connected to the respective node by a branch in the corresponding plurality of branches.

In some embodiments, the determining the second category includes assessing whether a category immediately subsequent to the first category in the initial instance of the exposure progression is appropriate for the subject to perform next. In some embodiments, the determining the second category further includes presenting, when the immediately subsequent category in the initial instance of the exposure progression is appropriate for the subject to perform next, the immediately subsequent category in the initial instance of the exposure progression as the second category for the subject to perform.

In some embodiments, the determining the second category further includes recommending, when the immediately subsequent category in the initial instance of the exposure progression is inappropriate for the subject to perform next, a category other than the immediately subsequent category in the initial instance of the exposure progression as the second category for the subject to perform next.

In some embodiments, the first biometric sensor is configured to capture biometric data elements associated with a physiological or psychological state of the subject at a predetermined sampling rate.

In some embodiments, the predetermined sampling rate between 40 milliseconds (ms) and 160 ms. In some embodiments, the predetermined sampling rate is adjustable or fixed.

In some embodiments, the first biometric sensor is a heart rate sensor, a heart rate variability sensor, a blood pressure sensor, an electrodermal activity sensor, a galvanic skin response sensor, an electroencephalogram sensor, an eye-tracking sensor, a recorder, a microphone, or a thermometer.

In some embodiments, the first subset of biometric data elements is captured by the first biometric sensor in response to a specific trigger, such as a specific trigger event configured to initiate capture of the first subset of biometric data elements.

In some embodiments, the first biometric sensor is a heart rate sensor. In some such embodiments, the first subset of biometric data elements is used to determine a heartbeat rate of the subject.

In some embodiments, the first biometric sensor is a heart rate variability sensor. In some such embodiments, the first subset of biometric data elements is used to determine beat-to-beat intervals of the subject, thereby providing an assessment of heart rate variability.

In some embodiments, the first biometric sensor is an eye-tracking sensor and the first subset of biometric data elements is used to determine a gaze fixation of the subject, a smooth motion of the subject, a saccade of the subject, a blink by the subject, a scan-path length of the subject, an eye openness of the subject, a pupil dilation of the subject, an eye position of the subject, a hypervigilance exhibited by the subject, a gaze avoidance exhibited by the subject, or any combination thereof.

In some embodiments, the first biometric sensor is an eye-tracking sensor. In some such embodiments, the first subset of biometric data elements is used to determine a gaze fixation of the subject. In some such embodiments, the gaze fixation is defined based on a spatial criterion and a temporal criterion on a region of interest in the first digital reality scene.

In some embodiments, the first biometric sensor is an eye-tracking sensor. In some such embodiments, the first subset of biometric data elements is used to determine a hypervigilance exhibited by the subject. In some such embodiments, the hypervigilance is defined as a time to a first fixation during a specific challenge in the first digital reality scene.

In some embodiments, the first biometric sensor is an eye-tracking sensor. In some such embodiments, the first subset of biometric data elements is used to determine a gaze avoidance exhibited by the subject. In some such embodiments, the gave avoidance is defined as a number of fixations exhibited by the subject during a specific challenge in the first digital reality scene divided by a total number of fixations exhibited by the subject in the first digital reality scene.

In some embodiments, the first biometric sensor is a recorder. In some such embodiments, a sentiment analysis or an emotion analysis is performed on the first subset of biometric data elements to assess whether the first challenge is successfully completed.

In some embodiments, the first subset of biometric data elements is transcribed (e.g., by a computational model) to create a transcription. In some such embodiments, the transcription is extracted to produce words. In some such embodiments, the sentiment analysis is performed on the extracted words.

In some embodiments, the first subset of biometric data elements is used to determine fundamental frequency, speech rate, pauses, duration of silence, voice intensity, voice onset time, pitch perturbations, loudness perturbations, voice breaks, pitch jumps, voice quality, sound quality or a combination thereof, to assess whether the first challenge is successfully completed by satisfying the at least one biometric threshold associated with the first proposed experience for the first challenge.

In some embodiments, the first subset of biometric data elements captured by the first biometric sensor is stored, which allows a replay of the first subset of biometric data elements after completion of the first digital reality scene.

In some embodiments, one or more specific key words is used in analysis of the first subset of biometric data elements to prevent spoofing.

In some embodiments, the first subset of biometric data elements is pre-processed to remove a background noise prior to using the first subset of biometric data elements to assess whether the first challenge is successfully completed by satisfying the at least one biometric threshold associated with the first proposed experience for the first challenge.

In some embodiments, the first subset of biometric data elements is captured by the first biometric sensor with an auto noise cancellation feature enabled.

In some embodiments, the method further includes receiving, in electronic form, a second plurality of data elements associated with the subject. In some such embodiments, the second plurality of data elements includes a second set of biometric data elements associated with an initial psychiatric or mental condition of the subject. Moreover, the corresponding threshold baseline characteristic is formed by the second plurality of biometric data elements.

In some embodiments, the method further includes obtaining, from the first biometric sensor in the at least one biometric sensor, a second set of biometric data elements when or before initiating the presenting the first digital reality scene. The corresponding threshold baseline characteristic is formed by the second set of biometric data elements.

In some embodiments, the obtaining the second set of biometric data elements is performed during an introduction or tutorial challenge.

In some embodiments, the introduction or tutorial challenge is presented in a digital reality scene. The digital reality scene includes a happy place (e.g., a digital space configured to calm or normalize a subject, such as by providing an educational content and/or a soothing content).

In some embodiments, the method further includes repeating, when a gate criterion in the at least one respective gate criterion associated with the first category is not satisfied, the presenting the first digital reality scene, the obtaining the first plurality of data elements, and the determining satisfaction of one or more thresholds (e.g., at least one biometric threshold, a corresponding first threshold baseline characteristic, a gate criterion, a combination thereof), one or more times for other challenges associated with the first category.

In some embodiments, the method further includes recommending, when the first challenge is determined to be unsuccessfully completed by failing to satisfy the at least one biometric threshold associated with the first proposed experience for the first challenge, a challenge of another proposed experience in the corresponding plurality of proposed experiences for the first category for the subject to perform next. The recommending the challenge is presented in a text, a graphic, an audio, or a combination thereof.

In some embodiments, the recommended challenge poses an equal or less challenging challenge than the first challenge of the first category. In some embodiments, the recommended challenge is the same first challenge designed for the first proposed experience of the first category. Moreover, in some embodiments, the recommended challenge is a challenge designed for a different proposed experience of the first category. In some embodiments, the recommended challenge is a challenge designed for a proposed experience of a different category in the plurality of categories. Furthermore, in some embodiments, the recommended challenge is a challenge other than any category in the plurality of categories.

In some embodiments, the method further includes repeating, in response to selection of the recommended challenge, the presenting the first digital reality scene, the obtaining the first plurality of data elements, and the determining satisfaction of one or more thresholds (e.g., at least one biometric threshold, a corresponding first threshold baseline characteristic, a gate criterion, a combination thereof) for the recommended challenge.

In some embodiments, the challenge is a unique mindfulness challenge customized for the first category, a universal mindfulness challenge that is accessible from each category in the plurality of categories, a unique cognitive reframing challenge customized for the first category, or a universal cognitive reframing challenge that is accessible from each category in the plurality of categories.

In some embodiments, the method further includes presenting, in response to selection of the challenge and on the display, a second digital reality scene that manifests the challenge.

In some embodiments, the method further includes obtaining, in coordination with the presenting the second digital reality scene, a third plurality of data elements from a subset of sensors in the plurality of sensors. The third plurality of data elements includes a third plurality of biometric data elements associated with the subject. Moreover, the third plurality of data elements is captured when the subject is completing the second digital reality scene that manifests the challenge. In some such embodiments, the method further includes determining a change or improvement by comparing the third plurality of biometric data elements against the corresponding threshold baseline characteristic or against the first plurality of biometric data elements from the obtaining the first plurality of data elements.

In some embodiments, the method further includes presenting, on the display prior to the determining the second category, a subjective evaluation option, such as an assessment. In some such embodiments, the method further includes performing, in response to selection of the subjective evaluation option, a subjective evaluation. The determining the second category is based, at least in part, on an outcome of the subjective evaluation.

In some embodiments, the subjective evaluation is based on a Clinical Global Impression Scale of Improvement (CGI), a Patient Global Impression Scale of Improvement (PGI), a Liebowitz Social Anxiety Scale (LSAS), or a combination thereof. In some embodiments, the subjective evaluation is based on a Minimal Clinically Important Difference (MCID) that considers the CGI, the PGI, the LSAS, or the combination thereof. In some embodiments, the subjective evaluation is based on a Generalized Anxiety Disorder (GAD), such as a GAD-2, GAD-7, etc. In some embodiments, the subjective evaluation is based on Patient Health Questionnaire (PHQ), such as a PHQ-2, PHQ-9, etc.

In some embodiments, the method further includes repeating the presenting the first digital reality scene, the obtaining the first plurality of data elements, and the determining satisfaction of one or more thresholds (e.g., at least one biometric threshold, a corresponding first threshold baseline characteristic, a gate criterion, a combination thereof) for a digital reality scene that manifests a challenge designed for a proposed experience of the second category. In some such embodiments, the method further includes repeating the determining the second category for the second category.

In some embodiments, in the obtaining the plurality of categories, the plurality of proposed experiences associated with the first category is originally arranged in an initial first sub-progression. In some embodiments, the initial first sub-progression is set by a system administrator, the subject, a health care worker associated with the subject, a model, or a combination thereof.

In some embodiments, the method further includes assessing whether a proposed experience immediately subsequent to the first proposed experience in the initial first sub-progression is appropriate for the subject to perform next. In some such embodiments, the method further includes presenting, when the immediately subsequent proposed experience is deemed appropriate for the subject to perform next, a digital reality scene that manifests a challenge designed for the immediately subsequent proposed experience in the initial first sub-progression. Furthermore, in some such embodiments, the method further includes repeating the obtaining the first plurality of data elements, and the determining satisfaction of one or more thresholds (e.g., at least one biometric threshold, a corresponding first threshold baseline characteristic, a gate criterion, a combination thereof) for the challenge designed for the immediately subsequent proposed experience in the initial exposure first sub-progression.

In some embodiments, the method further includes recommending, when the immediately subsequent proposed experience is deemed inappropriate for the subject to perform next, a proposed experience other than immediately subsequent proposed experience for the subject to perform next.

In some embodiments, the determining satisfaction of one or more thresholds (e.g., at least one biometric threshold, a corresponding first threshold baseline characteristic, a gate criterion, a combination thereof. Moreover, the method further includes determining whether the first set of biometric data elements satisfies a second biometric threshold in the at least one biometric threshold.

In some embodiments, one of the first and second biometric thresholds in the at least one biometric threshold is a required minimal change in a number of utterances compared to an utterance baseline of the subject. Accordingly, the other of the first and second biometric thresholds in the at least one biometric threshold is a required minimal change in assertiveness compared to an assertiveness baseline of the subject, a required minimal change in decibel level compared to a decibel level baseline of the subject, a required minimal change in pitch compared to a pitch baseline of the subject, or a combination thereof during the first digital reality scene that manifests the first challenge designed for the first proposed experience associated with the first category.

In some embodiments, the at least one biometric data element captured in the obtaining the first plurality of data elements includes a fourth set of biometric data elements captured by a second biometric sensor in the at least one biometric sensor. In some embodiments, the fourth set of biometric data elements is different than the first set of biometric data elements. Moreover, in some such embodiments, the determining satisfaction of one or more thresholds (e.g., at least one biometric threshold, a corresponding first threshold baseline characteristic, a gate criterion, a combination thereof) includes determining whether a comparison of the fourth set of biometric data elements against a third baseline characteristic satisfies a third biometric threshold in the at least one biometric threshold.

In some embodiments, one of the first and third biometric thresholds is a required minimal change in a number of words compared to a word baseline of the subject, a required minimal change in a number of utterances compared to an utterance baseline of the subject, (a required minimal change in assertiveness compared to an assertiveness baseline of the subject, a required minimal change in decibel level compared to a decibel level baseline of the subject, a required minimal change in pitch compared to a pitch baseline of the subject, or a combination thereof. Moreover, the other of the first and third biometric thresholds in the at least one biometric threshold is a required minimal change in a length of eye contact compared to an eye contact baseline of the subject, during the first digital reality scene that manifests the first challenge designed for the first proposed experience associated with the first category.

In some embodiments, each category in the plurality of categories is associated with a unique rank.

In some embodiments, the plurality of sensors includes a heart rate sensor. In some such embodiments, the corresponding threshold baseline characteristic is an initial heart rate of the subject.

In some embodiments, the plurality of sensors includes a blood pressure sensor. In some such embodiments, the corresponding threshold baseline characteristic is a systolic blood pressure of the subject or a diastolic blood pressure of the subject.

In some embodiments, the display is a head mounted display.

In some embodiments, the at least one respective gate criterion includes a ranking gate criterion associated with a hierarchical ranking of each category in the plurality of categories.

In some embodiments, the at least one respective gate criterion includes a medical practitioner gate criterion associated with an approval, from a medical practitioner associated with the subject, of the category in the plurality of categories corresponding to the at least one respective gate criterion.

In some embodiments, the at least one respective gate criterion includes an arrangement gate criterion associated with an order of one or more categories in the plurality of categories.

In some embodiments, the psychiatric or mental condition is a clinically diagnosed mental disorder or a sub-clinically diagnosed mental disorder.

In some embodiments, the psychiatric or mental condition includes being stressed in a social setting, fearing a social setting, or being overwhelmed in a social setting.

In some embodiments, the psychiatric or mental condition is a clinically diagnosed mental disorder. Moreover, the clinically diagnosed mental disorder is an anxiety disorder, a mood disorder, a psychotic disorder, an eating disorder, an impulse control disorder, an addiction disorder, a personality disorder, an obsessive-compulsive disorder, or a post-traumatic stress disorder.

In some embodiments, the psychiatric or mental condition is a clinically diagnosed mental disorder. Furthermore, the clinically diagnosed mental disorder is an anxiety disorder. In some such embodiments, the anxiety disorder includes a separation anxiety disorder, a selective mutism, a specific phobia, a social anxiety disorder, a panic disorder, an agoraphobia, a generalized anxiety disorder, a substance-induced anxiety disorder, or an anxiety disorder due to a medical condition of the subject.

In some embodiments, the psychiatric or mental condition is a clinically diagnosed mental disorder. In some such embodiments, the clinically diagnosed mental disorder is a mood disorder, in which the mood disorder includes a depression disorder, a bipolar disorder, or a cyclothymic disorder.

In some embodiments, the psychiatric or mental condition is a clinically diagnosed mental disorder. Moreover, the clinically diagnosed mental disorder is a psychotic disorder. In some such embodiments, the psychotic disorder includes a schizophrenia disorder, a delusion disorder, or a hallucination disorder.

In some embodiments, the psychiatric or mental condition is a clinically diagnosed mental disorder. Moreover, the clinically diagnosed mental disorder is an eating disorder, in which the eating disorder includes anorexia nervosa, bulimia nervosa, or binge eating disorder.

In some embodiments, the psychiatric or mental condition is a clinically diagnosed mental disorder. Moreover, the clinically diagnosed mental disorder is an impulse control disorder, and in which impulse control disorder includes a pyromania disorder, a kleptomania disorder, or a compulsive gambling disorder.

In some embodiments, the psychiatric or mental condition is a clinically diagnosed mental disorder. Furthermore, the clinically diagnosed mental disorder is an addiction disorder, in which the addiction disorder includes an alcohol disorder or a substance abuse disorder.

In some embodiments, the psychiatric or mental condition is a clinically diagnosed mental disorder. Moreover, the clinically diagnosed mental disorder is a personality disorder, in which the personality disorder includes an antisocial personality disorder, an obsessive-compulsive personality disorder, or a paranoid personality disorder.

In some embodiments, the corresponding digital reality scene is a virtual reality scene.

In some embodiments, the corresponding digital reality scene is an augmented reality scene.

In some embodiments, the corresponding digital reality scene is a mixed reality scene.

In some embodiments, a gate criterion associated with one category in the plurality of categories specifies a condition that is to be satisfied by the subject prior to advancement to another category in the plurality of categories.

In some embodiments, a respective gate criterion of a respective category in the plurality of categories is set by a system administrator, the subject, a model, a health care worker associated with the subject, or a combination thereof.

In some embodiments, a respective gate criterion of a first category in the plurality of categories is set by a system administrator or a health care worker associated with the subject, and a respective gate criterion of a second category in the plurality of categories is set by the subject.

In some embodiments, a respective biometric threshold of a respective proposed experience in the plurality of proposed experiences associated with a respective category in the plurality of categories is set a system administrator, the subject, a health care worker associated with the subject, a model, or a combination thereof.

In some embodiments, a respective biometric threshold of a respective proposed experience in the plurality of proposed experiences associated with the first category in the plurality of categories is set by a system administrator, the subject, a health care worker associated with the subject, a model, or a combination thereof.

In some embodiments, the respective biometric threshold of the respective proposed experience in the plurality of proposed experiences associated with the first category is an absolute parameter, a relative parameter, a normalized parameter, or any combination thereof.

In some embodiments, the respective biometric threshold of the respective proposed experience in the plurality of proposed experiences associated with the first category is an eye contact threshold, a heart rate threshold, an assertiveness threshold, a decibel level threshold, a pitch threshold, an utterance threshold, a word threshold, a sentiment analysis criterion, or a combination thereof that manifests the corresponding challenge designed for the first proposed experience associated with the first category.

In some embodiments, the respective biometric threshold of the respective proposed experience in the plurality of proposed experiences associated with the first category is an eye contact threshold. Moreover, the eye contact threshold includes a minimum length of eye contact, an increment of eye contact, or both of the minimum length of eye contact and the increment of eye contact.

In some embodiments, the respective biometric threshold of the respective proposed experience in the plurality of proposed experiences associated with the first category is a heart rate threshold. Moreover, the heart rate threshold includes a maximum heart rate, a reduction of heart rate, or both of the maximum heart rate and the reduction of heart rate.

In some embodiments, the respective biometric threshold of the respective proposed experience in the plurality of proposed experiences associated with the first category is an assertiveness threshold. Furthermore, the assertiveness threshold includes an absolute assertiveness threshold, a relative assertiveness threshold, or both of the absolute and relative assertiveness thresholds.

In some embodiments, the respective biometric threshold of the respective proposed experience in the plurality of proposed experiences associated with the first category is a decibel level threshold. Furthermore, the decibel level threshold includes a lower decibel level threshold, an upper decibel level threshold, a required increase of the decibel level, a required decrease of the decibel level, or any combination thereof.

In some embodiments, the respective biometric threshold of the respective proposed experience in the plurality of proposed experiences associated with the first category is a pitch threshold. Moreover, the pitch threshold includes a lower pitch threshold, an upper pitch threshold, a required increase of the pitch, a required decrease of the pitch, or any combination thereof.

In some embodiments, the respective biometric threshold of the respective proposed experience in the plurality of proposed experiences associated with the first category is an utterance threshold. The utterance threshold includes a minimum number of utterances, a maximum number of utterances, a required increase of the number of utterances, a required decrease of the number of utterances, or a combination thereof.

In some embodiments, the respective biometric threshold of the respective proposed experience in the plurality of proposed experiences associated with the first category is a word threshold. Furthermore, in some such embodiments, the word threshold includes a minimum number of words, a maximum number of words, a required increase of the number of words, a required decrease of the number of words, or a combination thereof.

In some embodiments, the respective biometric threshold of the respective proposed experience in the plurality of proposed experiences associated with the first category is a sentiment analysis criterion. In some such embodiments, the sentiment analysis criterion includes an excited sentiment threshold and an overexcited sentiment threshold.

In some embodiments, the method further includes determining whether the sentiment analysis criterion is satisfied or not satisfied by taking a cosine similarity measure or dot product of one or more utterances of the subject, made during the corresponding challenge designed for the first proposed experience associated with the first category, against each statement in a list of statements that are deemed to be characteristic of a predetermined sentiment.

In some embodiments, the predetermined sentiment is amusement, anger, anxiety, awkwardness, boredom, calmness, confusion, craving, disgust, empathetic pain, entrancement, excitement, fear, horror, interest, joy, annoyance, nostalgia, relief, sadness, satisfaction, or surprise.

In some embodiments, the plurality of categories includes one or more exposure categories, one or more cognitive behavioral therapy (CBT) categories, one or more mindfulness categories, or a combination thereof.

In some embodiments, the first category is a mindfulness category, and the second category is a CBT category. In some embodiments, the first category is an exposure category, and the second category is the CBT category.

Another aspect of the present disclosure is directed to providing non-transitory computer readable storage medium storing one or more programs. The one or more programs includes instructions, which when executed by a computer system cause the computers system to perform a method of the present disclosure.

Yet another aspect of the present disclosure is directed to providing use of a computer system for improving an ability of a subject to manage a psychiatric or mental condition exhibited by the subject. The computer system includes one or more processors, a display, and a memory coupled to the one or more processors. In some embodiments, the computer system includes audio speakers and/or a microphone. The memory includes one or more programs, configured to be executed by the one or more processors, that implement a method of the present disclosure.

Yet another aspect of the present disclosure is directed to providing a device for implementing an exposure progression. In some embodiments, the device is configured to improves an ability of a subject to manage a psychiatric or mental condition of the subject. Furthermore, the device includes one or more processors and a memory coupled to the one or more processors. The memory includes one or more programs configured to be executed by the one or more processors. The one or more programs is configured to cause the computer system to perform the methods of the present disclosure. In some embodiments, the device includes a display and/or audio circuitry. In some embodiments, the device includes an objective lens in optical communication with a two-dimensional pixelated detector.

BRIEF DESCRIPTION OF THE DRAWINGS

The file of this patent contains at least one drawing executed in color.

FIGS. 4A, 4B, 4C, 4D, 4E, 4F, 4G, 4H, 4I, 4J, 4K, 4L, 4M, 4N, 4O, 4P, 4Q, and 4R collectively illustrate exemplary methods for implementing an exposure progression that improves an ability of a subject to manage a psychiatric or mental condition of the subject, in which optional embodiments are indicated by dashed boxes, in accordance with some embodiments of the present disclosure.

FIGS. 8A, 8B, 8C, and 8D collectively illustrate user interfaces for obtaining an assessment or subjective evaluation of a subject at a client device, in accordance with an embodiment of the present disclosure.

FIG. 10A illustrates an exemplary regimen, in accordance with some embodiments of the present disclosure.

FIGS. 10B and 10C collectively illustrate another exemplary regimen, in accordance with some embodiments of the present disclosure.

FIG. 14 illustrates various logic functions that are used implemented in some embodiments of the present disclosure.

Figure 1:
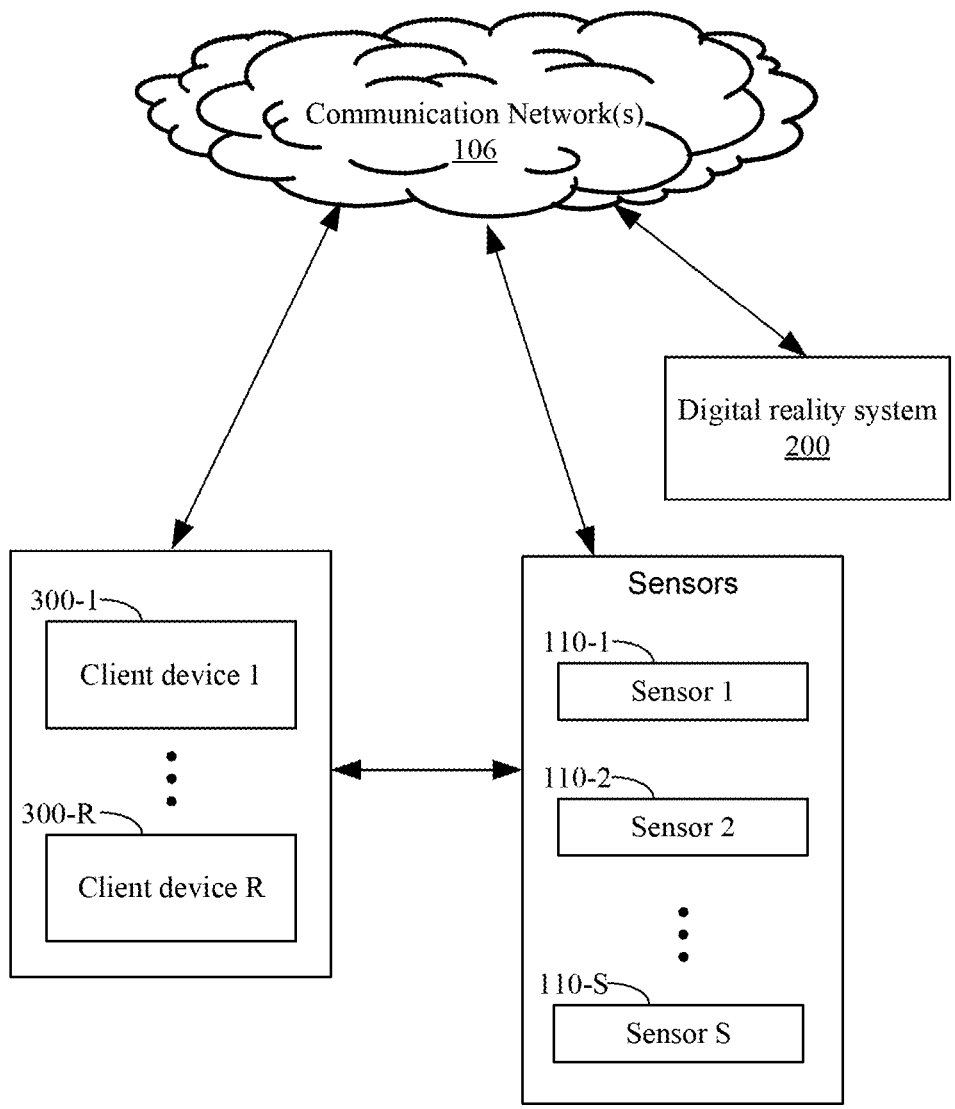
FIG. 1 illustrates a block diagram illustrating an embodiment of a system for displaying a digital reality scene, in accordance with an embodiment of the present disclosure.

It should be understood that the appended drawings are not necessarily to scale, presenting a somewhat simplified representation of various features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

The present disclosure provides systems and methods for improving an ability of a subject to manage a psychiatric or mental condition by implementing a personalized exposure progression for the subject. In some embodiments, the personalized exposure progression, as known as an exposure regimen, or regimen, is configured specifically for the subject, such that the exposure progression is targeted in a personalized fashion for the subject. Moreover, in some embodiments, the personalized exposure progression is configured dynamically, such that the exposure progression is flexible to change with the subject as the subject interacts with the systems and methods of the present disclosure. Accordingly, in some such embodiments, by at least combining exposure to digital reality, biometric data captured during the exposure to digital reality, historic accomplishments of a subject, or a combination thereof the systems, methods, and devices of the present disclosure create a personalized exposure progression that is tailored to the subject. Moreover, in some such embodiments, the personalized exposure progression is dynamically updated based on the timing and/or nature of the exposure experienced by the subject. This allows for subject-specific and condition-specific tailoring of a subject's personalized exposure progression.

In some embodiments, the personalized exposure progression is created or modified dynamically based, at least in part, on an initial assessment of a subject, the biometric data captured when the subject is completing one or more social challenges while exposed to a particular digital reality, a level of success that the subject has had in the one or more challenges (e.g., an exposure challenge, a social challenge, a CBT challenge, a mindfulness challenge, etc.), a subjective evaluation of and/or by the subject after completing one or more digital challenges, an evaluation or confirmation of a health care worker (e.g., medical practitioner) associated with the subject, an evaluation or confirmation by a computational model, or a combination thereof. By implementing the personalized exposure progression through, at least in part, a digital reality, the systems, methods, and devices of the present disclosure improve the likelihood of higher emotional and physiological arousal, engagement, a better clinical outcome for the subject, or a combination thereof, which improves the ability of the subject to manage their psychiatric or mental condition.

As such, the personalized exposure progression provided by the systems, methods, and devices of the present disclosure is designed to address a psychiatric or mental condition exhibited by a subject by improving an ability of the subject to manage the psychiatric or mental condition. In some such embodiments, the ability of the subject to manage the psychiatric or mental condition is actualized by educating the subject (e.g., about one or more coping exercises by way of a mindfulness challenge and/or a CBT challenge, about a frequency of occurrence of an event associated with the psychiatric or mental condition, about therapeutic practices that best fit the subject and/or the psychiatric or mental condition, about a thinking pattern exhibited by the subject, etc.), engaging with the subject (e.g., within a digital reality scene), treating the subject (e.g., by implementing for the subject and/or deeming the subject to have completed the personalized exposure progression), or a combination thereof. By way of example, in some embodiments, the systems, methods, and devices of the present disclosure are designed to address stressful and/or overwhelmed feelings associated with social situations, such as excessive worry, excessive anxiety, avoidance of a feared situation, and the like. As another non-limiting example, in some embodiments, the systems, methods, and devices of the present disclosure are designed to address a mental or psychiatric condition exhibited by the subject, such as worry about everyday events associated with a general anxiety disorder, such as excessive worry, excessive anxiety, difficulty concentrating, and the like. As yet another non-limiting example, in some embodiments, the systems, methods, and devices of the present disclosure are designed to address persistent sadness, anxiousness, emptiness, or a combination thereof associated with a major depressive disorder. As yet another non-limiting example, in some embodiments, the systems, methods, and devices of the present disclosure are designed to address dysphoria, anhedonia, apathy, irritability, anger, avolition, lack of motivation, sleep dysregulation, decreased energy, fatigue, behavior disturbances and/or disruptions detrimental to daily function, agitation, restlessness, or a combination thereof. As such, the systems, methods, and devices of the present disclosure address the psychiatric or mental condition by involving (e.g., by way of the digital reality scene) interactions with others, such as other users or non-player characters in various scenarios such as social interactions, work, school, or the like, while addressing both performance-based and/or interaction-based challenges (e.g., social challenges, focus challenges, etc.). In some embodiments, the systems, methods, and devices of the present disclosure address the psychiatric or mental condition by providing educational or therapeutical challenges using the digital reality scene, such as cognitive reframing training, cognitive reframing challenge, mindfulness training, mindfulness challenge, and alternative/additional exposure exercises. However, the present disclosure is not limited thereto. Accordingly, in various embodiments, the systems, methods, and devices of the present disclosure allow a subject to choose social challenge(s) that the subject wants to work on, based at least in part on, the initial assessment of the subject, biometric data captured while the subject is completing one or more social challenges, the level of success the subject has had in one or more social challenges, subjective evaluation of and/or by the subject after completing such social challenges, evaluation or confirmation of a health care worker associated with the subject, or a combination thereof. In some embodiments, a medical practitioner (e.g., clinician) is associated with a subject and is involved in the implementing the personalized exposure program. In some embodiments, the medical practitioner overrides the subject's selected personalized exposure program or modifies the personalized exposure program.

The systems, methods, and devices of the present disclosure allow subjects to re-visit challenges that have been completed already for repeated exposure practice.

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, and components have not been described in detail so as not to unnecessarily obscure aspects of the embodiments.

It will also be understood that, although the terms first, second, etc. may be used herein to describe various elements, these elements should not be limited by these terms. These terms are only used to distinguish one element from another. For instance, a first digital chart could be termed a second digital chart, and, similarly, a second digital chart could be termed a first digital chart, without departing from the scope of the present disclosure. The first digital chart and the second digital chart are both digital charts, but they are not the same digital chart.

The terminology used in the present disclosure is for the purpose of describing particular embodiments only and is not intended to be limiting of the invention. As used in the description of the invention and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The description herein includes example systems, methods, techniques, instruction sequences, and computing machine program products that embody illustrative implementations. For purposes of explanation, numerous specific details are set forth in order to provide an understanding of various implementations of the inventive subject matter. It will be evident, however, to those skilled in the art that implementations of the inventive subject matter may be practiced without these specific details. In general, well-known instruction instances, protocols, structures, and techniques have not been shown in detail.

The description herein, for purpose of explanation, is described with reference to specific implementations. However, the illustrative discussions are not intended to be exhaustive or to limit the implementations to the precise forms disclosed. Many modifications and variations are possible in view of the disclosed teachings. The implementations are chosen and described in order to best explain the principles and their practical applications, to thereby enable others skilled in the art to best utilize the implementations and various implementations with various modifications as are suited to the particular use contemplated.

In the interest of clarity, not all of the routine features of the implementations described herein are shown and described. It will be appreciated that, in the development of any such actual implementation, numerous implementation-specific decisions are made in order to achieve the designer's specific goals, such as compliance with use case- and business-related constraints, and that these specific goals will vary from one implementation to another and from one designer to another. Moreover, it will be appreciated that such a design effort might be complex and time-consuming, but nevertheless be a routine undertaking of engineering for those of ordering skill in the art having the benefit of the present disclosure.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

As used herein, the term "about" or "approximately" can mean within an acceptable error range for the particular value as determined by one of ordinary skill in the art, which can depend in part on how the value is measured or determined, e.g., the limitations of the measurement system. For example, "about" can mean within 1 or more than 1 standard deviation, per the practice in the art. "About" can mean a range of ±20%, ±10%, ±5%, or ±1% of a given value. Where particular values are described in the application and claims, unless otherwise stated, the term "about" means within an acceptable error range for the particular value. The term "about" can have the meaning as commonly understood by one of ordinary skill in the art. The term "about" can refer to ±10%. The term "about" can refer to ±5%.

As used herein, the term "equally spaced" means that a distance from a first feature to a corresponding second feature is the same for successive pairs of features unless expressly stated otherwise.

As used herein, the term "dynamically" means an ability to update a program while the program is currently running.

Additionally, the terms "client," "patient," "subject," and "user" are used interchangeably herein unless expressly stated otherwise.

Moreover, the terms "avatar" and "player character" are used interchangeably herein unless expressly stated otherwise.

In addition, the terms "therapy" and "treatment" are used interchangeably herein unless expressly stated otherwise.

Moreover, as used herein, the term "parameter" refers to any coefficient or, similarly, any value of an internal or external element (e.g., a weight and/or a hyperparameter) in an algorithm, model, regressor, and/or classifier that can affect (e.g., modify, tailor, and/or adjust) one or more inputs, outputs, and/or functions in the algorithm, model, regressor and/or classifier. For example, in some embodiments, a parameter refers to any coefficient, weight, and/or hyperparameter that can be used to control, modify, tailor, and/or adjust the behavior, learning, and/or performance of an algorithm, model, regressor, and/or classifier. In some instances, a parameter is used to increase or decrease the influence of an input (e.g., a feature) to an algorithm, model, regressor, and/or classifier. As a nonlimiting example, in some embodiments, a parameter is used to increase or decrease the influence of a node (e.g., of a neural network), where the node includes one or more activation functions. Assignment of parameters to specific inputs, outputs, and/or functions is not limited to any one paradigm for a given algorithm, model, regressor, and/or classifier but can be used in any suitable algorithm, model, regressor, and/or classifier architecture for a desired performance. In some embodiments, a parameter has a fixed value. In some embodiments, a value of a parameter is manually and/or automatically adjustable. In some embodiments, a value of a parameter is modified by a validation and/or training process for an algorithm, model, regressor, and/or classifier (e.g., by error minimization and/or backpropagation methods). In some embodiments, an algorithm, model, regressor, and/or classifier of the present disclosure includes a plurality of parameters. In some embodiments the plurality of parameters is n parameters, where: $n \geq 2$; $n \geq 5$; $n \geq 10$; $n \geq 25$; $n \geq 40$; $n \geq 50$; $n \geq 75$; $n \geq 100$; $n \geq 125$; $n \geq 150$; $n \geq 200$; $n \geq 225$; $n \geq 250$; $n \geq 350$; $n \geq 500$; $n \geq 600$; $n \geq 750$; $n \geq 1,000$; $n \geq 2,000$; $n \geq 4,000$; $n \geq 5,000$; $n \geq 7,500$; $n \geq 10,000$; $n \geq 20,000$; $n \geq 40,000$; $n \geq 75,000$; $n \geq 100,000$; $n \geq 200,000$; $n \geq 500,000$, $n \geq 1 \times 10^6$, $n\ 5 \times 10^6$, or $n \geq 1 \times 10^7$. In some embodiments, n is between 10,000 and $1 \times 10^7$, between 100,000 and $5 \times 10^6$, or between 500,000 and $1 \times 10^6$.

Furthermore, when a reference number is given an "$i^{th}$" denotation, the reference number refers to a generic component, set, or embodiment. For instance, a digital reality scene termed "digital reality scene i" refers to the $i^{th}$ digital reality scene in a plurality of digital reality scenes (e.g., a digital reality scene 40-$i$ in a plurality of digital reality scenes 40). In the present disclosure, unless expressly stated otherwise, descriptions of devices and systems will include implementations of one or more computers.

FIG. 1 depicts a block diagram of a distributed client-server system (e.g., distributed client-server system 100) according to some embodiments of the present disclosure. The system 100 facilitates preparing a regimen for improving an ability of a subject to manage a psychiatric or mental condition, such as a clinically diagnosed mental disorder, a sub-clinically diagnosed medical disorder, an undiagnosed condition (one that has not been diagnosed for the subject by a medical practitioner), or a combination thereof. In some embodiments, the system 100 facilitates preparing the regime for improving the general wellness of the subject, such as maintaining and/or encouraging a general state of health or a healthy activity for the subject. In some embodiments, the regime improves the general wellness of the subject by relates the role of a healthy lifestyle for the subject with helping to reduce the risk or impact of certain mental and/or psychiatric conditions. However, the present disclosure is not limited thereto. The system 100 generally includes a digital reality system (e.g., digital reality system 200) and one or more client devices 300 (e.g., a first client device 300-1, a second client device 300-2, . . . , a $R^{th}$ client device 300-R, etc.) in communication with the digital reality system through a communication network (e.g., communication network 106). In some embodiments, each client device is associated with at least one subject (e.g., a subject).

Figure 5A:
FIG. 5A illustrates an exemplary digital reality scene for social challenge training, in accordance with an embodiment of the present disclosure.
Figure 5B:
FIG. 5B illustrates an exemplary digital reality scene for social challenge training, in accordance with an embodiment of the present disclosure.

The system 100 also includes a plurality of sensors, such as sensor 110-1, sensor 110-2, . . . , sensor 110-S of FIGS. 5A and 5B. The plurality of sensors includes at least one biometric sensor (e.g., sensor 110-1 and/or sensor 110-2 being a biometric sensor or including a biometric sensor) configured to capture biometric data of a subject. In some embodiments, one or more sensors in the plurality of sensors are incorporated into a client device 300 or are components of the client device. In some embodiments, one or more sensors are in communication with one or more client devices (e.g., through ANT+ or Bluetooth or network interface of the client device). For example, in some embodiments, data captured by the one or more sensors is sent to and/or aggregated in the one or more client devices. In some embodiments, one or more sensors are in communication with a remote system, e.g., connected to the digital reality system 200 via the communication network 106, such that data captured by the one or more sensors can be sent to the remote system, which collects, stores, and/or processes the captured biometric data.

In some embodiments, the system 100 facilitates providing a regimen for a population of subjects, of which at least one subject exhibits a psychiatric or mental condition. In some embodiments, the regimen is prepared at the digital reality system and then provided to a subject through a graphical user interface (GUI) displayed on a respective client device 300. In some embodiments, a medical practitioner (e.g., clinician) associated with a subject prepares the regimen at a client device (e.g., the client device 300-1) and the subject performs the regimen at another client device (e.g., the client device 300-2). In some embodiments, a computational model prepares the regimen at the digital reality system and the subject performs the regimen at a client device (e.g., the client device 300-1). However, the present disclosure is not limited thereto.

Examples of the communication network 106 includes, but is not limited to, the World Wide Web (WWW), an intranet and/or a wireless network, such as a cellular telephone network, a wireless local area network (LAN) and/or a metropolitan area network (MAN), and other devices by wireless communication. The wireless communication optionally uses any of a plurality of communications standards, protocols and technologies, including Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11ac, IEEE 802.11ax, IEEE 802.11b, IEEE 802.11g and/or IEEE 802.11n), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of this document.

In some embodiments, the communication network 106 optionally includes the Internet, one or more local area networks (LANs), one or more wide area networks (WANs), other types of networks, or a combination of such networks.

It should be noted that the exemplary topology shown in FIG. 1 merely serves to describe the features of an embodiment of the present disclosure in a manner that will be readily understood to one of skill in the art. Other topologies of the system 100 are possible. For instance, in some embodiments, any of the illustrated devices and systems can, in fact, constitute several computer systems that are linked together in a network or be one or more virtual machines and/or containers in a cloud-computing environment. Moreover, rather than relying on a physical communications network 106, the illustrated devices and systems may wirelessly transmit information between each other.

Figure 2A:
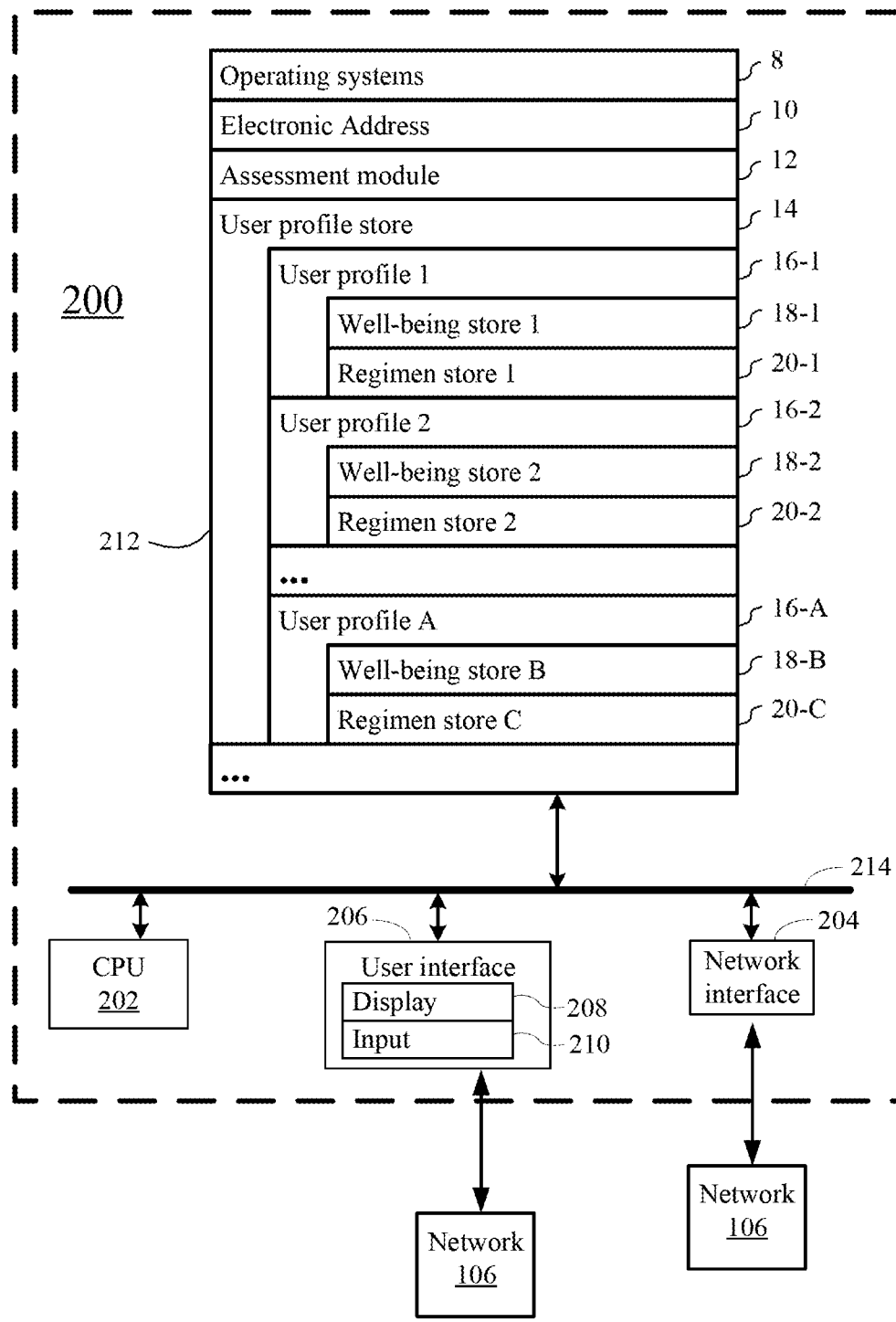
FIGS. 2A and 2B collectively illustrate a digital reality host system for facilitating a digital reality experience, in accordance with an embodiment of the present disclosure.
Figure 2B:
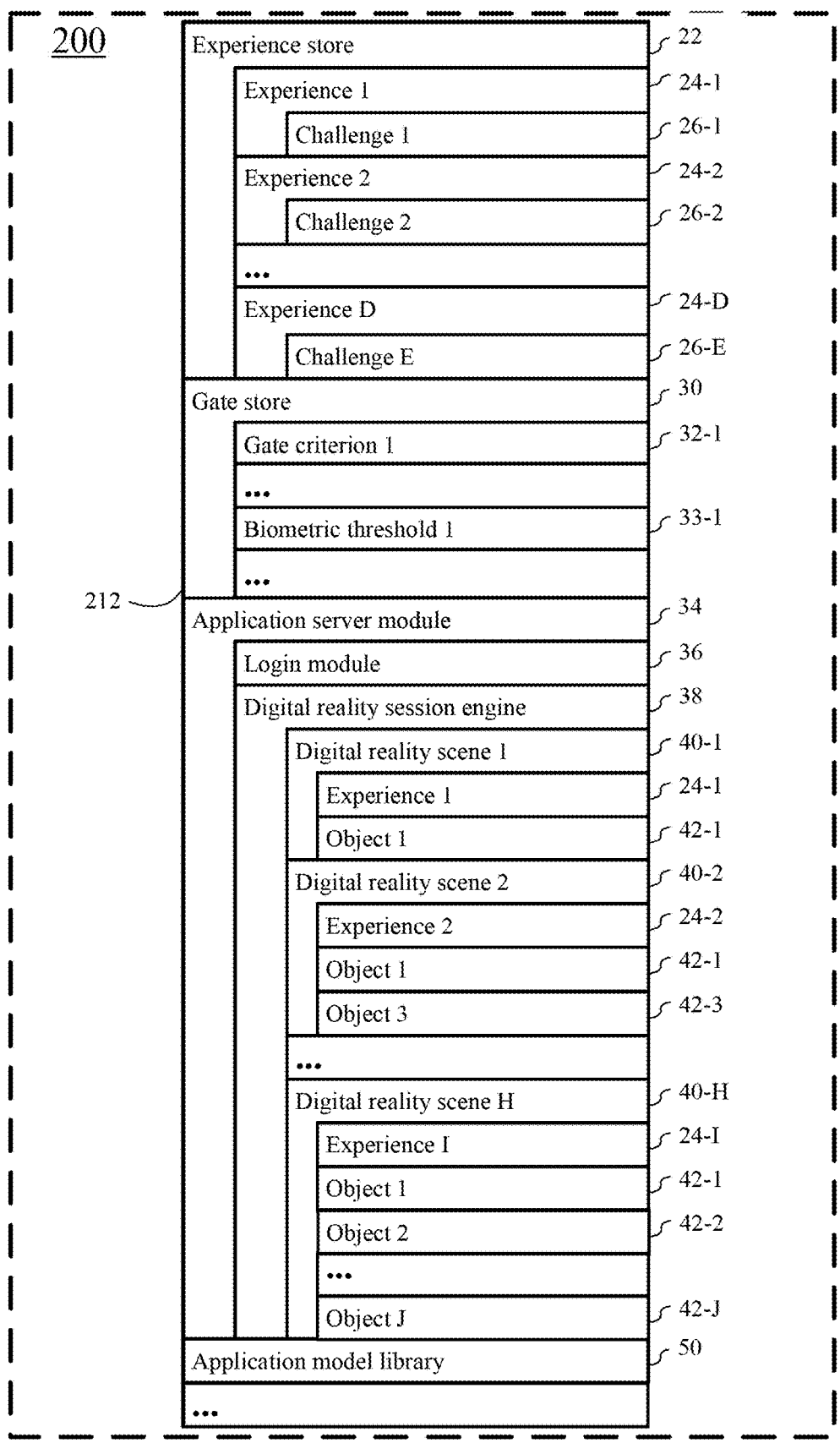

FIGS. 2A and 2B depict an exemplary digital reality system 200 for preparing a regimen for improving an ability of a subject to manage a psychiatric or mental condition exhibited by the subject. In various embodiments, the digital reality system 200 includes one or more processing units (CPUs) 202, a network or other communications interface 204, and memory 212.

Memory 212 includes high-speed random access memory, such as DRAM, SRAM, DDR RAM, or other random access solid state memory devices, and optionally also includes non-volatile memory, such as one or more magnetic disk storage devices, optical disk storage devices, flash memory devices, or other non-volatile solid state storage devices. Memory 212 may optionally include one or more storage devices remotely located from the CPU(s) 202. Memory 212, or alternatively the non-volatile memory device(s) within memory 212, includes a non-transitory computer readable storage medium. Access to memory 212 by other components of the digital reality system 200, such as the CPU(s) 202, is, optionally, controlled by a controller. In some embodiments, memory 212 can include mass storage that is remotely located with respect to the CPU(s) 202. In other words, some data stored in memory 212 may in fact be hosted on devices that are external to the digital reality system 200, but that can be electronically accessed by the digital reality system 200 over an Internet, intranet, or other form of network 106 or electronic cable using communication interface 204.

In some embodiments, the memory 212 of the digital reality system 200 for preparing a regimen for improving an ability of a subject to manage a psychiatric or mental condition exhibited by the subject stores:

an operating system 8 (e.g., ANDROID, iOS, DARWIN, RTXC, LINUX, UNIX, OS X, WINDOWS, or an embedded operating system such as VxWorks) that includes procedures for handling various basic system services;

an electronic address 10 associated with the digital reality system 200 that identifies the digital reality system 200, such as within a distributed computer system;

an optional assessment module 12 for obtaining an assessment of a subject that provides an identification of a plurality of proposed experiences through the assessment;

a user profile store 14 for retaining information associated with a population of users (e.g., user of client devices 300 of FIG. 1), including a user profile 16 for each user in the population of users, the user profile 16 including a corresponding well-being store 18 and a regimen store 20 associated with a subject of the user profile 16;

an experience store 22 including a plurality of experiences (e.g., first experience 24-1, second experience 24-2, . . . , experience 24-I of FIG. 2B), each experience 24 including a corresponding challenge 26;

a gate store 30 including a plurality of gate criteria (e.g., first gate criterion 32-1, second gate criterion 32-2, . . . , gate criterion G 32-G of FIG. 2B), each gate criterion 32 representing a condition for user engagement;

an application server module 34 that facilitates providing a plurality of digital reality scenes 40 to a population of client devices 300, the application server module 34 including a login module 36 for accessing a digital reality scene 40 and a digital reality session engine 38 that facilitates providing a plurality of digital reality scenes (e.g., first digital reality scene 40-1, second digital reality scene 40-2, . . . , digital reality scene H 40-H of FIG. 2B) for a population of users (e.g., client devices 300); and an application model library 50 that retains one or more models for providing an evaluation of a characteristic of a respective input, such as providing a first evaluation of whether completion of a corresponding challenge 26 satisfies one or more corresponding gate criteria 32.

In some embodiments, an electronic address 10 is associated with the digital reality system 200. The electronic address 10 is utilized to at least uniquely identify the digital reality system 200 from other devices and components of the distributed system 100 (e.g., uniquely identify digital reality system 200 from client device 300-1, client device 300-2, . . . or client device 300-R of FIG. 1). For instance, in some embodiments, the electronic address 10 is utilized to receive a request from a client device to participate in a respective digital reality scene via login module 36 of an application server module 34. As another non-limiting example, in some embodiments, the electronic address 10 is utilized to receive a plurality of data elements including a set of biometric data elements obtained when presenting a digital reality scene to a user at a remote client device 300. However, the present disclosure is not limited thereto.

In some embodiments, an assessment module 12 facilitates obtaining an assessment from a subject, such as a user of a respective client device or a medical practitioner associated with the user. In some embodiments, the assessment module 12 includes one or more assessments that is communicated to the respective client device (e.g., via communications network 106 of FIG. 1). For instance, in some embodiments, the assessment module 12 stores a standardized assessment that is provided to each subject. The standardized assessment provides a uniform assessment to each subject. In some embodiments, by utilizing a standardized assessment, the assessments obtained from multiple users is normalized in order to optimize identification of a plurality of proposed experiences (e.g., from experiences 24 of experience store 22 of FIG. 2B) between different users. However, the present disclosure is not limited thereto.

In some embodiments, the assessment includes a plurality of prompts answered by a subject. In some embodiments, through the answers to the plurality of prompts provided by the subject, an identification of a plurality of proposed experiences is obtained for the subject. For instance, an assessment for a social anxiety psychiatric or medical condition includes asking a user of a client device, e.g., client device 300-1, a question and providing multiple predetermined answers (e.g., none, mild, moderate, or severe). In some embodiments, user selection of a first answer from the predetermined answers forms the basis for the identification of the plurality of proposed experiences 24.

In some embodiments, the assessment module 12 includes one or more authorization criteria associated with approving an assessment obtained from a subject. For instance, in some embodiments, the assessment is provided to a first subject of a first client device 300-1, in which the first subject exhibits a psychiatric or mental condition. In some such embodiments, obtaining the assessment from the first subject is conditioned on satisfying a first authorization criterion. In some embodiments, this first authorization criterion is associated with the first subject obtaining an authorization of the assessment from a medical practitioner associated with the subject. By way of example, in some embodiments, the first authorization criterion requires that the medical practitioner and/or a computational model validate a certain aspect of the assessment, such as a truthfulness of the assessment, an accuracy of the assessment, a precision of the assessment, a consistency of the assessment, a competency of the assessment, a reasonableness of the assessment, a pass/fail of the assessment, a global rating scale of the assessment, or a combination thereof. In some embodiments, by adding a level of authorization, such as human authorization and/or computational model authorization, the digital reality system 200 ensures that a subject that exhibits a psychiatric or mental condition is capable of improving their ability to manage the psychiatric or mental condition when utilizing the systems, methods, and devices of the present disclosure, such as by ensuring the subject is providing honest answers to the assessment. In this way, in some such embodiments, the assessment module 12 prevents the subject from distorting the assessment, which would result in the production of a regimen that might not improve the ability of the subject to manage their psychiatric or mental condition.

In some embodiments, user profile store 14 retains a plurality of user profiles 16. Each respective user profile 16 is associated with a corresponding user of the digital reality system 200, such as a user of a client device that exhibits a psychiatric or mental condition and/or a medical practitioner associated with the user. For instance, in some embodiments, a respective user first customizes their profile (e.g., first user profile 16-1) at a client device by making a selection of a plurality of user login information, such as a password, an address (e.g., E-mail address, physical address, etc.), a personal name (e.g., a given name, a username, etc.), and the like. In some embodiments, the respective user provides, or is collected by the client device 300 (e.g., using optional GPS), one or more demographic characteristics (e.g., an age of the user, a weight of the user, a height of the user, a gender of the user, etc.) and/or one or more geographic characteristics (e.g., a region associated with the user, a physical address associated with the user, etc.). However, the present disclosure is not limited thereto. In some embodiments, the user profile uniquely identifies the respective user in a digital reality scene 40. In this way, each user profile 16 allows the digital reality system 200 to retain login information, privacy information (e.g., which psychiatric or mental condition is exhibited by a corresponding subject associated with a respective user profile 16) and other preferences, and/or biographical data. In some embodiments, a login name associated with a respective user is the same as the username displayed for the user. In other embodiments, a login name associated with a respective user is different from the username displayed for the user (e.g., displayed usernames with a digital reality scene 40 are different from associated user logins). In some embodiments, the user profile 16 includes some or all of a corresponding medical record of the subject associated with the user profile 16. In some embodiments, the digital reality system 200 stores a plurality of avatar information, including a plurality of traits for each avatar user, and/or a contact list of contacts within a digital reality scene 40. Accordingly, the systems, methods, and devices of the present disclosure allow for personalized a digital reality scene based on the information associated with the user using the user profile 16. By way of example, in some embodiments, a subject provides an age of the subject and, in accordance with the age of the subject, an appearance and/or an intensity level (e.g., a difficulty level) of a non-player character associated with a digital reality scene is modified based on the age of the subject.

Additionally, in some embodiments, each user profile 16 includes a well-being store (e.g., first user profile 16-1 includes first well-being store 18-1, second user profile 16-2 includes second well-being store 18-2, . . . , user profile A 16-A includes well-being store B 18-B, etc.). In some embodiments, the well-being store 18 retains a plurality of health information associated with the subject, such as an indication of a clinical diagnosis for a psychiatric or mental condition, a plurality of insurance information associated with an insurance provider of a corresponding subject, an electronic medical record, and the like. In some embodiments, the well-being store 18 includes a status of a treatment administered to a subject, such as a result of a previous treatment for the psychiatric or mental condition, a result of a previous regimen 20 provided to the subject, and the like.

In some embodiments, the well-being store 18 includes a plurality of biometric data elements that is associated with the respective user. For instance, in some embodiments, a set of biometric data elements is obtained when presenting a digital reality scene on a client device, and a plurality of biometric data elements from the set of biometric data elements (e.g., the first set of biometric data elements) is retained by the well-being store 18. As a non-limiting example, in some embodiments, the plurality of biometric data elements retained by the well-being store 18 includes a heart rate of the subject (e.g., a baseline heart rate, one or more heart rate zones of the subject, etc.). In some embodiments, the plurality of biometric data elements retained by the well-being store 18 includes a blood pressure of the subject (e.g., a baseline systolic blood pressure, a threshold diastolic blood pressure, etc.). Furthermore, in some embodiments, the plurality of biometric data elements includes a plurality of spatiotemporal data elements, which describe a spatial and temporal aspect of the user when engaging with a digital reality scene. Non-limiting examples of the plurality of spatiotemporal data elements includes an area of a portion of an eye of the user, a change in a position of the eye of the subject when addressing the corresponding challenge 26, a count of occurrences of the eye of the user at a predetermined reference position, and the like. In some embodiments, the plurality of biometric data elements retained by the well-being store 18 includes one or more vocal biometric data elements, such as vocal features associated with the use. As another non-limiting example, in some embodiments, the plurality of biometric data elements retained by the well-being store 18 includes a temporal vocal feature (e.g., a root mean square (RMS) energy of the vocal feature), a spectral vocal feature (e.g., a centroid of a spectrogram of the vocal feature, a roll-off of the spectrogram, etc.), a cepstral vocal feature (e.g., Mel Frequency Cepstral Coefficients (MFCC)), an entropy of the vocal feature (e.g., a spectral entropy, a probability density function entropy, etc.), or a combination thereof.

In some embodiments, the well-being store 18 includes one or more annotations. In some embodiments, each annotation is associated with the corresponding subject participating in a digital reality scene 40 and/or one or more assessments obtained from the subject. For instance, in some embodiments, the one or more assessments obtained from the subject that are stored by the well-being store 18 include a first assessment for obtaining the identification of the plurality of proposed experiences and/or a second assessment based on a proposed experience 24 conducted by the user. In some embodiments, the one or more annotations include a first annotation provided by the medical practitioner associated with the subject when the subject conducts the proposed experience. In some embodiments, the one or more annotations includes a second annotation provided by the subject. In some embodiments, the one ore annotations includes a third annotation provided by a computational model associated with the digital reality system 200.

In some embodiments, each user profile includes a regimen store (e.g., first user profile 16-1 includes first regimen store 20-1, second user profile 16-2 includes second regimen store 20-2, . . . , user profile A 16-A includes regimen store C 20-C, etc.) that retains information associated with a corresponding subject. By way of example, in some embodiments, the information retained by the regimen store of the user profile includes a plurality of sessions of a corresponding user engaging with the digital reality system. In some embodiments, the plurality of sessions includes an exposure session in which the subject engages with an exposure challenge, a cognitive behavioral therapy session in which the subject engages with a cognitive behavioral therapy challenge, a mindfulness based cognitive therapy in which the subject engages with a mindfulness challenge, or a combination thereof. From this, the user profile allows the systems, methods, and devices of the present disclosure to track various parameters associated with improving an ability of a subject to manage their psychiatric or mental condition. In some embodiments, the various parameters associated with improving an ability of a subject to manage their psychiatric or mental condition are retained by the regimen store 20 include, but are not limited to, a status of a respective exposure progression associated with the subject, a status of a respective interactive digital chart representing a respective exposure progression associated with the subject, availability of a respective exposure category or experience within a respective exposure progression associated with the subject, availability of other exposure categories or experiences for placement into a respective exposure progression, determination whether one or more gate criteria 32 are satisfied, a location of an avatar associated with the subject in a digital reality scene 40, or any combination thereof.

In some embodiments, by retaining a well-being store 18 and a regimen store 20 with each user profile 16, the digital reality system 200 allows each subject associated with a user profile to engage with the digital reality system 200 when and where the subject desires without losing their progress (e.g., progression through a regimen of the present disclosure) in improving their ability of manage their psychiatric or mental condition.

In some embodiments, an experience store 22 includes a plurality of experiences 24 (e.g., first experience 24-1, second experience 24-2, ..., experience 24-D of FIG. 2B). Each experience 24 includes a digital reality task in the form of a challenge (e.g., first challenge 26-1, second challenge 26-2, ..., challenge E 26-2 of FIG. 2B, etc.) that is designed to improve the ability of a subject to manage their psychiatric or mental condition. For instance, in some embodiments, each experience 24 is a challenge 26, which challenges the subject to perform a digital reality task in a within a digital reality scene 40.

In some embodiments, experiences 24 are grouped into categories, where each such category includes one or more experiences directed to challenge the subject to perform the same or similar challenges. For instance, in some embodiments, a first category includes one or more experiences 24 directed to general performance challenges of the subject, e.g., challenging the subject to give a presentation to an audience in a digital reality scene 40 or tell a story to a group in the digital reality scene 40.

In some embodiments, a second category includes one or more experiences directed to an exposure challenge. For instance, in some embodiments, the second category includes one or more experiences 24 designed to make the subject practice being assertive, e.g., challenging the subject to walk up to an individual in a digital reality scene 40 or reminding the individual in the digital reality scene 40 of a challenge assigned to the subject. In some embodiments, the second category includes one or more experiences 24 directed to interactions with individuals, e.g., challenging a subject to look at someone in the eyes in a digital reality scene 40. However, the present disclosure is not limited thereto.

Moreover, in some embodiments, a third category include one or more experiences directed to a CBT challenge. For instance, in some embodiments, the third category includes one or more experiences 24 designed to have the user self-identify harmful or negative evidence for a thought spoken by the user, evaluate if the self-identified evidence is sufficient to reframe the thought, reframing the thought in order to improve the psychiatric or mental condition of the subject, such as by modulating harm expectancy and/or a perception of control for the subject, or a combination thereof. In some embodiments, the third category includes one or more experiences 24 designed identify a negative thought or statement provided by the subject and/or disrupt a native cognitive pattern associated with a formation of the negative thought or statement by the subject with a new cognitive pattern associated with a formation of a positive or adaptive thought or statement.

Furthermore, in some embodiments, a fourth category include one or more experiences directed to a mindfulness challenge.

In some embodiments, an experience is directed to challenge the subject to perform a single challenge, e.g., a first challenge of giving a presentation, a second challenge of being assertive, a third challenge of gathering evidence, a fourth challenge of cognitive reframing, a fifth challenge of cognitive defusion, a sixth challenge of setting a goal, a seventh challenge of completing a mindfulness challenge, or the like. Accordingly, in some such embodiments, such an experience is associated with a single category. However, the present disclosure is not limited thereto. In some embodiments, an experience is directed to challenge the subject to perform multiple challenges, e.g., giving a presentation as well as being assertive. Accordingly, in some embodiments, such an experience is associated with a plurality of categories (e.g., two categories, three categories, four categories, five categories, etc.).

In some embodiments, each respective challenge 26 is associated with a specific setting, such as a specific digital reality scene 40. For instance, consider a first experience 24-1 is a first challenge 26-1 (e.g., an exposure challenge) that tasks a subject to walk up to a person in a first digital reality scene 40-1 that portrays a crowded, public setting, and a second experience 24-2 is a second challenge 26-2 (e.g., another exposure challenge) that tasks the subject to walk up to the person in a second digital reality scene 40-2 that portrays a quiet, private setting. Accordingly, both of the first experience 24-1 and the second experience 24-2 are associated with the exposure challenge of being assertive yet accomplish the goal of improving the ability of the subject to manage their psychiatric or mental condition at different granularities. In this way, in some embodiments, a corresponding experience 24 provides a broad categorization of content in a digital reality scene designed to improve the ability of the subject to manage their psychiatric or mental condition and a challenge provides a granular implementation of a corresponding experience.

Moreover, in some embodiments, each experience 24 of the experience store 22 is provided by the digital reality system 200 without association to a respective digital reality scene 40. This allows the digital reality system 200 to design and configure the respective digital reality scene based on an experience 24.

Furthermore, in some embodiments, a criterion store 30 facilitates retaining a plurality of criteria. In some embodiments, a criterion in the plurality of criteria is used to determine whether a challenge associated with an experience has been successfully completed by a subject, to identify a subsequent challenge for the subject to complete, to determine whether a category has been successfully completed by the subject, to identify a subsequent category for the subject to complete, or any combination thereof. For instance, in some embodiments, the criterion store 30 includes a plurality of gate criteria (e.g., gate criterion 32-1, gate criterion 32-2, ... ). In some embodiments, a gate criterion sets a condition for determining whether a category has been successfully completed, and/or for identifying a subsequent category or categories for a subject to complete. In some embodiments, a gate criterion sets a condition precedent for executing a category or a condition that must be achieved in order to deem the category complete. In some embodiments, the criterion store 30 also includes a plurality of biometric thresholds (e.g., biometric threshold 33-1, ... ). In some embodiments, a gate criterion includes a biometric threshold sets a condition for determining whether a challenge associated with an experience has been successfully completed, and/or for identifying a subsequent challenge for a subject to complete. In some embodiments, a biometric threshold sets a condition precedent of a gate criterion for executing a challenge associated with an experience or a condition that must be achieved in order to deem the challenge associated with the experience complete.

While FIG. 2B illustrates gate criteria and biometric thresholds separately, it should be noted that gate criteria and biometric thresholds can be arranged in the criterion store in other ways. For instance, in some embodiments, a category is associated with a gate criterion that includes one or more biometric thresholds for determining whether the challenge(s) of one or more experiences associated with the category has been successfully completed. In such embodiments, the criterion store may or may not include separate biometric thresholds. Moreover, while FIG. 2B illustrates only gate criteria and biometric thresholds, it should be noted that the criterion store can include other criteria. For instance, in some embodiments, the criterion store includes at least one criterion for emergent termination of a social challenge. Further, a criterion, either a gate criterion, a biometric threshold, or any other type, can be a standard criterion applicable to multiple subjects or a personalized criterion specifically designed for a single subject. In an embodiment, the criterion store includes at least one standard criterion. In another embodiment, the criterion store includes at least one personalized criterion. In still another embodiment, the criterion store includes both standard and personalized criteria.

In addition, in some embodiments, the digital reality system 200 includes an application server module 34 that facilitates providing access to a digital reality scene 40 for a user of a client device 300. In some embodiments, the application server module 34 sends each respective client device 300 data elements associated with a digital reality scene 40 when there is a request for such data elements by the respective client device 300, such as when the user logs into a client application 320 at the client device 300 or responsive to a determination by the computer system 200. For instance, a login module 36 of the application server 34 can verify the information provided by the user of the client device 300 against the information stored in a user profile 16 to ensure the correct user is requesting access to a digital reality scene 40. Accordingly, a population of users employ the client devices 300 to access the application server module 34 at the digital reality system 200 and to interact with a digital reality scene 40 that is hosted by the digital reality system 200.

In some embodiments, the application server module 34 also facilitates allowing the user of the client device 300 to configure a digital reality scene 40 in accordance with a determination that the user is a medical practitioner. For instance, in some embodiments, a user interface of a client device allows the user to configure one or more aspects of the digital reality scene, such as a number of non-player characters (NPCs) associated with one or more challenges such as a first social challenge 26-1 and a second social challenge 26-2. Examples of NPCs include other avatars associated with a digital reality scene 40 that the subject may interact with in (e.g., a coffee shop barista, a guest at a party, a co-worker, a transit worker, a menu narrator, a computer implemented communications agent, etc.). However, the present disclosure is not limited thereto.

In some embodiments, each respective digital reality scene 40 defines a digital domain for use by a population of users. A digital reality scene broadly means any space (e.g., digital space and/or real-world space) where digital reality content (e.g., an avatar, a digital reality object, etc.) is presented to a user, for instance, through a display of a client device. For example, in some embodiments, a digital reality scene 40 includes an avatar creation client application, a video game, a social networking website or forum, a messaging client application, or any other application where a user wants to have a digital representation.

In some embodiments, a digital reality scene 40 is configured for exposing a subject to a therapy for improving the psychiatric or mental condition of the subject. For instance, in some embodiments, the therapy for improving the psychiatric or mental condition of the subject is a cognitive therapy e.g., therapy provided by completing an experience associated with a CBT challenge) and/or an exposure therapy (e.g., therapy provided by completing an experience associated with an exposure challenge). As a non-limiting example, in some such embodiments, the cognitive therapy is cognitive behavioral therapy (CBT) or mindfulness based cognitive therapy (MBCT). Accordingly, in some embodiments, the digital reality scene is configured for exposing the subject to a cognitive reframing training, a cognitive reframing session, a mindfulness training, a mindfulness session, an exposure therapy (e.g., a digital reality scene for presenting a challenge), and/or other educational or therapeutical sessions. Additional details and information regarding exposing a subject to cognitive therapy can be found at Segal et al., 2018, "Mindfulness-based Cognitive Therapy for Depression," Guilford Publications, print; Hayes et al., 2018, "Process-based CBT: The Science and Core Clinical Competencies of Cognitive Behavior Therapy," New Harbinger Publications, print, each of which is hereby incorporated by reference in its entirety for all purposes.

Specifically, a respective digital reality scene 40 includes a plurality of objects (e.g., first object 42-1, second object 42-2, . . . , object J 42-J of digital reality scene H 40-H of FIG. 2B) that populates the respective digital reality scene 40. In some embodiments, the plurality of objects 42 includes a plurality of player character objects 42 (e.g., avatars) that represent and/or is controlled by the user, a plurality of NPC objects 42 that represent NPC in the respective digital reality scene that the user cannot directly control, and a plurality of scene objects 42 (e.g., objects that are not player character objects 42 or NPC objects 42, such as bodies of water in a digital reality scene 40, buildings, and furniture in the digital reality scene 40, etc.). As used herein, a digital reality scene refers to any space (e.g., digital space and/or real-world space) where digital reality content (e.g., an avatar, a digital reality object, etc.) is presented to a user through a display (e.g., a display of a client device 300).

However, the present disclosure is not limited thereto. For instance, in some embodiments, the object 42 is that is consumable by a user in the digital reality scene 40, such a video, a text, or an in-game consumable object (e.g., a digital reality drink object). Collectively, the plurality of objects 42 enables a user of a client device 300 to actively engage with the digital reality scene 40, such as one or more users that are online and interacting in the digital reality scene 40 and form the respective digital reality scene 40.

In some embodiments, each respective object 42 includes a plurality of attributes that describe not only how a respective object 42 interacts with a digital reality scene 40, such as with other objects 42 in the digital reality scene 40, but also how the respective object 42 interacts with other users in the digital reality scene 40. In some embodiments, attributes of an object 42 that can be modified or varied include a mass of the object 42, a volume of the object 42, a coefficient of friction of the object 42, a state of matter of the object 42, a rigidity of a body of the object 42, a position of the object 42, a health value of the object 42 (e.g., hit points of the object 42, energy points of the object, etc.), joints of the object 42, and the like. As a non-limiting example, consider a first attribute that describes a response to a collision with a respective object 42 (e.g., a hardness of the object 42, an adhesiveness of the object 42, etc.)

In some embodiments, the attributes associated with a respective object 42 are the same for each user in a digital reality scene 40. For example, if a respective object 42 has an attribute that makes the respective object 42 interactive with users, each user in the digital reality scene 40 can interact with the respective object 42. On the other hand, if the respective object 42 has an attribute that makes the respective object 42 interactive for a select group of users, such as those subjects that have an indication in a user profile 16 of exhibiting a psychiatric or mental condition, only the users in the select group of users can interact with the respective object 42. For example, in some embodiments, an administrator user of a digital reality scene 40 restricts interaction with a specific object 42 for all users except for the administer user or one or more particular users, such as those exhibiting a psychiatric or mental condition.

In some embodiments, the digital reality system 200 includes an application model library 50 that stores one or more models (e.g., classifiers, regressors, etc.). In some embodiments, the model is implemented as an artificial intelligence engine. For instance, in some embodiments, the model includes one or more gradient boosting models, one or more random forest models, one or more neural networks (NN), one or more regression models, one or more Naïve Bayes models, one or more machine learning algorithms (MLA), or a combination thereof. In some embodiments, an MLA or a NN is trained from a training data set (e.g., a first training data set including the user profile store 14, the experience store 22, the gate store 30, the application server module logs 34, or a combination thereof) that includes one or more features identified from a data set. By way of example, in some embodiments, the training data set includes data associated with a first user profile 16-1 and data associated with user tendencies in when confronted with an experience 24 in a digital reality scene 40.

Accordingly, in some embodiments, a first model is a neural network classification model, a second model is a Naïve Bayes classification model, and the like. Furthermore, in some embodiments, the model includes decision tree algorithm, a neural network algorithm, a support vector machine (SVM) algorithm, and the like. Moreover, in some embodiments, the model described herein is a logistic regression algorithm, a neural network algorithm, a convolutional neural network algorithm, a support vector machine (SVM) algorithm, a Naive Bayes algorithm, a nearest neighbor algorithm, a boosted trees algorithm, a random forest algorithm, a decision tree algorithm, a clustering algorithm, or a combination thereof.

In some embodiments, a model is utilized to normalize a value or data set, such as by transforming the value or a set of values to a common frame of reference for comparison purposes. For example, in some embodiments, when one or more pixel values corresponding to one or more pixels in a respective image is normalized to a predetermined statistic (e.g., a mean and/or standard deviation of one or more pixel values across one or more images), the pixel values of the respective pixels are compared to the respective statistic so that the amount by which the pixel values differ from the statistic is determined.

In some embodiments, an untrained model (e.g., "untrained classifier" and/or "untrained neural network") includes a machine learning model or algorithm, such as a classifier or a neural network, that has not been trained on a target dataset. In some embodiments, training a model (e.g., training a neural network) refers to the process of training an untrained or partially trained model (e.g., an untrained or partially trained neural network). For instance, consider the case of a plurality of training samples comprising a corresponding plurality of images (e.g., images capture when presenting a digital reality scene on a display of a client device 300), discussed below. The plurality of images is applied as collective input to an untrained or partially trained model, in conjunction with a corresponding measured indication of one or more objects (e.g., scene objects 42) for each respective image (hereinafter training dataset) to train the untrained or partially trained model on indications that identify objects related to morphological classes, thereby obtaining a trained model. Moreover, it will be appreciated that the term "untrained model" does not exclude the possibility that transfer learning techniques are used in such training of the untrained or partially trained model. For instance, Fernandes et al., 2017, "Transfer Learning with Partial Observability Applied to Cervical Cancer Screening," Pattern Recognition and Image Analysis: $8^{th}$ Iberian Conference Proceedings, 243-250, which is hereby incorporated by reference in its entirety for all purposes, provides non-limiting examples of such transfer learning. In instances where transfer learning is used, the untrained model described above is provided with additional data over and beyond that of the primary training dataset. That is, in non-limiting examples of transfer learning embodiments, the untrained model receives (i) the plurality of images and the measured indications for each respective image ("primary training dataset") and (ii) additional data. In some embodiments, this additional data is in the form of parameters (e.g., coefficients, weights, and/or hyperparameters) that were learned from another, auxiliary training dataset. Moreover, while a description of a single auxiliary training dataset has been disclosed, it will be appreciated that there is no limit on the number of auxiliary training datasets that may be used to complement the primary training dataset in training the untrained model in the present disclosure. For instance, in some embodiments, two or more auxiliary training datasets, three or more auxiliary training datasets, four or more auxiliary training datasets or five or more auxiliary training datasets are used to complement the primary training dataset through transfer learning, where each such auxiliary dataset is different than the primary training dataset. Any manner of transfer learning may be used in such embodiments. For instance, consider the case where there is a first auxiliary training dataset and a second auxiliary training dataset in addition to the primary training dataset. The parameters learned from the first auxiliary training dataset (by application of a first model to the first auxiliary training dataset) may be applied to the second auxiliary training dataset using transfer learning techniques (e.g., a second model that is the same or different from the first model), which in turn may result in a trained intermediate model whose parameters are then applied to the primary training dataset and this, in conjunction with the primary training dataset itself, is applied to the untrained model. Alternatively, a first set of parameters learned from the first auxiliary training dataset (by application of a first model to the first auxiliary training dataset) and a second set of parameters learned from the second auxiliary training dataset (by application of a second model that is the same or different from the first model to the second auxiliary training dataset) may each individually be applied to a separate instance of the primary training dataset (e.g., by separate independent matrix multiplications) and both such applications of the parameters to separate instances of the primary training dataset in conjunction with the primary training dataset itself (or some reduced form of the primary training dataset such as principal components or regression coefficients learned from the primary training set) may then be applied to the untrained model in order to train the untrained model. In some instances, additionally or alternatively, knowledge regarding objects related to morphological classes derived from an auxiliary training dataset is used, in conjunction with the object and/or class-labeled images in the primary training dataset, to train the untrained model.

As used herein, the term "model" refers to a machine learning model or algorithm.

In some embodiments, a model is an unsupervised learning algorithm. One example of an unsupervised learning algorithm is cluster analysis.

In some embodiments, a model is supervised machine learning. Non-limiting examples of supervised learning algorithms include, but are not limited to, logistic regression, neural networks, support vector machines, Naive Bayes algorithms, nearest neighbor algorithms, random forest algorithms, decision tree algorithms, boosted trees algorithms, multinomial logistic regression algorithms, linear models, linear regression, GradientBoosting, mixture models, hidden Markov models, Gaussian NB algorithms, linear discriminant analysis, or any combinations thereof. In some embodiments, a model is a multinomial classifier algorithm. In some embodiments, a model is a 2-stage stochastic gradient descent (SGD) model. In some embodiments, a model is a deep neural network (e.g., a deep-and-wide sample-level classifier).

Neural networks. In some embodiments, the model is a neural network (e.g., a convolutional neural network and/or a residual neural network). Neural network algorithms, also known as artificial neural networks (ANNs), include convolutional and/or residual neural network algorithms (deep learning algorithms). Neural networks can be machine learning algorithms that may be trained to map an input data set to an output data set, where the neural network includes an interconnected group of nodes organized into multiple layers of nodes. For example, the neural network architecture may include at least an input layer, one or more hidden layers, and an output layer. The neural network may include any total number of layers, and any number of hidden layers, where the hidden layers function as trainable feature extractors that allow mapping of a set of input data to an output value or set of output values. As used herein, a deep learning algorithm (DNN) can be a neural network comprising a plurality of hidden layers, e.g., two or more hidden layers. Each layer of the neural network can include a number of nodes (or "neurons"). A node can receive input that comes either directly from the input data or the output of nodes in previous layers, and perform a specific operation, e.g., a summation operation. In some embodiments, a connection from an input to a node is associated with a parameter (e.g., a weight and/or weighting factor). In some embodiments, the node may sum up the products of all pairs of inputs, xi, and their associated parameters. In some embodiments, the weighted sum is offset with a bias, b. In some embodiments, the output of a node or neuron may be gated using a threshold or activation function, f, which may be a linear or non-linear function. The activation function may be, for example, a rectified linear unit (ReLU) activation function, a Leaky ReLU activation function, or other function such as a saturating hyperbolic tangent, identity, binary step, logistic, arcTan, softsign, parametric rectified linear unit, exponential linear unit, softPlus, bent identity, softExponential, Sinusoid, Sine, Gaussian, or sigmoid function, or any combination thereof.

The weighting factors, bias values, and threshold values, or other computational parameters of the neural network, may be "taught" or "learned" in a training phase using one or more sets of training data. For example, the parameters may be trained using the input data from a training data set and a gradient descent or backward propagation method so that the output value(s) that the ANN computes are consistent with the examples included in the training data set. The parameters may be obtained from a back propagation neural network training process.

Any of a variety of neural networks may be suitable for use in performing the methods disclosed herein. Examples can include, but are not limited to, feedforward neural networks, radial basis function networks, recurrent neural networks, residual neural networks, convolutional neural networks, residual convolutional neural networks, and the like, or any combination thereof. In some embodiments, the machine learning makes use of a pre-trained and/or transfer-learned ANN or deep learning architecture. Convolutional and/or residual neural networks can be used for analyzing an image of a subject in accordance with the present disclosure.

For instance, a deep neural network model includes an input layer, a plurality of individually parameterized (e.g., weighted) convolutional layers, and an output scorer. The parameters (e.g., weights) of each of the convolutional layers as well as the input layer contribute to the plurality of parameters (e.g., weights) associated with the deep neural network model. In some embodiments, at least 100 parameters, at least 1000 parameters, at least 2000 parameters or at least 5000 parameters are associated with the deep neural network model. As such, deep neural network models require a computer to be used because they cannot be mentally solved. In other words, given an input to the model, the model output needs to be determined using a computer rather than mentally in such embodiments. See, for example, Krizhevsky et al., 2012, "Imagenet classification with deep convolutional neural networks," in *Advances in Neural Information Processing Systems* 2, Pereira, Burges, Bottou, Weinberger, eds., pp. 1097-1105, Curran Associates, Inc.; Zeiler, 2012 "ADADELTA: an adaptive learning rate method," CoRR, vol. abs/1212.5701; and Rumelhart et al., 1988, "Neurocomputing: Foundations of research," ch. Learning Representations by Back-propagating Errors, pp. 696-699, Cambridge, MA, USA: MIT Press, each of which is hereby incorporated by reference in its entirety for all purposes.

Neural network algorithms, including convolutional neural network algorithms, suitable for use as models are disclosed in, for example, Vincent et al., 2010, "Stacked denoising autoencoders: Learning useful representations in a deep network with a local denoising criterion," J Mach Learn Res 11, pp. 3371-3408; Larochelle et al., 2009, "Exploring strategies for training deep neural networks," J Mach Learn Res 10, pp. 1-40; and Hassoun, 1995, Fundamentals of Artificial Neural Networks, Massachusetts Institute of Technology, each of which is hereby incorporated by reference. Additional example neural networks suitable for use as models are disclosed in Duda et al., 2001, *Pattern Classification*, Second Edition, John Wiley & Sons, Inc., New York; and Hastie et al., 2001, *The Elements of Statistical Learning*, Springer-Verlag, New York, each of which is hereby incorporated by reference in its entirety for all purposes. Additional example neural networks suitable for use as models are also described in Draghici, 2003, *Data Analysis Tools for DNA Microarrays*, Chapman & Hall/CRC; and Mount, 2001, *Bioinformatics: sequence and genome analysis*, Cold Spring Harbor Laboratory Press, Cold Spring Harbor, New York, each of which is hereby incorporated by reference in its entirety for all purposes.

Support vector machines. In some embodiments, the model is a support vector machine (SVM). SVM algorithms suitable for use as models are described in, for example, Cristianini and Shawe-Taylor, 2000, "An Introduction to Support Vector Machines," Cambridge University Press, Cambridge; Boser et al., 1992, "A training algorithm for optimal margin classifiers," in Proceedings of the 5th Annual ACM Workshop on Computational Learning Theory, ACM Press, Pittsburgh, Pa., pp. 142-152; Vapnik, 1998, Statistical Learning Theory, Wiley, New York; Mount, 2001, Bioinformatics: sequence and genome analysis, Cold Spring Harbor Laboratory Press, Cold Spring Harbor, N.Y.; Duda, Pattern Classification, Second Edition, 2001, John Wiley & Sons, Inc., pp. 259, 262-265; and Hastie, 2001, The Elements of Statistical Learning, Springer, New York; and Furey et al., 2000, Bioinformatics 16, 906-914, each of which is hereby incorporated by reference in its entirety for all purposes. When used for classification, SVMs separate a given set of binary labeled data with a hyper-plane that is maximally distant from the labeled data. For cases in which no linear separation is possible, SVMs can work in combination with the technique of 'kernels', which automatically realizes a non-linear mapping to a feature space. The hyper-plane found by the SVM in feature space can correspond to a non-linear decision boundary in the input space. In some embodiments, the plurality of parameters (e.g., weights) associated with the SVM define the hyper-plane. In some embodiments, the hyper-plane is defined by at least 10, at least 20, at least 50, or at least 100 parameters and the SVM model requires a computer to calculate because it cannot be mentally solved.

Naïve Bayes algorithms. In some embodiments, the model is a Naive Bayes algorithm. Naïve Bayes classifiers suitable for use as models are disclosed, for example, in Ng et al., 2002, "On discriminative vs. generative classifiers: A comparison of logistic regression and naive Bayes," Advances in Neural Information Processing Systems, 14, which is hereby incorporated by reference in its entirety for all purposes. A Naive Bayes classifier is any classifier in a family of "probabilistic classifiers" based on applying Bayes' theorem with strong (naïve) independence assumptions between the features. In some embodiments, they are coupled with Kernel density estimation. See, for example, Hastie et al., 2001, *The elements of statistical learning: data mining, inference, and prediction*, eds. Tibshirani and Friedman, Springer, New York, which is hereby incorporated by reference in its entirety for all purposes.

Nearest neighbor algorithms. In some embodiments, a model is a nearest neighbor algorithm. Nearest neighbor models can be memory-based and include no model to be fit. For nearest neighbors, given a query point $x_0$ (a first image), the k training points $x_{(r)}$, r, . . . k (here the training images) closest in distance to $x_0$ are identified and then the point $x_0$ is classified using the k nearest neighbors. In some embodiments, the distance to these neighbors is a function of the values of a discriminating set. In some embodiments, Euclidean distance in feature space is used to determine distance as $d_{(i)} = \|x_{(i)} - x_{(o)}\|$. In some embodiments, when the nearest neighbor algorithm is used, the value data used to compute the linear discriminant is standardized to have mean zero and variance 1. The nearest neighbor rule can be refined to address issues of unequal class priors, differential misclassification costs, and feature selection. Many of these refinements involve some form of weighted voting for the neighbors. For more information on nearest neighbor analysis, see Duda, Pattern Classification, Second Edition, 2001, John Wiley & Sons, Inc; and Hastie, 2001, The Elements of Statistical Learning, Springer, New York, each of which is hereby incorporated by reference in its entirety for all purposes.

A k-nearest neighbor model is a non-parametric machine learning method in which the input consists of the k closest training examples in feature space. The output is a class membership. An object is classified by a plurality vote of its neighbors, with the object being assigned to the class most common among its k nearest neighbors (k is a positive integer, typically small). If k=1, then the object is simply assigned to the class of that single nearest neighbor. See, Duda et al., 2001, *Pattern Classification*, Second Edition, John Wiley & Sons, which is hereby incorporated by reference in its entirety for all purposes. In some embodiments, the number of distance calculations needed to solve the k-nearest neighbor model is such that a computer is used to solve the model for a given input because it cannot be mentally performed.

Random forest, decision tree, and boosted tree algorithms. In some embodiments, the model is a decision tree. Decision trees suitable for use as models are described generally by Duda, 2001, Pattern Classification, John Wiley & Sons, Inc., New York, pp. 395-396, which is hereby incorporated by reference. Tree-based methods partition the feature space into a set of rectangles, and then fit a model (like a constant) in each one. In some embodiments, the decision tree is random forest regression. One specific algorithm that can be used is a classification and regression tree (CART). Other specific decision tree algorithms include, but are not limited to, ID3, C4.5, MART, and Random Forests. CART, ID3, and C4.5 are described in Duda, 2001, Pattern Classification, John Wiley & Sons, Inc., New York, pp. 396-408 and pp. 411-412, which is hereby incorporated by reference in its entirety for all purposes. CART, MART, and C4.5 are described in Hastie et al., 2001, The Elements of Statistical Learning, Springer-Verlag, New York, Chapter 9, which is hereby incorporated by reference in its entirety for all purposes. Random Forests are described in Breiman, 1999, "Random Forests—Random Features," Technical Report 567, Statistics Department, U.C. Berkeley, September 1999, which is hereby incorporated by reference in its entirety for all purposes. In some embodiments, the decision tree model includes at least 10, at least 20, at least 50, or at least 100 parameters (e.g., weights and/or decisions) and requires a computer to calculate because it cannot be mentally solved.

Regression. In some embodiments, the model uses a regression algorithm. A regression algorithm can be any type of regression. For example, in some embodiments, the regression algorithm is logistic regression. In some embodiments, the regression algorithm is logistic regression with lasso, L2 or elastic net regularization. In some embodiments, those extracted features that have a corresponding regression coefficient that fails to satisfy a threshold value are pruned (removed from) consideration. In some embodiments, a generalization of the logistic regression model that handles multicategory responses is used as the model. Logistic regression algorithms are disclosed in Agresti, An Introduction to Categorical Data Analysis, 1996, Chapter 5, pp. 103-144, John Wiley & Son, New York, which is hereby incorporated by reference in its entirety for all purposes. In some embodiments, the model makes use of a regression model disclosed in Hastie et al., 2001, *The Elements of Statistical Learning*, Springer-Verlag, New York. In some embodiments, the logistic regression model includes at least 10, at least 20, at least 50, at least 100, or at least 1000 parameters (e.g., weights) and requires a computer to calculate because it cannot be mentally solved.

Linear discriminant analysis algorithms. Linear discriminant analysis (LDA), normal discriminant analysis (NDA), or discriminant function analysis can be a generalization of Fisher's linear discriminant, a method used in statistics, pattern recognition, and machine learning to find a linear combination of features that characterizes or separates two or more classes of objects or events. The resulting combination can be used as the model (e.g., a linear classifier) in some embodiments of the present disclosure.

Mixture model and Hidden Markov model. In some embodiments, the model is a mixture model, such as that described in McLachlan et al., Bioinformatics 18(3):413-422, 2002. In some embodiments, in particular, those embodiments including a temporal component, the model is a hidden Markov model such as described by Schliep et al., 2003, Bioinformatics 19(1):i255-i263.

Clustering. In some embodiments, the model is an unsupervised clustering model. In some embodiments, the model is a supervised clustering model. Clustering algorithms suitable for use as models are described, for example, at pages 211-256 of Duda and Hart, Pattern Classification and Scene Analysis, 1973, John Wiley & Sons, Inc., New York, (hereinafter "Duda 1973") which is hereby incorporated by reference in its entirety for all purposes. The clustering problem can be described as one of finding natural groupings in a dataset. To identify natural groupings, two issues can be addressed. First, a way to measure similarity (or dissimilarity) between two samples can be determined. This metric (e.g., similarity measure) can be used to ensure that the samples in one cluster are more like one another than they are to samples in other clusters. Second, a mechanism for partitioning the data into clusters using the similarity measure can be determined. One way to begin a clustering investigation can be to define a distance function and to compute the matrix of distances between all pairs of samples in a training dataset. If distance is a good measure of similarity, then the distance between reference entities in the same cluster can be significantly less than the distance between the reference entities in different clusters. However, clustering may not use a distance metric. For example, a nonmetric similarity function $s(x, x')$ can be used to compare two vectors $x$ and $x'$. $s(x, x')$ can be a symmetric function whose value is large when $x$ and $x'$ are somehow "similar." Once a method for measuring "similarity" or "dissimilarity" between points in a dataset has been selected, clustering can use a criterion function that measures the clustering quality of any partition of the data. Partitions of the data set that extremize the criterion function can be used to cluster the data. Particular exemplary clustering techniques that can be used in the present disclosure can include, but are not limited to, hierarchical clustering (agglomerative clustering using a nearest-neighbor algorithm, farthest-neighbor algorithm, the average linkage algorithm, the centroid algorithm, or the sum-of-squares algorithm), k-means clustering, fuzzy k-means clustering algorithm, and Jarvis-Patrick clustering. In some embodiments, the clustering includes unsupervised clustering (e.g., with no preconceived number of clusters and/or no predetermination of cluster assignments).

Ensembles of models and boosting. In some embodiments, an ensemble (two or more) of models is used. In some embodiments, a boosting technique such as AdaBoost is used in conjunction with many other types of learning algorithms to improve the performance of the model. In this approach, the output of any of the models disclosed herein, or their equivalents, is combined into a weighted sum that represents the final output of the boosted model. In some embodiments, the plurality of outputs from the models is combined using any measure of central tendency known in the art, including but not limited to a mean, median, mode, a weighted mean, weighted median, weighted mode, etc. In some embodiments, the plurality of outputs is combined using a voting method. In some embodiments, a respective model in the ensemble of models is weighted or unweighted.

The term "classification" can refer to any number(s) or other characters(s) that are associated with a particular property of a sample. For example, a "+" symbol (or the word "positive") can signify that a sample is classified as having a desired outcome or characteristic, whereas a "−" symbol (or the word "negative") can signify that a sample is classified as having an undesired outcome or characteristic. In another example, the term "classification" refers to a respective outcome or characteristic (e.g., high risk, medium risk, low risk). In some embodiments, the classification is binary (e.g., positive or negative) or has more levels of classification (e.g., a scale from 1 to 10 or 0 to 1). In some embodiments, the terms "cutoff" and "threshold" refer to predetermined numbers used in an operation. In one example, a cutoff value refers to a value above which results are excluded. In some embodiments, a threshold value is a value above or below which a particular classification applies. Either of these terms can be used in either of these contexts.

One of skill in the art will readily appreciate other models that are applicable to the systems and methods of the present disclosure. In some embodiments, the systems, methods, and devices of the present disclosure utilize more than one model to provide an evaluation (e.g., arrive at an evaluation given one or more inputs) with an increased accuracy. For instance, in some embodiments, each respective model arrives at a corresponding evaluation when provided a respective data set. Accordingly, each respective model can independently arrive at a result and then the result of each respective model is collectively verified through a comparison or amalgamation of the models. From this, a cumulative result is provided by the models. However, the present disclosure is not limited thereto.

In some embodiments, a respective model is tasked with performing a corresponding activity. As a non-limiting example, in some embodiments, the task performed by the respective model includes, but is not limited to, diagnosing a mental disorder, generating a manifestation of a corresponding challenging in the form of an experience 24 associated with a digital reality scene 40, identifying each category in a plurality of categories of an assessment obtained from an subject, conducting a validation of the assessment obtained from the subject, conducting a further validation of another validation by a medical practitioner of the assessment obtained from the subject, generating a respective gate criterion, generating a respective biometric threshold, generating an exposure progression including a plurality of categories arranged in an order, determining whether a challenge has been successfully completed, identifying a subsequent challenge for a subject to complete, determining whether a category has been successfully completed, identifying a subsequent category for a subject to complete, or any combination thereof. In some embodiments, each respective model of the present disclosure makes use of 10 or more parameters, 100 or more parameters, 1000 or more parameters, 10,000 or more parameters, or 100,000 or more parameters. In some embodiments, each respective model of the present disclosure cannot be mentally performed.

Each of the above identified modules and applications correspond to a set of executable instructions for performing one or more functions described above and the methods described in the present disclosure. These modules (e.g., sets of instructions) need not be implemented as separate software programs, procedures or modules, and thus various subsets of these modules are, optionally, combined or otherwise re-arranged in various embodiments of the present disclosure. In some embodiments, the memory 212 optionally stores a subset of the modules and data structures identified above. Furthermore, in some embodiments, the memory 212 stores additional modules and data structures not described above.

It should be appreciated that FIGS. 2A and 2B illustrates only an example of the digital reality system 200, and that the digital reality system 200 optionally has more or fewer components than shown, optionally combines two or more components, or optionally has a different configuration or arrangement of the components. The various components shown in FIGS. 2A and 2B are implemented in hardware, software, firmware, or a combination thereof, including one or more signal processing and/or application specific integrated circuits. Moreover, the digital reality system 200 can be a single device that includes all the functionality of the digital reality system 200. The client device 300 can also be a combination of multiple devices. For instance, the functionality of the digital reality system 200 may be spread across any number of networked computers and/or reside on each of several networked computers and/or by hosted on one or more virtual machines and/or containers at a remote location accessible across a communications network (e.g., communications network 106, network interface 204, or both). One of skill in the art will appreciate that a wide array of different computer topologies is possible for the digital reality system 200, and other devices and systems of the preset disclosure, and that all such topologies are within the scope of the present disclosure.

Figure 3:
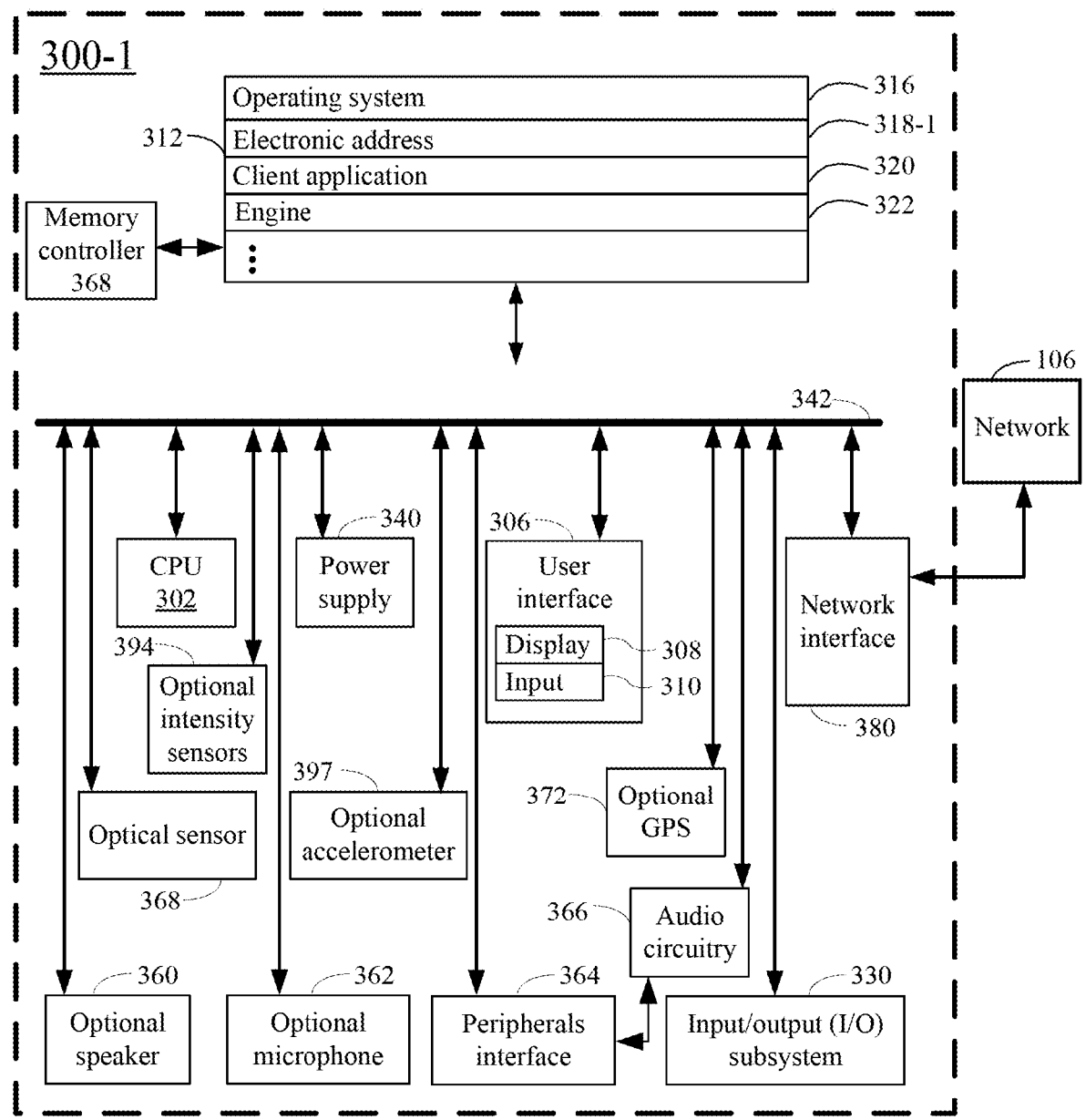
FIG. 3 illustrates a client device for displaying a digital reality scene, in accordance with an embodiment of the present disclosure.

Referring to FIG. 3, an exemplary client device 300 is provided (e.g., first client device 300-1). A client device 300 includes one or more processing units (CPUs) 302, one or more network or other communication interfaces 304, memory 312 (e.g., random access memory and/or non-volatile memory) optionally accessed by one or more controllers, and one or more communication busses 314 interconnecting the aforementioned components.

In some embodiments, a client device 300 includes a mobile device, such as a mobile phone, a tablet, a laptop computer, a wearable device such as a smart watch, and the like. In such embodiments, a respective digital reality scene 40 that is accessible through the client device 300 includes an augmented reality scene. In some embodiments, the respective digital reality scene accessible through the client device 300 includes a mixed reality scene. However, the present disclosure is not limited thereto. For instance, in some embodiments, the client device 300 is a desktop computer or other similar devices that accepts one or more wearable devices (e.g., wearable display). In some embodiments, the client device 300 is a standalone device that is dedicated to providing a digital reality scene 40 of the systems and methods of the present disclosure. Further, in some embodiments, each client device 300 enables a respective subject to provide information related to the respective subject (e.g., subject preferences, subject feedback, etc.).

In addition, the client device 300 includes a user interface 306. The user interface 306 typically includes a display device 308 for presenting media, such as a digital reality scene 40, and receiving instructions from the subject operating the client device 300. In some embodiments, the display device 308 is optionally integrated within the client device 300 (e.g., housed in the same chassis as the CPU 302 and memory 312), such as a smart (e.g., smart phone) device. In some embodiments, the client device 300 includes one or more input device(s) 310, which allow the subject to interact with the client device 300. In some embodiments, input devices 310 include a keyboard, a mouse, one or more cameras (e.g., an objective lens in communication with a two-dimensional pixelated detector) configured to determine a position of an object during a period of time (e.g., track a hand of a subject across space and/or time), and/or other input mechanisms. Alternatively, or in addition, in some embodiments, the display device 308 includes a touch-sensitive surface, e.g., where display 308 is a touch-sensitive display or client device 300 includes a touch pad.

In some embodiments, the client device 300 includes an input/output (I/O) subsystem 330 for interfacing with one or more peripheral devices with the client device 300. For instance, in some embodiments, audio is presented through an external device (e.g., speakers, headphones, etc.) that receives audio information from the client device 300 and/or a remote device (e.g., digital reality system 200), and presents audio data based on this audio information. In some embodiments, the input/output (I/O) subsystem 330 also includes, or interfaces with, an audio output device, such as speakers or an audio output for connecting with speakers, earphones, or headphones. In some embodiments, the input/output (I/O) subsystem 330 also includes voice recognition capabilities (e.g., to supplement or replace an input device 310).

In some embodiments, the client device 300 also includes one or more sensors (e.g., an accelerometer, a magnetometer, a proximity sensor, a gyroscope, etc.), an image capture device (e.g., a camera device or an image capture module and related components), a location module (e.g., a Global Positioning System (GPS) receiver or other navigation or geolocation system module/device and related components), or a combination thereof, and the like.

As described above, the client device 300 includes a user interface 306. The user interface 306 typically includes a display device 308, which is optionally integrated within the client device 300 (e.g., housed in the same chassis as the CPU and memory, such as with a smart phone or an all-in-one desktop computer client device 300). In some embodiments, the client device 300 includes a plurality of input device(s) 310, such as a keyboard, a mouse, and/or other input buttons (e.g., one or more sliders, one or more joysticks, one or more radio buttons, etc.). Alternatively, or in addition, in some embodiments, the display device 308 includes a touch-sensitive surface, e.g., where display 308 is a touch-sensitive display 308 or a respective client device 300 includes a touch pad.

In some embodiments, a pose of the client device 300 is determined based one or more characteristics, such as one or more local characteristics at the client device 300 (e.g., an acceleration of the client device) and/or one or more proximate characteristics near the client device 300 that are associated with a respective region of interest, such as a hand of a subject using the client device 300 or a hand controller of the client device 300. For instance, in some embodiments, the one or more proximate characteristics associated with the respective region of interest include an appearance of the region of interest. By way of example, in some embodiments a respective proximate characteristic is associated with a shape of the region of interest (e.g., a hand of a subject changing from an open first to a clenched fist, etc.), a color of the region of interest (e.g., evaluating a color of an article of clothing worn by the subject), a reflectance of the region of interest, or the like. In some embodiments, the one or more proximate characteristics associated with a respective region of interest is derived from information derived from a previous challenge of a respective digital reality scene (e.g., information retained by regimen store of a corresponding user profile), such as a workflow of an exposure progression. In some embodiments, the one or more proximate characteristics associated with a respective region of interest is based on a reference databased including a plurality of characteristics having an association with a predetermined region of interest. Additional details and information regarding determining pose based on characteristics of a region of interest can be found at Oe et al., 2005, "Estimating Camera Position and Posture by Using Feature Landmark Database," Scandinavian Conference on Image Analysis, pg. 171; Lee et al., 1998, "Fine Active Calibration of Camera Position/Orientation through Pattern Recognition," IEEE ISIE, print; Dettwiler et al., 1994, "Motion Tracking with an Active Camera," IEEE Transactions on Pattern Analysis and Machine Intelligence, 16(5), pg. 449; Kritikos et al., 2020, "Comparison between Full Body Motion Recognition Camera Interaction and Hand Controllers Interaction used in Virtual Reality Exposure Therapy for Acrophobia," Sensors, 20(5), pg. 1244, each of which is hereby incorporated by reference in its entirety for all purposes.

Furthermore, in some embodiments, the client device 300 includes a heads-up display (HUD) device, e.g., where display 308 is head-mounted on the user such as a virtual reality headset that facilitates presenting a virtual reality scene 40, an augmented reality headset that facilitates presenting an augmented reality scene 40, or a mixed reality headset that facilitates presenting a mixed reality scene 40. In such embodiments, the client device 300 includes the input device(s) 310 such as a haptic feedback device. Accordingly, the HUD client device 300 provides the functionality of a virtual reality client device 300 with synchronized haptic and audio feedback, an augmented reality client device 300 with synchronized haptic and audio feedback, a mixed reality client device 300 with synchronized haptic and audio feedback, or a combination thereof.

Figure 13:
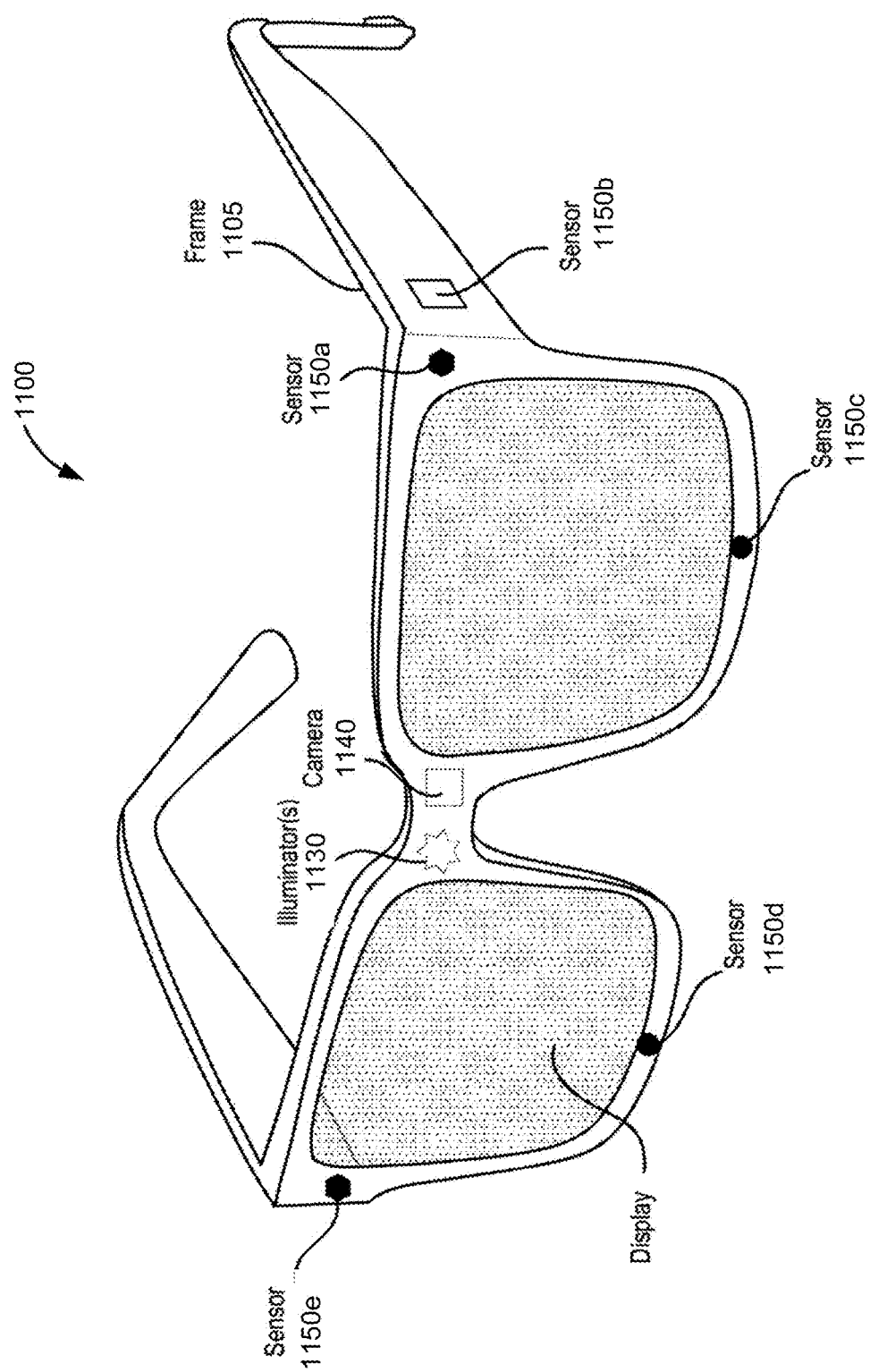
FIG. 13 illustrates another client device for displaying a digital reality scene, in accordance with an embodiment of the present disclosure.

In some embodiments, the display 308 is a wearable display, such as a smart watch, head mounted display or a smart garment client device (e.g., display 1100 of FIG. 13). One such non-limiting example of a wearable display 308 includes a near-eye display or a head mounted display. In other embodiments, the display 308 is a smart mobile device display (e.g., a smart phone), such as client device 300-1 of FIG. 8A. In some embodiments, display 308 is a head-mounted display (HMD) connected to host computer system 300, a standalone HMD, a mobile device or computing system, or any other hardware platform capable of providing artificial reality content to one or more viewers. FIG. 13 is a perspective view of an example of a near-eye display 1100 in the form of a pair of glasses for implementing some of the examples of displays 308 disclosed herein. In some embodiments, the near-eye display 1100 is configured to operate as a virtual reality display, an augmented reality display, and/or a mixed reality display. In some embodiments, the near-eye display 1100 includes a frame 1105 and a display 1110. In some embodiments, the display 1110 is configured to present content to a user. In some embodiments, the display 1100 includes display electronics and/or display optics. For example, in some embodiments, the display 1100 includes an LCD display panel, an LED display panel, or an optical display panel (e.g., a waveguide display assembly). In some embodiments, the near-eye display 1100 further includes various sensors 1150a, 1150b, 1150c, 1150d, and 1150e on or within frame 1105. In some embodiments, the various sensors 1150a-1150e include one or more depth sensors, motion sensors, position sensors, inertial sensors, recorder sensors (e.g., microphone sensors), or ambient light sensors. In some embodiments, the various sensors 1150a-1150e include one or more image sensors configured to generate image data representing different fields of views in different directions. In some embodiments, the various sensors 1150a-1150e are used as input devices to control or influence the displayed content of near-eye display 1100, and/or to provide an interactive VR/AR/MR experience to a user of near-eye display 1100. In some embodiments, the various sensors 1150a-1150e also are used for stereoscopic imaging.

In some embodiments, the near-eye display 1100 further includes one or more illuminators 1130 to project light into the physical environment. In some embodiments, the projected light is associated with different frequency bands (e.g., visible light, infra-red light, ultra-violet light, etc.) and, in such embodiments, serves various purposes. For example, in some embodiments, the illuminator(s) 1130 project light in a dark environment (or in an environment with low intensity of infra-red light, ultra-violet light, etc.) to assist sensors 1150a-1150e in capturing images of different objects within the dark environment. In some embodiments, the illuminator(s) 1130 are used to project certain light pattern onto the objects within the environment. In some embodiments, the illuminator(s) 1130 are used as locators.

In some embodiments, the near-eye display 1100 includes a high-resolution camera 1140. In some embodiments, the camera 1140 captures images of the physical environment in the field of view. In some embodiments, the captured images are processed, for example, by a virtual reality engine (e.g., engine 322 of FIG. 3) to add one or more virtual objects 42 to the captured images or modify physical objects in the captured images. In some embodiments, the processed images are displayed to the user by display 1100 for the AR or MR applications (e.g., client application 320 of FIG. 3) provided by the present disclosure.

Additionally, in some embodiments, the client device 300 includes, or is a component part of a digital reality kit for presenting a digital reality scene 40. Additional details and information regarding a digital reality kit can be found at United States Patent Application Publication no.: 2020/0121050 A1, entitled "Virtual Reality Kit," filed Oct. 18, 2019, which is hereby incorporated by reference in its entirety for all purposes.

In some embodiments, the client device 300 includes one or more readily available (e.g., off the shelf) components such a Pico Neo 3 pro (Pico Interactive Inc., San Francisco, California), Oculus Quest 2 (Oculus VR, Irvine, California), Snapchat Spectacles 3 (Snap Inc., Santa Monica, California), Google Cardboard (Google LLC, Mountain View, California), HTC VIVE Pro 2 (HTC Corporation, Taoyuan City, Taiwan), or the like. One of skill in the art will appreciate that the present disclosure is not limited thereto.

In some embodiments, the client device 300 presents media to a user through the display 308. Examples of media presented by the display 308 include one or more images, a video, audio (e.g., waveforms of an audio sample), or a combination thereof. In typical embodiments, the one or more images, the video, the audio, or the combination thereof is presented by the display through a digital reality scene 40. In some embodiments, the audio is presented through an external device (e.g., speakers, headphones, etc.) that receives audio information from the client device 300, the digital reality system 200, or both, and presents audio data based on this audio information. In some embodiments, the user interface 306 also includes an audio output device, such as speakers or an audio output for connecting with speakers, earphones, or headphones. In some embodiments, the user interface 306 also includes an audio input device (e.g., a microphone), and optional voice recognition capabilities (e.g., to supplement or replace the keyboard). Optionally, the client device 300 includes an audio input device 310 (e.g., a microphone) to capture audio (e.g., speech from a user). In some embodiments, the audio input device 310 is a single omni-directional microphone.

In some embodiments, the client device 300 also includes one or more of: one or more sensors (e.g., accelerometer, magnetometer, proximity sensor, gyroscope); an image capture device (e.g., a camera device or module and related components); and/or a location module (e.g., a Global Positioning System (GPS) receiver or other navigation or geolocation device and related components). In some embodiments, the sensors include one or more hardware devices that detect spatial and motion information about the client device 300. Spatial and motion information can include information about a position of the client device 300, an orientation of the client device 300, a velocity of the client device 300, a rotation of the client device 300, an acceleration of the client device 300, or a combination thereof. For instance, in some embodiments, the sensors include one or more inertial measurement units (IMUs) that detect rotation of the user's head while the user is utilizing (e.g., wearing) the client device 300. In some embodiments, this rotation information is used (e.g., by client application 320 of FIG. 3 and/or digital reality session engine 38 of FIG. 2B) to adjust the images displayed on the display 308 of the client device 300. In some embodiments, each IMU includes one or more gyroscopes, one or more accelerometers, and/or one or more magnetometers that collect the spatial and motion information. In some embodiments, the sensors include one or more cameras positioned on the client device 300.

Memory 312 includes high-speed random access memory, such as DRAM, SRAM, DDR RAM, or other random access solid state memory devices, and optionally also includes non-volatile memory, such as one or more magnetic disk storage devices, optical disk storage devices, flash memory devices, or other non-volatile solid state storage devices. Memory 312 may optionally include one or more storage devices remotely located from the CPU(s) 302. Memory 312, or alternatively the non-volatile memory device(s) within memory 312, includes a non-transitory computer readable storage medium. Access to memory 312 by other components of the client device 300, such as the CPU(s) 302 and the I/O subsystem 330, is, optionally, controlled by a controller. In some embodiments, memory 312 can include mass storage that is remotely located with respect to the CPU 302. In other words, some data stored in memory 312 may in fact be hosted on devices that are external to the client device 300, but that can be electronically accessed by the client device 300 over an Internet, intranet, or other form of network 106 or electronic cable using communication interface 304.

In some embodiments, the memory 312 of the client device 300 stores:
- an operating system 316 that includes procedures for handling various basic system services;
- an electronic address 318 associated with the client device 300 that identifies the client device 300 within a distributed system 100;
- a client application 320 for generating content for display through a graphical user interface presented on the display 308 of the client device 300; and
- an engine 322 that allows a client application 320 to operate in conjunction with the client device 300.

In some embodiments, an electronic address 318 is associated with the client device 300, which is utilized to at least uniquely identify the client device 300 from other devices and components of the distributed system 100. In some embodiments, the electronic address 318 associated with the client device 300 is used to determine a source of an assessment provided by the client device 300 (e.g., receiving an assessment from the digital reality system 200 and communicating one or more responses based on the assessment).

In some embodiments, each client application 320 is a group of instructions that, when executed by a processor, generates content for presentation to the user, such as a virtual reality scene 40, an augmented reality scene 40, a mixed reality scene 40. A client application 320 may generate content in response to inputs received from the user through movement of the client device 300, such as the inputs 310 of the client device. Here, the client application 320 includes a gaming application, a conferencing application, a video playback application, or a combination thereof. For instance, in some embodiments, the client application 320 facilitates providing one or more sessions of a digital reality scene, such as the digital reality scene 40-1, 40-2, . . . , or 40-H of FIG. 1. In some embodiments, the client application 320 is utilized to obtain an assessment from a subject that includes an identification of a plurality of proposed experiences 24. In some embodiments, the client application 320 is utilized to configure one or more criteria associated with an experience 24, and, optionally, configure the experience within a digital reality scene 40, such as a number of player characters and/or a number of non-player characters that can participate in the digital reality scene 40 at during a given challenge.

In some embodiments, an engine 322 is a software module that allows a client application 320 to operate in conjunction with the client device 300. In some embodiments, the engine 322 receives information from the sensors on the client device 300 and provides the information to a client application 320. Based on the received information, the engine 322 determines media content to provide to the client device 300 for presentation to the user through the display 308 or the one or more audio devices, and/or a type of haptic feedback. For example, if the engine 322 receives information from the sensors of the client device 300 indicating that the user has looked to the left, the engine 322 generates content for the display 308 that mirrors the user's movement in a digital reality scene 40. As another example, if the user hits a wall (e.g., in a digital reality scene 40), the engine 322 generates control signals for a haptic-feedback mechanism of the client device 300 to generate a vibration, and, optionally, audio that corresponds to the user action (e.g., sound of a human first striking a wooden wall, or sound of a human first hitting a Plexiglas wall, which would be different from the sound generated for the wooden wall). As yet another non-limiting example, in some embodiments, the engine 322 receives information from one or more sensors in electronic communication with the client device 300, in which the one or more sensors obtain biometric data from a user of the client device 300 such as an instantaneous heart rate of the user captured over a period of time. In such embodiments, the engine 322 generates content for the display 308 that is responsive to the biometric data from the user, such as changing a color of a first object 42-1 in a digital reality scene 40 from a first color of orange to a second color of violet in order to reflect a lowering of the instantaneous heart rate of the user. However, the present disclosure is not limited thereto.

Similarly, in some embodiments, the engine 322 receives information from the sensors of the client device 300 and provides the information from the sensors to a client application 320. Accordingly, in some embodiments, the application 320 uses the information to perform an action within a digital reality scene of the application 320. In this way, if the engine 322 receives information from the sensors that the user has raised his or her hand, a simulated hand in the digital reality scene 40 lifts to a corresponding height. However, the present disclosure is not limited thereto.

In some embodiments, the engine 322 generates control signals for the haptic-feedback mechanism, which cause a haptic-feedback mechanism to create one or more haptic ques. As described supra, the information received by the engine 322 can also include information from the client device 300. For example, in some embodiments, one or more cameras (e.g., inputs 310, I/O subsystem 330 of FIG. 3) disposed on the client device 300 captures movements of the client device 300, and the client application 320 can use this additional information to perform the action within a digital reality scene 40 of the client application 320.

In some embodiments, the engine 322 provides feedback to the user that the action was performed. In some embodiments, the provided feedback is visually provided through the display 308 of the client device 300, provided in an auditory manner through the one or more audio devices of the client device 300 (e.g., I/O subsystem 330), and/or provided in a haptic manner via one or more of the haptic-feedback mechanisms of the client device 300.

Additional details and information regarding utilizing an engine (e.g., digital reality session engine 38 of FIG. 2B, engine 322 of FIG. 3) can be found at United States Patent Application Publication no.: 2018/0254097 A1, entitled "Dynamic Multi-Sensory Simulation System for Effecting Behavior Change," filed Mar. 5, 2018; United States Patent Application Publication no.: 2020/0022632 A1, entitled "Digital Content Processing and Generation for a Virtual Environment," filed Jul. 16, 2019; and United States Patent Application Publication no.: 2020/0023157 A1, entitled "Dynamic Digital Content Delivery in a Virtual Environment," filed Jul. 16, 2019; each of which is hereby incorporated by reference in its entirety for all purposes.

Each of the above identified modules and applications correspond to a set of executable instructions for performing one or more functions described above and the methods described in the present disclosure. These modules (e.g., sets of instructions) need not be implemented as separate software programs, procedures or modules, and thus various subsets of these modules are, optionally, combined or otherwise re-arranged in various embodiments of the present disclosure. In some embodiments, the memory 312 optionally stores a subset of the modules and data structures identified above. Furthermore, in some embodiments, the memory 312 stores additional modules and data structures not described above.

It should be appreciated that FIG. 3 illustrates only an example of the client device 300, and that the client device 300 optionally has more or fewer components than shown, optionally combines two or more components, or optionally has a different configuration or arrangement of the components. The various components shown in FIG. 3 are implemented in hardware, software, firmware, or a combination thereof, including one or more signal processing and/or application specific integrated circuits. Moreover, the client device 300 can be a single device that includes all the functionality of the client device 300. The client device 300 can also be a combination of multiple devices. For instance, the functionality of the client device 300 may be spread across any number of networked computers and/or reside on each of several networked computers and/or by hosted on one or more virtual machines and/or containers at a remote location accessible across a communications network (e.g., communications network 106, network interface 304, or both). One of skill in the art will appreciate that a wide array of different computer topologies is possible for the client device 300, and other devices and systems of the preset disclosure, and that all such topologies are within the scope of the present disclosure.

Figure 4B:
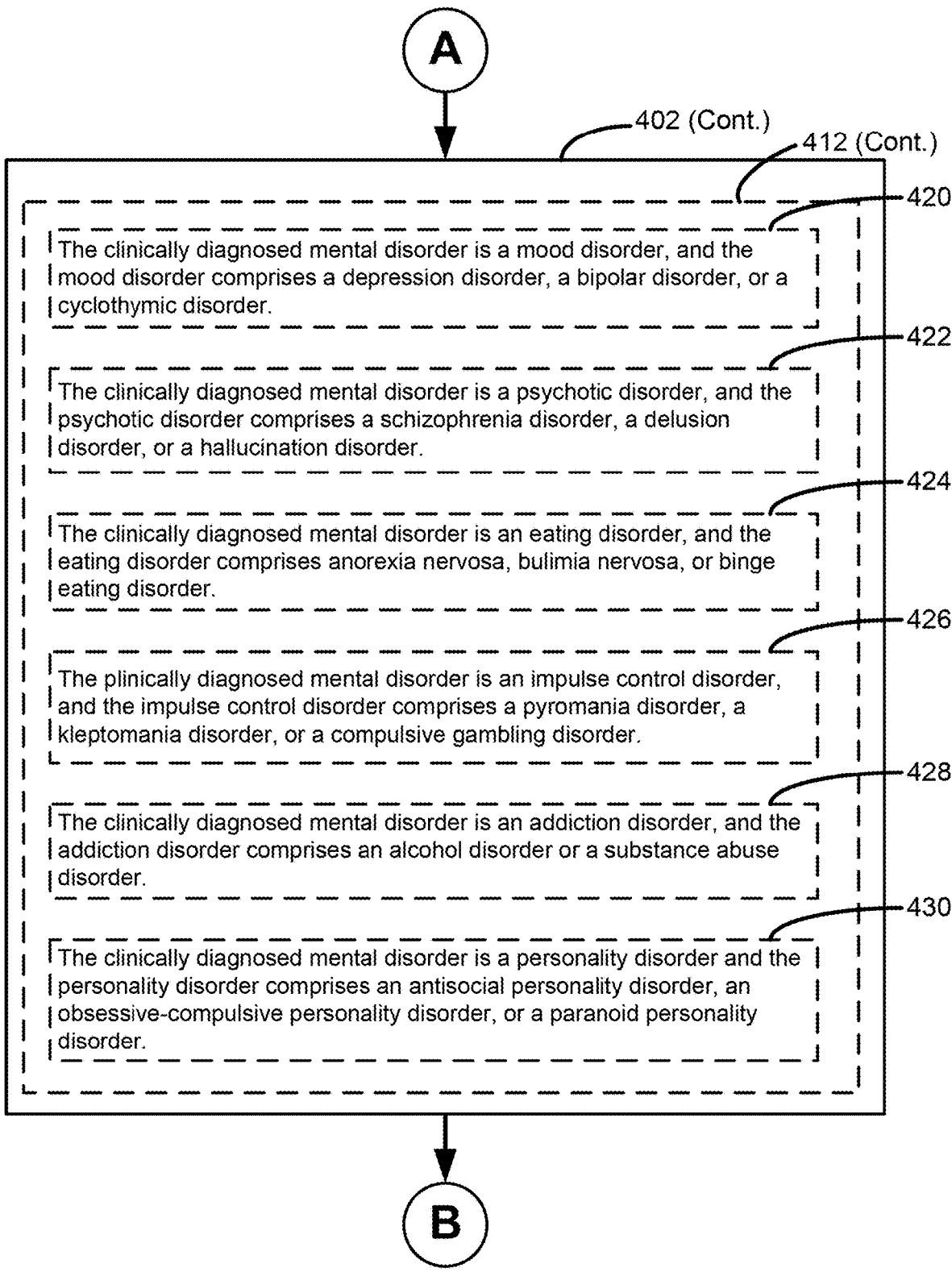
Figure 4D:
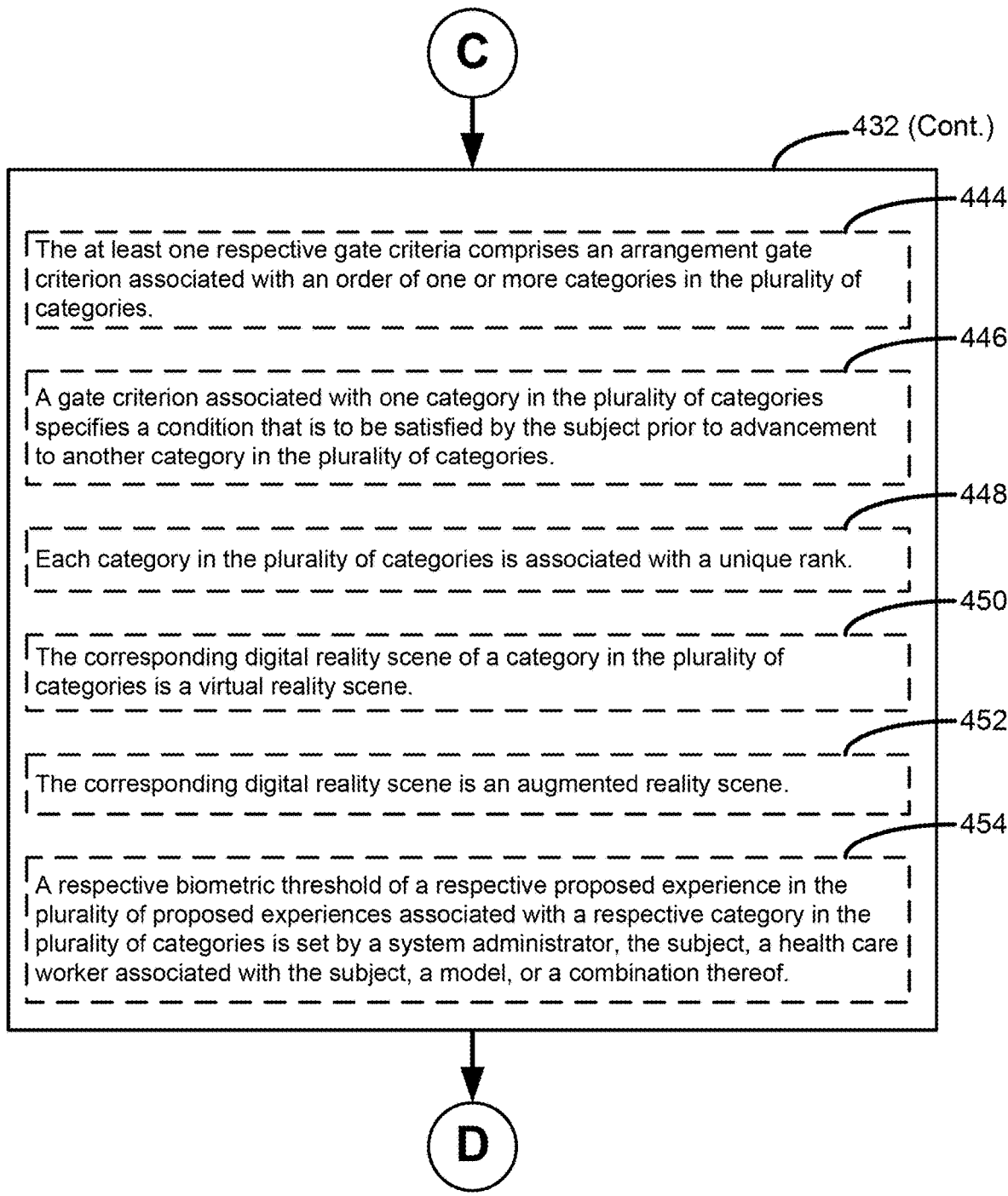
Figure 4E:
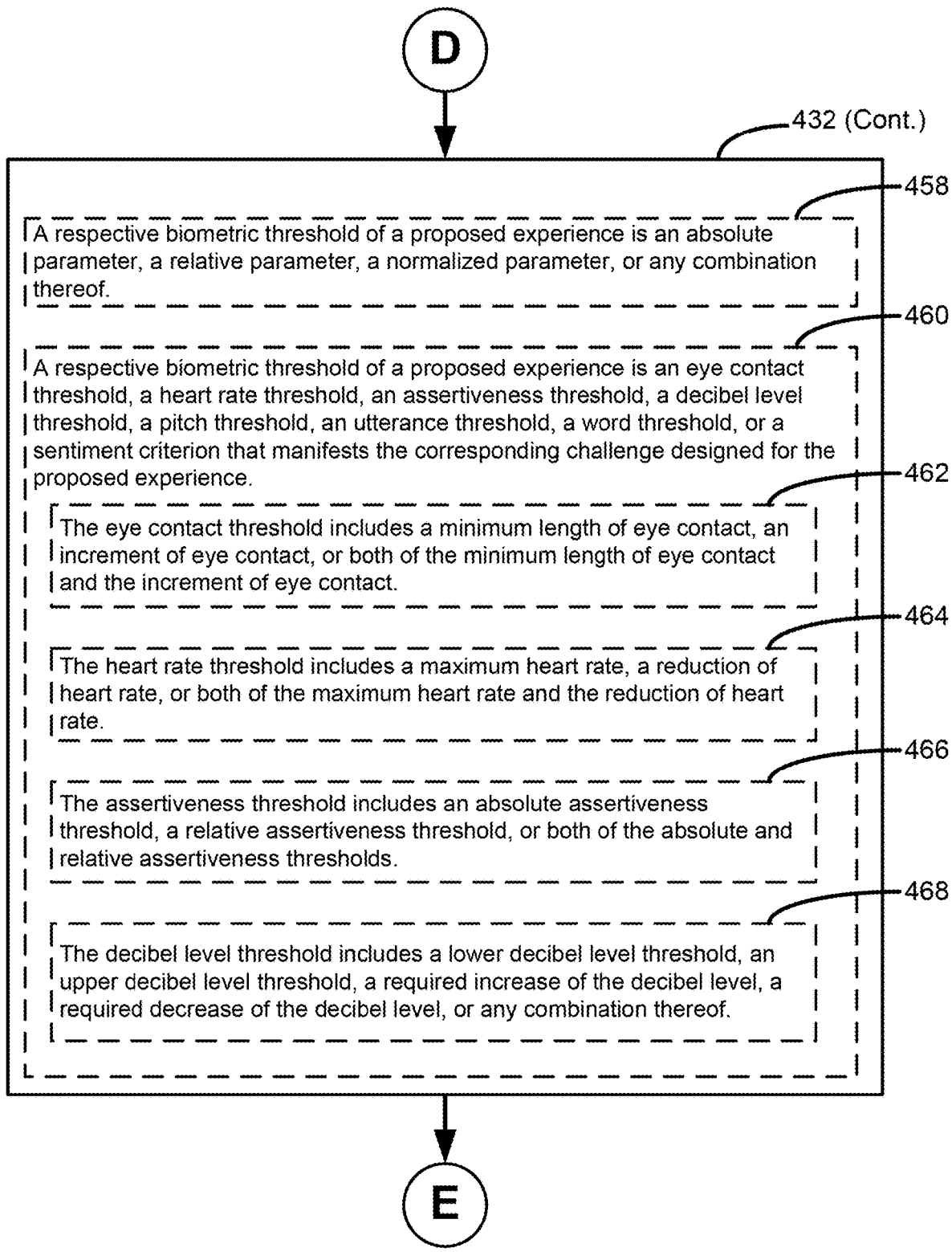
Figure 4F:
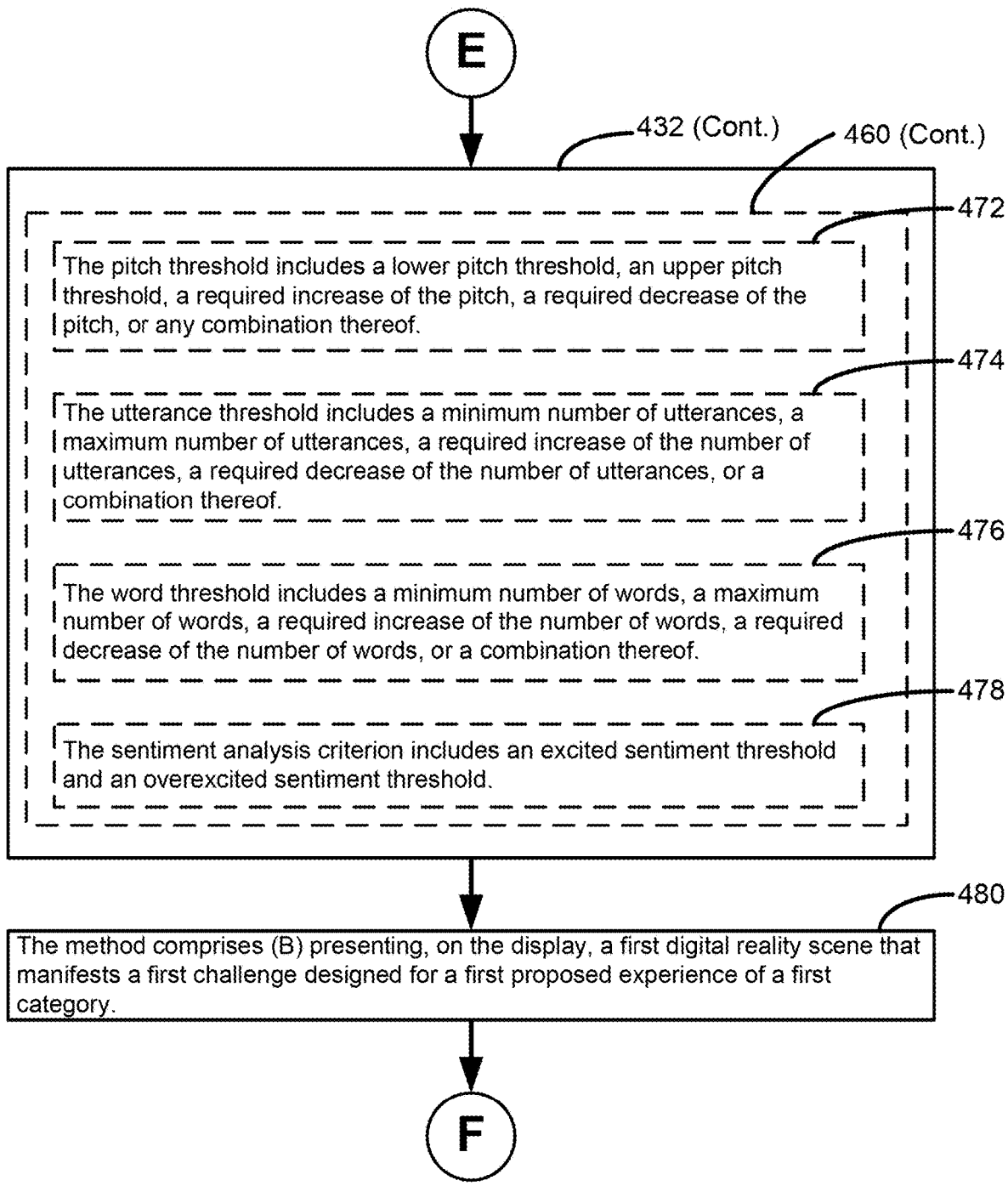
Figure 4G:
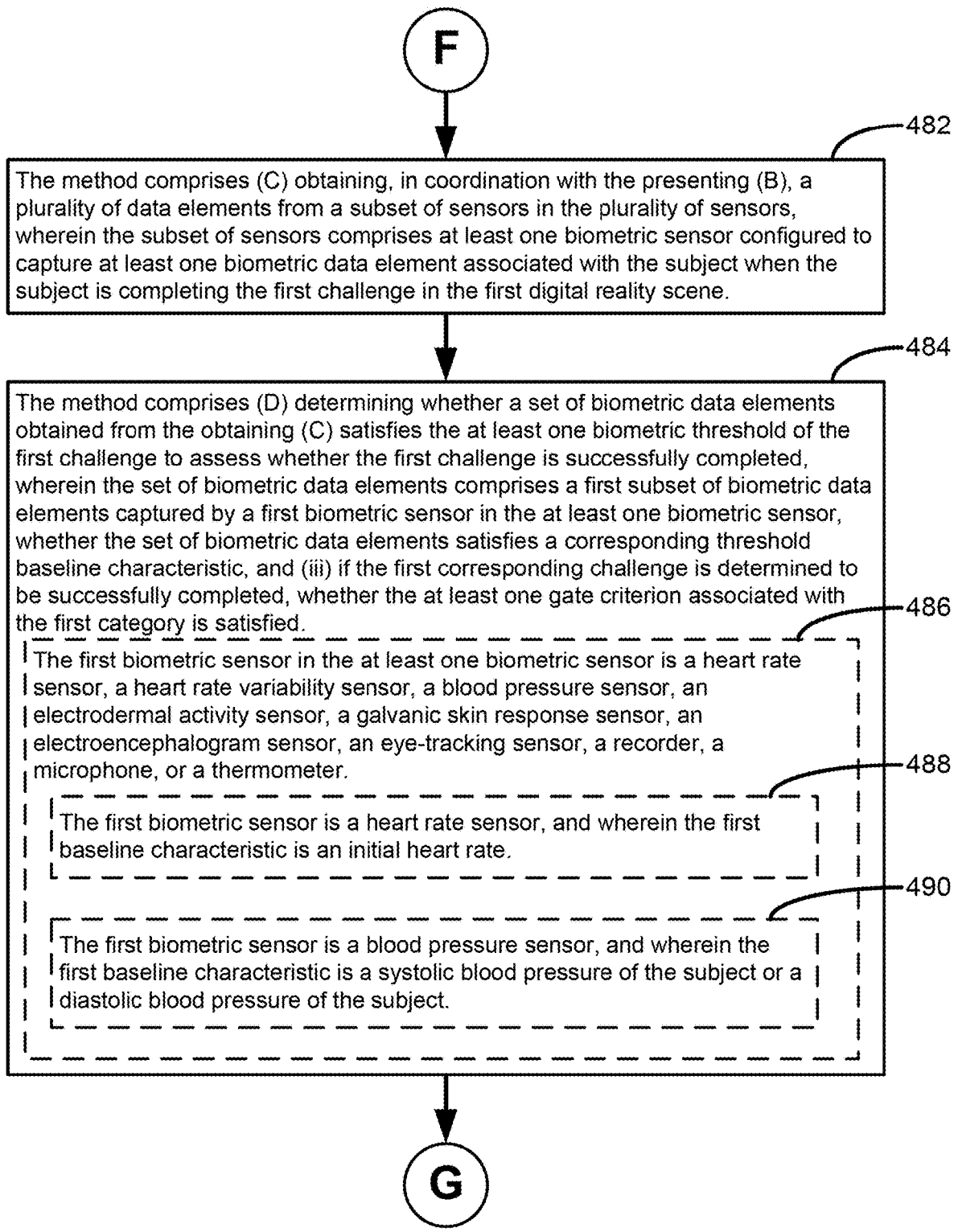
Figure 4H:
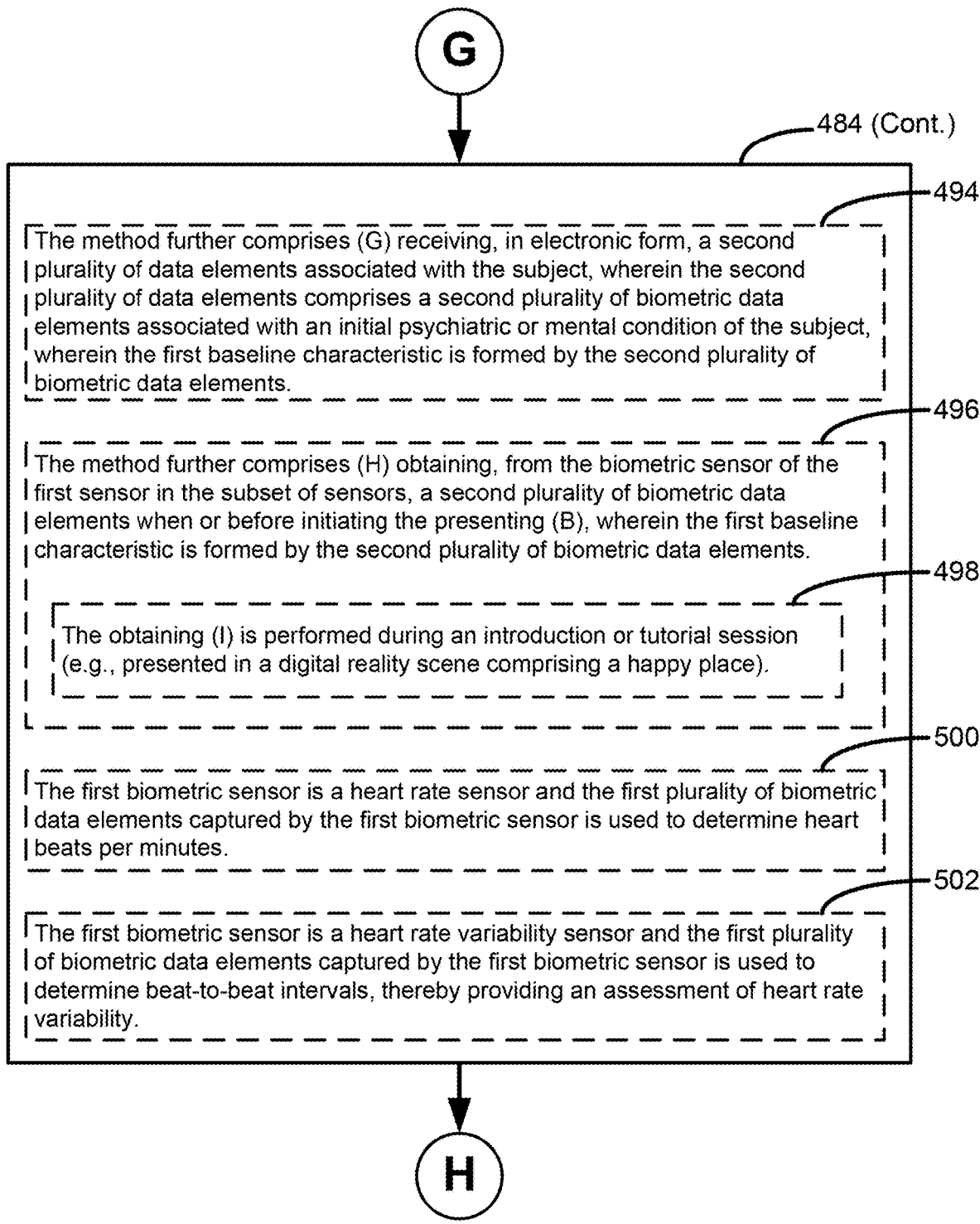
Figure 4I:
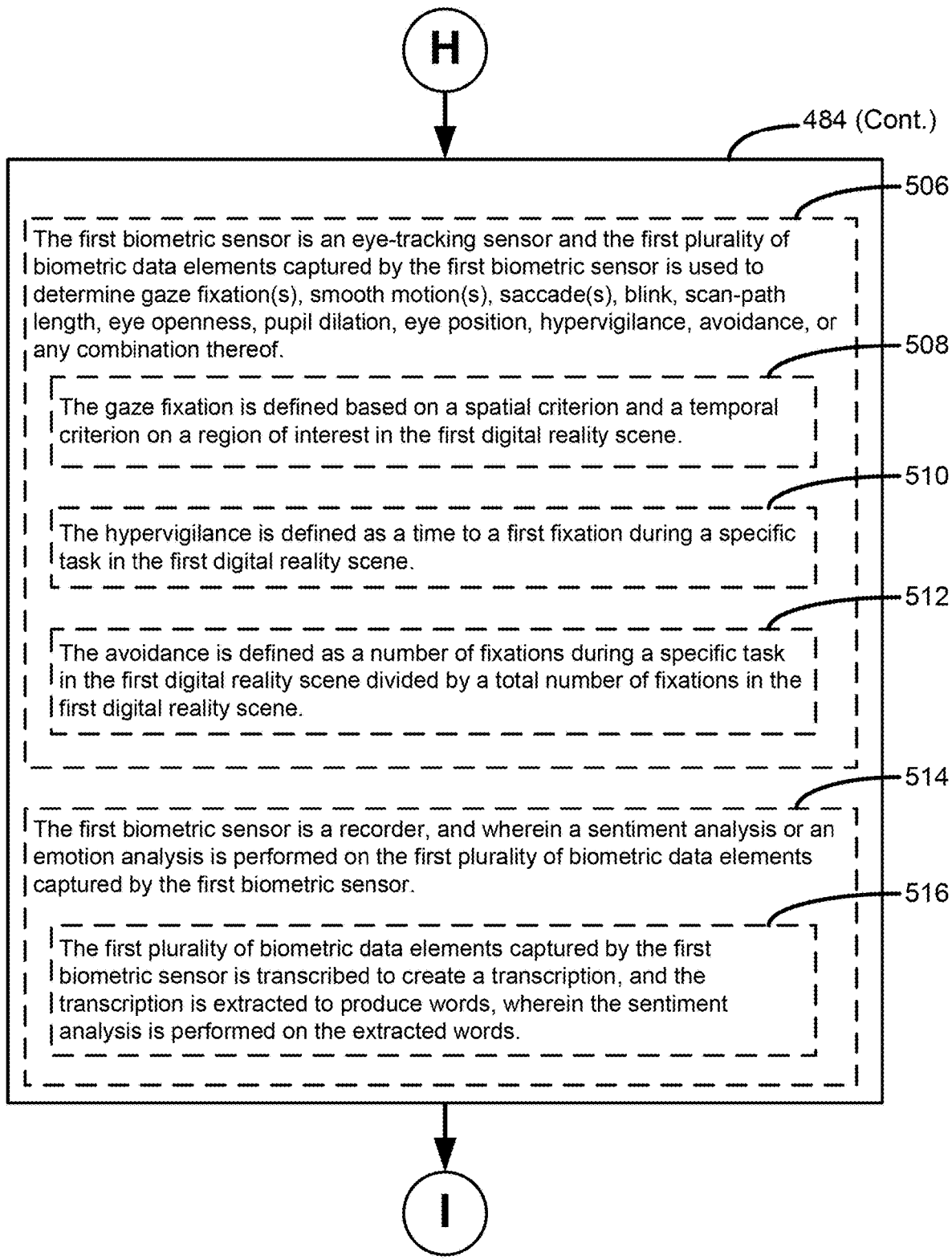
Figure 4J:
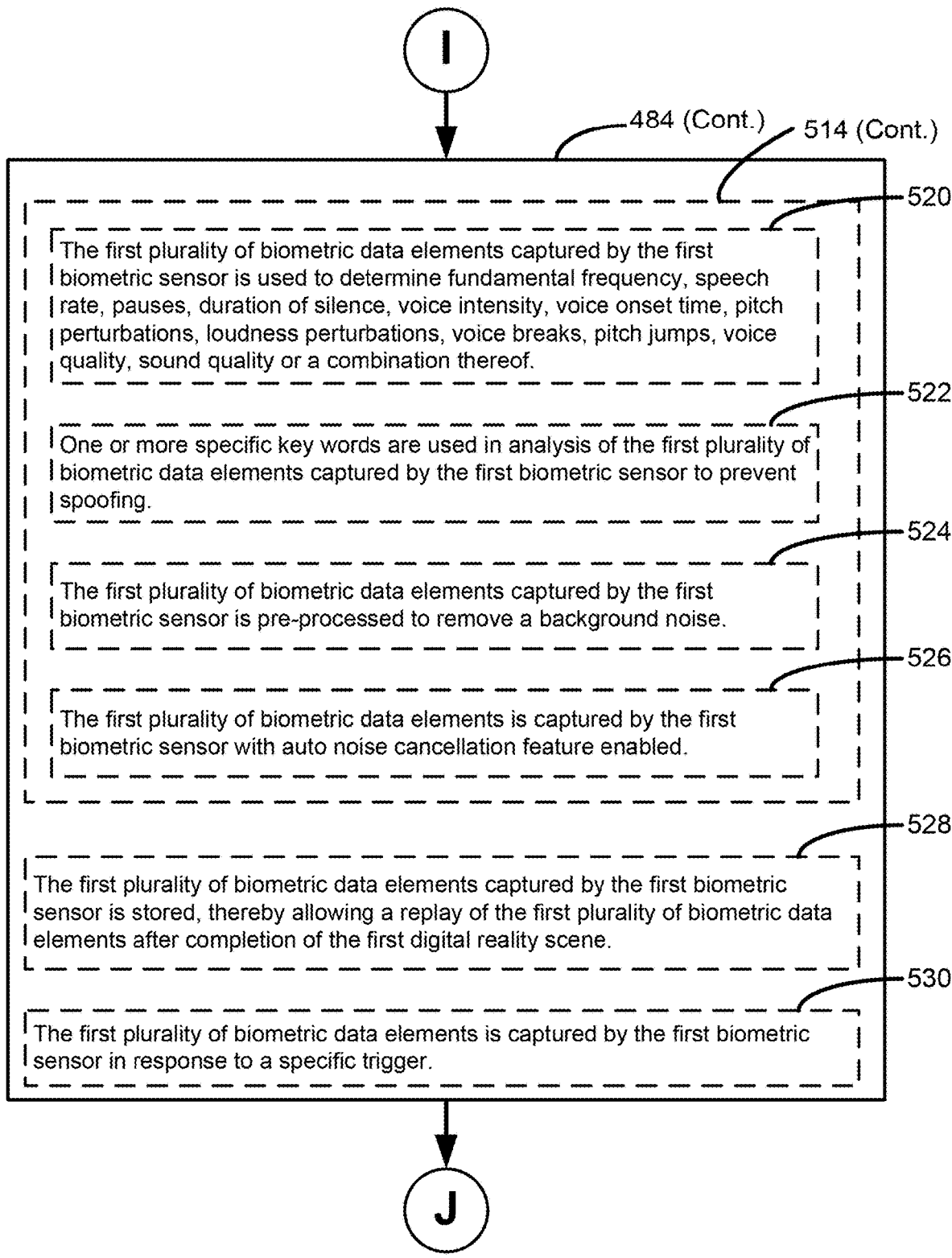
Figure 4K:
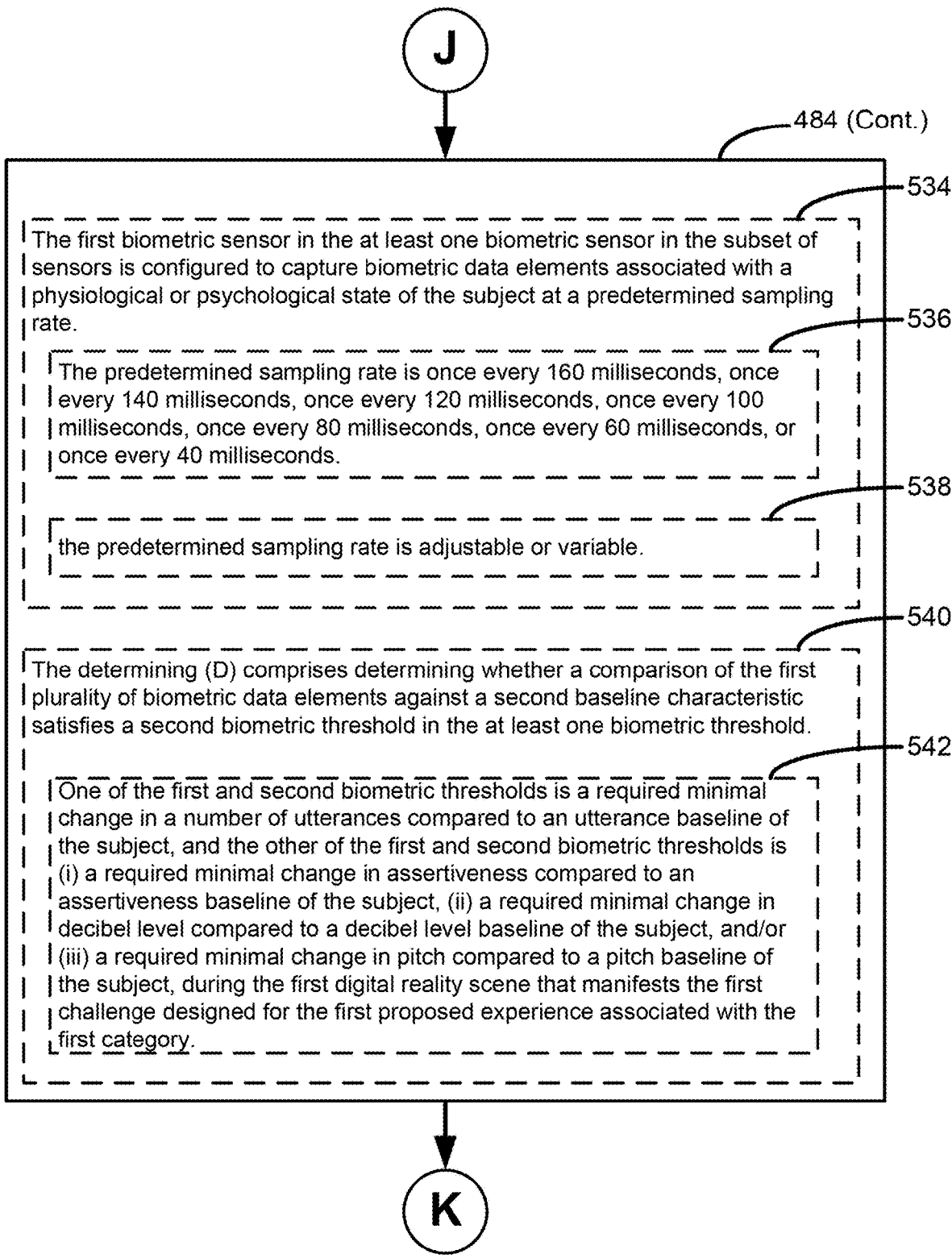
Figure 4L:
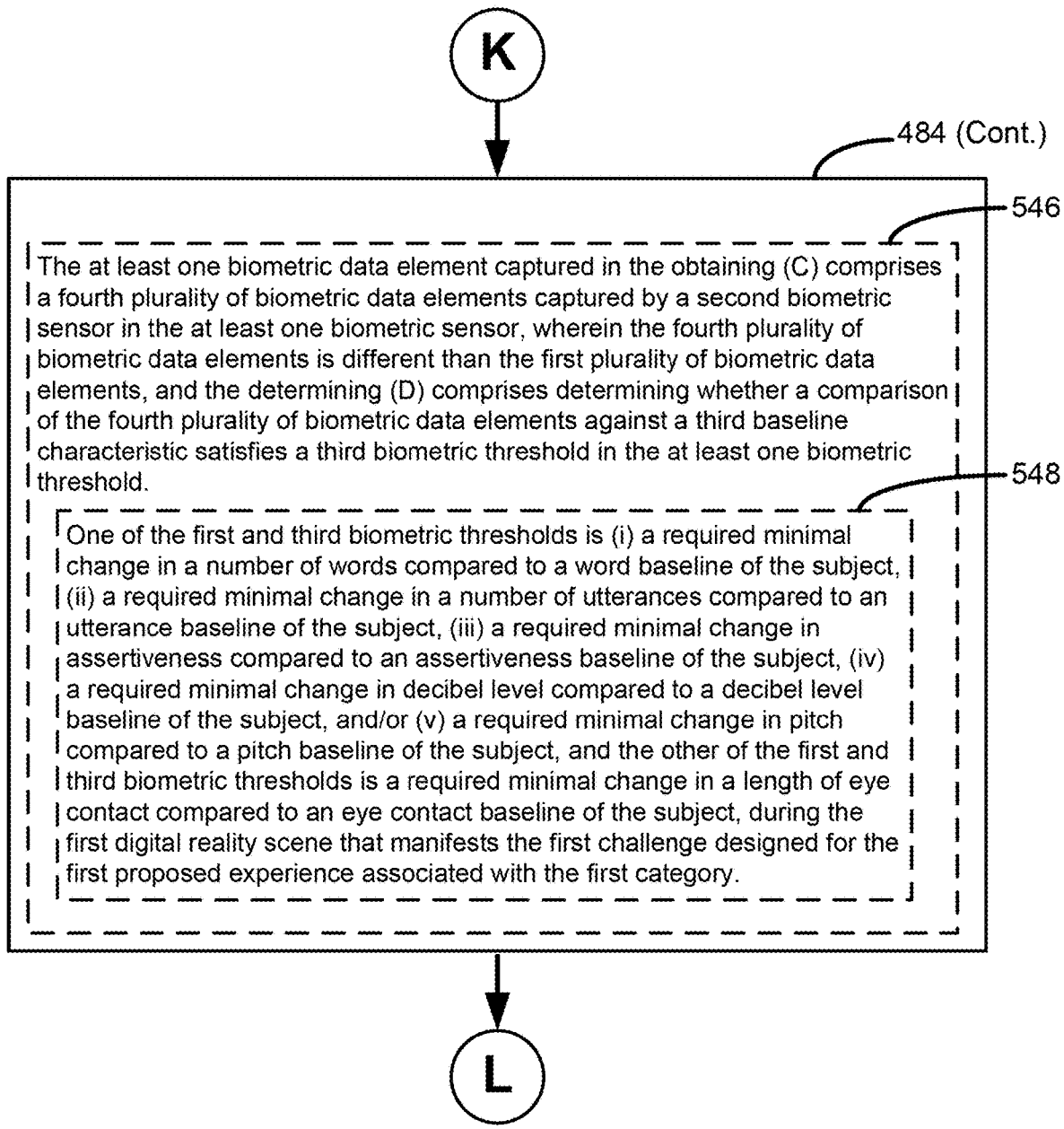
Figure 4M:
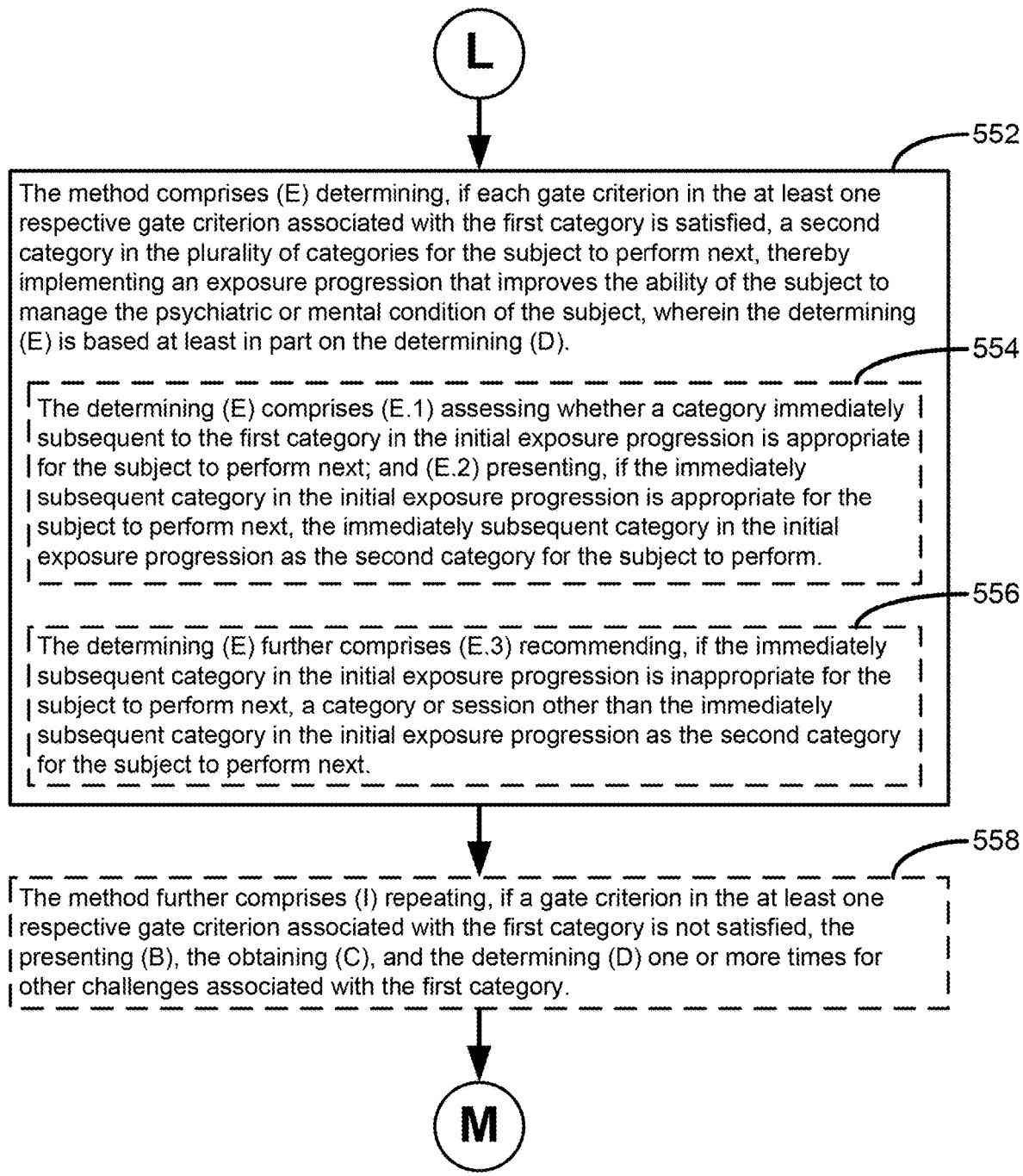
Figure 4N:
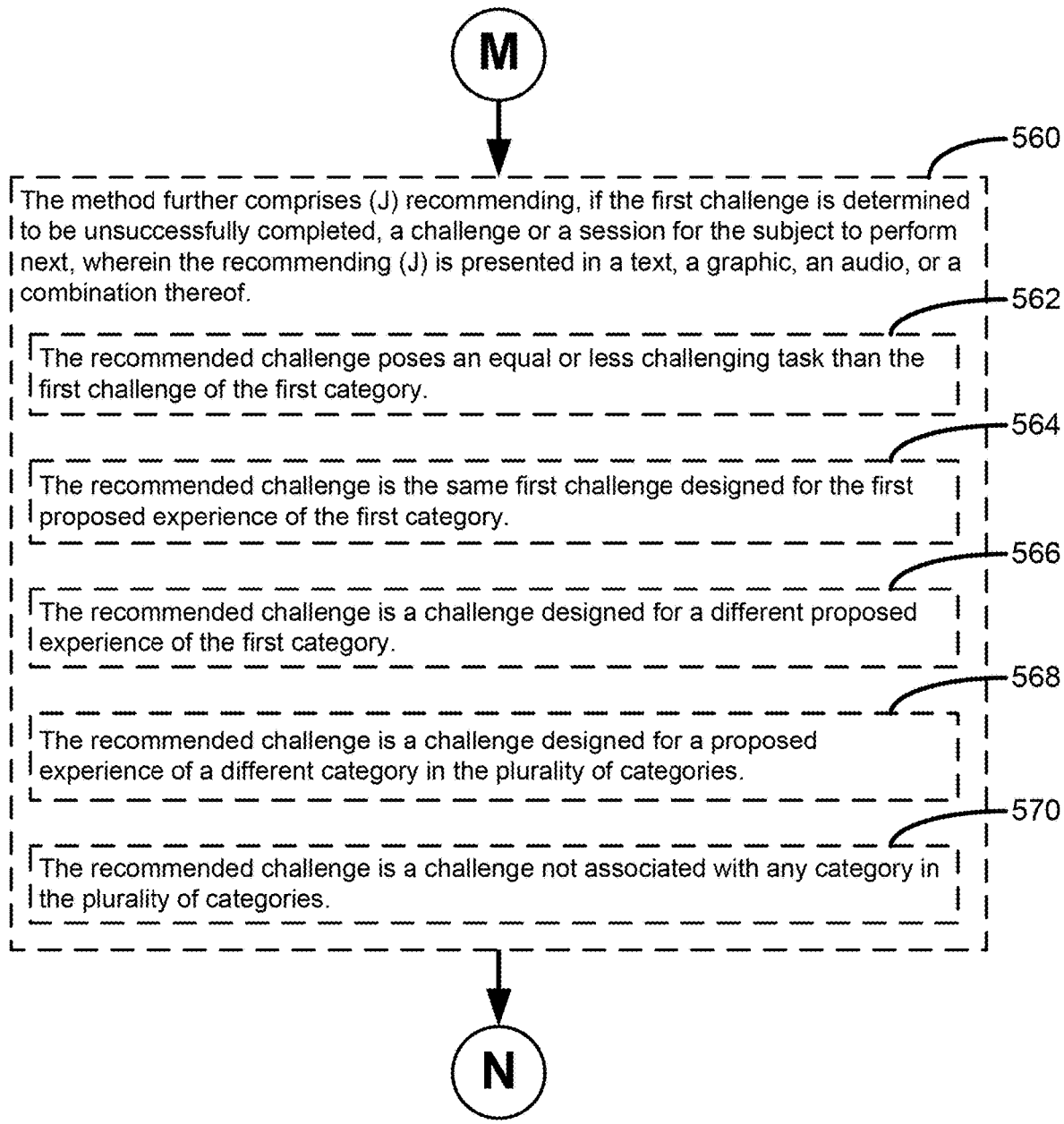
Figure 40:
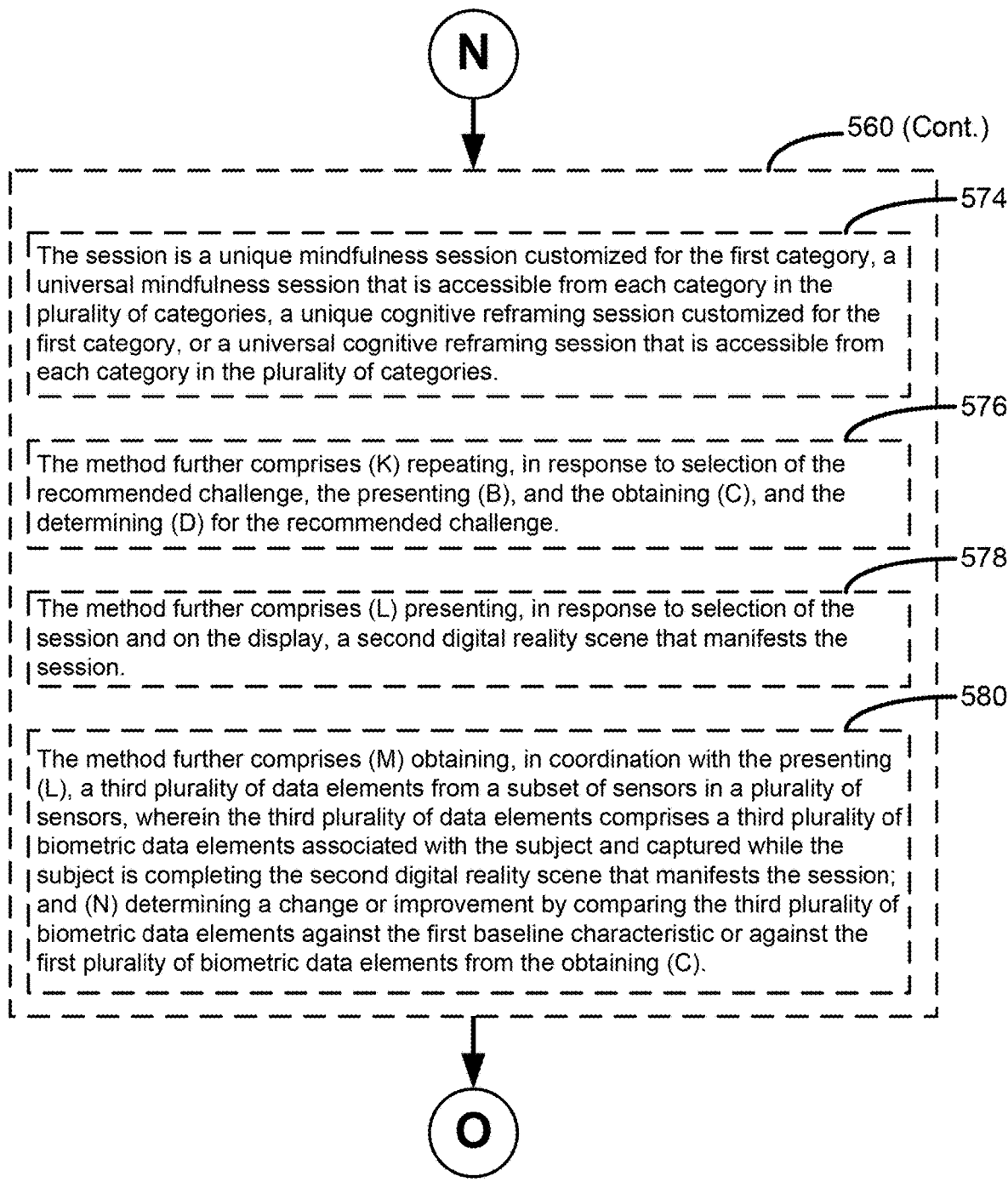
Figure 4P:
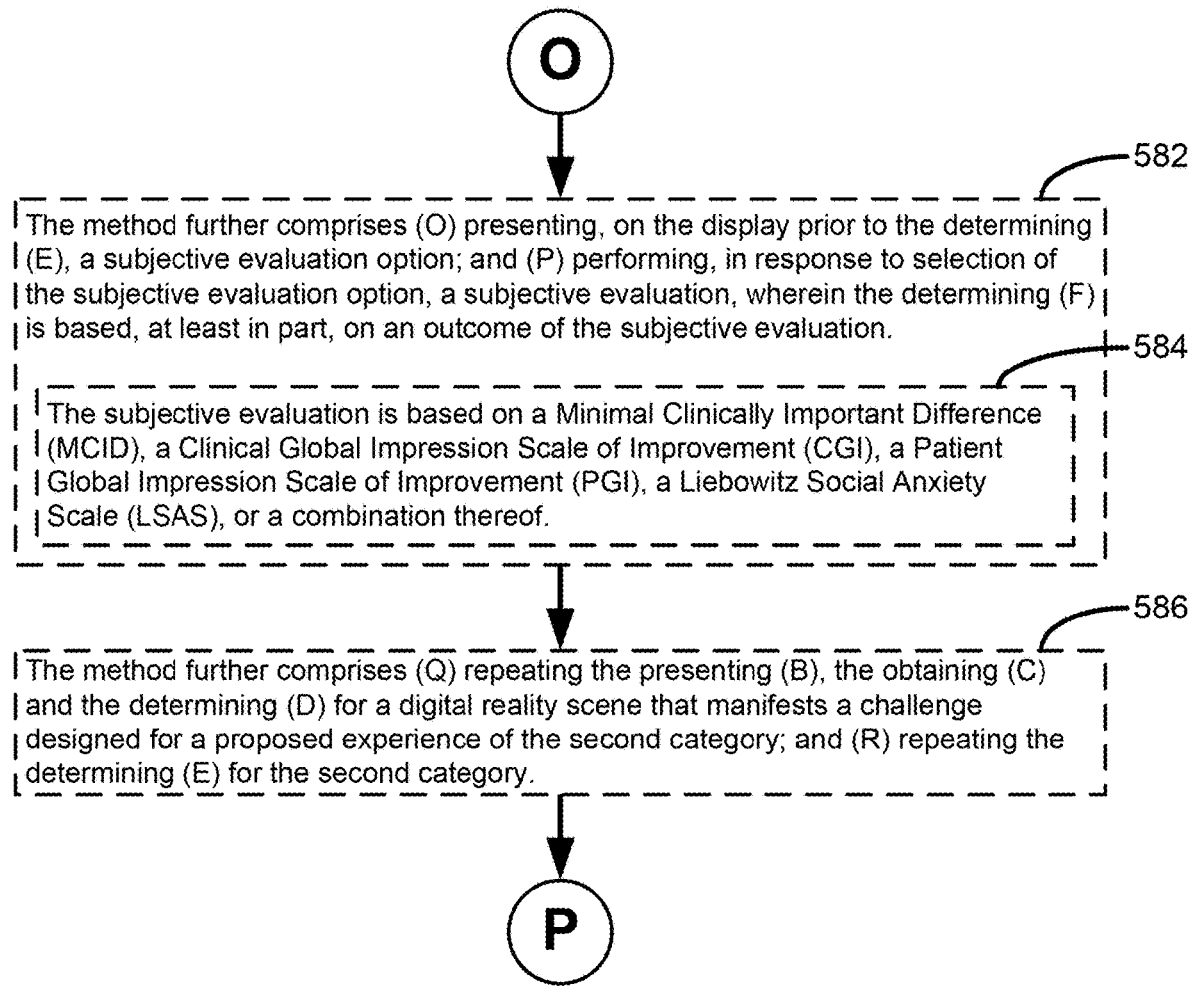

Referring now to FIGS. 4A-4R, there is depicted a flowchart illustrating an exemplary method 400 in accordance with some embodiments of the present disclosure. In the flowchart, the preferred parts of the method are shown in solid line boxes, whereas additional, optional, or alterative parts of the method are shown in dashed line boxes. The method prepares a regimen for improving an ability of a subject to manage a psychiatric or mental condition exhibited by the subject. In particular, the method 400 implements an exposure progression that improves an ability of a subject to manage a psychiatric or mental condition of the subject. In various embodiments, the method 400 combines digital reality (e.g., one or more virtual reality scenes), biometric capture, digital reality interaction from a subject, and/or other elements, to create or modify a personal exposure progression for each subject in a targeted and flexible fashion. Accordingly, in some such embodiments, the present disclosure not only provides an exposure progression tailored to each subject, but also personalizes the timing and/or nature of the exposure progression dynamically as the subject interacts with the exposure progression. For instance, in some embodiments, the present disclosure builds or revises a personal exposure progression dynamically, based at least in part on the level of success that the subject has had in one or more social challenges.

In some embodiments, the method 400 obtains a plurality of categories for the subject, where a respective category in the plurality of categories is associated with a corresponding plurality of proposed experiences, and each respective proposed experience in the corresponding plurality of proposed experiences is associated with a corresponding digital reality scene that manifests a corresponding challenge. The method 400 then presents, on the display, a first digital reality scene that manifests a first challenge designed for a first proposed experience of a first category. While the subject is completing the first challenge in the first digital reality scene, the method 400 obtains at least one biometric data element associated with the subject. In some embodiments, using the obtained biometric data elements, the method 400 determines whether the subject has completed the first challenge successfully. In some embodiments, in accordance with a determination that the subject has completed the first challenge successfully, the method 400 determines whether the subject has completed the first category successfully. In some embodiments, in accordance with a determination that the subject has completed the first category successfully, the method 400 determines a second category in the plurality of categories for the subject to perform next. As such, the method 400 implements an exposure progression for improving the ability of the subject to manage the psychiatric or mental condition of the subject.

In some embodiments, the method 400 includes, or provides, a comparison of the obtained biometric data elements against a baseline of a subject or a baseline of a population of users. By comparing the obtained biometric data elements against a baseline, the method and system of the present disclosure are able to analyze the change of the biometric measure (e.g., heart rate) over time, evaluate the stress or anxiety, if any, the subject is experiencing throughout a challenge, a status of an exposure progression and/or the entire program, or a combination thereof. In some embodiments, the method and system of the present disclosure are able to evaluate one or more assessments and/or provide one or more recommendations per exposure progression per subject. However, the present disclosure is not limited thereto.

Block 402. Referring to block 402, in various embodiments, the method 400 is provided at a computer system (e.g., system 100 of FIG. 1, digital reality system 200 of FIGS. 2A and 2B, client device 300 of FIG. 3, etc.) associated with the subject. The computer system includes one or more processors (e.g., CPU 202 of FIG. 2A, CPU 302 of FIG. 3, etc.), a display (e.g., a display of a client device 300), a plurality of sensors (e.g., sensor 110-1, sensor 110-2 of FIG. 1), and a memory (e.g., member 212 of FIG. 2A, memory 312 of FIG. 3, etc.) coupled to the one or more processors. The memory includes one or more programs configured to be executed by the one or more processors. Accordingly, in some such embodiments, the method 400 requires utilization of the computer system, such as in order to present information to a subject, and, therefore, cannot be mentally performed.

Block 404. Referring to block 404, the display can be any suitable display. For instance, in some embodiments, the display is a wearable display, such as display 308 of FIG. 13. Examples of a wearable display include, but are not limited to, a smart watch, a head mounted display, a smart garment, a near-eye display, and a smart mobile device display (e.g., a smart phone), such as display of FIG. 13. In some embodiments, the display is a head-mounted display (HMD) connected to a host computer system such as the client device 300 of FIG. 3. In some embodiments, the display is a standalone HMD, a mobile device or computing system, or any other hardware platform capable of providing artificial reality content to one or more viewers.

Blocks 406-410. Referring to blocks 406-410, in some embodiments, the plurality of sensors includes at least one biometric sensor (e.g., sensor 110-1 of FIG. 1) configured to collect measurable biometric signals associated with a physiological or psychological state of the subject. A biometric sensor in the at least one biometric sensor can be any suitable biometric sensor. Examples of a suitable biometric sensor include, but are not limited to, a heart rate sensor, a heart rate variability sensor, an electrodermal activity sensor, a galvanic skin response sensor, an electroencephalogram sensor, an eye-tracking sensor, a recorder, a microphone, a thermometer, and a camera. In some embodiments, a biometric sensor in the at least one biometric sensor is incorporated in or is a component of a wearable device such as a watch, wristband, headset, garment, vest, shirt, or other suitable device.

In some embodiments, a biometric sensor in the at least one biometric sensor is incorporated with a client device or is a component of a client device. For instance, in some embodiments, a microphone of a smart phone is used to capture voice date when the smart phone is used as a client device. In some embodiments, a biometric sensor in the at least one biometric sensor is in communication with one or more client devices such that data captured by the one or more sensors can be sent to and/or aggregated in the one or more client devices. For instance, in some embodiments, an eye tracking sensor configured to track eye movement is physically or wirelessly connected to a client device. In some embodiments, a biometric sensor in the at least one biometric sensor is in communication with a system, e.g., connected to the digital reality system 200 via the communication network 106, such that data captured by the one or more sensors can be sent to and/or aggregated on the system. In some embodiments, a biometric sensor in the at least one biometric sensor is in communication with one or more client devices and the digital reality system 200.

In some embodiments, the at least one biometric sensor consists of a single biometric sensor. In some embodiments, the at least one biometric sensor includes two, three, four, five or more than five biometric sensors, either of the same type or different types. For instance, as a non-limiting example, in some embodiments, the at least one biometric sensor includes two first biometric sensors positioned at different locations, e.g., one heart rate sensor positioned at a wrist of a subject and another heart rate sensor positioned at an arm of the subject. As another non-limiting example, in some embodiments, the at least one biometric sensor includes a first biometric sensor, e.g., a heart rate sensor to measure the heart rate of a subject, and a second biometric sensor that is different than the first biometric sensor, e.g., an eye-tracking sensor to track the eye movement of the subject. As a further non-limiting example, in some embodiments, the at least one biometric sensor includes one or more heart rate sensors, one or more heart rate variability sensors, one or more electrodermal activity sensors, one or more galvanic skin response sensors, one or more electroencephalogram sensors, one or more eye-tracking sensors, one or more recorders, one or more microphones, one or more thermometers, one or more cameras, or any combination thereof.

In some embodiments, a biometric sensor features other sensors and capabilities. A non-limiting example is a heart rate sensor that includes an accelerometer to collect additional data. Another non-limiting example is a mobile device that includes one or more cameras and/or microphones that can be used for capturing the facial expression and/or for recording the voice or speech.

The plurality of sensors can include other sensors. For instance, in some embodiments, the plurality of sensors includes, but is not limited to, an accelerometer, a magnetometer, a proximity sensor, a gyroscope, an image capture device (e.g., a camera device or an image capture module and related components), a location module (e.g., a Global Positioning System (GPS) receiver or other navigation or geolocation system module/device and related components), or a combination thereof, and the like.

In some embodiments, the plurality of sensors includes between 2 sensors and 100 sensors, between 2 sensors and 50 sensors, between 2 sensors and 20 sensors, between 2 sensors and 15 sensors, between 2 sensors and 10 sensors, between 2 sensors and 5 sensors, between 3 sensors and 100 sensors, between 3 sensors and 50 sensors, between 3 sensors and 20 sensors, between 3 sensors and 15 sensors, between 3 sensors and 10 sensors, between 3 sensors and 5 sensors, between 6 sensors and 100 sensors, between 6 sensors and 50 sensors, between 6 sensors and 20 sensors, between 6 sensors and 15 sensors, between 6 sensors and 10 sensors, between 12 sensors and 100 sensors, between 12 sensors and 50 sensors, between 12 sensors and 20 sensors, or between 12 sensors and 15 sensors. In some embodiments, the plurality of sensors includes at least 2 sensors, at least 3 sensors, at least 4 sensors, at least 5 sensors, at least 6 sensors, at least 8 sensors, at least 10 sensors, at least 12 sensors, at least 15 sensors, at least 20 sensors, at least 25 sensors, at least 50 sensors, at least 75 sensors, or at least 100 sensors. In some embodiments, the plurality of sensors includes at most 2 sensors, at most 3 sensors, at most 4 sensors, at most 5 sensors, at most 6 sensors, at most 8 sensors, at most 10 sensors, at most 12 sensors, at most 15 sensors, at most 20 sensors, at most 25 sensors, at most 50 sensors, at most 75 sensors, or at most 100 sensors.

In some embodiments, the plurality of sensors include a continuous sensor, which is configured to obtain an uninterrupted or recurring (e.g., periodic) stream of data elements from the subject. In some embodiments, the plurality of sensors include a passive sensor, which is configured to obtain information from an environment associated with the subject. Furthermore, in some embodiments, the plurality of sensors include a non-invasive sensor, which is configured to obtain a data element from the subject without introduction into a body of the subject. Accordingly, in some such embodiments, the method 400 is capable of providing an exposure progression that is unique to the subject based on the information (e.g., data) provided by the plurality of sensors associated with the computer system, which allows for improving the ability of the subject.

Blocks 412-430. Referring to block 412 through block 430, in some embodiments, the psychiatric or mental condition is a clinically diagnosed mental disorder or a subclinically diagnosed mental disorder. Examples of a psychiatric or mental condition include, but are not limited to, those being stressed in a social setting, fearing a social setting, or being overwhelmed in a social setting. For instance, in some embodiments, the clinically diagnosed mental disorder is an anxiety disorder such as a separation anxiety disorder, a selective mutism, a specific phobia, a social anxiety disorder, a panic disorder, an agoraphobia, a generalized anxiety disorder, a substance-induced anxiety disorder, or an anxiety disorder due to a medical condition of the subject. In some embodiments, the clinically diagnosed mental disorder is a mood disorder such as a depression disorder, a bipolar disorder, or a cyclothymic disorder. For instance, in some embodiments, the depression disorder is a major depression disorder. In some embodiments, the clinically diagnosed mental disorder is a psychotic disorder such as a schizophrenia disorder, a delusion disorder, or a hallucination disorder. In some embodiments, the clinically diagnosed mental disorder is an eating disorder such as anorexia nervosa, bulimia nervosa, or binge eating disorder. In some embodiments, the clinically diagnosed mental disorder is an impulse control disorder such as a pyromania disorder, a kleptomania disorder, or a compulsive gambling disorder. In some embodiments, the clinically diagnosed mental disorder includes, but is not limited to, a personality disorder, an obsessive-compulsive disorder, or a post-traumatic stress disorder. In some embodiments, the clinically diagnosed mental disorder is an addiction disorder such as an alcohol use disorder or a substance abuse disorder. In some embodiments, the clinically diagnosed mental disorder is a personality disorder such as an antisocial personality disorder, an obsessive-compulsive personality disorder, or a paranoid personality disorder. However, the present disclosure is not limited thereto.

Block 432. Referring to block 432, in various embodiments, the method includes obtaining a plurality of categories for the subject. In some embodiments, each respective category in the plurality of categories is directed to improving the ability of the subject to manage a psychiatric or mental condition of the subject. Each respective category in the plurality of categories is associated with a corresponding set of proposed experiences, e.g., experience 24-1, experience 24-2, . . . , and/or experience 24-I from the experience store 22 of the digital reality system 200. In some embodiments, each respective category in the plurality of categories is associated with a corresponding plurality of proposed experiences. Each respective category in the plurality of categories is also associated with at least one respective gate criterion in a plurality of gate criteria, e.g., gate criterion 32-1, gate criterion 32-2, . . . , from the criterion store 30 of the digital reality system 200.

For each respective category in the plurality of categories, each respective proposed experience (e.g., experience 24-1) in the corresponding set or plurality of proposed experiences is associated with a corresponding digital reality scene (e.g., digital reality scene 40-1) in a corresponding plurality of digital reality scenes. The corresponding digital reality scene (e.g., digital reality scene 40-1) in the corresponding plurality of digital reality scenes manifests a corresponding challenge (e.g., challenge 26-1), in a corresponding plurality of challenges, designed for the respective proposed experience of the respective category. For each respective category in the plurality of categories, each respective proposed experience (e.g., experience 24-1) in the corresponding set or plurality of proposed experiences is also associated with at least one biometric threshold in a plurality of biometric thresholds, e.g., biometric threshold 33-1, threshold 33-2, . . . , from the criterion store 30 of the digital reality system 200.

It should be noted that the plurality of categories can include any suitable number of categories. For instance, in some embodiments, the plurality of categories includes at least a first category and a second category. In some embodiments, the plurality of categories includes at least a first category, a second category, and a third category. In some embodiments, the plurality of categories includes more than three, more than four, more than five, more than ten, or more than twenty categories. In some embodiments, a category is directed to improving the ability of the subject to manage a psychiatric or mental condition in social interaction and/or interaction anxiety (e.g., going to a party, meeting strangers), public performance anxiety (e.g., giving a report to a small group), observation fear (e.g., writing while being observed), ingestion anxiety (e.g., eating and/or drinking), assertiveness anxiety (e.g., resisting a sale), or any combination thereof. However, the present disclosure is not limited thereto. In some embodiments, each respective category in the plurality of categories is directed to improving a unique ability of the subject to manage a psychiatric or mental condition of the subject. For instance, in some embodiments, a first category (e.g., an exposure category) is associated with improving an ability of the subject to confront a conflict associated with the subject, such as a fear inducing conflict. In some embodiments, a second category (e.g., a CBT category) is associated with improving an ability of the subject to reframe a thought associated with the subject. In some embodiments, a third category (e.g., a CBT category) is associated with improving an ability of the subject to use the thought associated with the subject. In some embodiments, a fourth category (e.g., a CBT category) is associated with improving an ability of the subject to defuse the thought associated with the subject.

In some embodiments, the plurality of obtained categories is a predetermined set of categories or a subset of the predetermined set of categories. In some embodiments, the plurality of obtained categories is selected by the subject, a medical practitioner associated with the subject, a model, or a combination thereof. For instance, in some embodiments, the plurality of obtained categories is first selected by the subject and then first selection is refined by the medical practitioner and/or the model to provide a second selection of categories. In some embodiments, the plurality of obtained categories is tailored based on the psychiatric or mental condition exhibited by the subject. For instance, consider a first user of a first client device 300-1 that exhibits a social anxiety disorder and a second user of a second client device 300-2 that exhibits an addiction disorder. The method 400 can obtain different pluralities of categories for the first and second users, each plurality of categories being unique to one user based on the psychiatric or mental condition exhibited by the user.

The corresponding set of proposed experiences can include any suitable number of proposed experiences, such as one, two, three, four, five, more than five, more than ten, more than twenty, more than fifty, more than a hundred proposed experiences. In some exemplary embodiments, each respective category in the plurality of categories is associated with a corresponding plurality of proposed experiences, e.g., associated with two, three, four, five, more than five, more than ten, more than twenty, more than fifty, more than a hundred proposed experiences. In some embodiments, each respective category in the plurality of categories is associated with between 2 categories and 100 categories, between 2 categories and 50 categories, between 2 categories and 25 categories, between 2 categories and 10 categories, between 2 categories and 5 categories, between 3 categories and 100 categories, between 3 categories and 50 categories, between 3 categories and 25 categories, between 3 categories and 10 categories, between 3 categories and 5 categories, between 7 categories and 100 categories, between 7 categories and 50 categories, between 7 categories and 25 categories, between 7 categories and 10 categories, between 30 categories and 100 categories, or between 30 categories and 50 categories.

In some embodiments, different categories in the plurality of categories are associated with the same number of proposed experiences or different numbers of proposed experiences. For instance, in some embodiments, a first category and a second category are associated with the same number (e.g., six) of proposed experiences whereas a third category is associated with a different number (e.g., eight) of proposed experiences than the first and second categories. In some embodiments, different categories in the plurality of categories are associated with completely different sets of proposed experiences or partially overlapped sets of proposed experience. In other words, in some embodiments, proposed experiences associated with one category are completely distinctive from proposed experiences associated with another category (e.g., no proposed experience is associated with two different categories) or overlap with proposed experiences associated with another category (e.g., at least one proposed experience is shared by two or more different categories). For instance, as a non-limiting example, in some embodiments, a first category is associated with a first set of proposed experiences consisting of experience 24-1, experience 24-2, experience 24-3 and experience 24-4 whereas a second category is associated with a second set of proposed experiences consisting of experience 24-5, experience 24-6, and experience 24-7 from the experience store 22 of the digital reality system 200. In such embodiments, no experience associated with the first category is the same as those associated with the second category. As another non-limiting example, in some alternative embodiments, a first category is associated with a first set of proposed experiences consisting of experience 24-1, experience 24-2, experience 24-3 and experience 24-4 whereas a second category is associated with a second set of proposed experiences consisting of experience 24-4, experience 24-5, and experience 24-6 from the experience store 22 of the digital reality system 200. In such embodiments, experience 24-4 is associated with both the first and second categories.

In some embodiments, a category is associated with first experience 24-1 and second experience 24-2 of FIG. 2B. First experience 24-1 is associated with a corresponding digital reality scene, e.g., first digital reality scene 40-1, that manifests a corresponding challenge, e.g., first challenge 26-1. Similarly, second experience 24-2 is associated with a corresponding digital reality scene, e.g., second digital reality scene 40-2, that manifests a corresponding challenge, e.g., second challenge 26-2.

In some embodiments, an experience is associated with a digital reality scene that manifests a challenge. For instance, in some embodiments, an experience is an exposure experience, such as in social interaction or interaction anxiety (e.g., meeting strangers). In some embodiments, an experience is an exposure experience associated with a digital reality scene that manifests a challenge in verbal/non-verbal performance, such as a performance by the subject in front of others or public speaking (e.g., giving a report to a small group). In some embodiments, an experience is an exposure experience associated with a digital reality scene that manifests a challenge in observation fear (e.g., writing while being observed). In some embodiments, an experience is an exposure experience associated with a digital reality scene that manifests a challenge in ingestion anxiety (eating and/or drinking). By way of example, FIGS. 5A and 5B illustrate exemplary digital reality scene for social challenge training.

In some embodiments, an experience is a CBT experience associated with a digital reality scene that manifests a challenge in gathering evidence associated with a thought of the subject. In some embodiments, an experience is a CBT experience associated with a digital reality scene that manifests a challenge in reframing a thought of the subject. In some embodiments, an experience is a CBT experience associated with a digital reality scene that manifests a challenge in defusing a thought of the subject. In some embodiments, an experience is mindfulness associated with a digital reality scene that manifests a challenge in being actively present (e.g., the ability of the subject to be fully present, aware of where the subject is and what the subject is doing, or the like).

In some embodiments, a category in the plurality of categories is associated with one or more experiences 24 directed to meeting strangers, for instance, at a wedding reception, at a work event, in a dating App, when starting school, or the like. In some embodiments, a category in the plurality of categories is associated with one or more experiences 24 directed to interacting with people, for instance, participating in a small group at work, participating in a small group, making small talk with a neighbor, asking questions to a coworker, receiving feedback from a manager, or the like. In some embodiments, a category in the plurality of categories is associated with one or more experiences 24 directed to performing in front of people, for instance, giving a presentation at work, giving a toast at a party, having a job interview, talking in front of a class, or the like.

In some embodiments, a category in the plurality of categories is associated with one or more experiences 24 directed to one or more exposure techniques, such as an exposure therapy technique. In some embodiments, through interaction with an exposure experience of the exposure category, a subject gradually confronts one or more anxiety triggers associated with the subject. In some embodiments, such as during a period of time, through the exposure to social experiences, the subject's anxiety lowers (e.g., as determined based one or more data sets obtained by a sensor and evaluated by a medical practitioner and/or a model of the present disclosure), builds self-confidence, and is able to expand their range of activities in the form of improving the ability of the subject.

For instance, in some embodiments, an exposure category includes one or more social interaction experiences 24 directed to performance in front of others. In some embodiments, the exposure category in the plurality of categories includes or is associated with one or more experiences 24 directed to interaction anxiety (e.g., specific challenges 26 for meeting strangers), public speaking (e.g., specific challenges 26 for giving a report to a small group), observation fear (e.g., specific challenges 26 for writing while being observed), ingestion anxiety (e.g., specific challenges 26 for eating and/or drinking), or any combination thereof. As a non-limiting example, consider an interaction anxiety of meeting strangers. A nonlimiting example of an exposure category configured for the interaction anxiety of meeting strangers includes a first proposed experience 24-1 of a corresponding first challenge 26-1 of looking at a unknown bartender in the eyes when grabbing a drink off the bar, a second proposed experience 24-2 of a corresponding second challenge 26-2 of introducing yourself to a player character in a digital reality scene 40 (e.g., another avatar) and say something about yourself, and a third proposed experience 24-3 of a corresponding third challenge 26-3 of attending an augmented digital reality scene 40 or a mixed digital reality scene 40. In other embodiments, an exposure category in the plurality of categories includes one or more experiences 24 directed to interaction anxiety (e.g., meeting strangers), nonverbal performance anxiety (e.g., taking a test), ingestion anxiety, public performance anxiety, assertiveness anxiety (e.g., resisting a high pressure salesperson), or any combination thereof. In some embodiments, an exposure category in the plurality of categories includes one or more experiences 24 directed to interacting with strangers (e.g., talking to face to face with someone you do not know very well, such as another non-player character or NPC in a digital reality scene), general performance (e.g., speaking up in a meeting, giving a prepared oral talk to a group, etc.), assertiveness (e.g., expressing disagreement or disapproval to someone you do not know very well), or any combination thereof.

More specifically, in some embodiments, the corresponding challenge 26 of a proposed exposure experience 24 includes: a first challenge 26-1 of using a telephone in public; a second challenge 26-2 of participating in small group activity; a third challenge 26-3 of eating in public; a fourth challenge 26-4 of drinking with others; a fifth challenge 26-6 of talking to someone in authority; a sixth challenge 26-6 of acting, performing, or speaking in front of an audience; a seventh challenge 26-7 of going to a party; an eight challenge 26-8 of working while being observed; a ninth challenge 26-9 of writing while being observed; a tenth challenge 26-10 of calling someone you do not know very well; an eleventh challenge 26-11 of talking face to face with someone you do not know very well; a twelfth challenge 26-12 of meeting strangers urinating in a public bathroom; a thirteenth challenge 26-13 of entering a room when others are already seating; a fourteenth challenge 26-14 of being the center of attention; a sixteenth challenge 26-16 of speaking up at a meeting; a seventeenth challenge 16-17 of taking a test of your ability, skill, or knowledge; an eighteenth challenge 26-18 of expressing disagreement or disapproval to someone you do not know very well; a ninetieth challenge 26-19 of looking someone who you do not know every well straight in the eyes (e.g., maintain eye contact); a twentieth challenge 26-20 of giving a prepared oral talk to a group; a twenty-first challenge 26-21 of trying to make someone's acquaintance for the purpose of a romantic and/or sexual relationship; a twenty-second challenge 26-22 of returning goods to a store for a refund; a twenty-third challenge 26-23 of giving a party; a twenty-fourth challenge 26-24 of resisting a high pressure sales person; or any sub-combination (e.g., any 2, 3, 4, 5, 6, 7, 8, 9, 10, 11, 12, 13, 14, 15, 16, 17, 18, 19, 20, 21, or 22 of the forgoing challenges) thereof.

Additional details and information regarding exposure therapy are found in U.S. Provisional Patent Application No. 63/223,871 filed Jul. 20, 2021, U.S. Provisional Patent Application No. 63/284,862 filed Dec. 1, 2021, U.S. patent application Ser. No. 17/869,670 filed Jul. 20, 2022, U.S. Provisional Patent Application No. 63/415,860 filed Oct. 13, 2022, and U.S. Provisional Patent Application No. 63/415,876 filed Oct. 13, 2022, each of which is hereby incorporated by reference in its entirety for all purposes.

In some embodiments, a category in the plurality of categories is associated with one or more experiences 24 directed to one or more CBT techniques, such as one or more cognitive reframing CBT techniques, one or more gathering evidence CBT techniques, one or more usefulness CBT techniques, or any combination thereof. In some embodiments, the one or more experiences for the CBT category include a challenge of identifying a thought or statement or statement obtained from the subject. In some embodiments, the one or more experiences for the CBT category include a challenge of disrupting a first (e.g., a native, an initial, etc.) cognitive pattern associated with a formation of the negative thought or statement by the subject with a second (e.g., new) cognitive pattern associated with a formation of a second thought or statement different than the first thought, such as a second positive or affirmative thought. In some embodiments, a CBT category in the plurality of categories includes one or more experiences directed implementation of cognitive restructuring challenge within a digital reality scene. As a non-limiting example, in some embodiments, the one or more experiences, of the CBT category causes behavioral activation for the subject when deemed complete by the subject, which is conducted via long-term and short-term goal settings within a client application, such as within a digital reality scene presented through the client application. In some embodiments, acceptance, and commitment therapy (ACT) and/or behavioral activation (BA) are forms of CBT techniques utilized within an experience in the one or more experiences provide challenges that are particularly effective for anxiety disorders and depression used by the systems, methods, and devices of the present disclosure. However, the present disclosure is not limited thereto.

In some embodiments, the one or more gather evidence experiences of the CBT category include implementation of cognitive restructuring challenges within a digital reality scene including a challenge: of having a subject self-identify harmful or negative evidence for a thought spoken by the subject; having the subject, a medical practitioner, a model, or any combination thereof evaluating if the self-identified evidence is sufficient to reframe the thought; having the subject reframing the thought in order to improve the psychiatric or mental condition of the subject, such as by modulating harm expectancy and/or a perception of control for the subject, or any combination thereof. In some embodiments, the one or more usefulness experiences for the CBT category include implementation of cognitive restructuring challenge within a digital reality scene by having the subject, a medical practitioner, a model, or any combination thereof identify a core belief associated with a thought and relating the core belief to one or more short and/or long term goals associated with the subject. In some embodiments, the one or more usefulness experiences for the CBT category include implementation of cognitive restructuring challenge within a digital reality scene by having the subject, a medical practitioner, a model, or any combination thereof identify a core belief associated with an anxious thought, such as a statement captured from the subject by a recorder sensor of the client device. In some embodiments, the usefulness CBT experience include implementation of cognitive restructuring challenge within a digital reality scene by having the subject, a medical practitioner, a model, or any combination thereof determine how useful or harmful the core belief is toward helping subject achieve one or more short term and/or long term goals. In some embodiments, the one or more defusion experiences for the CBT category include implementation of cognitive restructuring challenge within a digital reality scene by having the subject repeat a thought associated with the subject while speaking in the third-person within a digital reality scene. In some embodiments, the one or more defusion experiences include implementation of cognitive restructuring challenge within a digital reality scene by having the subject, a medical practitioner, a model, or any combination thereof determining, based one or more data sets obtained from a sensor in the plurality of sensors (e.g., based on a heart rate of the subject, based on a vocal feature of the subject, such as a cadence of the subject, etc.), if anxiety-inducing thoughts or statement have a reduced or inhibited effect (e.g., lose their intensity) for the subject.

Additional details and information regarding types of categories and/or proposed experiences is disclosed in Heimberg et al., 1999, Psychometric Properties of the Leibowitz Social Anxiety Scale," Psychological Medicine, 29(1), pg. 199; Safren et al., 1999, "Factor Structure of Social Fears: The Liebowitz Social Anxiety Scale," Journal of Anxiety Disorders, 13(3), pg. 253; Baker et al., 2002, "The Liebowitz Social Anxiety Scale as a Self-Report Instrument: A preliminary Psychometric Analysis," Behavior Research and Therapy, 40(6), pg. 701; Loenen I et al., "The Effectiveness of Virtual Reality Exposure-Based Cognitive Behavioral Therapy for Severe Anxiety Disorders, Obsessive-Compulsive Disorder, and Posttraumatic Stress Disorder: Meta-analysis," J Med Internet Res. 2022 Feb. 10; 24(2); Wu et al., "Virtual Reality-Assisted Cognitive Behavioral Therapy for Anxiety Disorders: A Systematic Review and Meta-Analysis," Front Psychiatry. 2021 Jul. 23; 12:575094; Garland et al., "Biobehavioral Mechanisms of Mindfulness as a Treatment for Chronic Stress: An RDoC Perspective," Chronic Stress (Thousand Oaks). 2017 February, 1:2470547017711912; Hofmann et al., 2017, "Mindfulness-Based Interventions for Anxiety and Depression," Psychiatr. Clin. North Am., 40(4), pg. 739-749; Creswell et al., "Mindfulness Training and Physical Health: Mechanisms and Outcomes," Psychosom Med. 2019 April, 81(3): 224-232; Seabrook et al., "Understanding How Virtual Reality Can Support Mindfulness Practice: Mixed Methods Study." J Med Internet Res. 2020 Mar. 18, 22(3); Navarro-Haro et al., "Meditation experts try Virtual Reality Mindfulness: A pilot study evaluation of the feasibility and acceptability of Virtual Reality to facilitate mindfulness practice in people attending a Mindfulness conference," PLoS One. 2017 Nov. 22, 12(11); Chandrasiri et al., "A virtual reality approach to mindfulness skills training," Virtual Reality 24, 143-149 (2020); Bluett et al., 2014, "Acceptance and commitment therapy for anxiety and OCD spectrum disorders: an empirical review," J Anxiety Disord., 28(6), pg. 612-24; Zawn et al., 2021, "What is behavioral activation?," Medical News Today, Oct. 24, 2021; celik et al., "Acrophobia treatment with virtual reality-assisted acceptance and commitment therapy: two case reports," 2020; Paul et al., "Virtual Reality Behavioral Activation as an Intervention for Major Depressive Disorder: Case Report," JMIR mental health, 7(11), 2020, each of which is hereby incorporated by reference in its entirety for all purposes. By using these aforementioned different limited types of proposed experiences (e.g., interactive, performance, and/or assertiveness), the subject can follow and track progress of the regimen 20 more easily. Moreover, in some embodiments, the different types of proposed experiences are configured for a respective psychiatric or mental condition. For instance, in some embodiments, an addiction disorder condition requires use of a first experience whereas a social anxiety disorder requires use of a second experience different from the first experience. However, the present disclosure is not limited thereto.

Blocks 434-436. Referring to blocks 434-436, in some embodiments, the at least one gate criteria is set by a system administrator (e.g., administrator of a digital reality system 200), a model or algorithm, a user (e.g., the subject), a medical practitioner associated with the subject, or any combination thereof. For instance, in some embodiments, a gate criterion is set by a system administrator, who configures a gate criterion to be conditioned on receipt of payment from a subject (e.g., for access to the digital reality system 200, for access to a specific digital reality scene 40, and the like). However, the present disclosure is not limited thereto, and one of skill in the art of the present disclosure will appreciate that other respective gate criteria set by a system administrator are within the scope of the present disclosure. In some embodiments, the gate criteria set by the system is a geographic gate criteria, which places a geographic restriction on utilizing the systems, methods, and devices of the present disclosure within one or more geographic regions, such as by limiting the subject and/or a medical practitioner from using the system when outside of a first geographic region. However, the present disclosure is not limited thereto.

In some embodiments, a gate criterion is set by the subject (e.g., a user of a first client device 300-1). For instance, in some embodiments, the gate criterion is a number challenges completed, such as a number of short term goals accomplished by the subject, a number of reframed thoughts by the subject, a number of exposure challenges completed by the subject, a period of time interacting with a digital reality scene, or a combination thereof.

In some embodiments, the gate criterion is set by a health care worker, such as a medical practitioner, associated with the subject (e.g., a user of a second client device 300-2, via client application 320). In some embodiments, a gate criterion of a first category is set by the system administrator or the health care worker associated with the subject whereas a gate criterion of a second category is set by the subject.

In some embodiments, the at least one gate criteria is further modified by the medical practitioner associated with the subject or the model based on a classification, a clustering, or other parameters associated with the user that indicate changing a respective gate criterion in the at least one gate criteria would improve the likelihood of engagement and/or a better clinical outcome. For instance, in some embodiments, the medical practitioner associated with the subject or the model based on a classification changes a first gate criterion associated with a reframed thought threshold that must be satisfied by the subject, a second gate criterion associated with an exposure challenge threshold that must be satisfied by the subject, or the like.

Blocks 438-448. Referring to blocks 438-448, in some embodiments, the at least one respective gate criterion associated with a respective category includes a ranking gate criterion. In some embodiments, the ranking gate criterion is associated with a hierarchical ranking of each category in the plurality of categories. In some embodiments, the ranking gate criterion includes a subjective rating from highest to lowest (e.g., user-provided rating of "mild," "moderate," "severe," or "no reaction), an objective rating from highest to lowest (e.g., a ranking from most effective to least effective as determined by the digital reality system 200 or a medical practitioner associated with the subject), or a combination thereof. In some embodiments, each category in the hierarchical ranking is a weak order ranking or a total preorder ranking, such as a competition ranking, a dense ranking, an ordinal ranking, a fractional ranking, or a combination thereof. For instance, in some embodiments, the first ranking gate criterion is ranked higher than the second ranking gate criterion, ranked lower than the second ranking gate criterion, or ranked equal to the second ranking gate criterion.

In some embodiments, the at least one respective gate criterion associated with a respective category includes a difficulty gate criterion. The difficulty gate criterion is associated with a complexity or level of demand required by the subject to satisfy a respective challenge. For instance, in some embodiments, based on a respective age of the subject the difficulty gate criterion modifies how one or more NPC characters in a digital reality scene engage with the subject, such as how the tone and/or speech of the NPC characters is used to address the subject within the digital reality scene. However, the present disclosure is not limited thereto. In some embodiments, the difficulty gate criterion is utilized to determine if a level of interaction by the subject with a digital reality scene, such as how much interaction or oversight by a medical practitioner is required to progress through the exposure progression.

In some embodiments, the at least one respective gate criterion associated with a respective category includes a medical practitioner gate criterion. The medical practitioner gate criterion is associated with an approval from the medical practitioner associated with the subject. In this way, the medical practitioner associated with the subject can provide oversight to improving the psychiatric or mental condition exhibited by the subject by either approving or denying access to the category and proposed experiences that are associated with the categories. For instance, the medical practitioner can deny accesses to a particular category and particular proposed experience to a particular user until the medical practitioner believes the user is "ready" for the particular category and proposed experience.

In some embodiments, the at least one respective gate criterion associated with a respective category includes a user gate criterion. In some embodiments, the user gate criterion is associated with an approval or confirmation of a selection of a category from the subject. In this way, the user can actively engage in selection of a particular category to work with or deny a category if the user feels not ready for the particular category and proposed experience(s) associated with the particular category.

In some embodiments, a gate criterion sets a condition for determining whether a category has been successfully completed, and/or for identifying a subsequent category or categories for a subject to complete. In some embodiments, a gate criterion sets a condition precedent for executing a category or a condition that must be achieved in order to deem the category complete. A non-limiting example of a condition precedent is a requirement that some category or categories (e.g., first category) be successfully completed before the user is allowed to invoke a particular category (e.g., second category). For instance, in some embodiments, a first condition precedent is a requirement that a first tutorial category be successfully completed before the user is allowed to invoke a second category different than the first tutorial category. Another non-limiting example of a condition that must be achieved in order to deem a category complete is a minimum number of the proposed experiences associated with the categories that must be successfully completed.

In some embodiments, the at least one respective gate criterion associated with a respective category includes an arrangement gate criterion. The arrangement gate criterion is associated with an order of one or more categories in the plurality of categories, such as an order of one or more categories in a sequence of categories that form a story or common narrative thread. For instance, consider a set of three categories, A, B and C that form a story or a common narrative thread. To realize the story or common narrative thread in the correct order of A, B, and then C, a first arrangement gate criterion is imposed on B that requires A to be completed before B is initiated, and a second arrangement gate criterion is imposed on C that requires both A and B to be completed before C is initiated.

Blocks 450-452. Referring to blocks 450-452, the corresponding digital reality scene can be a virtual reality scene, an augmented reality scene, or a mixed reality scene. For instance, in some embodiments, the corresponding digital reality scene is a virtual reality scene that facilitates a fully digital immersion, allowing for one or more digital objects (e.g., objects 42 of FIG. 2B) within a digital space (e.g., three-dimensional digital space). In some alternative embodiments, the corresponding digital reality scene is an augmented reality scene that presents an augmentation of the real world using digital objects. In other embodiments, the corresponding digital reality scene is a mixed reality scene 40 that provides spatial mapping and data contextualization in real-time, allowing for one or more digital objects within a digital space that is correlated to a user space (e.g., a field of view of the user or client device 300). Additional detains and information regarding types of digital reality scene can be found at Parveau et al., 2018, 3iVClass: A New Classification Method for Virtual, Augmented and Mixed Realities," Procedia Computer Science, 141, pg. 263, which is hereby incorporated by reference in its entirety for all purposes. Accordingly, presenting a challenge within a digital reality scene, the subject becomes immersed in the experience, which improves interaction between the subject and the systems and methods of the present disclosure in order to improve the ability of the subject.

Block 454. Referring to block 454, in some embodiments, a respective biometric threshold (e.g., biometric threshold 33-1) of a respective proposed experience (e.g., experience 24-1) in the plurality of proposed experiences is set by a system administrator, the subject, a health care worker associated with the subject, a model or algorithm, or any combination thereof. For instance, as a non-limiting example, in some embodiments, a biometric threshold of a proposed experience is set by the subject (e.g., a user of a first client device 300-1), such as a maximum heartrate threshold or the like. As another non-limiting example, in some embodiments, a biometric threshold of a proposed experience is set by a health care worker (e.g., a medical practitioner) associated with the subject, such as by configuring a threshold vocal feature required to be satisfied by the subject. As still another non-limiting example, in some embodiments, a biometric threshold of a first proposed experience (e.g., experience 24-1) in the plurality of proposed experiences is set by the subject and a biometric threshold of a second proposed experience (e.g., experience 24-2) in the plurality of proposed experience is set by a health care worker associated with the subject. In some embodiments, a biometric threshold of a proposed experience is further modified by a medical practitioner associated with the subject or the model based on a classification, a clustering, or other parameters associated with the user that indicate changing a biometric threshold would improve the likelihood of engagement and/or a better clinical outcome.

In some embodiments, a biometric threshold sets a condition, at least in part, for determining whether a challenge associated with a proposed experience has been successfully completed, and/or for identifying a subsequent challenge/experience for a subject to complete. In some embodiments, a biometric threshold sets a condition, at least in part, precedent for executing a digital reality scene associated with a proposed experience or a condition that must be achieved in order to deem the challenge/experience complete. A non-limiting example of a condition precedent is a requirement that some challenges (e.g., attending a small party, reframing a thought, determining usefulness of core belief, etc.) be successfully completed before the subject is allowed to invoke a particular challenge (e.g., speaking in front of a large audience, defusing a thought, etc.). A non-limiting example of a condition that must be achieved in order to deem a challenge complete is a minimum length (e.g., a duration of a period of time) of eye contact with a designated portion of the corresponding digital reality scene that is associated with the corresponding challenge. As another non-limiting example of a condition that must be achieved in order to deem a challenge complete is a threshold root mean square of a data set captured by a recorder, such as a representation of a continuous power of a voice of the subject. As yet another non-limiting example of a condition that must be achieved in order to deem a challenge complete is a threshold voice entropy, which describes a capacity of a vocal feature obtained from the subject, such as how much information is conveyed by the vocal feature.

Block 458. Referring to block 458, a biometric threshold can be an absolute parameter, a relative parameter, a normalized parameter, or the like. For instance, in some embodiments, a biometric threshold of an experience is an absolute parameter. Non-limiting examples of absolute biometric thresholds include, but are not limited to, a minimum number of utterances required for a subject while the subject is completing a corresponding challenge of the experience, the lowest decibel level of one or more utterances for a subject to be heard, a minimum length of eye contact required for a subject while the subject is completing a corresponding challenge of the experience, a threshold spectral entropy of a vocal feature (e.g., a measure of irregularity of the vocal feature), a threshold PDF entropy of the vocal feature (e.g., a measure of stability of the vocal feature), or a combination thereof. In some embodiments, a biometric threshold of an experience is a relative parameter, e.g., relative to each subject's baseline or relative to a population's baseline. A non-limiting example of relative biometric thresholds is a variation in the decibel level against a decibel level baseline of a subject (e.g., decibel level when speaking under no pressure), for determining the reduction in subjective anxiety or improvement in the biometric measures achieved by the subject during a corresponding challenge of the experience. Another non-limiting example of relative biometric thresholds is a condition for determining whether a subject has reached a state of relaxation based on the subject's heart rate relative to the subject's or population's baseline heart rate indicative of a state of relaxation. Yet another non-limiting example of relative biometric thresholds is a condition for determining whether a subject has reached a state of relaxation based on the PDF entropy of a vocal feature obtained from the subject using a recorder to the subject's or population's baseline PDF entropy indicative of a state of relaxation. In some embodiments, a biometric threshold of an experience is a normalized parameter, such as an assertiveness based on a scale. In some embodiments, a biometric threshold of an experience includes a combination of absolute, relative and/or normalized parameters. However, the present disclosure is not limited thereto.

Block 460. Referring to block 460, a biometric threshold can be set for a variety of biometric measures. Examples of biometric thresholds include, but are not limited to, an eye contact threshold, a heart rate threshold, an assertiveness threshold, a decibel level threshold, a pitch threshold, an utterance threshold, a word threshold, a sentiment criterion, or the like.

Block 462. Referring to block 462, in some embodiments, a biometric threshold of a proposed experience is an eye contact threshold. In some embodiments, the eye contact threshold includes a threshold length of eye contact, e.g., a minimum eye contact duration, for the subject during the corresponding digital reality scene that manifests the corresponding challenge designed for the proposed experience. In some embodiments, the threshold length of eye contact is at least 2 seconds, at least 3 seconds, at least 5 seconds, at least 10 seconds, or at least 30 seconds. In some embodiments, the threshold length of eye contact is at most 2 seconds, at most 3 seconds, at most 5 seconds, at most 10 seconds, or at most 30 seconds. In some embodiments, the threshold eye contact is between 2 seconds and 30 seconds, between 2 seconds and 10 seconds, between 3 seconds and 30 seconds, between 3 seconds and 10 seconds, between 4 seconds and 30 seconds, between 4 seconds and 10 seconds, between 5 seconds and 30 seconds, or between 5 seconds and 10 seconds. Alternatively, optionally or additionally, in some embodiments, the biometric threshold of the proposed experience includes an increment of eye contact, e.g., an increased length of eye contact compared to an eye contact baseline of the subject, for the subject during the corresponding digital reality scene that manifests the corresponding challenge designed for the proposed experience. In some embodiments, the increment of eye contact is at least 1 second, at least 2 seconds, at least 3 seconds, at least 5 seconds, or at least 10 second. In some embodiments, the increment of eye contact is at most 1 second, at most 2 seconds, at most 3 seconds, at most 5 seconds, or at most 10 second. In some embodiments, the increment of eye contact is between 1 second and 10 seconds, between 1 second and 5 seconds, between 2 seconds and 10 seconds, between 2 seconds and 5 seconds, between 3 seconds and 10 seconds, between 3 seconds and 5 seconds, between 4 seconds and 10 seconds, or between 4 seconds and 5 seconds.

In some embodiments, the required minimum length of eye contact and/or the required increment of eye contact are with a portion of the corresponding digital reality scene of the proposed experience. For instance, as a non-limiting example, in the digital reality scene illustrated in FIG. 5A, the required minimum length of eye contact and/or the required increment of eye contact are with a portion of the digital reality scene where the subject is engaging with (e.g., talking to) a player character, e.g., object 42-1. The digital reality scene illustrated in FIG. 5B, the required minimum length of eye contact and/or the required increment of eye contact are with a portion of the digital reality scene where the subject is engaging with (e.g., talking to) a player character, e.g., object 42-2.

Block 464. Referring to block 464, in some embodiments, a biometric threshold of a proposed experience includes a heart rate threshold that manifests the corresponding challenge designed for the proposed experience. In some embodiments, the heart rate threshold includes a maximum heart rate, e.g., maximum heart beats per minute (bpm), for the subject during the corresponding digital reality scene that manifests the corresponding challenge designed for the proposed experience. In some embodiments, the threshold heart rate is at most 200 bpm, at most 190 bpm, at most 180 bpm, at most 170 bpm, at most 160 bpm, at most 150 bpm, at most 140 bpm, at most 130 bpm, or the like. In some embodiments, the threshold heart rate is at least 200 bpm, at least 190 bpm, at least 180 bpm, at least 170 bpm, at least 160 bpm, at least 150 bpm, at least 140 bpm, at least 130 bpm, or the like. In some embodiments, the threshold heart rate is between 55 bmp and 100 bmp, between 90 bmp and 120 bmp, between 105 bmp and 140 bmp, between 120 bmp and 120 bmp, between 135 bmp and 180 bmp, or between 150 bmp or 200 bmp.

Alternatively, optionally or additionally, in some embodiments, the biometric threshold of the proposed experience includes a reduction of heart rate, e.g., reduced heartbeat(s) per minute compared to a heart rate baseline of the subject, for the subject during the corresponding digital reality scene that manifests the corresponding challenge designed for the proposed experience. In some embodiments, the reduction of heart rate is at least 2 bpm, at least 4 bpm, at least 6 bpm, at least 8 bpm, at least 10 bpm, at least 15 bpm, at least 20 bpm, at least 25 bpm, at least 30 bpm, at least 40 bpm, at least 50 bpm, or the like. In some embodiments, the reduction of heart rate is at most 2 bpm, at most 4 bpm, at most 6 bpm, at most 8 bpm, at most 10 bpm, at most 15 bpm, at most 20 bpm, at most 25 bpm, at most 30 bpm, at most 40 bpm, at most 50 bpm, or the like. In some embodiments, the reduction of heart rate is between 2 bmp and 50 bmp, between 2 bmp and 40 bmp, between 2 bmp and 30 bmp, between 2 bmp and 20 bmp, between 2 bmp and 10 bmp, between 2 bmp and 5 bmp, between 4 bmp and 50 bmp, between 4 bmp and 40 bmp, between 4 bmp and 30 bmp, between 4 bmp and 20 bmp, between 4 bmp and 10 bmp, between 4 bmp and 5 bmp, between 7 bmp and 50 bmp, between 7 bmp and 40 bmp, between 7 bmp and 30 bmp, between 7 bmp and 20 bmp, between 7 bmp and 10 bmp, between 15 bmp and 50 bmp, between 15 bmp and 40 bmp, between 15 bmp and 30 bmp, between 15 bmp and 20 bmp, between 25 bmp and 50 bmp, between 25 bmp and 40 bmp, or between 25 bmp and 30 bmp.

Blocks 466-472. Referring to blocks 4666-472, in some embodiments, a biometric threshold of a proposed experience includes an assertiveness, a decibel level, a pitch, or a combination thereof of one or more utterances by the subject during the corresponding digital reality scene that manifests the corresponding challenge designed for the proposed experience. In some embodiments, like the eye contact threshold and/or the heart rate threshold, the assertiveness threshold can include an absolute assertiveness threshold, a relative assertiveness threshold, or both. The decibel level threshold can include an absolute decibel level threshold, a relative decibel level threshold, or both. The pitch threshold can include an absolute pitch threshold, a relative pitch threshold, or both. The relative assertiveness, decibel level or pitch threshold sets a condition, in comparison with a baseline of the subject, for determining an improvement achieved by the subject during the corresponding challenge.

In some embodiments, the absolute assertiveness threshold is represented by a score, e.g., 50 in a scale of 1 to 100, or by a range with a lower threshold and upper threshold, e.g., 40-60 in a scale of 1 to 100, or the like. In some embodiments, an utterance with a score above the absolute assertiveness threshold indicates that the subject is projecting with assertiveness or confidence. In some embodiments, the relative assertiveness threshold is a required increase or decrease of an assertiveness compared to an assertiveness baseline of the subject and is set to be, e.g., 2, 3, 4, 5, 10, 15, 20 or the like.

In some embodiments, the absolute decibel level threshold is presented by a range with a lower decibel level threshold and an upper decibel level threshold, e.g., 30-85 dB, 40-80 dB, 50-70 dB, or the like. An utterance at a decibel below the lower decibel level threshold is not loud enough to be heard, and an utterance at a decibel level above the upper decibel level threshold is too loud. Generally, 0 dB is the minimum sound level a person with good hearing can hear. 130 dB is the point where the sound is painful. A quiet whisper would produce a sound at a decibel level of about 30 dB. A normal conversation would produce a sound at a decibel level of about 60 dB. A loud singing would produce a sound at a decibel level of about 70 dB.

In some embodiments, the relative decibel level threshold is a required increase or decrease of the decibel level compared to a decibel level baseline of the subject. In some embodiments, the relative decibel level threshold is at least 1 dB, at least 2 dB, at least 3 dB, at least 4 dB, at least 5 dB, at least 6 dB, at least 7 dB, at least 8 dB, at least 9 dB, at least 10 dB, or the like. In some embodiments, the relative decibel level threshold is at most 1 dB, at most 2 dB, at most 3 dB, at most 4 dB, at most 5 dB, at most 6 dB, at most 7 dB, at most 8 dB, at most 9 dB, at most 10 dB, or the like. For some subjects, e.g., those who usually speak too softly, the relative decibel level threshold sets a condition for the subject to increase the decibel level. For some other subjects, e.g., those who usually speak too loudly, the relative decibel level threshold sets a condition for the subject to decrease the decibel level.

In some embodiments, the absolute pitch threshold is presented by a range with a lower pitch threshold and an upper pitch threshold, e.g., 0.1 kHz-15 kHz, 0.3 kHz-10 kHz, 0.5 kHz-5 kHz, or the like. In some embodiments, the relative pitch threshold is a required increase or decrease of the pitch compared to a pitch baseline of the subject. In some embodiments, the relative pitch threshold is at least 10 Hz, at least 20 Hz, at least 30 Hz, at least 40 Hz, at least 50 Hz, at least 60 Hz, at least 70 Hz, at least 80 Hz, at least 90 Hz, at least 100 Hz, at least 150 Hz, at least 200 Hz, at least 250 Hz, at least 300 Hz, or the like. In some embodiments, the relative pitch threshold is at most 10 Hz, at most 20 Hz, at most 30 Hz, at most 40 Hz, at most 50 Hz, at most 60 Hz, at most 70 Hz, at most 80 Hz, at most 90 Hz, at most 100 Hz, at most 150 Hz, at most 200 Hz, at most 250 Hz, at most 300 Hz, or the like. For some subjects, e.g., those who usually speak at a lower pitch, the relative pitch threshold sets a condition for the subject to increase the pitch. For some subjects, e.g., those who usually speak at a higher pitch, the relative pitch threshold sets a condition for the subject to decrease the pitch.

In some embodiments, the pitch threshold and the decibel level threshold are correlated with each other, e.g., based on hearing sensitivity of human hearing. Generally, human ear perceives frequencies between 20 Hz (lowest pitch) to 20 kHz (highest pitch). Hearing sensitivity of human ears, however, varies at frequencies between 20 Hz and 20 kHz. For instance, at around 2 kHz, a good ear can hear sounds with a decibel level between 0 dB and 120 dB. Hearing sensitivity narrows as the frequency lowers or increases. For instance, at frequencies close to 20 Hz, human ear can generally hear sounds with the decibel level between 80 dB and 100 dB, and at frequencies close to 20 kHz, human ear can generally hear sounds with the decibel level between 60 dB and 80 dB. In view of the hearing sensitivity, in some embodiments, the decibel level threshold is set to be a relatively larger range or increment when the pitch threshold is at around 1 kHz to 2 kHz and a relatively smaller range or increment when the pitch threshold is below kHz or above 2 kHz. However, the present disclosure is not limited thereto. For instance, in some embodiments, the pitch threshold and the decibel level threshold are set independently from each other, with or without taking into consideration of hearing sensitivity.

Blocks 474-476. Referring to blocks 474-476, in some embodiments, a biometric threshold of a proposed experience includes an utterance threshold for the subject during the corresponding digital reality scene that manifests the corresponding challenge designed for the proposed experience. In some embodiments, the utterance threshold includes an absolute utterance threshold represented by a range with a minimum number of utterances and a maximum number of utterances. Generally, the minimum number of utterances sets a condition that encourages subjects to speak out, whereas the maximum number of utterances sets a condition that discourages subject from talking incessantly. In some embodiments, the threshold number of utterances is at least 2 utterances, at least 3 utterances, at least 5 utterances, at least 10 utterances, or at least 30 utterances. In some embodiments, the threshold number of utterances is at most 100 utterances, at most 90 utterances, at most 70 utterances, or at most 60 utterances. In some embodiments, the threshold number of utterances is between 2 utterances and 100 utterances, between 2 utterances and 80 utterances, between 2 utterances and 50 utterances, between 2 utterances and 20 utterances, between 2 utterances and 10 utterances, between 5 utterances and 100 utterances, between 5 utterances and 80 utterances, between 5 utterances and 50 utterances, between 5 utterances and 20 utterances, between 5 utterances and 10 utterances, between 15 utterances and 100 utterances, between 15 utterances and 80 utterances, between 15 utterances and 50 utterances, between 15 utterances and 20 utterances, between 35 utterances and 100 utterances, between 35 utterances and 80 utterances, or between 35 utterances and 50 utterances.

Alternatively, optionally or additionally, in some embodiments, the utterance threshold includes a relative utterance threshold, e.g., an increase or decrease of the number of utterances compared to an utterance baseline of the subject, for the subject during the corresponding digital reality scene that manifests the corresponding challenge designed for the proposed experience. In some embodiments, the relative utterance threshold is at least 1 utterance, at least 2 utterances, at least 3 utterances, at least 5 utterances, at least 10 utterances, at least 15 utterances, or at least 20 utterances. For some subjects, e.g., those who tend to be quiet when getting nervous, the relative utterance threshold encourages them to speak more. For some subject, e.g., those who tend to talk incessantly when getting nervous, the relative utterance threshold encourages them to speak less.

In some embodiments, a biometric threshold of a proposed experience includes a word threshold for the subject during the corresponding digital reality scene that manifests the corresponding challenge designed for the proposed experience. Similar to the utterance threshold, in some embodiments, the word threshold includes an absolute word threshold represented by a range with a minimum number of words and a maximum number of words, and/or a relative word threshold requiring an increase or decrease of the number of words compared to a word baseline of the subject.

Block 478. Referring to block 478, in some embodiments, a biometric threshold of a proposed experience is a satisfaction or failure to satisfy a sentiment analysis criterion by the subject during the corresponding digital reality scene that manifests the corresponding challenge designed for the proposed experience. In some embodiments, the sentiment analysis criterion includes an excited sentiment threshold and an overexcited sentiment threshold. However, the present disclosure is not limited thereto. For instance, in some embodiments, the sentiment analysis criterion is utilized to determine a change in sentiment when comparing a first thought or statement obtained from the subject and a second thought or statement obtained from the subject, such as a change from a neutral sentiment to a positive sentiment, from a negative sentiment to a neutral sentiment, or from a negative sentiment to a positive sentiment. In some embodiments, the sentiment analysis criterion is associated with a determination that a thought or statement associated with the subject is further associated with a first sentiment. In some embodiments, the first sentiment is an all-or-nothing sentiment, an overgeneralization sentiment, a filter sentiment, a disqualifying the positive sentiment, a mind reading sentiment, a catastrophizing sentiment, an emotional reasoning sentiment, a labeling sentiment, a personalization sentiment, or a combination thereof.

In some embodiments, the all-or-nothing sentiment is associated with the thought or statement from subject describing binary (e.g., black and white) classifications by the subject. In some embodiments, the overgeneralization sentiment is associated with the thought or statement from the subject describing a singular event as a never-ending, or patterned, event. In some embodiments, the filter sentiment is associated with the thought or statement from the subject describing a single detail excessively. In some embodiments, the disqualifying the positive sentiment is associated with the thought or statement from the subject describing a rejection of a positive event. In some embodiments, the mind reading sentiment is associated with the thought or statement from the subject describes an arbitrary third-party description associated with the subject. In some embodiments, the catastrophizing sentiment is associated with the thought or statement from the subject describing an exaggeration of aspect of an event. In some embodiments, the emotional reasoning sentiment is associated with the thought or statement from the subject describing a portrayal of an internal emotion with an external feature. In some embodiments, the labeling sentiment is associated with the thought or statement from the subject describing attaching one or more labels to an action by the subject. In some embodiments, the personalization sentiment is associated with the thought or statement from the subject describing the subject as a source of responsibility or action. However, the present disclosure is not limited thereto. Additional details and information regarding the sentiment of the present disclosure is found at Burns et al., 1981, "Feeling Good: The New Mood Therapy," New York, pg. 393, print, which is hereby incorporated by reference in its entirety for all purposes.

It should be noted that, in some embodiments, biometric thresholds of different experiences can be different, even though they are the same type of biometric thresholds. For instance, as a non-limiting example, suppose a first proposed experience is associated with a first digital reality scene for an exposure category, in which the subject is talking, face-to-face, to one person in a private setting. A second proposed experience for the exposure category is associated with a second digital reality scene, in which the subject is speaking before an audience in a party with background noises. In such embodiments, the decibel level threshold of the second proposed experience would be generally higher than the decibel level threshold of the first proposed experience, e.g., 60-80 dB for the second proposed experience and 40-60 dB for the first proposed experiences. However, the present disclosure is not limited thereto.

Also, it should be noted that biometric thresholds of a same experience can be different for different subjects. For instance, as a non-limiting example, suppose a first subject and a second subject engage in the same exposure (e.g., social) challenge, e.g., having a job interview. The first subject tends to be quiet when nervous, whereas the second subject tends to talk incessantly with an elevated (e.g., increased) heart rate and/or with changing pitch when nervous. In such embodiments, the biometric thresholds (absolute and/or relative thresholds) for the first and second subjects would be generally different, e.g., the utterance threshold for the first subject would be set for encouraging the first subject to speak more whereas the utterance threshold for the second subject would be set for encouraging the second subject to speak less.

Further, it should be noted that a biometric threshold of an experience can be reset or modified by the subject, a health care worker associated with the subject, a model/algorithm, or any combination thereof. For instance, as a non-limiting example, suppose a subject engages a social challenge for a second time (e.g., after an initial attempt at the social challenge of an exposure category), after taking some educational or therapeutic challenges (e.g., a mindfulness and/or cognitive reframing challenge) and having achieved some improvement in managing a psychiatric or mental condition. The biometric threshold of the experience when the subject engages with the corresponding challenge can be reset or modified in accordance with the progress that the subject has achieved.

Block 480. Referring to block 480, the method includes presenting, on the display, a first digital reality scene that manifests a first challenge designed for a first proposed experience of a first category. For instance, as a non-limiting example, in some embodiments, the method presents a first digital reality scene 40-1 on the display. The first digital reality scene 40-1 manifests a first challenge 26-1 (e.g., a fear) designed for a first experience 24-1. In some embodiments, the challenge is unique for the experience. However, the present disclosure is not limited thereto.

The first digital reality scene can be any suitable type of digital reality scenes, including but not limited to a virtual reality scene, an augmented reality scene, or a mixed reality scene. In some embodiments, the first digital reality scene is dependent on a type of display of a respective client device 300. For instance, in some embodiments, for a first client device 300-1 having processing capabilities to display a virtual reality scene, the first digital reality scene is a virtual reality scene. For a second client device 300-1 having processing capabilities to display an augment reality scene, the first digital reality scene is an augmented reality scene. In some embodiments, the first digital reality scene is dependent on a type of experience. For instance, a first experience is associated with a virtual reality scene and a second experience is associated with an augmented reality scene. In some embodiments, the first digital reality scene is dependent on a type of challenge. For instance, a first challenge is associated with a virtual reality scene and a second challenge is associated with a mixed reality scene.

Block 482. Referring to block 482, the method includes (C) obtaining, in coordination with the presenting (B), a plurality of data elements from all or a subset of sensors in the plurality of sensors (e.g., sensor 110-1, sensor 110-2, . . . of FIG. 1). The subset of sensors includes at least one biometric sensor (e.g., sensor 110-1). The at least one biometric sensor is configured to capture at least one biometric data element associated with the subject while the subject is completing the first challenge in the first digital reality scene. In some embodiments, the at least one biometric sensor includes, but is not limited to, a heart rate sensor, a heart rate variability sensor, a blood sensor, an electrodermal activity sensor, a galvanic skin response sensor, an electroencephalogram sensor, an eye-tracking sensor, a recorder, a microphone, a thermometer, a heatmap sensor, a camera, or any combination thereof. For instance, in some embodiments, the at least one biometric sensor includes the recorder, the microphone, the camera, or a combination thereof, which is utilized to capture a vocal feature (e.g., utterance) from the subject.

Blocks 484-490. Referring to blocks 484-490, the method includes (D) determining whether the set of biometric data elements (e.g., the first set of biometric data elements) obtained from the obtaining (C) satisfies the at least one biometric threshold of the first challenge to assess whether the first challenge is successfully completed. The set of biometric data element includes a first plurality of biometric data elements captured by a first biometric sensor (e.g., sensor 110-1 of FIG. 1) in the at least one biometric sensor. The at least one biometric threshold includes a first biometric threshold (e.g., biometric threshold 33-1 from the criterion store 30 of the digital reality system 200 of FIG. 2B). The determining (D) includes determining whether a comparison of the first plurality of biometric data elements against a corresponding threshold baseline characteristic satisfies the first biometric threshold.

Figure 6A:
FIG. 6A illustrates an exemplary digital reality scene for introduction or educational training, in accordance with an embodiment of the present disclosure.

By comparing the first plurality of biometric data elements against the corresponding threshold baseline characteristic, the method and system of the present disclosure are able to evaluate the improvement of each subject based on the subject specific values, specific challenges, and/or population values. In an embodiment, the corresponding threshold baseline characteristic is a biometric baseline of the subject captured at the beginning of the corresponding challenge of the first digital reality scene. In another embodiment, the corresponding threshold baseline characteristic is a biometric baseline of the subject captured when the subject is at a relaxing state, such as in a happy place or when initiating an experience, so that the baseline does not reflect anticipatory anxiety towards the challenge. FIG. 6A illustrates a non-limiting example of a happy place, where the subject can play an introduction or educational video (e.g., psychoeducational challenge requiring the subject to watch a duration of the introduction or educational video). In still another embodiment, the corresponding threshold baseline characteristic is a biometric baseline of the subject captured before the subject starts any challenge and/or experience.

For instance, in some embodiments, the first biometric sensor is a heart rate sensor, and the corresponding threshold baseline characteristic is an initial heart rate of the subject captured at the beginning of the corresponding challenge of the first digital reality scene, when the subject is at a relaxing state, or before the subject starts any experience and/or challenge. In such embodiments, the comparison of the first plurality of biometric data elements against the corresponding threshold baseline characteristic provides the change of the heart rate over time based on the subject's specific initial values. By comparing the first plurality of biometric data elements against the corresponding threshold baseline characteristic, the method and system of the present disclosure are able to distinguish improvements by different subjects, or by the same subject during different challenges, or by the same subject while repeating the social challenge. For instance, the method and system of the present disclosure are able to distinguish an improvement achieved by a first subject whose heart rate drops from a high initial heart rate (e.g., 140 beats per minute) to a moderate heart rate (e.g., 120 beats per minute), from an improvement by a second subject whose heart rate drops from a moderate initial heart rate (e.g., 125 beats per minute) to a moderate heart rate (e.g., 120 beats per minute), and from a deterioration by a third subject whose heart rate increases from a moderate initial heart rate (e.g., 110 beats per minute) to a moderate heart rate (e.g., 120 beats per minute). However, the present disclosure is not limited thereto.

The first biometric sensor can be any suitable biometric sensor, including but not limited to a heart rate sensor, a heart rate variability sensor, a blood sensor, an electrodermal activity sensor, a galvanic skin response sensor, an electroencephalogram sensor, an eye-tracking sensor, a recorder, a microphone, a thermometer, a heatmap sensor, a camera, or any combination thereof. For instance, as a non-limiting example, in some embodiments, the at least one biometric sensor includes a heart rate sensor configured to capture the heart rate of the subject while the subject is completing the first challenge in the first digital reality scene. As another non-limiting example, in some embodiments, the at least one biometric sensor includes a heart rate sensor variability configured to capture the heart rate variability of the subject while the subject is completing the first challenge in the first digital reality scene. As yet another non-limiting example, in some embodiments, the at least one biometric sensor includes a microphone or recorder or the like, configured to record the utterances of the subject while the subject is completing the first challenge in the first digital reality scene, in which one or more vocal features is identified and evaluated from the utterances obtained from the subject. As still another non-limiting example, in some embodiments, the first biometric sensor is a blood pressure sensor, and the corresponding threshold baseline characteristic is a systolic blood pressure of the subject or a diastolic blood pressure of the subject. In some embodiments, the systolic or diastolic blood pressure is captured at the beginning of the corresponding challenge of the first digital reality scene. In some embodiments, the systolic or diastolic blood pressure is captured when the subject is at a relaxing state. In some embodiments, the systolic or diastolic blood pressure is captured before the subject starts any educational or therapeutical program.

Blocks 494-498. Referring to blocks 494-498, in some embodiments, the method further includes (H) receiving, in electronic form, a second plurality of data elements associated with the subject. The second plurality of data elements includes a second plurality of biometric data elements associated with an initial psychiatric or mental condition of the subject. The first base line characteristic is formed from the second plurality of biometric data elements.

Figure 6B:
FIG. 6B illustrates an exemplary digital reality scene for mindfulness training, in accordance with an embodiment of the present disclosure.
Figure 6C:
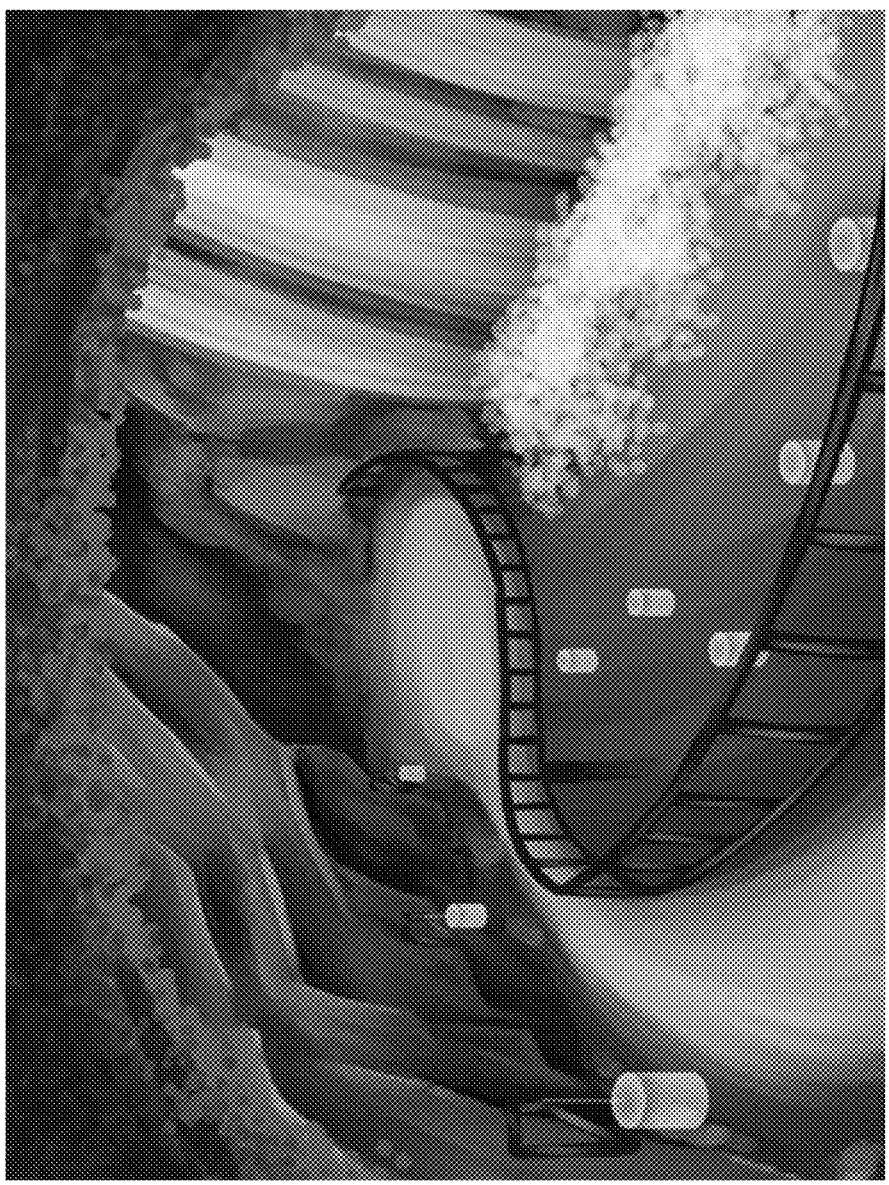
FIG. 6C illustrates an exemplary digital reality scene for cognitive reframing training, in accordance with an embodiment of the present disclosure.

For instance, in an embodiment, the second plurality of biometric data elements (e.g., heart rate, pitch, decibel level, an entropy, a temporal feature, etc. of the subject) is obtained or captured at the beginning of the corresponding challenge of the first digital reality scene. In another embodiment, the second plurality of biometric data elements is obtained or captured when the subject is at a relaxing state, e.g., during an introduction or tutorial challenge presented in a digital reality scene comprising a happy place such as the happy place illustrated in FIGS. 6A, 6B, and 6C. In still another embodiment, the second plurality of biometric data elements is obtained or captured during a mindfulness challenge. FIG. 6B illustrates a non-limiting example of a digital reality scene, where the subject can start a mindfulness challenge by having the avatar press the play button. In some embodiments, the second plurality of biometric data elements is obtained or captured during a CBT challenge. FIGS. 9A through 9D illustrate a non-limiting example of a digital reality scene, where the subject can start a CBT challenge, such as a gather evidence challenge, but interacting with a digital reality object, such as a digital reality recording object. In some embodiments, the second plurality of biometric data elements is obtained when or before initiating the presenting (B) of the first digital reality scene that manifests the first challenge designed for the first proposed experience of the first category. However, the present disclosure is not limited thereto. For instance, in some embodiments, the second plurality of biometric data elements is obtained before starting the entire program (e.g., before executing the client application at the client device), during a previous challenge, or the like. In some embodiments, the second plurality of biometric data elements is an average value over subject's previous challenge(s) or an average value over a population of users associated with the subject, such as a population of users having a similar condition as the subject.

Block 500. Referring to block 500, in some embodiments, the first biometric sensor is a heart rate sensor and the first plurality of biometric data elements captured by the first biometric sensor is used to determine heart beats per minutes. The method of the present disclosure can use any suitable type of a heart rate sensor to capture the biometric data elements. For instance, in some embodiments, the heart rate sensor is an electrical heart rate sensor (e.g., electrocardiography or ECG) that includes electrodes placed on the subject's chest to monitor electrical activity of the subject's heart. In some embodiments, the heart rate sensor is an optical heart rate sensor (e.g., photoplethysmography or PPG) that includes one or more light sources (e.g., LEDs) to detect the volume of blood flow under the subject's skin. In some embodiments, the optical heart rate sensor is a wearable/mobile device or is incorporated with a wearable/mobile device, such as watches, activity trackers, arm straps, and mobile phones.

Block 502. Referring to block 502, in some embodiments, the first biometric sensor is a heart rate variability sensor and the first plurality of biometric data elements captured by the first biometric sensor is used to determine beat-to-beat intervals, thereby providing an assessment of heart rate variability (HRV). HRV has been frequently applied as a reliable indicator of health status, stress, and mental effort. Studies have linked HRV to cardiovascular diseases, posttraumatic stress disorder, depression, and fibromyalgia. HRV has been proposed as a sensitive index of autonomic stress reactivity such as in panic disorder and work stress and mental effort.

In some embodiments, the heart rate variability sensor includes a chest-worn electrocardiogram sensor or a wearable/mobile photoplethysmogram (PPG) sensor that captures and provides heart signals for the HRV analysis. In some embodiments, the heart rate variability sensor is a non-contact sensor. For instance, in an embodiment, the heart rate variability sensor includes a camera that takes images or video of the subject while the subject is completing a challenge. The images or video taken by the camera are then used to extract arterial pulse information and derive the HRV. Additional information regarding a non-contact sensor can be found at "The PhysioCam: A Novel Non-Contact Sensor to Measure Heart Rate Variability in Clinical and Field Applications," Davila et al., Front Public Health, November 2017, Volume 5, Article 300, which is hereby incorporated by reference in its entirety for all purposes.

Blocks 506-512. Referring to blocks 506-512, in some embodiments, the first biometric sensor is an eye-tracking sensor. An eye-tracking sensor can be mounted on or incorporated with a device (e.g., a desktop, a stand, a wall or the like), a pair of eyeglasses, a virtual reality headset, or the like. It generally includes a projector that projects light (e.g., near-infrared light) on the eyes of a user, a camera that takes images of the user's eye, and/or an algorithm that processes the images to determine the eyes' position, gaze point and/or other features. In some embodiments, an eye-tracking sensor does not include image processing capability, instead, biometric data elements taken by such an eye-tracking sensor are sent to a client device (e.g., client device 300-1) or a remote system (e.g., digital reality system 200) for image processing. In some embodiment, an eye-tracking sensor is based on optical tracking of corneal reflections to assess visual attention, e.g., tracking the pupil center and where light reflects from the cornea. The light reflecting from the cornea and the center of the pupil are used to determine the movement and direction of the eye.

In some embodiments, the first plurality of biometric data elements captured by the first biometric sensor is used to determine gaze fixation(s), smooth motion(s), saccade(s), blink, scan-path length, eye openness, pupil dilation, eye position, hypervigilance or hyperscanning, avoidance, or any combination thereof.

In some embodiments, the gaze fixation is defined based on a spatial criterion and a temporal criterion on a region of interest (ROI) in a digital reality scene (e.g., eyes of object 42-2 in the digital reality scene illustrated in FIG. 6B). In some embodiments, the spatial criterion is a diameter of 0.8° visual angle, 0.9° visual angle, 1° visual angle, 1.1° visual angle, 1.2° visual angle, 1.3° visual angle, or the like, and the temporal criterion is a minimum of 120 ms, 130 ms, 140 ms, 150 ms, or the like. In some embodiments, the spatial criterion is a diameter visual angle between 0.8° and 1.3°, between 0.8° and 1.2°, between 0.8° and 1.1°, between 0.8° and 1°, between 0.8° and 0.9°, between 0.9° and 1.3°, between 0.9° and 1.2°, between 0.9° and 1.1°, between 0.9° and 1°, between 1° and 1.3°, between 1° and 1.2°, between 1° and 1.1°, between 1.1° and 1.3°, between 1.1° and 1.2°, or between 1.1° and 1.3°. In some embodiments, the spatial criterion is a diameter visual angle of at least 0.8°, at least 0.9°, at least 1°, at least 1.1°, at least 1.2°, or at least 1.3°. In some embodiments, the spatial criterion is a diameter visual angle of at most 0.8°, at most 0.9°, at most 1°, at most 1.1°, at most 1.2°, or at most 1.3°. In some embodiments, the temporal criterion is a period of time between 120 ms and 150 ms, between 120 ms and 145 ms, between 120 ms and 140 ms, between 120 ms and 135 ms, between 120 ms and 130 ms, between 120 ms and 125 ms, between 125 ms and 150 ms, between 125 ms and 145 ms, between 125 ms and 140 ms, between 125 ms and 135 ms, between 125 ms and 130 ms, between 130 ms and 130 ms, between 130 ms and 145 ms, between 130 ms and 140 ms, between 130 ms and 135 ms, between 135 ms and 150 ms, between 135 ms and 145 ms, between 135 ms and 140 ms, between 140 ms and 150 ms, between 140 ms and 145 ms, or between 145 ms and 150 ms. In some embodiments, the temporal criterion is at least 120 ms, at least 125 ms, at least 130 ms, at least 135 ms, at least 140 ms, at least 145 ms, or at least 150 ms. In some embodiments, the temporal criterion is at most 120 ms, at most 125 ms, at most 130 ms, at most 135 ms, at most 140 ms, at most 145 ms, or at most 150 ms.

In some embodiments, the hypervigilance is defined as a time to a first fixation during a specific challenge in the digital reality scene. In some embodiments, the avoidance is defined as a number of fixations during a specific challenge in the digital reality scene divided by a total number of fixations in the first digital reality scene. Research has suggested that socially anxious humans guide their initial attention to emotionally threatening information (hypervigilance) and avoid the negative information subsequently (attentional avoidance) to reduce emotional distress. Additional information regarding eye-tracking can be found at "Gaze Behavior in Social Fear Conditioning: An Eye-Tracking Study in Virtual Reality," Reichenberger et al., Frontiers in Psychology, published 23 Jan. 2020, and at "Capturing Hypervigilance: Attention Biases in Elevated Trait Anxiety and Post-traumatic Stress Disorder" by Lorana H. Stewart submitted for the degree of Doctor of Philosophy, University College London, September 2011, each of which is hereby incorporated by reference in its entirety for all purposes.

In some embodiments, the method delimits one or more ROIs for objects (e.g., eyes of an avatar, face of an avatar, non-player object, etc.) in a digital reality scene. In some embodiments, the method determines the percentage of time a subject spends with his/her gaze within each ROI, the mean number of gaze fixations within each ROI, the median duration of gaze fixations within each ROI, the mean distance of gaze fixations with respect to the centre of each ROI, or any combination thereof.

However, the present disclosure is not limited thereto. For instance, in some embodiments, the method records the scan path of the subject's eyes and examines the subject's facial expressions using one or more models. In some embodiments, examination of the subject's facial expressions is performed by a health care worker associated with the subject. In some embodiments, the method determines other eye activities or features such as change in eye position when addressing the corresponding challenge, count of occurrences of the eyes at a predetermined reference position, or the like.

Blocks 514-520. Referring to blocks 514-520, in some embodiments, the first biometric sensor is a recorder. The method of the present disclosure can use any suitable recorder to capture the biometric data elements. Examples of recorders include, but are not limited to, online voice recorder, microphone recorder, USB flash drive voice recorder, portable digital recorders, voice-activated recorders, audio recorder, video recorder, and vibration responsive sensors.

In some embodiments, the recorder is utilized to obtain a statement, an utterance, a vocal feature, or a combination thereof from the subject. In some embodiments, emotions expressed in a voice are generally analyzed at a plurality of levels: the physiological level, the phonatory-articulatory level, the acoustic level, or a combination thereof. In some embodiments, the physiological level describes, for instance, nerve impulses or muscle innervation patterns of the major structures involved in the voice-production process. The phonatory-articulatory level describes, for instance, the position or movement of the major structures such as the vocal folds. The acoustic level describes, for instance, characteristics of the speech wave form emanating from the mouth. Most of the current methods for measurement at the physiological and phonatory-articulatory levels are rather intrusive and require specialized equipment as well as a high level of expertise. In contract, acoustic cues of vocal emotion expression may be obtained objectively, economically, and unobtrusively from speech recordings, with no requirement for any special equipment.

In some embodiments, a biometric threshold is associated with one or more voice cues. In some embodiments, the one or more vocal cues include: (a) a fundamental frequency (e.g., F0, such as a correlate of the perceived pitch), (b) a vocal perturbation (e.g., short-term variability in sound production), (c) a voice quality (e.g., a correlate of the perceived 'timbre'), (d) an intensity (e.g., a correlate of the perceived loudness), (e) one or more temporal aspects of speech (e.g., speech rate), as well as various combinations of these aspects (e.g., prosodic features). In some embodiments, the first plurality of biometric data elements captured by the first biometric sensor is used to determine a fundamental frequency, a speech rate, one or more pauses (e.g., pauses in speaking by the subject), a duration of silence by the subject, a voice intensity, a voice onset time, one or more pitch perturbations, one or more loudness perturbations, one or more voice breaks, one or more pitch jumps, a voice quality (e.g., stuttering, shaky, "like", "um"), a sound quality (e.g., pitch changes, stuttering), or a combination thereof.

In some embodiments, the first plurality of biometric data elements captured by the first biometric sensor (e.g., the recorder) is transcribed, such as by one or more computational models, to create a transcription, such as a text object that represents the utterance obtained from the subject through the recorder. For instance, in some embodiments, the transcription is then extracted by one or more models to produce a set of one or more words. In some embodiments, the first plurality of biometric data elements includes a waveform data, the method first segments the first plurality of biometric data elements captured by the first biometric sensor (e.g., the voice recorded by the recorder) into one or more voiced and unvoiced sounds, one or more words, one or more syllables, or a combination, thereby segmenting the waveform data or the transcription to allow a quantitative description of relatively homogeneous and thus comparable parts of each utterance. As yet another non-limiting example, in some embodiments, the first plurality of biometric data elements including the waveform data is inputted to a NN computational model, such as a 1-dimensional CNN in order to extract a vocal feature. However, the present disclosure is not limited thereto.

In some embodiments, an utterance can be a word, a short phrase, or a complex sentence with many embedded clauses. Non-limiting examples of utterances include, but are not limited to, one or more spoken phrases or words such as "ok?" "uhhuh." "not on the floor!" "the pink one." and "yeah, well, I thought she was going to, but she never did."

In some embodiments, segmenting the recorded voice is based on the pause(s) in the recorded voice, e.g., two utterances separated by a pause of at least 2 seconds, at least 2.5 seconds, at least 3 seconds, at least 3.5 seconds, or at least 4 seconds. In some embodiments, segmenting the recorded voice is based on a pause of at most 2 seconds, at most 2.5 seconds, at most 3 seconds, at most 3.5 seconds, or at most 4 seconds. In some embodiments, an utterance is never more than one complete sentence long, i.e., two complete sentences segmented into two utterances even though there is no detectable pause between the two complete sentences.

In some embodiments, the first plurality of biometric data elements includes, or is utilized to determine, a plurality of vocal features. In some embodiments, a vocal feature is a phenome associated with the utterance, such as a pitch, a cadence, an inflection, or the like. In some embodiments, the plurality of vocal features includes between 5 phonemes and 200 phonemes, between 5 phonemes and 150 phonemes, between 5 phonemes and 100 phonemes, between 5 phonemes and 80 phonemes, between 5 phonemes and 60 phonemes, between 5 phonemes and 40 phonemes, between 5 phonemes and 20 phonemes, between 15 phonemes and 200 phonemes, between 15 phonemes and 150 phonemes, between 15 phonemes and 100 phonemes, between 15 phonemes and 80 phonemes, between 15 phonemes and 60 phonemes, between 15 phonemes and 40 phonemes, between 15 phonemes and 20 phonemes, between 35 phonemes and 200 phonemes, between 35 phonemes and 150 phonemes, between 35 phonemes and 100 phonemes, between 35 phonemes and 80 phonemes, between 35 phonemes and 60 phonemes, between 35 phonemes and 40 phonemes, between 60 phonemes and 200 phonemes, between 60 phonemes and 150 phonemes, between 60 phonemes and 100 phonemes, between 60 phonemes and 80 phonemes, between 80 phonemes and 200 phonemes, between 80 phonemes and 150 phonemes, or between 80 phonemes and 100 phonemes. In some embodiments, the plurality of vocal features includes at least 5 phonemes, at least 10 phonemes, at least 15 phonemes, at least 20 phonemes, at least 25 phonemes, at least 30 phonemes, at least 35 phonemes, at least 40 phonemes, at least 45 phonemes, at least 50 phonemes, at least 55 phonemes, at least 60 phonemes, at least 65 phonemes, at least 70 phonemes, at least 75 phonemes, at least 80 phonemes, at least 85 phonemes, at least 90 phonemes, at least 95 phonemes, at least 100 phonemes, at least 105 phonemes, at least 110 phonemes, at least 115 phonemes, at least 120 phonemes, at least 125 phonemes, at least 130 phonemes, at least 135 phonemes, at least 140 phonemes, at least 145 phonemes, at least 150 phonemes, at least 155 phonemes, at least 160 phonemes, at least 165 phonemes, at least 170 phonemes, at least 175 phonemes, at least 180 phonemes, at least 185 phonemes, at least 190 phonemes, at least 195 phonemes, or at least 200 phonemes. In some embodiments, the plurality of vocal features includes at most 5 phonemes, at most 10 phonemes, at most 15 phonemes, at most 20 phonemes, at most 25 phonemes, at most 30 phonemes, at most 35 phonemes, at most 40 phonemes, at most 45 phonemes, at most 50 phonemes, at most 55 phonemes, at most 60 phonemes, at most 65 phonemes, at most 70 phonemes, at most 75 phonemes, at most 80 phonemes, at most 85 phonemes, at most 90 phonemes, at most 95 phonemes, at most 100 phonemes, at most 105 phonemes, at most 110 phonemes, at most 115 phonemes, at most 120 phonemes, at most 125 phonemes, at most 130 phonemes, at most 135 phonemes, at most 140 phonemes, at most 145 phonemes, at most 150 phonemes, at most 155 phonemes, at most 160 phonemes, at most 165 phonemes, at most 170 phonemes, at most 175 phonemes, at most 180 phonemes, at most 185 phonemes, at most 190 phonemes, at most 195 phonemes, or at most 200 phonemes.

In some embodiments, the method then extracts various voice cues of relevance to speech emotion. In some embodiments, the various voice cues include, but are not limited to, a fundamental frequency, a speech rate, one or more pauses, a voice intensity, a voice onset time, a jitter (e.g., one or more pitch perturbations), a shimmer (e.g., one or more loudness perturbations), one or more voice breaks, one or more pitch jumps, one or more measures of voice quality (e.g., the relative extent of high- versus low-frequency energy in the spectrum, the frequency and bandwidth of energy peaks in the spectrum due to natural resonances of the vocal tract called formants, etc.), or a combination thereof. Several measures may be obtained for each type of cue. In some embodiments, extraction of voice cues is unsupervised, e.g., automatically without human involvement. In some embodiments, extraction of the various voice cues is supervised, e.g., carefully checked by the subject, a system administrator or a health care worker associated with the subject.

In some embodiments, a sentiment analysis or an emotion analysis is performed on the first plurality of biometric data elements captured by the recorder. For instance, in some embodiments, the sentiment analysis is performed on words, phrases, and/or sentences extracted from the first plurality of biometric data elements. In some embodiments, the predetermined sentiment is amusement, anger, anxiety, awkwardness, boredom, calmness, confusion, craving, disgust, empathetic pain, entrancement, excitement, fear, horror, interest, joy, annoyance, nostalgia, relief, sadness, satisfaction, or surprise.

In some embodiments, the sentiment analysis is performed based at least in part on lexicons (e.g., lists of words and the emotions they convey), sentiment analysis dictionaries (e.g., a dictionary containing information about the emotions or polarity expressed by words, phrases, or concepts), libraries (e.g., a library computing a set of prosodic and spectra features that supports emotion recognition), complex machine learning algorithms (e.g., Naive Bayes, Support Vector Machine, Maximum Entropy), or a combination thereof.

In some embodiments, the sentiment analysis is performed using a distance metric, such as a cosine similarity measure or dot product of one or more utterances of the subject made during the corresponding challenge against each statement in a list of statements that are deemed to be characteristic of a predetermined sentiment. In some embodiments, the sentiment analysis is based on those described in Duda et al., 1973, "Pattern Classification and Scene Analysis," Wiley, Print., and/or that described in Salton et al., 1983, "Introduction to Modern Information Retrieval," McGraw-Hill Book Co., Print, each of which is hereby incorporated by reference in their entirety. For instance, consider $X^p=[X_1^p, \ldots, X_n^p]$ and $X^q=[X_1^q, \ldots, X_n^q]$ to be two vectors representing, respectively, the utterances made by the subject and statement in a list of statements that are deemed to be characteristic of a predetermined sentiment. The similarity measure may be determined using the following formula:

$$d(X^p, X^q) = 1 - \frac{\sum_{i=1}^{n} X_i^p X_i^q}{\sqrt{\sum_{i=1}^{n} X_i^{p^2} \cdot \sum_{i=1}^{n} X_i^{q^2}}}$$

Table 1 below shows various other types of measures for distance and further describes the nomenclature of the above-identified formula.

Table 1. Exemplary distance metrics for the distance based classification model 208. Consider $X^p=[X_1^p, \ldots, X_n^p]$ and $X^q=[X_1^q, \ldots, X_n^q]$ to be two pattern vectors (be two vectors representing, respectively, the utterances made by the subject and statement in a list of statements). Also consider $\max_i$ and $\min_i$ to be the maximum value and the minimum value of an $i^{th}$ attribute of the patterns in a data set (e.g., a text string), respectively. The distance between $X^p$ and $X^q$ is defined as follows for each distance metric:

| Type | Distance Metric |
|---|---|
| Euclidean | $d(X^p, X^q) = \sqrt{\sum_{i=1}^{n}(X_i^p - X_i^q)^2}$ |
| Manhattan | $d(X^p, X^q) = \sum_{i=1}^{n}|X_i^p - X_i^q|$ |
| Maximum Value | $d(X_p, X_q) = \mathrm{argmax}_i |X_i^p - X_i^q|$ |
| Normalized Euclidean | $d(X^p, X^q) = \sqrt{\frac{1}{n}\sum_{i=1}^{n}\left(\frac{X_i^p - X_i^q}{\max_i - \min_i}\right)^2}$ |
| Normalized Manhattan | $d(X^p, X^q) = \frac{1}{n}\sum_{i=1}^{n}\frac{|X_i^p - X_i^q|}{\max_i - \min_i}$ |
| Normalized Maximum Value | $d(X^p, X^q) = \mathrm{argmax}_i \frac{|X_i^p - X_i^q|}{\max_i - \min_i}$ |
| Dice Coefficient | $d(X^p, X^q) = 1 - \frac{2\sum_{i=1}^{n} X_i^p X_i^q}{\sum_{i=1}^{n} X_i^{p^2} + \sum_{i=1}^{n} X_i^{q^2}}$ |
| Cosine coefficient | $d(X^p, X^q) = 1 - \frac{\sum_{i=1}^{n} X_i^p X_i^q}{\sqrt{\sum_{i=1}^{n} X_i^{p^2} \cdot \sum_{i=1}^{n} X_i^{q^2}}}$ |
| Jaccard coefficient | $d(X^p, X^q) = 1 - \frac{\sum_{i=1}^{n} X_i^p X_i^q}{\sum_{i=1}^{n} X_i^{p^2} + \sum_{i=1}^{n} X_i^{q^2} - \sum_{i=1}^{n} X_i^p X_i^q}$ |

One of skill in the art will appreciate that other sentiments are within the domain of the systems and methods of the present disclosure. Additional information regarding sentimental analysis or analysis of voice data can be found at "Sentiment Analysis and Opinion Mining," Bing Liu, Morgan & Clypool Publishers, May 2012, "Speech motion analysis," Juslin et al., (2008), Scholarpedia, 3(10):4240, each of which is hereby incorporated by reference in its entirety for all purposes. Additional details and information regarding the distance-based classification model can be learned from Yang et al., 1999, "DistAI: An Inter-pattern Distance-based Constructive Learning Algorithm," Intelligent Data Analysis, 3(1), pg. 55.

Blocks 522-526. Referring to blocks 522-526, in some embodiments, the first plurality of biometric data elements captured by the first biometric sensor is stored, thereby allowing a replay of the first plurality of biometric data elements after completion of the first digital reality scene. For instance, as a non-limiting example, in an embodiment, the first plurality of biometric data elements captured by the first biometric sensor (e.g., the recorded voice) is stored in the recorder. As another non-limiting example, in another embodiment, the first plurality of biometric data elements captured by the first biometric sensor is sent to and stored in a client device (e.g., client device 300-1), a remote system (e.g., digital reality system 200), or the like.

In some embodiments, one or more specific key words is used in analysis of the first plurality of biometric data elements captured by the first biometric sensor to prevent spoofing. For instance, as a non-limiting example, in some embodiments where a challenge is for a subject to request a napkin from a non-player character (e.g., a bartender), the subject needs to say the specific word "Napkin" or "Napkins" in order to start the conversation. As another non-limiting example, in some embodiments, where a challenge for a subject to reframe a thought, the subject needs to say a first word (e.g., "will") or cannot say a second word (e.g., "cannot") during the conversation. However, the present disclosure is not limited thereto.

In some embodiments, the first plurality of biometric data elements captured by the first biometric sensor is pre-processed to remove a background noise, such as by modulating a waveform data in the first plurality of biometric data elements. Alternatively, in some embodiments, the first plurality of biometric data elements is captured by the first biometric sensor with auto noise cancellation feature enabled.

Block 528. Referring to block 528, in some embodiments, the first plurality of biometric data elements captured by the first biometric sensor (e.g., recorder, camera, eye-tracking sensor) is stored, thereby allowing a replay of the first plurality of biometric data elements after completion of the first digital reality scene. For instance, as a non-limiting example, in an embodiment, the first plurality of biometric data elements (e.g., the recorded voice) captured by the first biometric sensor is stored in the recorder. As another non-limiting example, in another embodiment, the first plurality of biometric data elements captured by the first biometric sensor is sent to and stored in a client device (e.g., client device 300-1), a remote system (e.g., digital reality system 200), or the like. As still another non-liming example, the first plurality of biometric data elements (e.g., images or video) captured by the first biometric sensor is stored in the camera, or sent to and stored in a client device (e.g., client device 300-1), or sent to and stored in a remote system (e.g., digital reality system 200), or the like. For instance, in some embodiments, when completing a CBT challenge, a first thought or statement obtained by the subject associated with the first plurality of biometric data elements (e.g., waveform data of the first thought or statement) is stored, which allows the subject to reframe the first thought or statement (e.g., complete the first challenge) at a future time.

Block 530. Referring to block 530, in some embodiments, the first plurality of biometric data elements is captured by the first biometric sensor in response to a specific trigger. For instance, as a non-limiting example, in some embodiments where the first biometric sensor is or includes an eye-tracking sensor, the first plurality of biometric data elements is captured in response to the subject looking at a specific object of the digital reality scene, e.g., looking at another player characterizer such as a bartender in the eye. As another non-limiting example, in some embodiments, the first plurality of biometric data elements is captured in response to a selection or de-selection of a check box by the subject or a health care worker associated with the subject. As still another non-limiting example, the first plurality of biometric data elements is captured in response to a voice command from the subject or a health care worker associated with the subject. In some embodiments, the specific trigger includes changing a state of an input of the client device, such as by pressing a button input or moving a location of a sensor of the client device. In some embodiments, the specific trigger is associated with an interaction with a digital reality object in the digital reality scene, such as interacting with a digital reality recording object.

However, the present disclosure is not limited thereto, and any suitable triggers can be used to start and/or stop capturing biometric data elements. For instance, in some embodiments, the first plurality of biometric data elements is captured in response to a touch on the first biometric sensor, switch of an input mechanism, by the subject or a health care worker associated with the subject, by a change in a state of a digital reality scene (e.g., interacting with a digital reality object, etc.), or a combination thereof. In some embodiments, the first plurality of biometric data elements is captured in response to one or more specific key words provided by the subject, such as one or more specific key words obtained through the recorder.

Blocks 534-538. Referring to blocks 534-538, in some embodiments, the first biometric sensor in the at least one biometric sensor is configured to capture biometric data elements associated with a physiological or psychological state of the subject at a predetermined sampling rate, such as a recurring sampling rate, a periodic sampling rate, a non-periodic sampling rate, etc. For instance, in some embodiments, the first biometric sensor captures biometric data elements at a predetermined sampling rate of once every 200 milliseconds or less, once every 160 milliseconds or less, once every 140 milliseconds or less, once every 120 milliseconds or less, once every 100 milliseconds or less, once every 80 milliseconds or less, once every 60 milliseconds or less, once every 40 milliseconds or less, once every 30 milliseconds or less, once every 20 milliseconds or less, or once 10 milliseconds or less. In some embodiments, the first biometric sensor captures biometric data elements at a predetermined sampling rate of once every 200 milliseconds or more, once every 160 milliseconds or more, once every 140 milliseconds or more, once every 120 milliseconds or more, once every 100 milliseconds or more, once every 80 milliseconds or more, once every 60 milliseconds or more, once every 40 milliseconds or more, once every 30 milliseconds or more, once every 20 milliseconds or more, or once 10 milliseconds or more. In some embodiments, the first biometric sensor captures biometric data elements at a predetermined sampling rate between 10 ms and 200 ms, between 10 ms and 150 ms, between 10 ms and 100 ms, between 10 ms and 50 ms, between 25 ms and 200 ms, between 25 ms and 150 ms, between 25 ms and 100 ms, between 25 ms and 50 ms, between 60 ms and 200 ms, between 60 ms and 150 ms, between 60 ms and 100 ms, between 130 ms and 200 ms, or between 130 ms and 150 ms.

In some embodiments, the predetermined sampling rate is constant while the subject is completing the first challenge in the first digital reality scene. In some other embodiments, the predetermined sampling rate is adjustable or variable, e.g., adjusted or varied responsive to the earlier captured biometric data elements. For instance, in an embodiment, the method adjusts (e.g., increases) the predetermined sampling rate when it detects a dramatic variation in biometric measures (e.g., a sudden increase of the heart rate) over a relatively short period of time. In another embodiment, the method adjusts (e.g., decreases) the predetermined sampling rate when it does not detect a change in biometric measures over a relatively long period of time (e.g., a consist and normal heart rate).

In some embodiments, the first biometric sensor captures biometric data elements at a constant predetermined sampling rate while the subject is completing a portion of the first digital reality scene, and at an adjustable or variable predetermined sampling rate while the subject is completing another portion of the first digital reality scene.

In some embodiments, the first biometric sensor captures biometric data elements intermittently while the subject is completing the corresponding first challenge of the first digital reality scene. For instance, as a non-limiting example, in some embodiments, the first biometric sensor starts to capture biometric data elements while the subject speaks in the first digital reality scene and stops collecting biometric data elements while other player character (e.g., object 42-2 of FIG. 6B) in the first digital reality scene speaks, while the method or system provides instruction, or when the subject is not speaking.

Blocks 540-542. Referring to blocks 540-542, in some embodiments, the determining (D) includes determining whether a comparison of the first plurality of biometric data elements against a second baseline characteristic satisfies a second biometric threshold in the at least one biometric threshold. For instance, as a non-limiting example, suppose that the first biometric sensor is a recorder, and the first plurality of biometric data elements is the voice of the subject recorded during at least a portion of the first digital reality scene that manifests the first challenge designed for the first proposed experience associated with the first category. The recorded voice is segmented into one or more utterances. The determining (D) includes determining whether a comparison of the first plurality of biometric data elements against a corresponding threshold baseline characteristic (e.g., an utterance baseline of the subject at a relaxing state, a pitch baseline of the subject, a cadence baseline of the subject, an inflection baseline of the subject, a vernacular baseline of the subject, a grammar baseline of the subject, etc.) satisfies a first biometric threshold (e.g., a relative utterance threshold, a relative pitch threshold, a relative cadence threshold, a relative inflection threshold, a relative vernacular threshold, a relative grammar threshold, etc.) and against a second baseline characteristic (e.g., a decibel level or pitch baseline of the subject at a relaxing state, a PDF entropy baseline of the subject, etc.) satisfies a second biometric threshold (e.g., a relative decibel level or pitch threshold, a relative PDF entropy threshold, etc.).

It should be noted that in embodiments where the first plurality of biometric data elements is a recorded voice, the first or second biometric threshold can be any threshold related to utterance, including but not limited to, a relative utterance threshold, a relative assertiveness threshold, a relative decibel level threshold, a relative pitch threshold, or any combination thereof. For instance, in an embodiment, the first biometric threshold is a required minimal change in a number of utterances compared to an utterance baseline of the subject, and the second biometric threshold is (i) a required minimal change in assertiveness compared to an assertiveness baseline of the subject, (ii) a required minimal change in decibel level compared to a decibel level baseline of the subject, and/or (iii) a required minimal change in pitch compared to a pitch baseline of the subject, during the first digital reality scene that manifests the first challenge designed for the first proposed experience associated with the first category. In another embodiment, the first biometric threshold is (i) a required minimal change in assertiveness compared to an assertiveness baseline of the subject, (ii) a required minimal change in decibel level compared to a decibel level baseline of the subject, and/or (iii) a required minimal change in pitch compared to a pitch baseline of the subject, and the second biometric threshold is a required minimal change in a number of utterances compared to an utterance baseline of the subject, during the first digital reality scene that manifests the first challenge designed for the first proposed experience associated with the first category. However, the present disclosure is not limited thereto.

Blocks 546-548. Referring to blocks 546-548, in some embodiments, the at least biometric data element captured in the obtaining (C) includes a fourth plurality of biometric data elements captured by a second biometric sensor (e.g., sensor 110-2 of FIG. 1) in the at least one biometric sensor. The fourth plurality of biometric data elements is different than the first plurality of biometric data elements.

For instance, as a non-limiting example, the first biometric sensor is a recorder and the first plurality of biometric data elements is a recorded voice captured by the recorder, whereas the second biometric sensor is an eye-tracking sensor and the fourth plurality of biometric data elements is an eye-tracking data (e.g., images) captured by the eye-tracking sensor, or vice versa. In such embodiments, any threshold related to voice or eye-tracking can be used. For instance, as a non-limiting example, one of the first and third biometric thresholds is (i) a required minimal change in a number of words compared to a word baseline of the subject, (ii) a required minimal change in a number of utterances compared to an utterance baseline of the subject, (iii) a required minimal change in assertiveness compared to an assertiveness baseline of the subject, (iv) a required minimal change in decibel level compared to a decibel level baseline of the subject, and/or (v) a required minimal change in pitch compared to a pitch baseline of the subject, and the other of the first and third biometric thresholds is a required minimal change in a length of eye contact compared to an eye contact baseline of the subject, during the first digital reality scene that manifests the first challenge designed for the first proposed experience associated with the first category.

As another non-limiting example, the first biometric sensor is a recorder and the first plurality of biometric data elements is a recorded voice captured by the recorder, whereas the second biometric sensor is a heart rate sensor and the fourth plurality of biometric data elements is a heart rate data captured by the heart rate sensor, or vice versa. In such embodiments, any threshold related to voice or heart rate can be used. For instance, as a non-limiting example, one of the first and third biometric thresholds is (i) a required minimal change in a number of words compared to a word baseline of the subject, (ii) a required minimal change in a number of utterances compared to an utterance baseline of the subject, (iii) a required minimal change in assertiveness compared to an assertiveness baseline of the subject, (iv) a required minimal change in decibel level compared to a decibel level baseline of the subject, and/or (v) a required minimal change in pitch compared to a pitch baseline of the subject, and the other of the first and third biometric thresholds is a required minimal change in heart rate compared to a heart rate baseline of the subject.

As a further non-limiting example, the first biometric sensor is a heart rate sensor and the first plurality of biometric data elements is a heart rate data captured by the heart rate sensor, whereas the second biometric sensor is a heart rate sensor and the fourth plurality of biometric data elements is a heart rate data captured by the heart rate sensor. In such embodiments, any threshold related to heart rate or eye-tracking can be used. For instance, as a non-limiting example, one of the first and third biometric thresholds is a required minimal change in heart rate compared to a heart rate baseline of the subject, and the other of the first and third biometric thresholds is a required minimal change in a length of eye contact compared to an eye contact baseline of the subject, during the first digital reality scene that manifests the first challenge designed for the first proposed experience associated with the first category.

In some embodiments, the determining (D) includes determining whether a comparison of the fourth plurality of biometric data elements against a third baseline characteristic satisfies a third biometric threshold in the at least one biometric threshold. For instance, as a non-limiting example, in the embodiment where the fourth plurality of biometric data elements is an eye-tracking data captured by the eye-tracking sensor, the determining (D) determines whether a comparison of the eye-tracking data (e.g., length of eye contact) against an eye contact baseline characteristic (e.g., length of eye contact of the subject at a relaxing state) satisfies an eye-contact threshold. As another non-limiting example, in the embodiment where the fourth plurality of biometric data elements is a heart rate data captured by the heart rate sensor, the determining (D) determines whether a comparison of the heart rate data (e.g., heart beats per minute) against a heart rate baseline characteristic (e.g., heart beats per minute of the subject at a relaxing state) satisfies a heart rate threshold.

In some embodiments, the method includes determining, if the first challenge is determined to be successfully completed, whether the at least one gate criterion associated with the first category is satisfied. In some embodiments, this determination if the first challenge is determined to be successfully completed is based at least in part on an outcome of the determining whether the first set of biometric data elements satisfies the at least one biometric threshold associated with the first proposed experience for of the first challenge, in which the at least one biometric threshold includes a first biometric threshold, to assess whether the first challenge is successfully completed by satisfying the at least one biometric threshold associated with the first proposed experience for the first challenge, in which the first set of biometric data elements includes a first subset of biometric data elements captured by a first biometric sensor in the at least one biometric sensor; whether the first set of biometric data elements satisfies a corresponding first threshold baseline characteristic; whether the at least one gate criterion associated with the first category is satisfied; or a combination thereof. For instance, as a non-limiting example, suppose the at least one gate criterion associated with the first category includes a single gate criterion that requires the subject to successfully complete a minimal number (e.g., 3, 4 or 5) of challenges, such as a threshold number of exposure challenges, a threshold number of CBT challenges (e.g., a threshold number of reframed thoughts, etc.), or the like. In such embodiments, the determining determines whether the number of challenges that the subject has successfully completed meets or exceeds the required minimal number of challenges. As another non-limiting example, suppose the at least one gate criterion associated with the first category includes a first gate criterion and a second gate criterion. The first gate criterion requires the subject to successfully complete a threshold number of challenges and the second gate criterion that requires the subject to successfully complete one or more specific challenges (e.g., challenge 26-2) associated with the first category. In such embodiments, the determining (E) determines not only whether the number of challenges that the subject has successfully completed meets or exceeds the required minimal number of challenges, but also whether the subject has successfully completed each of the required one or more specific challenges.

Block 552. Referring to block 552, the method includes (E) determining, if each gate criterion in the at least one respective gate criterion associated with the first category is satisfied, a second category in the plurality of categories for the subject to perform next based at least in part on an outcome of the determining (D) (e.g., successful completion of the first set of biometric data elements satisfying the at least one biometric threshold associated with the first proposed experience for of the first challenge, the at least one biometric threshold includes a first biometric threshold, satisfying the at least one biometric threshold associated with the first proposed experience for the first challenge, in which the first set of biometric data elements includes a first subset of biometric data elements captured by a first biometric sensor in the at least one biometric sensor; successful completion of whether the first set of biometric data elements satisfies a corresponding first threshold baseline characteristic; and successful completion of whether the at least one gate criterion associated with the first category is satisfied), thereby implementing an exposure progression that improves the ability of the subject to manage the psychiatric or mental condition of the subject. For instance, as a non-limiting example, suppose that the obtained plurality of categories for the subject is a set of three categories A, B and C, and that category A is the first category that the subject has been successfully completely (e.g., each gate criterion in the at least one respective gate criterion associated with the first category is satisfied). The determining (E) determines whether category B or category C should be the second category for the subject to perform next.

The determining (E) of a second category for the subject to perform next is based at least in part on the determining (D) of whether the at least one biometric data element satisfies the at least one biometric threshold of the first challenge and the determining (E) of whether the at least one gate criterion associated with the first category is satisfied. For instance, in some embodiments, the determining (E) of a second category for the subject to perform next is based not only on the number of challenges that the subject has successfully completed, but also on how well the subject has completed these challenges (e.g., meets the requirements, exceeds some requirements, exceeds most requirements, exceeds all requirements) and/or how much improvement that the subject has achieved through these challenges (e.g., merely, moderate, significant). In some embodiments, the determining (E) of a second category for the subject to perform next is based not only on whether the subject has successfully completed each of the required one or more specific challenges, but also on any additional challenges that the subject has intended or successfully completed. In some embodiments, the determining (E) of a second category for the subject to perform next is based, additionally or optionally, on other substances, including but not limited to, performance of the subject during other educational or therapeutical challenge, performance of a population of users during the same challenges, or the like. As such, the method of the present disclosure not only provides an exposure progression tailored to each subject, but also personalizes the timing and/or nature of the exposure practice. It builds or revises a personal exposure progression dynamically, based at least in part on the level of success that the subject has had in one or more social challenges.

Blocks 554-556. Referring to block 554-556, in some embodiments, the determining (E) of a second category for the subject to perform next includes (E.1) assessing whether a category immediately subsequent to the first category in the initial exposure progression (e.g., an initial exposure progression based on the assessment from the subject and/or other data as exemplified by at least block 480) is appropriate for the subject to perform next. In some embodiments, the determining (E) of a second category for the subject to perform next also includes (E.2) presenting, if the immediately subsequent category in the initial exposure progression is appropriate for the subject to perform next, the immediately subsequent category in the initial exposure progression as the second category for the subject to perform. In some embodiments, the determining (E) of a second category for the subject to perform next further includes (E.3) recommending, if the immediately subsequent category in the initial exposure progression is inappropriate for the subject to perform next, a category other than the immediately subsequent category in the initial exposure progression as the second category for the subject to perform next.

For instance, as a non-limiting example, suppose that the obtained plurality of categories for the subject is a set of three categories A (e.g., an exposure category), B (e.g., a CBT category), and C (e.g., a mindfulness category), which is in an initial exposure progression with category A as the first category immediately followed by category B and then category C. If it is determined that the subject has successfully completed category A (the first category in the initial exposure progression), the method determines, in the assessing (E.1), whether category B (the category immediately subsequent to category A in the initial exposure progression) is appropriate for the subject to perform next. If it is determined that category B is appropriate for the subject to perform next, the method presents, in the presenting (E.2), category B (e.g., on the display) for the subject to perform. If it is determined that category B is not appropriate for the subject to perform next, the method recommends, in the recommending (E.3) category C or other educational/therapeutical challenge (e.g., mindfulness or cognitive reframing challenge) for the subject to perform. The recommendation can be done, for instance, by placing an indicator (e.g., text, graphic or the like) on the display, through an audio or the like.

Block 558. Referring to block 558, in some embodiments, the method further includes (I) repeating, if a gate criterion in the at least one respective gate criterion associated with the first category is not satisfied, the presenting (B), the obtaining (C), and the determining (D) one or more times for other challenges associated with the first category. For instance, as a non-limiting example, suppose that the at least one gate criterion associated with the first category includes a first gate criterion that requires the subject to successfully complete a minimal number of three challenges. If it is determined that the subject has successfully completed just one challenge (e.g., challenge 26-1) associated with the first category, then the repeating (J) repeats the presenting (B), the obtaining (C), and the determining (D) at least two times for other challenges (e.g., challenge 26-2, challenge 26-3) associated with the first category. If it is determined that the subject has successfully completed two challenges (e.g., challenge 26-1, challenge 26-2), then the repeating (I) repeats the presenting (B), the obtaining (C), and the determining (D) at least one time for another challenge (e.g., challenge 26-3) associated with the first category.

As another non-limiting example, suppose that the at least one gate criterion associated with the first category includes a second gate criterion that requires the subject to successfully complete one or more specific challenges (e.g., challenge 26-4) associated with the first category. If it is determined that the subject has not successfully completed each of the required one or more specific challenges, the method would inform the subject the requirement and recommend the required specific challenges to the subject, even if the subject has successfully completed the required minimal number of challenges associated with the first category. In some embodiments, upon selection of the one or more required challenges (e.g., challenge 26-4) by the subject or a health care worker associated with the subject, the repeating (I) repeats the presenting (B), the obtaining (C), and the determining (D) one or more times for the one or more required challenges associated with the first category.

Blocks 560-574. Referring to 560-570, in some embodiments, the method further includes (J) recommending, if the first challenge is determined to be unsuccessfully completed, a challenge for the subject to perform next. The recommended challenge can be, but is not limited to, a challenge that poses an equal or less challenging challenge than the first challenge of the first category, the same first challenge designed for the first proposed experience of the first category, a challenge designed for a different proposed experience of the first category, a challenge designed for a proposed experience of a different category (e.g., a second category) in the plurality of categories, a challenge not associated with any category in the plurality of categories, or the like. In some embodiments, the commendation is based at least in part on the performance of the subject on the first challenge and/or other challenge(s).

For instance, as a non-limiting example, suppose that the plurality of category includes a first category associated with four challenges (e.g., challenge 26-1, challenge 26-2, challenge 26-3 and challenge 26-4) and a second category associated with three challenges (e.g., challenge 26-5, challenge 26-6 and challenge 26-7) and that challenge 26-2 poses an equal or less challenging challenge than challenge 26-1. In an embodiment, if it is determined that challenge 26-1 is not successfully completed, the method recommends, in the recommending (K), challenge 26-2 for the subject to perform next. In another embodiment, if it is determined that challenge 26-1 is not successfully performed, the method recommends, in the recommending (K), challenge 26-1 for the subject to perform next (i.e., repeating the same challenge one or more times). In a further embodiment, if it is determined that challenge 26-1 is not successfully performed, the method recommends, in the recommending (J), recommends challenge 26-5, which is not associated with the first category, for the subject to perform next. In an alternative embodiment, the method recommends, in the recommending (J), a challenge for the subject to perform next.

The recommended challenge can be, but is not limited to, a mindfulness challenge, a cognitive reframing challenge, or the like. In some embodiments, the challenge is a unique mindfulness challenge customized for the first category, a universal mindfulness challenge that is accessible from each category in the plurality of categories, a unique cognitive reframing challenge customized for the first category, or a universal cognitive reframing challenge that is accessible from each category in the plurality of categories.

The recommendation can be presented to the subject in any suitable ways. For instance, in some embodiments, the recommendation is presented in a text, a graphic, an audio (e.g., spoken by a digital reality host), or a combination thereof. Through recommendation, the systems, methods, and devices of the present disclosure improves the likelihood of engagement and/or a better clinical outcome.

Block 576. Referring to block 576, in some embodiments, the method further includes (K) repeating, in response to selection of the recommended challenge, the presenting (B), and the obtaining (C), and the determining (D) for the recommended challenge. For instance, in response to selection of the recommended challenge, the method presents, similar to that disclosed herein and exemplified by at least block 480, the digital reality scene that manifests the recommended challenge. In coordination with the presenting of the digital reality scene that manifests the recommended challenge, the method obtains, similar to that disclosed herein and exemplified by at least block 482, a plurality of data elements from all or a subset of sensors in the plurality of sensors, where the at least one biometric sensor captures at least one biometric data element associated with the subject while the subject is completing the recommended challenge. Based on the at least one biometric data element captured while the subject is completing the recommended challenge, the method determines, similar to that disclosed herein and exemplified by at least block 484, whether the recommended challenge is successfully completed.

Block 578. Referring to block 578, in some embodiments, the method further includes (L) presenting, in response to selection of the challenge and on the display, a second digital reality scene that manifests the challenge. For instance, in embodiments where the recommended challenge is a mindfulness challenge, the method presents a digital reality scene that manifests the mindfulness challenge, e.g., a digital reality scene that guide the subject to focus on the present moment. In some embodiments, the digital reality scene that manifests the mindfulness challenge is a mediation scene, such as the digital reality scene illustrated in FIG. 6B. However, the present disclosure is not limited thereto. For instance, in some embodiments, the recommended challenge is a cognitive challenge manifested by a digital reality scene such as the digital reality scene illustrated in FIG. 6C.

Block 580. Referring to block 580, in some embodiments, the method further includes (M) obtaining, in coordination with the presenting (L) of the second digital reality scene that manifests the challenge, a third plurality of data elements from a subset of sensors in a plurality of sensors. The third plurality of data elements includes a third plurality of biometric data elements associated with the subject and captured (e.g., by the first biometric sensor in the at least one biometric sensor) while the subject is completing the second digital reality scene that manifests the challenge. For instance, as a non-limiting example, suppose that the corresponding threshold baseline characteristic is a heart rate of the subject captured during a training or educational challenge at a happy place, the first plurality of biometric data elements from the obtaining (C) is a heart rate of the subject captured while the subject is completing the first challenge in the first digital reality scene, and the third plurality of biometric data elements is a heart rate captured while the subject is completing a mindfulness challenge.

In some embodiments, the method also includes (N) determining a change or improvement by comparing the third plurality of biometric data elements against the corresponding threshold baseline characteristic or against the first plurality of biometric data elements from the obtaining (C). In some embodiments, the comparison of the third plurality of biometric data elements against the corresponding threshold baseline characteristic or against the first plurality of biometric data elements from the obtaining (C) reveals the effectiveness of the mindfulness challenge, and provides insight for improving the likelihood of engagement and/or a better clinical outcome by using other challenges along with social challenges.

It should be noted that the present disclosure is not limited to a mindfulness challenge and heart rate biometric measures. Any suitable educational or therapeutical program (e.g., introduction, training, cognitive reframing) can be a challenge and any suitable biometric data (e.g., voice, eye movement) can be captured during the educational or therapeutical program. By comparing the biometric data obtained during educational or therapeutical program against a baseline or the biometric data elements obtained during the first challenge, the method can determine the effect of the educational or therapeutical program.

Blocks 582-584. Referring to blocks 582-584, in some embodiments, the method further includes (O) presenting, on the display prior to the determining (E), a subjective evaluation option, e.g., asking the subject whether the subject would like to conduct an evaluation on the challenge(s)/category that the subject has completed, the challenge(s)/category that the subject has not completed, or both. In some embodiment, the method further includes (P) performing, in response to selection of the subjective evaluation option, a subjective evaluation.

In some embodiments, the subjective evaluation is performed through a user interface of a client device (e.g., user interface 306 of client device 300-1 of FIG. 3). In some other embodiments, the subjective evaluation is performed through a web browser in communication with the client device or digital reality system 200. In some embodiments, the subjective evaluation is self-administered by the subject without supervision of a health care worker (e.g., a medical practitioner) associated with the subject. In some other embodiments, the subjective evaluation is performed by the subject but with supervision of a health care worker associated with the subject.

Referring to FIGS. 8A-8C, in some embodiments, the subjective evaluation includes a plurality of prompts for the subject to answer. For instance, in some embodiments, the subjective evaluation includes more than 2, more than 5, more than 10, more than 15, more than 20, more than 30, more than 50, more than 100, or more than 200 prompts for the subject to answer. In some embodiments, the subjective evaluation includes about twelve prompts for a subject to answer. In alternative embodiments, the subjective evaluation includes about twenty-four prompts.

In some embodiments, the subjective evaluation is based on a Minimal Clinically Important Difference (MCID), a Clinical Global Impression Scale of Improvement (CGI), a Patient Global Impression Scale of Improvement (PGI), a Liebowitz Social Anxiety Scale (LSAS), or a combination thereof. In some embodiments, the MCID, CGI, PGI, and/or LSAS is a part of assessment module 12 of FIG. 2A.

The MCID refers to the smallest benefit of value to the subject. It captures both the magnitude of the improvement and the value the subject places on the change. The MCID defines the smallest amount an outcome must change to be meaningful to the subject. Additional details and information regarding MCID assessments can be found at Kaplan, R., 2005, "The Minimally Clinically Important Difference in Generic Utility-based Measures," COPD: Journal of Chronic Obstructive Pulmonary Disease, 2(1), pg. 91, which is hereby incorporated by reference in its entirety for all purposes.

The CGI evaluations a severity and/or changes in an ability of the subject to manage the psychiatric or mental condition. Additional details and information regarding CGI scale assessments can be found at Pérez et al., 2007, "The Clinical Global Impression Scale for Borderline Personality Disorder Patients (CHI-BPD): A Scale Sensible to Detect Changes," Actas Españolas de Psiquiatria, 35(4), pg. 229, which is hereby incorporated by reference in its entirety for all purposes.

The PGI provides a patient rated format, as opposed to a clinician rated format of the CGI scale assessment. Additional details and information regarding the PGI assessment can be found at Faith et al., 2007, "Twelve Years-Experience with the Patient Generated Index (PGI) of Quality of Life: A Graded Structured Review," Quality of Life Research, 16(4), pg. 705, which is hereby incorporated by reference in its entirety for all purposes.

The LSAS assesses social anxiety disorder in clinical research and practice. It includes a self-reported (LSAS-SR) and a clinician-administered (LSAS-CA). Additional details and information regarding an LSAS assessment is found at Rytwinski et al., 2009, "Screening for Social Anxiety Disorder with the Self-Report Version of the Liebowitz Social Anxiety Scale," Depression and Anxiety, 26(1), pg. 34, which is hereby incorporated by reference in its entirety for all purposes.

In some embodiments, the determining (E) of a category in the plurality of categories for the subject to perform next is based, at least in part, on an outcome of the subjective evaluation. For instance, as a non-limiting example, suppose that the obtained plurality of categories for the subject is a set of three categories A, B and C. The three categories are initially ranked, by the subject, a health care worker associated with the subject, and/or the model, in the order of category A followed by category B and then category C before the subject starts the program. After the subject has successfully completed the required challenges and/or other requirements associated with category A, the subjective evaluation indicates that the subject considers category C less challenging than category B. In determining the category for the subject to perform next, the method takes the subjective evaluation into consideration. For instance, in an embodiment, upon confirmation of the subjective evaluation by a health care worker associated with the subject and/or the model, the method determines category C, instead of category B, to be the next category for the subject to perform. The method 400, based at least in part on the subjective evaluation and/or other factors (e.g., the level of success that the subject have had in one or more social challenges, evaluation or confirmation of a health care worker associated with the subject), builds or revises a personal exposure progression dynamically and personalizes the timing and/or nature of the exposure practice.

It should be noted that the presenting (O) of a subjective evaluation option and the performing (P) of the subjective evaluation option can be conducted in other times. For instance, as a non-limiting example, they can be conducted after a subject has successfully completed one or more challenges associated with a category (e.g., the first, second, or third category) but has not yet successfully completed all of the requirement associated with the category. As another non-limiting example, they can be conducted after a subject fails to successfully complete a challenge associated with a category one or more times. As a further non-limiting example, in some embodiments, the method allows the subject to start, terminate or resume the subjective evaluation at any time when desired.

The subjective evaluation can be used in various ways. For instance, it can be used for ranking or re-ranking the experiences associated with a category in the plurality of categories, for ranking or re-ranking the plurality of categories, for recommending alternative or additional challenges or categories, for recommending educational or therapeutical challenges (e.g., mindfulness challenges, recognitive reframing challenges, etc.), or a combination thereof. FIG. 8D illustrates a non-limiting example of the use of the subjective evaluation, e.g., recommending a goal, a challenge, etc.

Block 586. Referring to block 586, in some embodiments, the method further includes (Q) repeating the presenting (B), the obtaining (C) and the determining (D) for a digital reality scene that manifests a challenge designed for a proposed experience of the second category; and (R) repeating the determining (E) for the second category.

For instance, as a non-limiting example, suppose that the second category is associated with experience **26-*j*, and that experience 26-*j* is associated with digital reality scene 40-*j* that manifests challenge 26-*j* designed for experience 26-*j* of the second category. The method presents, similar to that disclosed herein and exemplified by at least block 480, digital reality scene 40-*j* that manifests challenge 26-*j*. In coordination with the presenting of digital reality scene 40-*j*, the method obtains, similar to that disclosed herein and exemplified by at least block 482, a plurality of data elements from all or a subset of sensors in the plurality of sensors, where the at least one biometric sensor captures at least one biometric data element associated with the subject while the subject is completing challenge 26-*j*. Based on the at least one biometric data element captured while the subject is completing challenge 26-*j*, the method determines, similar to that disclosed herein and exemplified by at least block 484, whether challenge 26-*j* is successfully completed. If it is determined that challenge 26-*j* is successfully completed, the method determines, similar to that disclosed herein and exemplified by at least block 550**, whether the at least one gate criterion associated with the second category is satisfied.

Figure 7A:
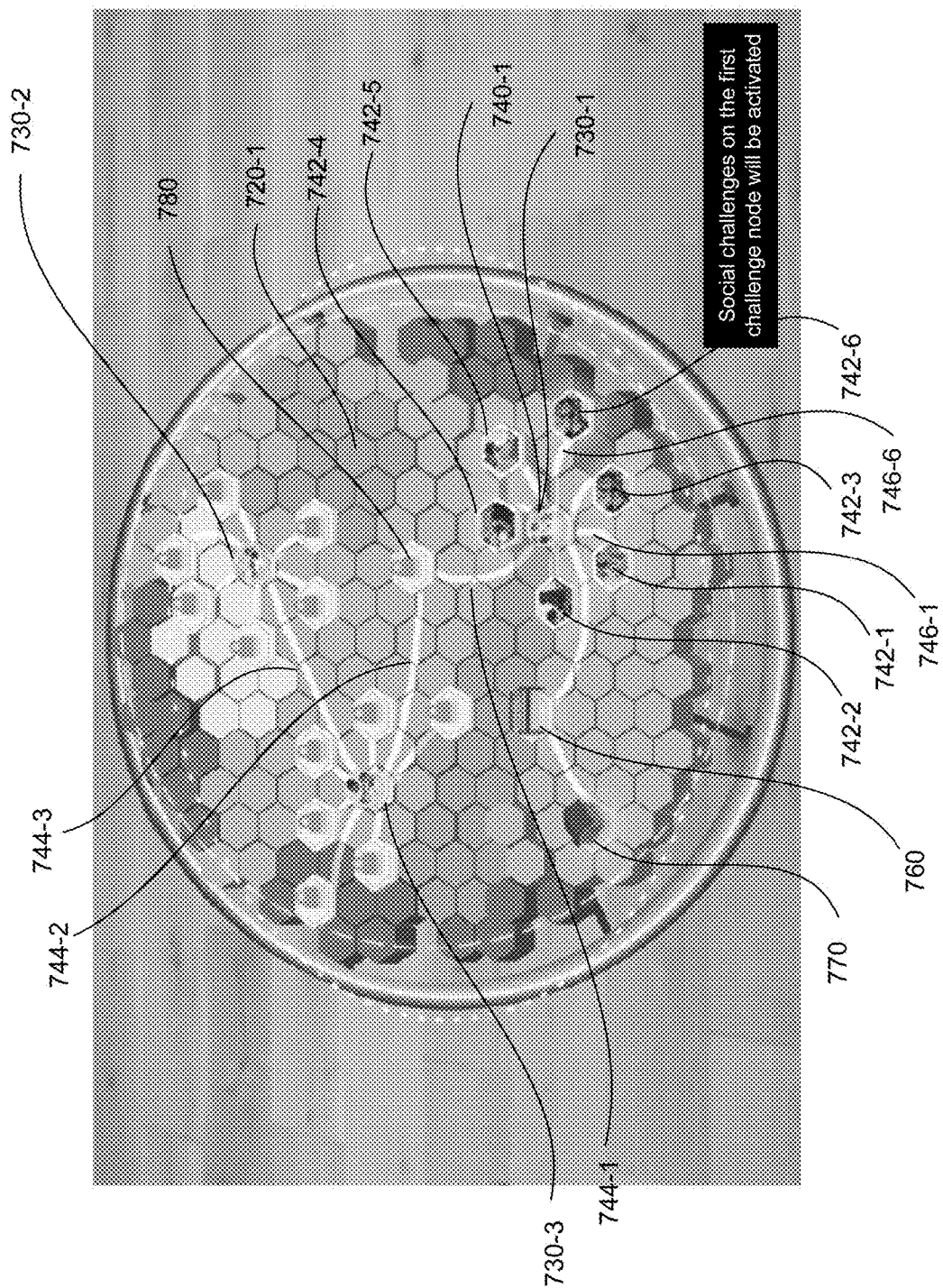
FIG. 7A illustrates an exemplary digital reality scene for presenting an initial category hierarchy in a graph that includes a proposed subject experience progression, in accordance with an embodiment of the present disclosure.
Figure 7B:
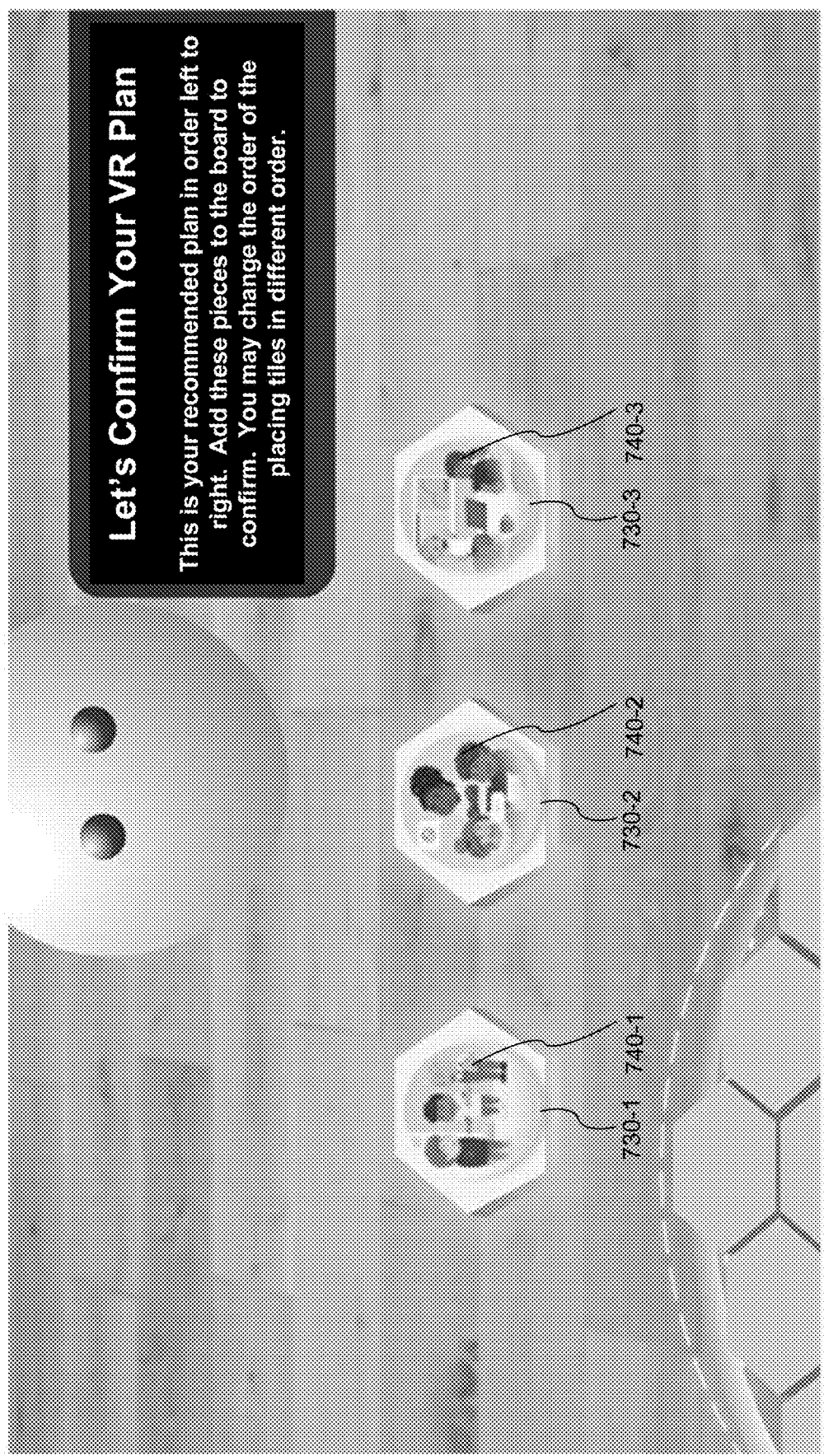
FIG. 7B illustrates an exemplary digital reality scene for presenting a recommended category hierarchy and allowing a user to personalize the category hierarchy, in accordance with an embodiment of the present disclosure.
Figure 9A:
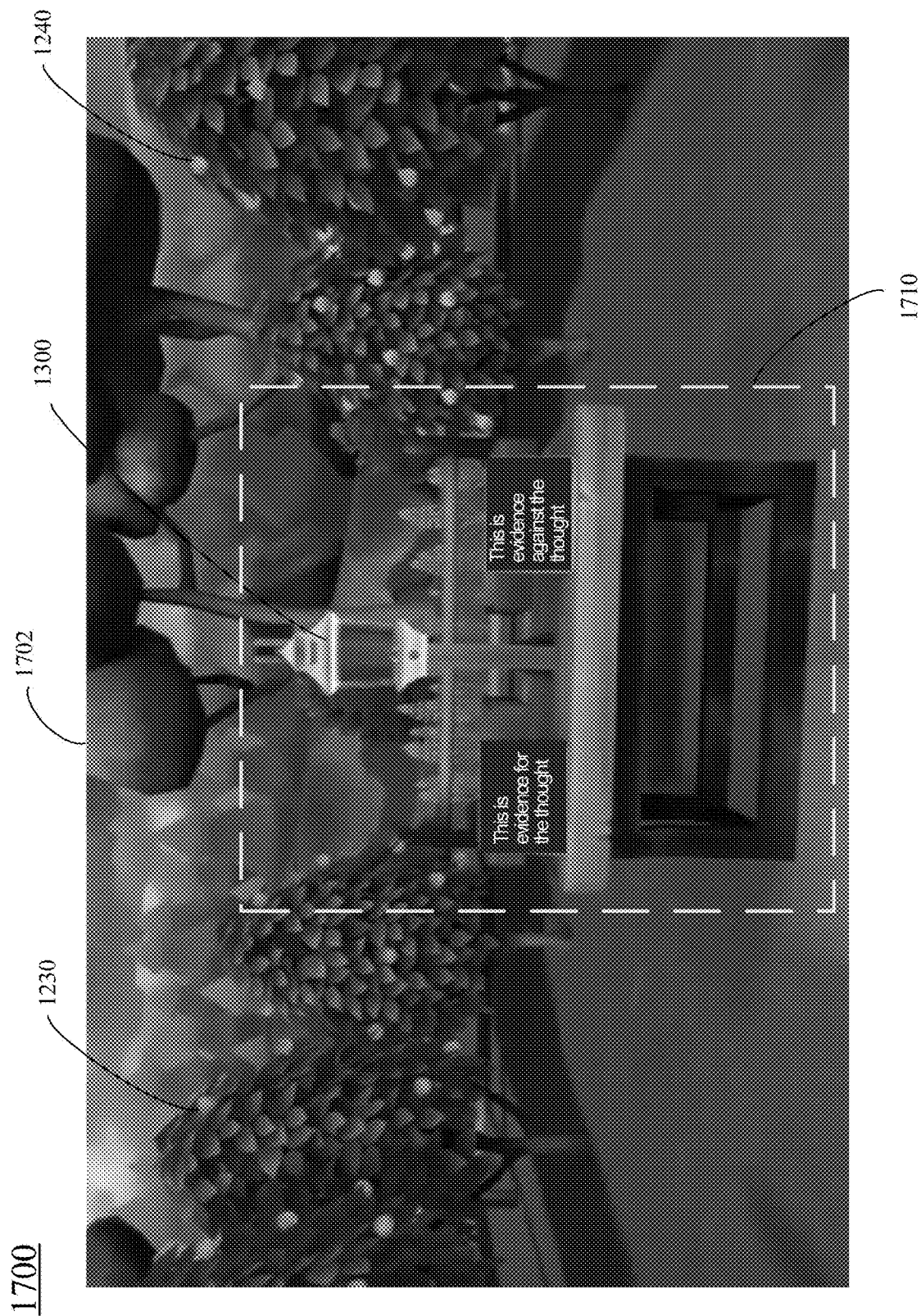
FIG. 9A illustrates another exemplary digital reality scene for cognitive reframing training, in accordance with an embodiment of the present disclosure.
Figure 9B:
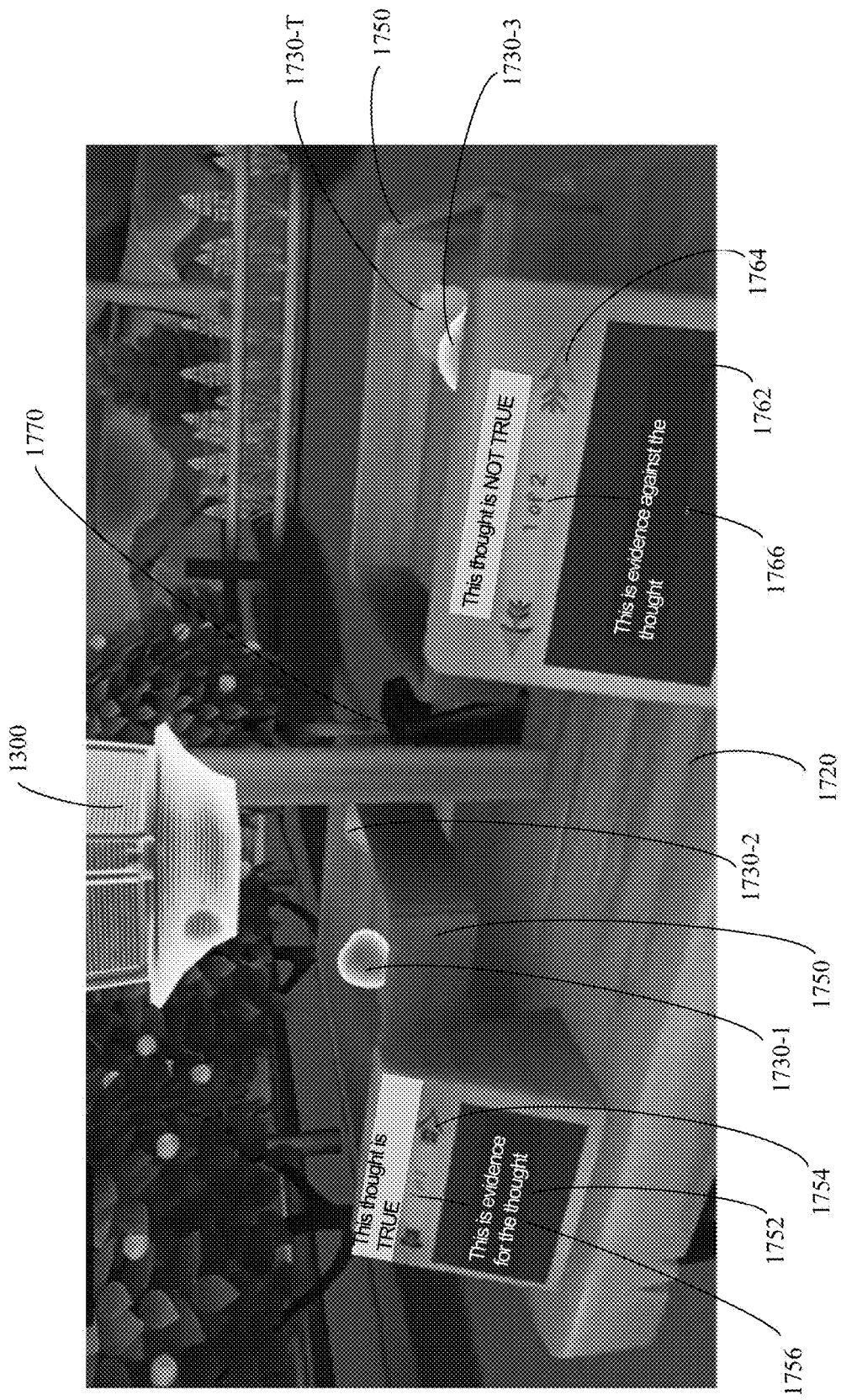
FIG. 9B illustrates yet another exemplary digital reality scene for cognitive reframing training, in accordance with an embodiment of the present disclosure.
Figure 9C:
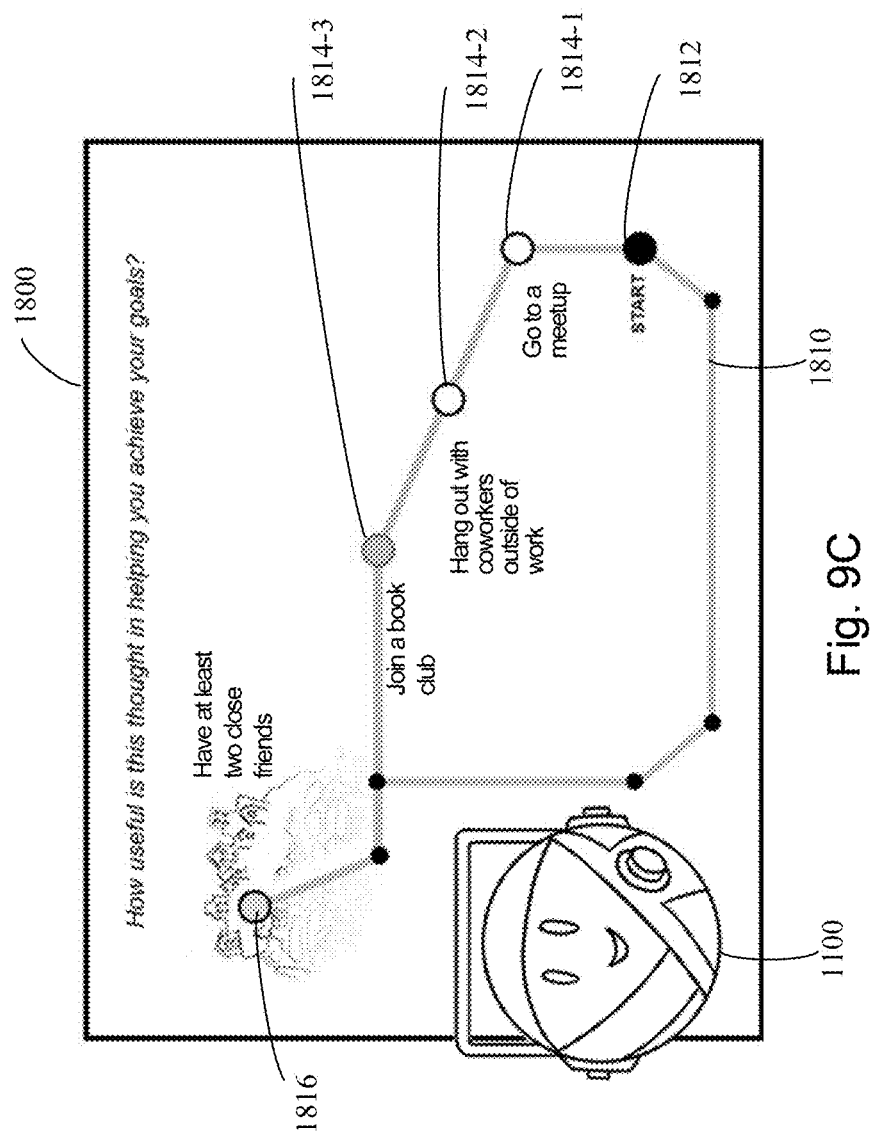
FIG. 9C illustrates yet another exemplary digital reality scene for cognitive reframing training, in accordance with an embodiment of the present disclosure.
Figure 9D:
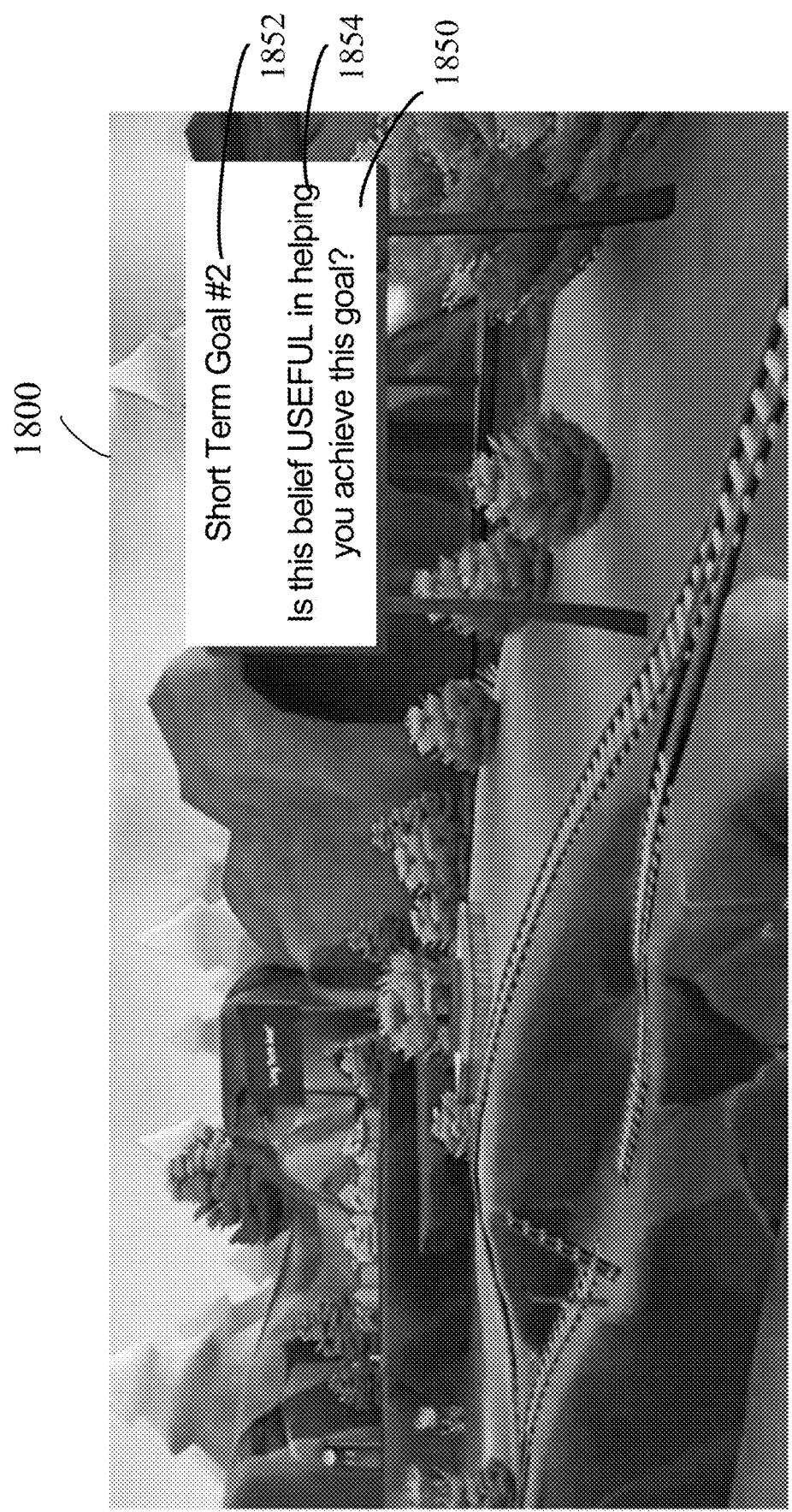
FIG. 9D illustrates yet another exemplary digital reality scene for cognitive reframing training, in accordance with an embodiment of the present disclosure.
Figure 11A:
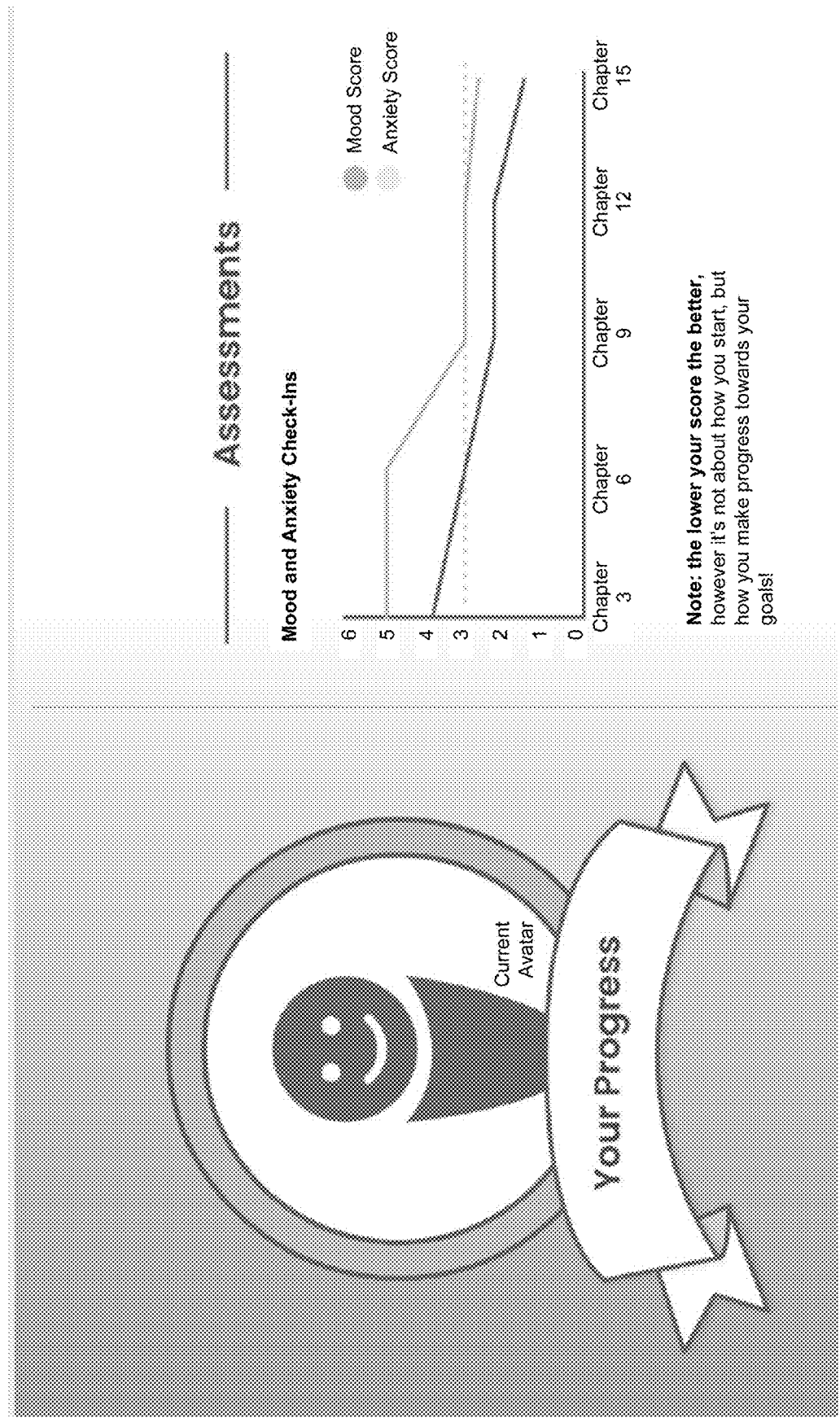
FIGS. 11A and 11B illustrates an exemplary user interface of a DR scene or a client application configured present progress of a subject within an interactive DR activity, in accordance with some embodiments of the present disclosure.
Figure 11B:
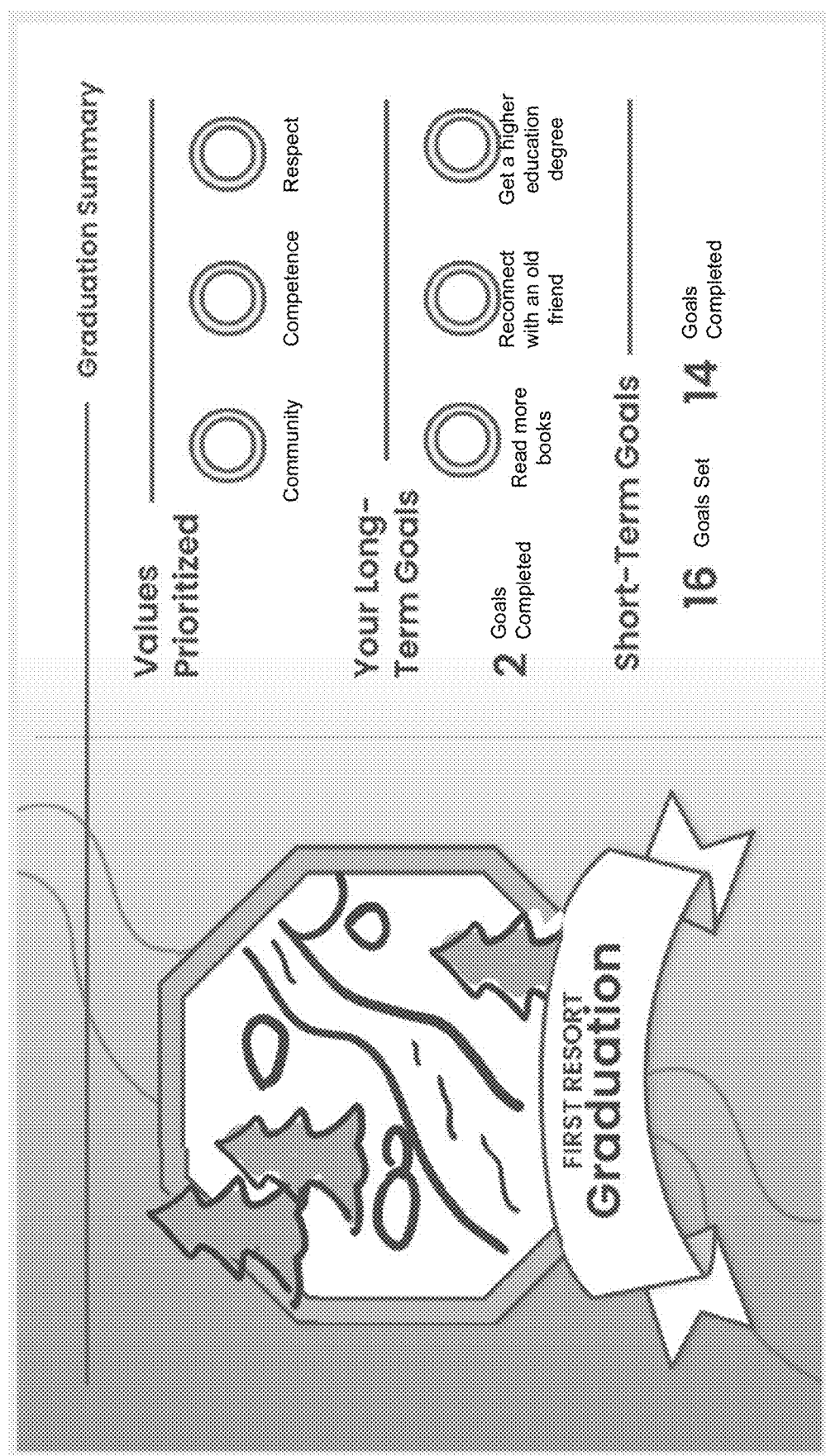

Block 588. Referring to block 588, in some embodiments, the plurality of categories obtained in the obtaining (A) is originally arranged in an initial category hierarchy, thereby forming an initial exposure progression. For instance, referring to FIG. 7A, in some embodiments, the obtained plurality of categories for a subject includes a first category 740-1, a second category 740-2 and a third category 740-3. Among these three categories, the first category 740-1 is considered least challenging for the subject, the third category 740-3 is considered more challenging for the subject, and the second category 740-2 is considered most challenging for the subject. The plurality of categories is originally arranged in an initial category hierarchy. For instance, FIG. 7B illustrates the first, second and third categories placed in an order. The plurality of categories arranged in an initial category hierarchy forms an initial exposure progression.

In some embodiments, the initial category hierarchy is set by (i) a system administrator, (ii) the subject, (iii) a health care worker associated with the subject, (iv) a model, or (v) a combination thereof. For instance, as a non-limiting example, in some embodiments, whether a category is considered more or less challenging is determined from an assessment and/or subjective evaluation, e.g., through the assessment module 12 that facilitates obtaining an assessment and/or subjective evaluation from the subject. By responding to the assessment, the subject provides input to the selection and order of categories and at least helps in the formation of the initial exposure progression. As another non-limiting example, in some embodiments, whether a category is considered more or less challenging is determined by the medical practitioner associated with the subject, such as by having the medical practitioner evaluate some or all of the assessment obtained by the subject and generating an initial exposure progression.

As yet another non-limiting example, in some embodiments, the initial category progression is generated at least in part by a model. For instance, in some embodiments, the model obtains at least the assessment from the subject and, optionally or additionally, other data (e.g., user profile data of FIG. 2A), and generates the initial exposure progression based on the assessment from the subject and/or other data. In some embodiments, the model obtains a subjective rating from highest to lowest (e.g., user-provided rating of "mild," "moderate," "severe," or "no reaction), an objective rating from highest to lowest (e.g., a ranking from most effective to least effective as determined by a digital reality system 200 or a medical practitioner associated with the subject) and/or other data, and generates the initial exposure progression based on the subjective rating, objective rating, and/or other data. In some embodiments, the medical practitioner and the model generate the initial exposure progression, such as by having the medical practitioner provide input and/or supervision for the model.

As yet another non-limiting example, in some embodiments, a recommended exposure progression is generated by (i) a system administrator, (ii) the subject, (iii) a health care worker associated with the subject, (iv) a model, or (v) a combination thereof. The recommended exposure progression is presented to the subject. In some embodiments, the subject either confirms the recommended exposure progression, or changes the order of the categories to create an initial exposure progression that is different than the recommended exposure progression. For instance, by way of example, FIG. 7B illustrates a recommended exposure progression with first category 740-1, second category 740-2, and third category 740-3 placed in an order from the left to the right in the figure. FIG. 7A illustrates the change in the order of the categories made by the subject, showing an initial exposure progression with an order of first category 740-1 followed by third category 740-3 and then second category 740-2.

Blocks 590-592. Referring to blocks 590-592, in some embodiments, the method further includes (F) presenting a graph on the display to represent an initial instance of the exposure progression (e.g., graph of user interface 700 of FIG. 7A, graph of user interface 1800 of FIG. 9D, graph of user interface 1400 of FIG. 12A, graph of user interface 1400 of FIG. 12B, etc.). The presenting (F) is generally performed prior to the presenting (B) of the first digital reality scene that manifests the first challenge designed for the first proposed experience of the first category.

The graph includes a plurality of nodes and a plurality of edges. For instance, as a non-limiting example, FIG. 7B illustrates three nodes, i.e., node 730-1, node 730-2, and node 730-3. For each respective node in the plurality of nodes, the graph further includes a corresponding plurality of experience graphics displayed adjacent to the respective node. For instance, as a non-limiting example, FIG. 7A illustrates experience graphics, e.g., experience graphic 742-1, experience graphic 742-2, experience graphic 742-3, . . . , displayed adjacent to node 730-1. An experience graphic represents a proposed experience. For instance, in some embodiments, experience 742-1 represents experience 24-1, and experience graphic 742-2 represents experience 24-2. FIG. 7A also illustrates a plurality of experience graphics displayed adjacent to node 730-2 and a plurality of experience graphics displayed adjacent to node 730-3.

In the graph, each respective node in the plurality of nodes corresponds to a respective category in the plurality of categories. For instance, in the illustrated embodiments, node 730-1 corresponds to (e.g., represents) first category 740-1 (e.g., first exposure category, first CBT category, etc.), node 730-2 corresponds to second category 740-2 (e.g., second exposure category, first mindfulness category, etc.), and node 730-3 corresponds to third category 740-3 (e.g., second mindfulness category, second CBT category, etc.).

In the graph, each respective node in the plurality of nodes is also associated with a corresponding plurality of proposed experiences. For instance, as a non-limiting example, node 730-1 is associated with a first experience 24-1 (e.g., meeting strangers at a first party), a second experience 24-2 (e.g., meeting strangers at a second party), a third experience 24-3 (e.g., meeting strangers at a wedding reception), a fourth experience 24-4 (e.g., meeting strangers at a work event), a fifth experience 24-5 (e.g., meeting strangers in a dating App) and a sixth experience 24-6 (e.g., meeting strangers when starting school). Node 730-2 and node 730-3 each are associated with experiences, for instance, experiences from the experience store 22 of the digital reality system 200.

In the graph, each respective node in the plurality of nodes is further associated with the at least one respective gate criterion in the plurality of gate criteria. That is, each respective node in the plurality of nodes is associated with the same gate criterion or criteria as the category it corresponds to. In some embodiments, the method displays a completion status of each respective gate criterion associated with each respective node in the graph.

In some embodiments, a gate criterion associated with one node in the graph specifies a condition that is to be satisfied by the subject prior to advancement to another node in the graph. For instance, in the embodiment illustrated in FIG. 7A, a gate criterion associated with node 730-1 in the graph specifies a condition that is to be satisfied by the subject prior to advancement to node 730-3 in the graph. A gate criterion associated with node 730-3 in the graph specifies a condition that is to be satisfied by the subject prior to advancement to node 730-2 in the graph.

In some embodiments, a gate criterion associated with one node in the graph specifies a condition that is to be satisfied by the subject prior to activate the node in the graph. For instance, in the embodiment illustrated in FIG. 7A, a gate criterion associated with node 730-1 in the graph specifies a condition that is to be satisfied by the subject prior to activate node 730-1 in the graph. A gate criterion associated with node 730-3 in the graph specifies a condition that is to be satisfied by the subject prior to activate node 730-3 in the graph.

In the graph, for each respective node in the plurality of nodes, each respective experience graphic in the corresponding plurality of experience graphic corresponds to a respective proposed experience in the plurality of proposed experiences. For instance, as a non-limiting example, experience graphic 742-1 displayed adjacent to node 730-1 in FIG. 7A corresponds to (e.g., represents) experience 24-1 of the first category. Similarly, experience graphic 742-2, experience graphic 742-3, experience graphic 742-4, experience graphic 742-5 and experience graphic 742-6 correspond to experience 24-2, experience 24-3, experience 24-4, experience 24-5, and experience 24-6 of the first category.

In the graph, for each respective node in the plurality of nodes, each respective experience graphic in the corresponding plurality of experience graphic is also associated with the at least one biometric threshold in the plurality of biometric thresholds. That is, each respective experience graphic in the plurality of experience graphics is associated with the same biometric threshold(s) as the experience it corresponds to.

In some embodiments, each respective node in the plurality of nodes is connected by an edge in the plurality of edges to at least one other node in the graph. For instance, by way of example, FIG. 7A illustrates that node 730-1 (first node selected and placed in the graph by the user) is connected to node 730-3 (second selected and placed in the graph by the user) by edge 744-1 and edge 744-2. Node 730-3 is connected to node 730-2 (third node selected and placed in the graph by the user) by edge 744-3.

In some embodiments, each respective edge in the plurality of edges represents a progression within the graph between a respective initial node and a respective subsequent node in the graph upon successful completion by a subject of the category represented by the respective initial node (e.g., a required number of corresponding challenges associated with the category represented by the respective initial node). For instance, as a non-limiting example, suppose that node 730-1 is the respective initial node and node 730-3 is the respective subsequent node in the graph. Node 730-1 is associated with six proposed experiences, each proposed experience associated with a corresponding digital reality scene that manifests a corresponding challenge. In order to advance to node 730-3, a subject has to successfully complete a minimum number (e.g., 3, 4 or 5) of corresponding challenges associated with node 730-1. Without successful completion of the minimum number of corresponding challenges associated with node 730-1, the subject cannot advance to node 730-3 (e.g., node 730-3 would not be activated to allow access of the proposed experiences associated with node 730-3) unless a health care worker (e.g., a medical practitioner) associated with the subject intervenes.

In some embodiments, for each respective node in the plurality of nodes, the graph further includes a plurality of branches such as branch 746-1, branch 746-2 and branch 746-3. In some embodiments, each experience graphic in the plurality of experience graphics is connected to the respective node in the plurality of nodes by a branch in the plurality of branches. For instance, as a non-limiting example, FIG. 7A illustrates that each of experience graphic 742-1, experience graphic 742-2, experience graphic 742-3, experience graphic 742-4, experience graphic 742-5, and experience graphic 742-6 is connected to node 730-1 by a branch. Specifically, experience graphic 742-1 is connected to node 730-1 by branch 746-1, and experience graphic 742-6 is connected to node 730-1 by branch 746-6.

It should be noted that the graph can include other optional, alternative or additional elements. For instance, the graph can include one or more nodes, e.g., node 760 and node 770, representing other educational or therapeutical challenges such as cognitive reframing training, cognitive reframing challenge, mindfulness training, mindfulness challenge, and alternative/additional exposure exercises. The graph can also include other elements such as landmarks/landscapes. The graph can also be modified, animated or the like. Additional information regarding presenting a graph on a display can be found at U.S. Provisional Application No. 63/223,871, which is hereby incorporated by reference in its entirety for all purposes.

Block 594. Referring to block 594, in some embodiments, the obtained plurality of proposed experiences associated with the first category is originally arranged in an initial first experience hierarchy, thereby forming an initial first sub-progression (e.g., an initial first experience progression within the first category). For instance, in some embodiments, the obtained plurality of proposed experiences associated with the first category includes a first experience 24-1 (e.g., a first exposure experience of meeting strangers at a first party, a first CBT experience of reframing a thought), a second experience 24-2 (e.g., a second exposure experience of meeting strangers at a second party, a second CBT experience of determining usefulness of a thought), a third experience 24-3 (e.g., a third exposure experience of meeting strangers at a wedding reception, a third CBT experience of defusing a thought), a fourth experience 24-4 (e.g., a fourth exposure experience of meeting strangers at a work event), a fifth experience 24-5 (e.g., a fifth exposure experience of meeting strangers in a dating App) and a sixth experience 24-6 (e.g., a sixth exposure experience of meeting strangers when starting school). In some embodiments, among these six experiences, the sixth category is considered least challenging for the subject, followed by the third experience, first experience, second experience and fourth experience. The fifth experience is considered most challenging for the subject. In such cases, the six experiences are originally arranged in an initial first experience hierarchy, i.e., in an order of the sixth experience, third experience, first experience, second experience, fourth experience, and fifth experience. The plurality of experiences arranged in an initial first experience hierarchy forms initial first sub-progression. However, the present disclosure is not limited thereto.

In some embodiments, the experience graphics corresponding to the plurality of proposed experiences associated with the first category are arranged in a specific order on the graph to represent the initial first experience hierarchy. For instance, as a non-limiting example, FIG. 7A illustrates experience graphic 742-6, experience graphic 742-3, experience graphic 742-1, experience graphic 742-2, experience graphic 742-4, and experience graphic 742-5 arranged in a clock-wise manner adjacent to node 730-1. However, the present disclosure is not limited thereto. For instance, in some embodiments, the experience graphics are arranged on the graph in a counter-clock-wise manner. In some embodiments, the experience graphics are arranged on the graph in an ascending manner. In some embodiments, the experience graphics are arranged on the graph in a descending manner. In some embodiments, the experience graphics are not arranged on the graph in an order, and the initial first experience hierarchy is represented by other indicators such as numbers, texts or the like.

In some embodiments, the initial first experience hierarchy is set by (i) a system administrator, (ii) the subject, (iii) a health care worker associated with the subject, (iv) a model, or (v) a combination thereof. Generating the initial first experience hierarchy is similar to generating the initial category exposure progression described above. For instance, in some embodiments, whether an experience is considered more or less challenging is determined (i) from an assessment or a subjective evaluation, e.g., through the assessment module 12 that facilitates obtaining an assessment/subjective evaluation from the subject, and/or (ii) by the medical practitioner associated with the subject, e.g., having the medical practitioner evaluate some or all of the assessment obtained by the subject and generate the initial first experience progression. In some embodiments, the initial first experience hierarchy is generated at least in part by a model, based at least in part on the assessment from the subject and/or other data (e.g., user profile data of FIG. 2A). In some embodiments, the medical practitioner and the model generate the initial first experience progression, such as by having the medical practitioner provide input and/or supervision for the model. In some embodiments, the initial first experience progression is generated by the subject who modifies a recommended first experience progression.

In some embodiments, the plurality of proposed experiences associated with a second category is originally arranged in an initial second experience hierarchy, thereby forming an initial second sub-progression (e.g., an initial experience progression within the second category). In some embodiments, the plurality of proposed experiences associated with each respective category in the plurality of categories is originally arranged in an initial experience hierarchy, thereby forming a plurality of initial sub-progressions.

In some embodiments, each category in the plurality of categories is associated with a unique rank within a respective experience hierarchy, such as a first unique ranking of projected efficacy or a second unique ranking of interest by subject. For instance, in some embodiments, the unique rank is configured to define a relative position within the hierarchy. In some embodiments, the unique rank provides an indexing of each category in the plurality of categories, such that no two categories have the same ranking within the indexing of the plurality of categories. However, the present disclosure is not limited thereto.

Blocks 596-602. Referring to blocks 596-602, in some embodiments, the method further includes (S) assessing whether a proposed experience immediately subsequent to the first proposed experience in the initial first sub-progression is appropriate for the subject to perform next. For instance, as a non-limiting example, suppose that the subject has successfully completed challenge 26-$m$ designed for experience 24-$m$ and experience 24-$n$ is immediately subsequent to experience 24-$m$ in the initial experience hierarchy (e.g., the first sub-progression). The method assesses whether experience 24-$n$ is appropriate for the subject to perform next. In some embodiments, the assessment of whether experience 24-$n$ is appropriate for the subject to perform next is based, at least in part, on the level of success that the subject have had in challenge 26-$m$ designed for experience 24-$m$.

In some embodiments, the method further includes (T) presenting, if the immediately subsequent proposed experience is appropriate for the subject to perform next, a digital reality scene that manifests a challenge designed for the immediately subsequent proposed experience in the initial first sub-progression. For instance, as a non-limiting example, if it is determined that experience 24-$n$ is appropriate for the subject to perform next, the method presents, similar to that disclosed herein and exemplified by at least block 480, digital reality scene 40-$n$ that manifests challenge 26-$n$.

In some embodiments, the method further includes (U) repeating the obtaining (C), and the determining (D) for the challenge designed for the immediately subsequent proposed experience in the initial first sub-progression. For instance, as a non-limiting example, the method obtains, similar to that disclosed herein and exemplified by at least block 482, a plurality of data elements from all or a subset of sensors in the plurality of sensors, where the at least one biometric sensor captures at least one biometric data element associated with the subject while the subject is completing challenge 26-$n$. Based on the at least one biometric data element captured while the subject is completing challenge 26-$n$, the method determines, similar to that disclosed herein and exemplified by at least block 484, whether challenge 26-$n$ is successfully completed.

In some embodiments, the method further includes (V) recommending, if the immediately subsequent proposed experience is inappropriate for the subject to perform next, a proposed experience other than the immediately subsequent proposed experience for the subject to perform next. For instance, as a non-limiting example, if it is determined that experience 26-$n$ is inappropriate for the subject to perform next, the method recommends experience 26-$o$ for the subject to perform next, where experience 26-$o$ is associated with the same category as experience 26-$m$ but not immediately subsequent to experience 26-$m$ in the initial experience hierarchy. However, the present disclosure is not limited thereto. For instance, in some alternative embodiments, the method recommends an experience associated with a different category than experience 26-$m$, an experience not associated with any of the plurality of categories, an educational challenge, a mindfulness challenge, a cognitive reframing challenge, or the like.

It should be noted that the processes illustrated in the FIGS. 4A-4R are not necessarily in order. For instance, in some embodiments, the presenting (F) of a graph as exemplified by at least block 590 is performed prior to the presenting (B) of the first digital reality scene that manifests the first challenge designed for the first proposed experience of the first category as exemplified by at least block 480. In some embodiments, the presenting (O) of a subjective evaluation option and the performing (P) of the subjective evaluation as exemplified by at least block 582 is performed prior to the obtaining (A) of a plurality of categories for the subject as exemplified by at least block 432. In some embodiments, the presenting (O) of a subjective evaluation option and the performing (P) of the subjective evaluation as exemplified by at least block 582 is performed after the repeating (Q) and (R) for the second category as exemplified by at least block 586.

It should also be noted that the method can include the additional, optional and/or alternative processes exemplified in the flowchart in any meaningful and useful combinations. For instance, in some embodiments, the method include generate a report for the subject and/or present the report to the subject.

It should further be noted that the processes disclosed herein and exemplified in the flowchart can be, but do not have to be, executed in full. The subject and/or a health care worker associated with the subject can start, terminate, resume or restart the processes when needed or desired.

Furthermore, in some embodiments, the present disclosure is directed to providing a device (e.g., client device 300 of FIG. 3 and/or digital reality system 200 of FIGS. 2A and 2B) for implementing an exposure progression. The device is configured to improves an ability of a subject to manage a psychiatric or mental condition of the subject. Furthermore, the device includes one or more processors and a memory coupled to the one or more processors. The memory includes one or more programs configured to be executed by the one or more processors. The one or more programs is configured to cause the computer system to perform the methods of the present disclosure. In some embodiments, the device includes a display and/or audio circuitry (e.g., a speaker). In some embodiments, the device includes an objective lens in optical communication with a two-dimensional pixelated detector.

Referring to FIGS. 10A, 10B, and 10C there is depicted various therapeutic exposure progressions that utilize the devices, systems and/or methods of the present disclosure for treatment of individuals (e.g., individuals 18 years or older) with a mental health issue, such as social anxiety disorder or major depressive order. In some embodiments, the exposure progression is built to be used at home by a subject (e.g., a patient) while giving a healthcare professional (e.g., a clinician) associated with the subject the ability to asynchronously monitor and adjust the exposure progression (e.g., if necessary) for the subject. In some embodiments, the use of the systems and/or methods of the present disclosure provides a treatment of a psychiatric or mental condition exhibited by the subject.

That is, in some embodiments, the present disclosure includes a method of treating a psychiatric or mental condition by using the systems and/or methods of the present disclosure. In some embodiments, the method of treating a psychiatric or mental condition includes a combination therapy and/or one or more adjunctive therapies with any psychiatric medication (e.g., a pharmaceutical composition that is administered to a subject in order to treat a psychiatric or mental condition exhibited by the subject). In some embodiments, the pharmaceutical composition includes at least one selected from the group consisting of: a selective serotonin reuptake inhibitor (SSRIs) pharmaceutical composition; a selective serotonin and norepinephrine inhibitors (SNRIs) pharmaceutical composition; a norepinephrine-dopamine reuptake inhibitor (NDRIs) pharmaceutical composition; a NMethyl-D-aspartate receptor antagonist pharmaceutical composition; a serotonergic pharmaceutical composition; a tricyclic antidepressant pharmaceutical composition; a monoamine oxidase inhibitor (MAOIs) pharmaceutical composition; a tetracyclic antidepressant pharmaceutical composition; a L-methylfolate pharmaceutical composition; a benzodiazepine pharmaceutical composition; and a beta-blocker pharmaceutical composition. In some embodiments, the pharmaceutical composition includes at least one selected from the group consisting of: chlorpromazine, perphenazine, trifluoperazine, mesoridazine, a fluphenazine, thiothixene, molindone, thioridazine, loxapine, haloperidol, aripiprazole, clozapine, ziprasidone, risperidone, quetiapine pharmaceutical composition, an olanzapine, citalopram, escitalopram, fluvoxamine, paroxetine, fluoxetine, sertraline, clomipramine, amoxapine, amitriptyline, desipramine, nortriptyline, doxepin, trimipramine, imipramine, protiptyline, desvenlafaxine, venlafaxine, duloxetine, lorazepam, buspirone, propranolol, clonazepam, chlordiazepoxide, oxazepam, atenolol, clorazepate, diazepam, laprazolam, amphetamine, dextroamphetamine, methyphenidate, lamotrigine, ketamine, and lithium.

In some embodiments, the exposure progression includes a plurality of categories, each category in the plurality of categories directed to improving the ability of the subject, such as an ability to reframe a cognitive thought, an ability to be exposed to a stress, an ability to defuse a thought, or the like. Moreover, each category is associated with a proposed experience that manifests a corresponding challenge in a corresponding digital reality scene associated with the proposed experience.

For instance, in some embodiments, a first category of exposure progression is associated with a plurality of education experiences designed to educate the subject, such as a first educational experience educating the subject on long-term goal setting and a second educational experience educating the subject on short-term goal settings. In some embodiments, an education experience manifests a challenge in a corresponding digitally reality scene through one or more psychoeducation, interactive challenges. In some embodiments, the one or more psychoeducational interactive challenges help the subject understand the underly biopsychosocial drivers of their mental and behavioral health. In some embodiments, the exposure to the education experiences, such as by completing the challenges, provides an ability or the subject of a strong foundation and understanding of psychoeducational materials support effective transdiagnostic therapies.

In some embodiments, the exposure progression is configured (e.g., prescribed) by a qualified healthcare professional with a dosage of one or more challenges per a time period. In some embodiments, the time period can be a day, two days, three days, four days, five days, a week, two weeks, three weeks, a month, or more than a month. In some embodiments, the period of time is between 1 hour and 1 year, between 1 hour and 6 months, between 1 hour and 1 month, between 1 hour and 1 fortnight, between 1 hour and 1 week, between 1 hour and 1 day, between 1 hour and 12 hours, between 6 hours and 1 year, between 6 hours and 6 months, between 6 hours and 1 month, between 6 hours and 1 fortnight, between 6 hours and 1 week, between 6 hours and 1 day, between 6 hours and 12 hours, between 1 day and 1 year, between 1 day and 6 months, between 1 day and 1 month, between 1 day and 1 fortnight, between 1 day and 1 week, between 5 days and 1 year, between 5 days and 6 months, between 5 days and 1 month, between 5 days and 1 fortnight, between 5 days and 1 week, between 30 days and 1 year, between 30 days and 6 months, or between 30 days and 1 month. In some embodiments, the period of time is at least 1 hour, at least 6 hours, at least 12 hours, at least 1 day, at least 2 days, at least 5 days, at least 14 days, at least 20 days, at least 30 days, at least 31 days, at least 60 days, at least 2 months, at least 3 months, at least 4 months, at least 5 months, at least 6 months, at least 1 year, or at least 2 years. In some embodiments, the period of time is at most 1 hour, at most 6 hours, at most 12 hours, at most 1 day, at most 2 days, at most 5 days, at most 14 days, at most 20 days, at most 30 days, at most 31 days, at most 60 days, at most 2 months, at most 3 months, at most 4 months, at most 5 months, at most 6 months, at most 1 year, or at most 2 years. In some embodiments, the period of time is a duration of time the subject interacts, or is presented, with a digital reality scene. However, the present disclosure is not limited thereto. A time period for a challenge can be the same as or different from a time period for another challenge. As a non-limiting example, FIGS. 10A and 10B illustrates an outline of the exposure progression 2300 planned over the course of eight weeks with three challenges per week. In some embodiments, the exposure progression includes one or more psychoeducation challenges, one or more exposure challenges (e.g., social challenge practice), one or more mindfulness challenges, one or more cognitive reframing challenges, one or more goal settings challenges, or a combination thereof. In some embodiments, the exposure progression is allocated, or divided, into a plurality of chapters. In some embodiments, the plurality of chapters includes between 1 chapter and 100 chapters, between 2 chapters and 100 chapters, between 2 chapters and 50 chapters, between 2 chapters and 30 chapters, between 2 chapters and 24 chapters, between 2 chapters and 20 chapters, between 2 chapters and 12 chapters, between 2 chapters and 5 chapters, between 3 chapters and 100 chapters, between 3 chapters and 50 chapters, between 3 chapters and 30 chapters, between 3 chapters and 24 chapters, between 3 chapters and 20 chapters, between 3 chapters and 12 chapters, between 3 chapters and 5 chapters, between 5 chapters and 100 chapters, between 5 chapters and 50 chapters, between 5 chapters and 30 chapters, between 5 chapters and 24 chapters, between 5 chapters and 20 chapters, between 5 chapters and 12 chapters, between 10 chapters and 100 chapters, between 10 chapters and 50 chapters, between 10 chapters and 30 chapters, between 10 chapters and 24 chapters, between 10 chapters and 20 chapters, between 10 chapters and 12 chapters, between 10 chapters and 5 chapters, between 18 chapters and 100 chapters, between 18 chapters and 50 chapters, between 18 chapters and 30 chapters, between 18 chapters and 24 chapters, or between 18 chapters and 20 chapters. In some embodiments, the plurality of chapters includes at least 1 chapter, at least 3 chapters, at least 5 chapters, at least 6 chapters, at least 12 chapters, at least 14 chapters, at least 20 chapters, at least 24 chapters, at least 30 chapters, at least 31 chapters, or at least 60 chapters. In some embodiments, the plurality of chapters includes at most 1 chapter, at most 3 chapters, at most 5 chapters, at most 6 chapters, at most 12 chapters, at most 14 chapters, at most 20 chapters, at most 24 chapters, at most 30 chapters, at most 31 chapters, or at most 60 chapters.

Some of the psychoeducation, social challenge practice, mindfulness practice, cognitive reframing practice and goal settings are required and some of them are not required. In some embodiments, social challenge practice is always required.

In some embodiments, the exposure progression is configured to prevent the subject from moving any faster than prescribed (e.g., no more three challenges a week). In various embodiments, the exposure progression is configured to allow the subject to slow down his/her pace if the subject chooses or if the healthcare professional associated with the subject makes that suggestion, such as by making the subject repeat a first experience and/or a first challenge. For instance, in some embodiments, the exposure progression is configured to allow the subject to complete a challenge in about a week, about two weeks or more than two weeks if the subject chooses. In various embodiments, the exposure progression is also configured to allow the subject to go back into the exposure progression and do optional content anytime the subject chooses. For example, if a first chapter the subject completes the required content in the morning and wants to go back into the exposure progression later in the day to do a mindfulness practice, the exposure progression is configured to allow the subject to access the mindfulness practice of the first chapter. However, the present disclosure is not limited thereto.

In some embodiments, a client application, such as companion app 2100, is provided to or accessible by the subject and/or a healthcare professional. In some embodiments, the client application 2100 includes one or more functions that are alternative, additional or optional to those in the exposure progression. In some embodiments, the client application is used by a healthcare professional to prescribe the exposure progression for the subject, by the subject to track his/her progress, log his/her mood and thoughts, add short-term goals, by a healthcare professional associated with the subject to monitor the subject's progress and revise the exposure progression if needed, or any combination thereof.

In some embodiments, once in the exposure progression (e.g., once the subject has indicated the exposure progression, such as by interacting with a first experience and/or a first challenge), the subject can move through the exposure progression as prescribed by the healthcare professional. For instance, in some embodiments, once the subject is registered for the exposure progression, has a unique PIN, and syncs his/her headset, the subject can start the experience in virtual/digital reality. In some embodiments, when the subject begins the experience in digital reality, the subject immediately finds himself/herself in a DR environment, such as the DR environment 1000 simulating a beautiful and scenic place called the lake house. In some embodiments, when in the DR environment 1000 (e.g., the lake house), the subject can explore and/or teleport around the DR environment 1000, get familiar with the surroundings, and/or have the option to choose an avatar to represent himself/herself during the exposure progression.

In some embodiments, when the subject is ready to begin the exposure progression, a DR assistant, such as the DR assistant 1100, will appear (e.g., knock at the door) and a first chapter of required content will begin. In some embodiments, the DR assistant will navigate the subject to his/her first experience and/or first challenge, such as a psychoeducation challenge. Psychoeducation can take place in any suitable DR area within the exposure progression and in any suitable format. For instance, in some embodiments, psychoeducation primarily takes place in a designated area 1010 called the theater room or education room, and is displayed on a DR object, such as a TV screen as a video.

In some embodiments, only one psychoeducation experiences are available in chapter 1, but throughout the exposure progression the subject will go through several psychoeducational videos. In some embodiments, the topics of psychoeducational videos include, but are not limited to, education on (i) think, feel, do and cognitive behavioral therapy, (ii) mindfulness, (iii) goal setting, (iv) exposure therapy, (v) cognitive reframing and linking emotions and behaviors, (vi) different cognitive distortions types, (vii) gathering evidence cognitive reframing technique, (viii) usefulness cognitive reframing technique, and/or (ix) maintenance for preparing to graduate the exposure progression.

In some embodiments, a psychoeducational video can be short video or long video. For instance, in some embodiments, the psychoeducational video can last for about one minute, about two minutes, about three minutes, about four minutes, about five munities, about six minutes, about seven minutes, about eight minutes, or more than eight minutes. In an embodiment, each psychoeducational video takes about three to five minutes to complete.

In some embodiments, the subject will learn and experience mindfulness in a second chapter. Mindfulness is an option at any time for the subject from the second chapter forward, and the subject will have access to a suitable number of mindfulness practices. For instance, the subject can have access to more than two, more than four, more than six, more than eight, more than ten, more than twelve, more than fourteen, more than sixteen, more than eighteen, or more than twenty mindfulness practices. In some embodiments, the subject can select the voice (e.g., male or female) the subject prefers for guiding the subject through the mindfulness practices, and/or the location (e.g., a site or an environment) that the subject would like to experience while in his/her mindfulness practice. As a non-limiting example, FIG. 14 illustrates that a subject is allowed to choose a location among a number of locations (e.g., locates 2410-1, 2410-2) to practice mindfulness.

In some embodiments, a third chapter is directed to goal setting. In some embodiments, the third chapter includes education on why goal setting is important and beneficial, and teaches the subject on goal setting through one or more interactive activities. In some embodiments, goal setting is performed in the exposure progression 2300 or in the client application 2100. For instance, as a non-limiting example, in some embodiments, long-term goal setting is performed in the exposure progression (e.g., using the DR journey object 1022 in the study room), and short-term goal setting is performed (e.g., entered, recorded, or the like) in the client application. As another non-limiting example, in some embodiments, both long-term goal setting and short-term goal setting are performed in the client application. As a further non-limiting example, in some embodiments, both long-term goal setting and short-term goal setting are performed in the exposure progression. In some embodiments, a subject will set his/her long-term goals (e.g., three long-term goals) using the DR journey object 1022 in the study room of the lake house. In some embodiments, a subject will set his/her short-term goals using the client application 2100.

Figure 12A:
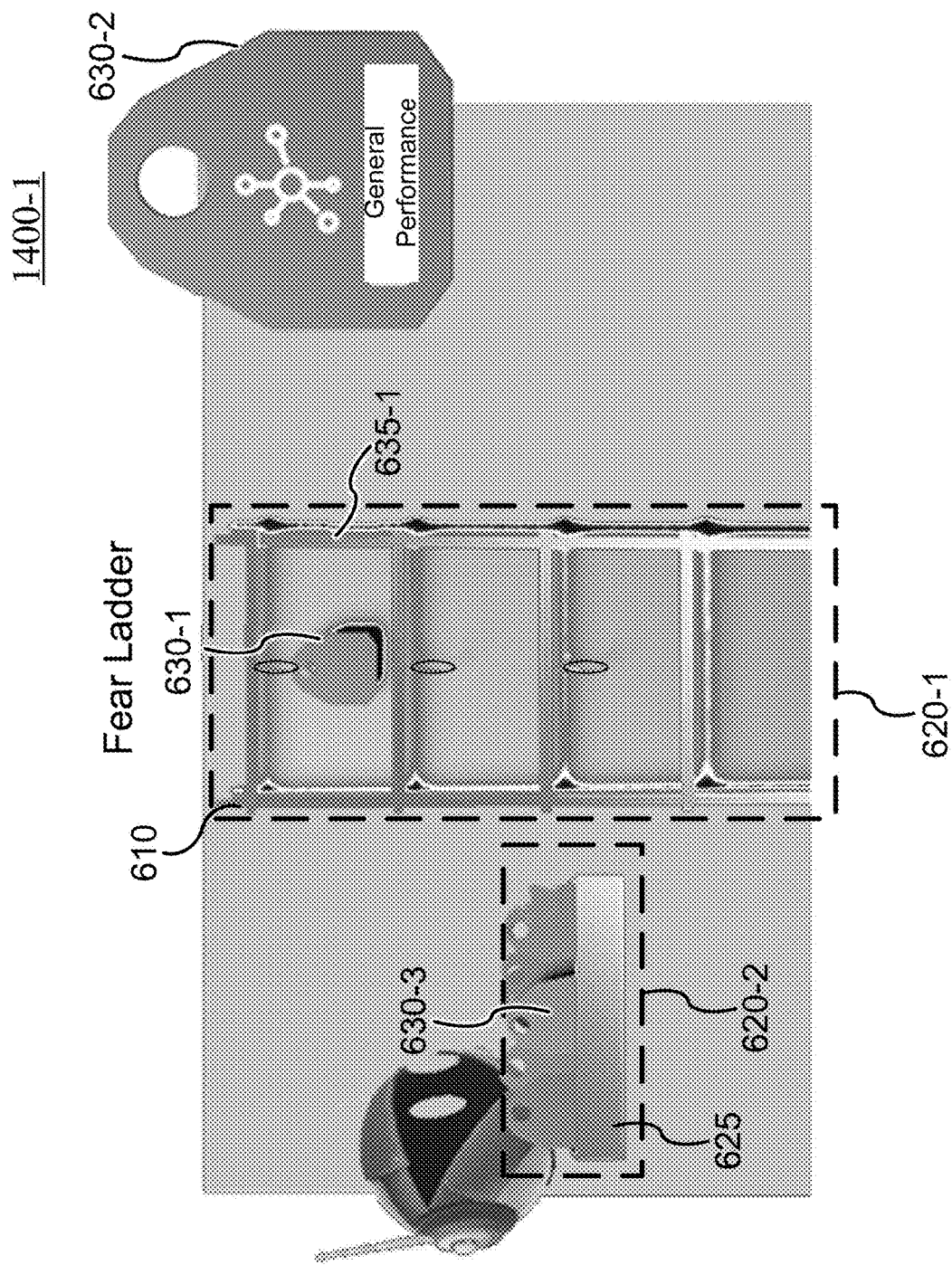
FIGS. 12A and 12B collectively illustrate another exemplary regimen, in accordance with some embodiments of the present disclosure.
Figure 12B:

In some embodiments, the exposure therapy includes a plurality of social challenges that are personalized by the subject while in the exposure progression and/or a healthcare professional associated with the subject. For instance, in some embodiments, the subject is guided by the DR assistant to personalize how the subject will move through his/her exposures by setting his/her hierarchy of different fear categories. A fear hierarchy can include two, three, four, five, five, six, seven, eight, nine, ten, or more than ten fear categories. Aa a non-limiting example, FIGS. 12A and 12B illustrate a hierarchy with three different fear categories: general performance, being assertive, and interacting with strangers.

In some embodiments, a fear hierarchy of social challenges is set by the subject in a designated area in the exposure progression, such as the designated area 1020 in the interactive DR environment 1000 (e.g., the study room in the lake house). To help the subject to set the fear hierarchy, in some embodiments, the designated area includes a plurality of DR category objects each representing a fear category, and a DR hierarchy object for the subject to place selected fear categories in an order, thereby forming a fear hierarchy. The plurality of DR category objects and the DR hierarchy object can be configured to simulate any real or nonreal, existent or non-existent items, devices, images, texts, symbols, cartoons, or the like. As a non-limiting example, FIG. 12A illustrates a DR hierarchy object 2610 simulating a ladder and a plurality of DR category objects (e.g., a category object 2620-1, a category object 2620-2 and/or a category object 2620-3) simulating placards. In some embodiments, a fear title 2622 and/or an icon 2624 of a respective category is displayed on a corresponding placard.

The DR assistant will walk the subject through the process of setting his/her fear hierarchy, explaining the subject will want to set the categories in a way where the subject can work his/her way up the ladder to his/her most feared social fear category. The subject will select placards and hang the selected placards on the ladder. The least feared category will be placed at the lowest level of the ladder and the most feared category will be placed at the highest level of the ladder. In some embodiments, the DR assistant will ask the subject to confirm the choices before the fear hierarchy is finalized.

A fear hierarchy of social challenges can be set in other ways, such as those disclosed in U.S. Provisional Patent Application No. 63/223,871 filed Jul. 20, 2021, U.S. Provisional Patent Application No. 63/284,862 filed Dec. 1, 2021, and U.S. patent application Ser. No. 17/869,670 filed Jul. 20, 2022, each of which is hereby incorporated by reference in its entirety for all purposes.

In some embodiments, the subject will start with his/her least feared category and work his/her way up to his/her most feared category. In some embodiment, each category is mapped to one or more interactive challenges. In some embodiments, challenges are set in a variety of different experiences realized through digital reality scenes that are known to trigger the psychiatric or mental condition exhibited by the subject. For instance, in some embodiments, a subject with social anxiety disorder, the exposure challenges are set in school cafeteria, classroom, job interviews, dates at a park, a traveling at an airport, and/or house BBQ/parties. In some embodiments, the subject must practice exposure challenges for a number of times (e.g., at least 5 times, at least 10 times, at least 15 times, at least 20 times, at least 25 times, at least 30 times, at most 5 times, at most 10 times, at most 15 times, at most 20 times, at most 25 times, at most 30 times, between 5 times and 30 times, between 5 times and 20 times, between 10 times and 30 times, between 10 times and 20 times, or the like) to move his/her way up his/her fear ladder as the subject moves through the exposure progression.

In some embodiments, before and/or after a challenge, the subject is required to answer an assessment, such as select his/her subjective units of distress (SUDS) to track his/her stress levels from the challenge, as the subject moves throughout the exposure progression. In some embodiments, before and/or after each and every challenge, the subject is required to select his/her SUDS to track his/her stress levels from the challenges as the subject moves throughout the exposure progression. The SUDS is a self-assessment tool for measuring the intensity of anxiety, anger, agitation, stress or other feelings and is generally rated on a scale from a first number to a second number. As a non-limiting example, in some embodiments, a SUDS is rated on a scale from 0 (e.g., not stressed at all) to 10 (e.g., extremely stressed). In some embodiments, selection of the SUDS is self-administered by the subject without supervision of a health care worker (e.g., a medical practitioner) associated with the subject. In some other embodiments, selection of the SUDS is performed by the subject but with supervision of a health care worker associated with the subject. In some embodiments, the assessment includes a GAD assessment (e.g., GAD-2 assessment) and/or a PHQ assessment (e.g., PHQ-2 assessment).

In some embodiments, the subject begins to learn and practice CBT techniques using a fourth chapter. In some embodiments, a CBT experience takes place in a digital reality scene simulating a woods environment. In some embodiments, the experience is configured to facility a combination of interactive psychoeducation challenges, such as led by the digital reality hose, and practice challenges. For instance, in some embodiments, a fifth chapter is associated with a first CBT experience that is associated with a first challenge to have the subject understanding how thoughts, emotions, and behaviors are linked. In some embodiments, a sixth chapter is associated with a second CBT experience that is associated with a second challenge for having the subject labeling cognitive distortions with different distortion types. In some embodiments, a seventh chapter a third CBT experience that is associated with a third challenge for having the subject gather evidence associated with a thought that helps the subject literally record evidence for and against a cognitive distortion associated with the thought. In some embodiments, an eighth CBT experience that is associated with a fourth challenge includes having the subject learns about how useful certain thoughts are to achieving his/her short and/or long-term goals.

Accordingly, the present disclosure allows for providing a personalized exposure therapy through digital reality in order to improve an ability of a subject to manage a mental or psychiatric condition exhibited by the subject.

REFERENCES CITED AND ALTERNATIVE EMBODIMENTS

All references cited herein are incorporated herein by reference in their entirety and for all purposes to the same extent as if each individual publication or patent or patent application was specifically and individually indicated to be incorporated by reference in its entirety for all purposes.

The present invention can be implemented as a computer program product that includes a computer program mechanism embedded in a non-transitory computer-readable storage medium. For instance, the computer program product could contain instructions for operating the user interfaces disclosed herein. These program modules can be stored on a CD-ROM, DVD, magnetic disk storage product, USB key, or any other non-transitory computer readable data or program storage product.

Many modifications and variations of this invention can be made without departing from its spirit and scope, as will be apparent to those skilled in the art. The specific embodiments described herein are offered by way of example only. The embodiments were chosen and described in order to best explain the principles of the invention and its practical applications, to thereby enable others skilled in the art to best utilize the invention and various embodiments with various modifications as are suited to the particular use contemplated. The invention is to be limited only by the terms of the appended claims, along with the full scope of equivalents to which such claims are entitled.

What is claimed is:

1. A method for implementing an exposure progression that improves an ability of a subject to manage a social anxiety disorder exhibited by the subject, the method comprising:

at a computer system associated with the subject, the computer system comprising one or more processors, a wearable display, a plurality of sensors, and a memory coupled to the one or more processors, the memory comprising one or more programs configured to be executed by the one or more processors, the one or more programs singularly or collectively comprising instructions for:

(A) generating, in electronic form, from an assessment data store, a first assessment for display at the wearable display, wherein the first assessment comprises a first set of prompts that elicits a response from the subject;

(B) determining if a plurality of assessment responses provided by the subject responsive to the first assessment satisfies one or more authorization criterion, wherein when the plurality of assessment responses satisfies an authorization criterion in the one or more authorization criterion, the one or more programs singularly or collectively obtains a baseline characteristic of the social anxiety disorder exhibited by the subject and an identification of a first set of categories for the subject, and when the plurality of assessment responses satisfies no authorization criteria in the one or more authorization criterion, repeating the generating (A) and determining (B) for one or more prompts in the first set of prompts;

(C) forming an initial instance of a corresponding exposure progression for the subject in accordance with the identification of the first set of categories, wherein:

the first set of categories is selected from a plurality of categories, each respective category in the plurality of categories (i) is directed to improving a particular ability of the subject to manage the social anxiety disorder exhibited by the subject, (ii) is associated with a corresponding plurality of proposed experiences, and (iii) is associated with at least one respective gate criterion in a plurality of gate criteria, and for each respective category in the plurality of categories, each respective proposed experience in the corresponding plurality of proposed experiences (i) is associated with a corresponding virtual reality scene, in a corresponding plurality of virtual reality scenes, that manifests a corresponding challenge, in a corresponding plurality of challenges, designed to evoke the social anxiety disorder of the subject during the respective proposed experience of the respective category, and (ii) is associated with at least one threshold, in a plurality of thresholds, for the corresponding challenge of the respective proposed experience, and the initial instance of the corresponding exposure progression comprises a first sequence of virtual reality events comprising an order of a first category and a second category in the first set of categories, wherein the first and second is selected from the group consisting of: an exposure category, a cognitive reframing therapy category, and a mindfulness category;

(D) presenting, on the wearable display, the first sequence of virtual reality events comprising a first virtual reality scene that manifests a first challenge designed for a first proposed experience of the first category in the first set of categories through a first plurality of interactable virtual reality objects, a second virtual reality scene that manifests a second challenge designed for a second proposed experience of the second category in the first set of categories different from the first category through a second plurality of interactable virtual reality objects, and a second assessment comprising a second set of prompts different from the first set of prompts in accordance with the initial instance of the corresponding exposure progression;

(E) obtaining, concurrent with the presenting (D), a first plurality of data elements, the first plurality of data elements comprising a first set of data elements, from a subset of sensors in the plurality of sensors, wherein the first set of data elements is selected in accordance with the first sequence of virtual reality events, and wherein the subset of sensors comprises a first sensor that captures at least one data element in waveform associated with the subject when the subject is completing the first challenge in the first virtual reality scene and a second sensor that captures at least one data element associated with the subject when the subject is completing the second challenge in the second virtual reality scene, and wherein the obtaining (E) comprises transcribing the at least one data element in waveform, thereby obtaining a vocal feature associated with the subject when the subject is completing the first challenge in the first virtual reality scene;

(F) determining:
- (i) whether the first plurality of data elements satisfies the at least one threshold associated with the first proposed experience for the first challenge and the at least one threshold associated with the second proposed experience for the second challenge, wherein each of the at least one threshold comprises a threshold to assess whether a respective challenge is successfully completed by satisfying the at least one threshold associated with a corresponding proposed experience for the respective challenge, and wherein the first plurality of data elements comprises a first subset of data elements captured by the first sensor,
- (ii) whether the first plurality of data elements satisfies a corresponding first threshold baseline characteristic defined by the initial instance of the corresponding exposure progression,
- (iii) whether the at least one respective gate criterion associated with the first category is satisfied, and
- (iv) whether the at least one respective gate criterion associated with the second category is satisfied;

(G) forming an updated instance of the corresponding exposure progression, wherein:
when each gate criterion in the at least one respective gate criterion associated with the first category and each gate criterion in the at least one respective gate criterion associated with the second category are satisfied, the first sequence of virtual reality events is updated to comprise a third category in the plurality of categories for the subject to perform next, thereby forming a second sequence of virtual reality events associated with the updated instance of the corresponding exposure progression different from the first sequence of virtual reality events, and
when each gate criterion in the at least one respective gate criterion associated with the first category and each gate criterion in the at least one respective gate criterion associated with the second category are not satisfied, the first sequence of virtual reality events is updated to comprise either of the first category or the second category for the subject to perform next, thereby forming a third sequence of virtual reality events associated with the updated instance of the corresponding exposure progression different from the second sequence of virtual reality events and the first sequence of virtual reality events, wherein the forming (G) is based at least in part on an outcome of the determining (F);

(H) presenting, on the wearable display, either the second sequence of virtual reality events or the third sequence of virtual reality events, thereby implementing the exposure progression that improves the ability of the subject to manage the social anxiety disorder exhibited by the subject; and (I) obtaining, concurrent with the presenting (H), a second plurality of data elements, the first plurality of data elements comprising a first set of data elements, from the subset of sensors in the plurality of sensors when the subject is completing the second sequence of virtual reality events or the third sequence of virtual reality events.

2. The method of claim 1, wherein the first sequence of virtual reality events is originally arranged in the initial instance of the corresponding exposure progression that is set by (i) a system administrator, (ii) the subject, (iii) a health care worker associated with the subject, (iv) a model, or (v) a combination thereof.

3. The method of claim 2, further comprising:
(J) presenting, on the wearable display prior to the presenting (D), a graph to represent the initial instance of the exposure progression, wherein the graph comprises a plurality of nodes and a plurality of edges and wherein, for each respective node in the plurality of nodes, the graph further comprises a corresponding plurality of experience graphics displayed adjacent to the respective node, wherein:
each respective node in the plurality of nodes (i) corresponds to a respective category in the plurality of categories, (ii) is associated with the corresponding plurality of proposed experiences associated with the respective category corresponding to the respective node, and (iii) is associated with the at least one respective gate criterion in the plurality of gate criteria associated with the respective category corresponding to the respective node,
for each respective node in the plurality of nodes, each respective experience graphic in the corresponding plurality of experience graphics (i) corresponds to a respective proposed experience in the corresponding plurality of proposed experiences associated with the respective category corresponding to the respective node, and (ii) is associated with the at least one threshold in the plurality of thresholds for the corresponding challenge of the respective proposed experience,
each respective node in the plurality of nodes is connected, by an edge in the plurality of edges, to at least one other node in the plurality of nodes, and
each respective edge in the plurality of edges represents a progression within the graph between a respective initial node and a respective subsequent node in the graph upon successful completion by a subject of a required number of corresponding challenges associated with the respective initial node.

4. The method of claim 2, wherein the forming (G) comprises:
assessing whether a category immediately subsequent to the first category in the initial instance of the corresponding exposure progression is appropriate for the subject to perform next; and
presenting, when the immediately subsequent category in the initial instance of the corresponding exposure progression is appropriate for the subject to perform next, the immediately subsequent category in the initial instance of the corresponding exposure progression as the third category for the subject to perform.

5. The method of claim 4, wherein the forming (G) further comprises:
recommending, when the immediately subsequent category in the initial instance of the corresponding exposure progression is inappropriate for the subject to perform next, the first category or the second category for the subject to perform next.

6. The method of claim 1, wherein the first sensor is a recorder, and the first subset of data elements comprises a temporal data element, a spectral data element, a cepstral data element, an entropy data element, or a combination thereof.

7. The method of claim 1, wherein the first subset of data elements captured by the first sensor is stored in a corresponding user profile, thereby allowing a replay of the first subset of data elements after completion of the first virtual reality scene.

8. The method of claim 1, further comprising:
(K) receiving, in electronic form a second plurality of data elements associated with the subject, wherein the second plurality of data elements comprises a second plurality of data elements associated with an initial psychiatric or mental condition of the subject, wherein the corresponding threshold baseline characteristic is formed by the second plurality of data elements.

9. The method of claim 1, further comprising:
(L) obtaining, from the first sensor, a second plurality of data elements when or before initiating the presenting (D), wherein the corresponding threshold baseline characteristic is formed by the second plurality of data elements.

10. The method of claim 1, further comprising:
(M) repeating, when a gate criterion in the at least one respective gate criterion associated with the first category is not satisfied, the presenting (D), the obtaining (E), and the determining (F) one or more times for challenges of other proposed experiences in the corresponding plurality of proposed experiences associated with the first category.

11. The method of claim 1, further comprising:
(N) recommending, when the first challenge is determined to be unsuccessfully completed by failing to satisfy the at least one threshold associated with the first proposed experience for the first challenge, a challenge of another proposed experience in the corresponding plurality of proposed experiences for the first category for the subject to perform next, wherein the recommending (N) is presented, in a text, a graphic, an audio, or a combination thereof.

12. The method of claim 11, wherein the recommended challenge poses an equal or less challenging challenge than the first challenge of the first category, is the same first challenge designed for the first proposed experience of the first category, a challenge designed for a different proposed experience of the first category, or a challenge designed for a proposed experience of a different category in the plurality of categories.

13. The method of claim 1, further comprising:
(O) presenting, on the wearable display prior to the determining (F), the second assessment comprising a subjective evaluation option; and
(P) performing, in response to selection of the subjective evaluation option, a subjective evaluation,
wherein the determining (F) is based, at least in part, on an outcome of the subjective evaluation.

14. The method of claim 13, wherein the subjective evaluation is based on a Minimal Clinically Important Difference (MCID), a Clinical Global Impression Scale of Improvement (CGI), a Patient Global Impression Scale of Improvement (PGI), a Liebowitz Social Anxiety Scale (LSAS), a Generalized Anxiety Disorder (GAD), a Patient Health Questionnaire (PHQ), or a combination thereof.

15. The method of claim 1, wherein the determining (F) further comprises determining whether the first plurality of data elements satisfies a second threshold in the at least one threshold.

16. The method of claim 1, wherein the at least one respective gate criterion comprises a medical practitioner gate criterion associated with an approval, from a medical practitioner associated with the subject, of the category in the plurality of categories corresponding to the at least one respective gate criterion.

17. The method of claim 1, wherein the at least one respective gate criterion comprises an arrangement gate criterion associated with an order of one or more categories in the plurality of categories.

18. The method of claim 1, wherein a gate criterion associated with one category in the plurality of categories specifies a condition that is to be satisfied by the subject prior to advancement to another category in the plurality of categories.

19. The method of claim 18, wherein a respective gate criterion of a respective category in the plurality of categories is set by (i) a system administrator, (ii) the subject, (iii) a model, or (iv) a health care worker associated with the subject.

20. The method of claim 19, wherein
a respective gate criterion of a first category in the plurality of categories is set by a system administrator or a health care worker associated with the subject, and
a respective gate criterion of a second category in the plurality of categories is set by the subject.

21. The method of claim 1, wherein the at least one threshold of the first proposed experience is an eye contact threshold, a heart rate threshold, an assertiveness threshold, a decibel level threshold, a pitch threshold, an utterance threshold, a word threshold, or a sentiment analysis criterion that manifests the corresponding challenge designed for the first proposed experience associated with the first category.

22. The method of claim 1, wherein the at least one threshold of the first proposed experience is an utterance threshold, wherein the utterance threshold comprises a minimum number of utterances, a maximum number of utterances, a required increase of the number of utterances, a required decrease of the number of utterances, or a combination thereof.

23. The method of claim 1, wherein the first category is a mindfulness category or an exposure category and the second category is a cognitive reframing category.

24. The method of claim 1, further comprising administering:
when each gate criterion in the at least one respective gate criterion associated with the first category and each gate criterion in the at least one respective gate criterion associated with the second category are satisfied, the second sequence of virtual reality events, and
when each gate criterion in the at least one respective gate criterion associated with the first category and each gate criterion in the at least one respective gate criterion associated with the second category are not satisfied, some or all of the first sequence of virtual reality events.

25. The method of claim 1, wherein the corresponding first threshold baseline characteristic is a comparison of the first set of data elements against a baseline of the subject obtained, prior to the obtaining (A).

26. The method of claim 1, wherein the corresponding challenge manifested by the corresponding virtual reality scene for each respective proposed experience in the corresponding plurality of proposed experiences for the exposure category comprises a fear inducing conflict.

27. The method of claim 1, wherein the corresponding challenge manifested by the corresponding virtual reality scene for each respective proposed experience in the corresponding plurality of proposed experiences for the cognitive reframing category comprises disrupting a first cognitive pattern associated with the subject with a formation of a second cognitive reframing pattern different from the first cognitive framing pattern.

28. The method of claim 1, wherein the corresponding challenge manifested by the corresponding virtual reality scene for each respective proposed experience in the corresponding plurality of proposed experiences for the mindfulness category comprises modulating a perception of control for the subject.

29. A computer system for implementing an exposure progression that improves an ability of a subject to manage a social anxiety disorder exhibited by the subject, the computer system comprising one or more processors, a wearable display, a plurality of sensors, and a memory coupled to the one or more processors, the memory comprising one or more programs configured to be executed by the one or more processors, thereby causing the computer system to perform a method comprising:
- (A) generating, in electronic form, from an assessment data store, a first assessment for display at the wearable display, wherein the first assessment comprises a first set of prompts that elicits a response from the subject;
- (B) determining if a plurality of assessment responses provided by the subject responsive to the first assessment satisfies one or more authorization criterion, wherein
  - when the plurality of assessment responses satisfies an authorization criterion in the one or more authorization criterion, the one or more programs singularly or collectively obtains a baseline characteristic of the social anxiety disorder exhibited by the subject and an identification of a first set of categories for the subject, and
  - when the plurality of assessment responses satisfies no authorization criteria in the one or more authorization criterion, repeating the generating (A) and determining (B) for one or more prompts in the first set of prompts;
- (C) forming an initial instance of a corresponding exposure progression for the subject in accordance with the identification of the first set of categories, wherein:
  - the first set of categories is selected from a plurality of categories,
  - each respective category in the plurality of categories (i) is directed to improving a particular ability of the subject to manage the social anxiety disorder exhibited by the subject, (ii) is associated with a corresponding plurality of proposed experiences, and (iii) is associated with at least one respective gate criterion in a plurality of gate criteria, and
  - for each respective category in the plurality of categories, each respective proposed experience in the corresponding plurality of proposed experiences (i) is associated with a corresponding virtual reality scene, in a corresponding plurality of virtual reality scenes, that manifests a corresponding challenge, in a corresponding plurality of challenges, designed to evoke the social anxiety disorder of the subject during the respective proposed experience of the respective category, and (ii) is associated with at least one threshold, in a plurality of thresholds, for the corresponding challenge of the respective proposed experience, and
  - the initial instance of the corresponding exposure progression comprises a first sequence of virtual reality events comprising an order of a first category and a second category in the first set of categories, wherein the first and second is selected from the group consisting of: an exposure category, a cognitive reframing therapy category, and a mindfulness category;
- (D) presenting, on the wearable display, the first sequence of virtual reality events comprising a first virtual reality scene that manifests a first challenge designed for a first proposed experience of the first category in the first set of categories through a first plurality of interactable virtual reality objects, a second virtual reality scene that manifests a second challenge designed for a second proposed experience of the second category in the first set of categories different from the first category through a second plurality of interactable virtual reality objects, and a second assessment comprising a second set of prompts different from the first set of prompts in accordance with the initial instance of the corresponding exposure progression;
- (E) obtaining, concurrent with the presenting (D), a first plurality of data elements, the first plurality of data elements comprising a first set of data elements, from a subset of sensors in the plurality of sensors, wherein the first set of biometric data elements is selected in accordance with the first sequence of virtual reality events, and wherein the subset of sensors comprises a first sensor that captures at least one data element in waveform associated with the subject when the subject is completing the first challenge in the first virtual reality scene and a second sensor that captures at least one data element associated with the subject when the subject is completing the second challenge in the second virtual reality scene, and wherein the obtaining (E) comprises transcribing the at least one data element in waveform, thereby obtaining a vocal feature associated with the subject when the subject is completing the first challenge in the first virtual reality scene;
- (F) determining:
  - (i) whether the first plurality of data elements satisfies the at least one threshold associated with the first proposed experience for the first challenge and the at least one threshold associated with the second proposed experience for the second challenge, wherein each of the at least one threshold comprises a threshold to assess whether a respective challenge is successfully completed by satisfying the at least one threshold associated with a corresponding proposed experience for the respective challenge, and wherein the first plurality of data elements comprises a first subset of data elements captured by the first sensor,
  - (ii) whether the first plurality of data elements satisfies a corresponding first threshold baseline characteristic defined by the initial instance of the corresponding exposure progression,
  - (iii) whether the at least one respective gate criterion associated with the first category is satisfied, and
  - (iv) whether the at least one respective gate criterion associated with the second category is satisfied;
- (G) forming an updated instance of the corresponding exposure progression, wherein:
  - when each gate criterion in the at least one respective gate criterion associated with the first category and each gate criterion in the at least one respective gate criterion associated with the second category are satisfied, the first sequence of virtual reality events is updated to comprise a third category in the plurality of categories for the subject to perform next, thereby forming a second sequence of virtual reality events associated with the updated instance of the corresponding exposure progression different from the first sequence of virtual reality events, and when each gate criterion in the at least one respective gate criterion associated with the first category and each gate criterion in the at least one respective gate criterion associated with the second category are not satisfied, the first sequence of virtual reality events is updated to comprise either of the first category or the second category for the subject to perform next, thereby forming a third sequence of virtual reality events associated with the updated instance of the corresponding exposure progression different from the second sequence of virtual reality events and the first sequence of virtual reality events, wherein the forming (G) is based at least in part on an outcome of the determining (F);

(H) presenting, on the wearable display, either the second sequence of virtual reality events or the third sequence of virtual reality events, thereby implementing the exposure progression that improves the ability of the subject to manage the social anxiety disorder exhibited by the subject; and (I) obtaining, concurrent with the presenting (H), a second plurality of data elements, the first plurality of data elements comprising a first set of data elements, from the subset of sensors in the plurality of sensors when the subject is completing the second sequence of virtual reality events or the third sequence of virtual reality events.

30. A non-transitory computer readable storage medium storing one or more programs, the one or more programs comprising instructions, which when executed by a computer system cause the computer system to perform a method comprising:

(A) generating, in electronic form, from an assessment data store, a first assessment for display at the wearable display, wherein the first assessment comprises a first set of prompts that elicits a response from the subject;

(B) determining if a plurality of assessment responses provided by the subject responsive to the first assessment satisfies one or more authorization criterion, wherein when the plurality of assessment responses satisfies an authorization criterion in the one or more authorization criterion, the one or more programs singularly or collectively obtains a baseline characteristic of the social anxiety disorder exhibited by the subject and an identification of a first set of categories for the subject, and when the plurality of assessment responses satisfies no authorization criteria in the one or more authorization criterion, repeating the generating (A) and determining (B) for one or more prompts in the first set of prompts;

(C) forming an initial instance of a corresponding exposure progression for the subject in accordance with the identification of the first set of categories, wherein:

the first set of categories is selected from a plurality of categories, each respective category in the plurality of categories (i) is directed to improving a particular ability of the subject to manage the social anxiety disorder exhibited by the subject, (ii) is associated with a corresponding plurality of proposed experiences, and (iii) is associated with at least one respective gate criterion in a plurality of gate criteria, and for each respective category in the plurality of categories, each respective proposed experience in the corresponding plurality of proposed experiences (i) is associated with a corresponding virtual reality scene, in a corresponding plurality of virtual reality scenes, that manifests a corresponding challenge, in a corresponding plurality of challenges, designed to evoke the social anxiety disorder of the subject during the respective proposed experience of the respective category, and (ii) is associated with at least one threshold, in a plurality of thresholds, for the corresponding challenge of the respective proposed experience, and the initial instance of the corresponding exposure progression comprises a first sequence of virtual reality events comprising an order of a first category and a second category in the first set of categories, wherein the first and second is selected from the group consisting of: an exposure category, a cognitive reframing therapy category, and a mindfulness category;

(D) presenting, on the wearable display, the first sequence of virtual reality events comprising a first virtual reality scene that manifests a first challenge designed for a first proposed experience of the first category in the first set of categories through a first plurality of interactable virtual reality objects, a second virtual reality scene that manifests a second challenge designed for a second proposed experience of the second category in the first set of categories different from the first category through a second plurality of interactable virtual reality objects, and a second assessment comprising a second set of prompts different from the first set of prompts in accordance with the initial instance of the corresponding exposure progression;

(E) obtaining, concurrent with the presenting (D), a first plurality of data elements, the first plurality of data elements comprising a first set of data elements, from a subset of sensors in the plurality of sensors, wherein the first set of data elements is selected in accordance with the first sequence of virtual reality events, and wherein the subset of sensors comprises a first sensor that captures at least one data element in waveform associated with the subject when the subject is completing the first challenge in the first virtual reality scene and a second sensor that captures at least one data element associated with the subject when the subject is completing the second challenge in the second virtual reality scene, and wherein the obtaining (E) comprises transcribing the at least one data element in waveform, thereby obtaining a vocal feature associated with the subject when the subject is completing the first challenge in the first virtual reality scene;

(F) determining:

(i) whether the first plurality of data elements satisfies the at least one threshold associated with the first proposed experience for the first challenge and the at least one threshold associated with the second proposed experience for the second challenge, wherein each of the at least one threshold comprises a threshold to assess whether a respective challenge is successfully completed by satisfying the at least one threshold associated with a corresponding proposed experience for the respective challenge, and wherein the first plurality of data elements comprises a first subset of data elements captured by the first sensor, (ii) whether the first plurality of data elements satisfies a corresponding first threshold baseline characteristic defined by the initial instance of the corresponding exposure progression, (iii) whether the at least one respective gate criterion associated with the first category is satisfied, and (iv) whether the at least one respective gate criterion associated with the second category is satisfied;

(G) forming an updated instance of the corresponding exposure progression, wherein:

when each gate criterion in the at least one respective gate criterion associated with the first category and each gate criterion in the at least one respective gate criterion associated with the second category are satisfied, the first sequence of virtual reality events is updated to comprise a third category in the plurality of categories for the subject to perform next, thereby forming a second sequence of virtual reality events associated with the updated instance of the corresponding exposure progression different from the first sequence of virtual reality events, and when each gate criterion in the at least one respective gate criterion associated with the first category and each gate criterion in the at least one respective gate criterion associated with the second category are not satisfied, the first sequence of virtual reality events is updated to comprise either of the first category or the second category for the subject to perform next, thereby forming a third sequence of virtual reality events associated with the updated instance of the corresponding exposure progression different from the second sequence of virtual reality events and the first sequence of virtual reality events, wherein the forming (G) is based at least in part on an outcome of the determining (F);

(H) presenting, on the wearable display, either the second sequence of virtual reality events or the third sequence of virtual reality events, thereby implementing the exposure progression that improves the ability of the subject to manage the social anxiety disorder exhibited by the subject; and (I) obtaining, concurrent with the presenting (H), a second plurality of data elements, the first plurality of data elements comprising a first set of data elements, from the subset of sensors in the plurality of sensors when the subject is completing the second sequence of virtual reality events or the third sequence of virtual reality events.

31. A method for implementing an exposure progression that improves an ability of a subject to manage a social anxiety disorder exhibited by the subject, the method comprising:

at a computer system associated with the subject, the computer system comprising one or more processors, a wearable display, a plurality of sensors, and a memory coupled to the one or more processors, the memory comprising one or more programs configured to be executed by the one or more processors to perform the method, the one or more programs singularly or collectively comprising instructions for:

(A) generating, in electronic form, from an assessment data store, a first assessment for display at the wearable display, wherein the first assessment comprises a first set of prompts that elicits a response from the subject;

(B) determining if a plurality of assessment responses provided by the subject responsive to the first assessment satisfies one or more authorization criterion, wherein when the plurality of assessment responses satisfies an authorization criterion in the one or more authorization criterion, the one or more programs singularly or collectively obtains a baseline characteristic of the social anxiety disorder exhibited by the subject and an identification of a first set of categories for the subject, and when the plurality of assessment responses satisfies no authorization criteria in the one or more authorization criterion, repeating the generating (A) and determining (B) for one or more prompts in the first set of prompts;

(C) forming an initial instance of a corresponding exposure progression for the subject in accordance with the identification of the first set of categories, wherein:

the first set of categories is selected from a plurality of categories, each respective category in the plurality of categories (i) is directed to improving a particular ability of the subject to manage the social anxiety disorder exhibited by the subject, (ii) is associated with a corresponding plurality of proposed experiences, and (iii) is associated with at least one respective gate criterion in a plurality of gate criteria, and for each respective category in the plurality of categories, each respective proposed experience in the corresponding plurality of proposed experiences (i) is associated with a corresponding virtual reality scene, in a corresponding plurality of virtual reality scenes, that manifests a corresponding challenge, in a corresponding plurality of challenges, designed to evoke the social anxiety disorder of the subject during the respective proposed experience of the respective category, and (ii) is associated with at least one threshold, in a plurality of thresholds, for the corresponding challenge of the respective proposed experience, and the initial instance of the corresponding exposure progression comprises a first sequence of virtual reality events comprising an order of a first category and a second category in the first set of categories, wherein the first and second is selected from the group consisting of: an exposure category, a cognitive reframing therapy category, and a mindfulness category;

(D) presenting, on the wearable display, the first sequence of virtual reality events comprising a first virtual reality scene that manifests a first challenge designed for a first proposed experience of the first category in the first set of categories through a first plurality of interactable virtual reality objects, a second virtual reality scene that manifests a second challenge designed for a second proposed experience of the second category in the first set of categories different from the first category through a second plurality of interactable virtual reality objects, and a second assessment comprising a second set of prompts different from the first set of prompts in accordance with the initial instance of the corresponding exposure progression;

(E1) obtaining, in coordination with the presenting (D), a first subset of data elements of the subject, using a first sensor in the plurality of sensors operating at a first sampling rate, while the subject is incurring a first portion of the first sequence of virtual reality events;
(E2) determining, responsive to a content of the first set of data elements, using the one or more programs, whether to adjust the first sampling rate of the first sensor to a second sampling rate, other than the first sampling rate, based on an evaluation of the content of the first subset of data;
(E3) obtaining, in coordination with the presenting (D), a second subset of data elements of the subject, using the first sensor in the plurality of sensors operating:
  (i) at the first sampling rate when the evaluation of the content of the first subset of data does not indicate that the second sampling rate is warranted, or
  (ii) at the second sampling rate when the evaluation of the content of the first subject of data indicates that the different second sampling rate is warranted, while the subject is incurring a second portion of the first sequence of virtual reality events,
wherein the first subset of data and the second subset of data combine to form a first set of data elements;
(F) determining:
  (i) whether the first plurality of data elements satisfies the at least one threshold associated with the first proposed experience for the first challenge and the at least one threshold associated with the second proposed experience for the second challenge, wherein each of the at least one threshold comprises a threshold to assess whether a respective challenge is successfully completed by satisfying the at least one threshold associated with a corresponding proposed experience for the respective challenge, and wherein the first plurality of data elements comprises a first subset of data elements captured by the first sensor,
  (ii) whether the first plurality of data elements satisfies a corresponding first threshold baseline characteristic defined by the initial instance of the corresponding exposure progression,
  (iii) whether the at least one respective gate criterion associated with the first category is satisfied, and
  (iv) whether the at least one respective gate criterion associated with the second category is satisfied;
(G) forming an updated instance of the corresponding exposure progression, wherein:
  when each gate criterion in the at least one respective gate criterion associated with the first category and each gate criterion in the at least one respective gate criterion associated with the second category are satisfied, the first sequence of virtual reality events is updated to comprise a third category in the plurality of categories for the subject to perform next, thereby forming a second sequence of virtual reality events associated with the updated instance of the corresponding exposure progression different from the first sequence of virtual reality events, and
  when each gate criterion in the at least one respective gate criterion associated with the first category and each gate criterion in the at least one respective gate criterion associated with the second category are not satisfied, the first sequence of virtual reality events is updated to comprise either of the first category or the second category for the subject to perform next, thereby forming a third sequence of virtual reality events associated with the updated instance of the corresponding exposure progression different from the second sequence of virtual reality events and the first sequence of virtual reality events, wherein the forming (G) is based at least in part on an outcome of the determining (F);
(H) presenting, on the wearable display, either the second sequence of virtual reality events or the third sequence of virtual reality events, thereby implementing the exposure progression that improves the ability of the subject to manage the social anxiety disorder exhibited by the subject; and
(I) obtaining, concurrent with the presenting (H), a second plurality of data elements, the first plurality of data elements comprising a first set of data elements, from the subset of sensors in the plurality of sensors when the subject is completing the second sequence of virtual reality events or the third sequence of virtual reality events.

32. The method of claim 31, wherein the first sensor measures heart rate and the (E2) determining adjusts the first sampling rate of the first sensor to the second sampling rate when a heartrate in the content of the first subset of data includes a variation in the heart rate.

33. The method of claim 31, wherein the first sensor measures speech and the (E2) determining adjusts the first sampling rate of the first sensor to the second sampling rate when the content of the first subset of data indicates the subject is not speaking.

* * * * *